United States Patent
Vlahov et al.

(10) Patent No.: US 9,505,747 B2
(45) Date of Patent: Nov. 29, 2016

(54) PROCESSES FOR PREPARING TUBULYSIN DERIVATIVES AND CONJUGATES THEREOF

(71) Applicant: Endocyte, Inc., West Lafayette, IN (US)

(72) Inventors: Iontcho Radoslavov Vlahov, West Lafayette, IN (US); Hari Krishna R. Santhapuram, West Lafayette, IN (US); Paul Joseph Kleindl, Lebanon, IN (US); Christopher Paul Leamon, West Lafayette, IN (US); Fei You, West Lafayette, IN (US)

(73) Assignee: Endocyte, Inc., West Lafayette, IN (US)

( * ) Notice: Subject to any disclaimer, the term of this patent is extended or adjusted under 35 U.S.C. 154(b) by 0 days.

(21) Appl. No.: 14/388,311

(22) PCT Filed: Mar. 29, 2013

(86) PCT No.: PCT/US2013/034672
§ 371 (c)(1),
(2) Date: Sep. 26, 2014

(87) PCT Pub. No.: WO2013/149185
PCT Pub. Date: Oct. 3, 2013

(65) Prior Publication Data
US 2015/0051399 A1 Feb. 19, 2015

Related U.S. Application Data

(60) Provisional application No. 61/617,386, filed on Mar. 29, 2012, provisional application No. 61/684,450, filed on Aug. 17, 2012, provisional application No. 61/771,451, filed on Mar. 1, 2013, provisional application No. 61/794,720, filed on Mar. 15, 2013.

(51) Int. Cl.
| | |
|---|---|
| *C07D 277/56* | (2006.01) |
| *A61K 38/00* | (2006.01) |
| *C07D 417/14* | (2006.01) |
| *C07K 5/02* | (2006.01) |
| *C07K 7/02* | (2006.01) |
| *C07D 213/71* | (2006.01) |
| *C07C 241/02* | (2006.01) |
| *C07D 213/76* | (2006.01) |
| *C07D 417/12* | (2006.01) |
| *C07F 7/18* | (2006.01) |

(52) U.S. Cl.
CPC .......... *C07D 417/14* (2013.01); *C07C 241/02* (2013.01); *C07D 213/71* (2013.01); *C07D 213/76* (2013.01); *C07D 277/56* (2013.01); *C07D 417/12* (2013.01); *C07F 7/188* (2013.01); *C07F 7/1892* (2013.01); *C07K 5/02* (2013.01); *C07K 7/02* (2013.01)

(58) Field of Classification Search
CPC .............................. C07D 277/56; A61K 38/00
USPC ...................................................... 546/208
See application file for complete search history.

(56) References Cited

U.S. PATENT DOCUMENTS

| | | | |
|---|---|---|---|
| 2,515,483 | A | 7/1950 | Wolf et al. |
| 2,816,110 | A | 12/1957 | Sletzinger et al. |
| 3,387,001 | A | 6/1968 | Hargrove et al. |
| 3,392,173 | A | 7/1968 | Hargrove et al. |
| 4,166,810 | A | 9/1979 | Cullinan et al. |
| 4,203,898 | A | 5/1980 | Cullinan et al. |
| 4,316,885 | A | 2/1982 | Rakhit |
| 4,337,339 | A | 6/1982 | Farina et al. |
| 4,639,456 | A | 1/1987 | Trouet et al. |
| 4,650,803 | A | 3/1987 | Stella et al. |
| 4,691,024 | A | 9/1987 | Sirahata |
| 4,713,249 | A | 12/1987 | Schroder |
| 4,801,688 | A | 1/1989 | Laguzza et al. |
| 4,866,180 | A | 9/1989 | Vyas et al. |
| 4,870,162 | A | 9/1989 | Trouet et al. |
| 5,006,652 | A | 4/1991 | Cullinan et al. |
| 5,094,849 | A | 3/1992 | Cullinan et al. |

(Continued)

FOREIGN PATENT DOCUMENTS

| | | |
|---|---|---|
| CA | 2372841 | 11/2000 |
| CA | 2376175 | 12/2000 |

(Continued)

OTHER PUBLICATIONS

PCT Search Report and Written Opinion for PCT/US2013/034672, completed Jun. 19, 2013.

(Continued)

*Primary Examiner* — John Mabry
(74) *Attorney, Agent, or Firm* — Barnes & Thornburg LLP

(57) ABSTRACT

The invention described herein pertains to processes for preparing tubulysin derivatives, conjugates of tubulysins, and intermediates therefore. In one illustrative embodiment of the invention, processes for derivatives or analogs of natural tubulysins including compounds of formula (T). In another embodiment, vitamin receptor binding conjugates of tubulysins are described. The processes include one or more steps described herein. In another embodiment, a process is described for preparing a compound of formula B, wherein R5 and R6 are as described in the various embodiments herein, such as each being independently selected from optionally substituted alkyl or optionally substituted cycloalkyl; and R8 is C1-C6 n-alkyl; wherein the process comprises the step of treating a compound of formula A with a silylating agent, such as triethylsilyl chloride, and a base, such as imidazole in an aprotic solvent.

20 Claims, No Drawings

(56) References Cited

U.S. PATENT DOCUMENTS

| | | |
|---|---|---|
| 5,100,883 A | 3/1992 | Schiehser |
| 5,108,921 A | 4/1992 | Low et al. |
| 5,118,677 A | 6/1992 | Caufield |
| 5,118,678 A | 6/1992 | Kao et al. |
| 5,120,842 A | 6/1992 | Failli et al. |
| 5,130,307 A | 7/1992 | Failli et al. |
| 5,138,051 A | 8/1992 | Hughes et al. |
| 5,140,104 A | 8/1992 | Coughlin et al. |
| 5,151,413 A | 9/1992 | Caufield et al. |
| 5,169,851 A | 12/1992 | Hughes et al. |
| 5,194,447 A | 3/1993 | Kao |
| 5,221,670 A | 6/1993 | Caufield |
| 5,233,036 A | 8/1993 | Hughes |
| 5,258,389 A | 11/1993 | Goulet et al. |
| 5,260,300 A | 11/1993 | Hu |
| 5,266,333 A | 11/1993 | Cady |
| 5,302,584 A | 4/1994 | Kao et al. |
| 5,362,718 A | 11/1994 | Skotnicki et al. |
| 5,378,696 A | 1/1995 | Caufield |
| 5,385,908 A | 1/1995 | Nelson et al. |
| 5,385,909 A | 1/1995 | Nelson et al. |
| 5,385,910 A | 1/1995 | Ocain et al. |
| 5,389,639 A | 2/1995 | Failli et al. |
| 5,391,730 A | 2/1995 | Skotnicki et al. |
| 5,416,016 A | 5/1995 | Low et al. |
| 5,417,982 A | 5/1995 | Modi |
| 5,463,048 A | 10/1995 | Skotnicki et al. |
| 5,491,231 A | 2/1996 | Nelson et al. |
| 5,547,668 A | 8/1996 | Kranz et al. |
| 5,552,545 A | 9/1996 | Pearce et al. |
| 5,562,907 A | 10/1996 | Arnon |
| 5,583,020 A | 12/1996 | Sullivan |
| 5,627,165 A | 5/1997 | Glazier |
| 5,635,382 A | 6/1997 | Low et al. |
| 5,672,486 A | 9/1997 | Soulillou |
| 5,688,488 A | 11/1997 | Low et al. |
| 5,998,603 A | 12/1999 | Cook |
| 6,004,555 A | 12/1999 | Thorpe et al. |
| 6,030,941 A | 2/2000 | Summerton et al. |
| 6,056,973 A | 5/2000 | Allen |
| 6,077,499 A | 6/2000 | Griffiths |
| 6,093,382 A | 7/2000 | Wedeking et al. |
| 6,171,614 B1 | 1/2001 | Chaikof et al. |
| 6,171,859 B1 | 1/2001 | Herrnstadt et al. |
| 6,177,404 B1 | 1/2001 | DeFeo-Jones et al. |
| 6,184,042 B1 | 2/2001 | Neumann et al. |
| 6,207,157 B1 | 3/2001 | Gu et al. |
| 6,290,929 B1 | 9/2001 | Camden et al. |
| 6,291,673 B1 | 9/2001 | Fuchs et al. |
| 6,291,684 B1 | 9/2001 | Borzilleri et al. |
| 6,315,978 B1 | 11/2001 | Grissom et al. |
| 6,335,434 B1 | 1/2002 | Guzaev et al. |
| 6,340,701 B1 | 1/2002 | Chari et al. |
| 6,342,244 B1 | 1/2002 | Zalipski et al. |
| 6,365,179 B1 | 4/2002 | Zalipsky et al. |
| 6,399,625 B1 | 6/2002 | Zhu |
| 6,399,626 B1 | 6/2002 | Zhu et al. |
| 6,399,638 B1 | 6/2002 | Vite et al. |
| 6,432,973 B1 | 8/2002 | Zhu et al. |
| 6,440,991 B1 | 8/2002 | Zhu et al. |
| 6,511,986 B2 | 1/2003 | Zhang et al. |
| 6,541,612 B2 | 4/2003 | Mulnar-Kimber et al. |
| 6,548,505 B1 | 4/2003 | Martin et al. |
| 6,596,757 B1 | 7/2003 | Chari et al. |
| 6,617,333 B2 | 9/2003 | Raibindran et al. |
| 6,670,355 B2 | 12/2003 | Azrulan et al. |
| 6,677,357 B2 | 1/2004 | Zhu et al. |
| 6,680,330 B2 | 1/2004 | Zhu et al. |
| 6,713,607 B2 | 3/2004 | Caggiano et al. |
| 6,800,653 B2 | 10/2004 | Regueiro-Ren et al. |
| 6,821,731 B2 | 11/2004 | Gillis et al. |
| 6,915,855 B2 | 7/2005 | Steele et al. |
| 6,958,153 B1 | 10/2005 | Ormerod et al. |
| 7,019,014 B2 | 3/2006 | Bernan et al. |
| 7,029,674 B2 | 4/2006 | Carreno et al. |
| 7,033,594 B2 | 4/2006 | Low et al. |
| 7,060,709 B2 | 6/2006 | Cooperstone et al. |
| 7,060,797 B2 | 6/2006 | O'Toole et al. |
| 7,067,111 B1 | 6/2006 | Yang et al. |
| 7,074,804 B2 | 7/2006 | Zhu et al. |
| 7,105,328 B2 | 9/2006 | Wood et al. |
| 7,122,361 B2 | 10/2006 | Liu et al. |
| 7,128,893 B2 | 10/2006 | Leamon et al. |
| 7,153,957 B2 | 12/2006 | Chew et al. |
| 7,279,562 B2 | 10/2007 | Molnar-Kimber et al. |
| 7,582,744 B2 | 9/2009 | Manoharan et al. |
| 7,601,332 B2 | 10/2009 | Vlahov et al. |
| 7,754,885 B2 | 7/2010 | Hoefle et al. |
| 7,776,814 B2 | 8/2010 | Dömling et al. |
| 7,816,377 B2 | 10/2010 | Dömling et al. |
| 7,875,612 B2 | 1/2011 | Green et al. |
| 7,910,594 B2 | 3/2011 | Vlahov et al. |
| 8,044,200 B2 | 10/2011 | Xu et al. |
| 8,105,568 B2 | 1/2012 | Vlahov et al. |
| 8,288,557 B2 | 10/2012 | Vlahov et al. |
| 8,383,122 B2 | 2/2013 | Dai et al. |
| 8,394,922 B2 | 3/2013 | Cheng et al. |
| 8,465,724 B2 | 6/2013 | Vlahov et al. |
| 8,470,822 B2 | 6/2013 | Green et al. |
| 8,476,451 B2 | 7/2013 | Ellman et al. |
| 8,497,365 B2 | 7/2013 | Davis et al. |
| 8,546,425 B2 | 10/2013 | Leamon et al. |
| 8,580,820 B2 | 11/2013 | Zanda et al. |
| 8,765,096 B2 | 7/2014 | Leamon |
| 8,802,632 B2 | 8/2014 | Cheng et al. |
| 8,889,880 B2 | 11/2014 | Vlahov et al. |
| 9,090,563 B2 | 7/2015 | Vlahov et al. |
| 2001/0031252 A1 | 10/2001 | Low et al. |
| 2002/0151088 A1 | 10/2002 | Molnar-Kimber et al. |
| 2003/0086900 A1 | 5/2003 | Low et al. |
| 2003/0162234 A1 | 8/2003 | Jallad |
| 2003/0194409 A1 | 10/2003 | Rothman et al. |
| 2004/0018203 A1 | 1/2004 | Pastan et al. |
| 2004/0033195 A1 | 2/2004 | Leamon et al. |
| 2004/0047917 A1 | 3/2004 | Wilson et al. |
| 2005/0004010 A1 | 1/2005 | Collins et al. |
| 2005/0026068 A1 | 2/2005 | Gogolides et al. |
| 2005/0107325 A1 | 5/2005 | Manoharan et al. |
| 2005/0227985 A9 | 10/2005 | Green et al. |
| 2005/0239713 A1 | 10/2005 | Domling et al. |
| 2005/0239739 A1 | 10/2005 | Matulic-Adamic et al. |
| 2005/0249740 A1 | 11/2005 | Doemling |
| 2006/0019911 A1 | 1/2006 | Papisov |
| 2006/0058266 A1 | 3/2006 | Manoharan et al. |
| 2006/0105975 A1 | 5/2006 | Pendergrast et al. |
| 2006/0128754 A1 | 6/2006 | Hoefle et al. |
| 2006/0217360 A1 | 9/2006 | Hoefle et al. |
| 2006/0222653 A1 | 10/2006 | Abel et al. |
| 2007/0009434 A1 | 1/2007 | Low et al. |
| 2007/0134332 A1 | 6/2007 | Turnell et al. |
| 2007/0275904 A1 | 11/2007 | Vite et al. |
| 2008/0096893 A1 | 4/2008 | Zebala |
| 2008/0280937 A1 | 11/2008 | Leamon et al. |
| 2009/0247614 A1 | 10/2009 | Manoharan et al. |
| 2010/0004276 A1 | 1/2010 | Vlahov et al. |
| 2010/0040669 A1 | 2/2010 | Higuchi |
| 2010/0048490 A1 | 2/2010 | Vlahov et al. |
| 2010/0074863 A1 | 3/2010 | Or et al. |
| 2010/0104626 A1 | 4/2010 | Leamon et al. |
| 2010/0129314 A1 | 5/2010 | Singh et al. |
| 2010/0240701 A1 | 9/2010 | Vlahov et al. |
| 2010/0323973 A1 | 12/2010 | Leamon et al. |
| 2011/0027274 A1 | 2/2011 | Cheng et al. |
| 2011/0166319 A1 | 7/2011 | Dai et al. |
| 2011/0172254 A1 | 7/2011 | Leamon et al. |
| 2011/0245295 A1 | 10/2011 | Chai et al. |
| 2012/0022245 A1 | 1/2012 | Low et al. |
| 2012/0065149 A1 | 3/2012 | Vlahov et al. |
| 2012/0129779 A1 | 5/2012 | Richter |
| 2012/0252738 A1 | 10/2012 | Richter |
| 2012/0252739 A1 | 10/2012 | Richter |
| 2012/0258905 A1 | 10/2012 | Leamon et al. |
| 2012/0259100 A1 | 10/2012 | Jin |
| 2012/0322741 A1 | 12/2012 | Low et al. |

(56) References Cited

U.S. PATENT DOCUMENTS

| | | |
|---|---|---|
| 2013/0029900 A1 | 1/2013 | Widdison |
| 2013/0116195 A1 | 5/2013 | Leamon et al. |
| 2013/0137139 A1 | 5/2013 | Vlahov et al. |
| 2013/0184435 A1 | 7/2013 | Vlahov et al. |
| 2013/0203680 A1 | 8/2013 | Leamon et al. |
| 2013/0217638 A1 | 8/2013 | Wessjohann et al. |
| 2013/0224228 A1 | 8/2013 | Jackson et al. |
| 2013/0281678 A1 | 10/2013 | Dai et al. |
| 2014/0058063 A1 | 2/2014 | Vlahov et al. |
| 2014/0058064 A1 | 2/2014 | Vlahov et al. |
| 2014/0066594 A1 | 3/2014 | Vlahov et al. |
| 2014/0073761 A1 | 3/2014 | Leamon et al. |
| 2014/0073763 A1 | 3/2014 | Low et al. |
| 2014/0080175 A1 | 3/2014 | Vlahov et al. |
| 2014/0107316 A1 | 4/2014 | Vlahov et al. |
| 2014/0193437 A1 | 7/2014 | Lin et al. |
| 2014/0227295 A1 | 8/2014 | Cong et al. |
| 2014/0227298 A1 | 8/2014 | Cong et al. |
| 2014/0249315 A1 | 9/2014 | Vlahov et al. |
| 2014/0309406 A1 | 10/2014 | Li et al. |
| 2014/0323690 A1 | 10/2014 | Cheng et al. |

FOREIGN PATENT DOCUMENTS

| | | |
|---|---|---|
| EP | 0 116 208 A1 | 8/1984 |
| EP | 0 163 550 A2 | 12/1985 |
| EP | 0 247 792 | 12/1987 |
| EP | 0 280 741 A1 | 9/1988 |
| EP | 0 354 728 | 2/1990 |
| JP | 59-175493 | 10/1984 |
| JP | 60-255789 | 12/1985 |
| WO | WO85/05554 | 12/1985 |
| WO | WO 88/01622 | 3/1988 |
| WO | WO 90/12096 | 10/1990 |
| WO | WO 91/07418 | 5/1991 |
| WO | WO95/15335 | 6/1995 |
| WO | WO 96/36367 | 11/1996 |
| WO | WO 98/08859 | 3/1998 |
| WO | WO 98/10651 | 3/1998 |
| WO | WO 99/20626 | 4/1999 |
| WO | WO 99/61055 | 12/1999 |
| WO | WO 00/35477 | 6/2000 |
| WO | WO 00/66091 | 11/2000 |
| WO | WO 00/74721 | 12/2000 |
| WO | WO01/13957 | 3/2001 |
| WO | WO 01/28592 | 4/2001 |
| WO | WO 01/74187 | 10/2001 |
| WO | WO02/059272 | 8/2002 |
| WO | WO 02/085908 | 10/2002 |
| WO | WO 02/087424 | 11/2002 |
| WO | WO 02/098868 | 12/2002 |
| WO | WO03/050295 | 6/2003 |
| WO | WO03/092742 | 11/2003 |
| WO | WO 03/097647 | 11/2003 |
| WO | 2004/005326 | 1/2004 |
| WO | WO 2004/005326 | 1/2004 |
| WO | WO 2004/005327 | 1/2004 |
| WO | WO 2004/012735 | 2/2004 |
| WO | WO2004/022099 | 3/2004 |
| WO | WO2004/037210 | 5/2004 |
| WO | 2004/046170 | 6/2004 |
| WO | WO 2004/046170 | 6/2004 |
| WO | WO 2004/054622 | 7/2004 |
| WO | WO 2004/069159 | 8/2004 |
| WO | WO 2005/074901 | 8/2005 |
| WO | WO 2005/112919 | 12/2005 |
| WO | WO2005/115912 | 12/2005 |
| WO | WO 2006/012527 | 2/2006 |
| WO | WO 2006/042146 | 4/2006 |
| WO | WO2006/089007 | 8/2006 |
| WO | WO 2006/101845 | 9/2006 |
| WO | WO 2006/105141 | 10/2006 |
| WO | WO2007/002222 | 1/2007 |
| WO | WO 2007/022493 | 2/2007 |
| WO | WO 2007/022494 | 2/2007 |
| WO | WO2007/022512 | 2/2007 |
| WO | WO2007/140298 | 12/2007 |
| WO | WO 2008/057437 | 5/2008 |
| WO | WO 2008/101231 | 8/2008 |
| WO | WO 2008/112873 | 9/2008 |
| WO | 2008/112873 | 11/2008 |
| WO | WO 2009/002993 | 12/2008 |
| WO | WO 2009/055562 | 4/2009 |
| WO | WO 2010/045598 | 4/2010 |
| WO | WO 2010/033733 | 5/2010 |
| WO | WO 2011/069116 | 6/2011 |
| WO | WO2011/069116 | 6/2011 |
| WO | WO2011/106639 | 9/2011 |
| WO | WO 2011/130598 | 10/2011 |
| WO | WO2012/019123 | 2/2012 |
| WO | WO 2012/047525 | 4/2012 |
| WO | WO 2013/126797 | 8/2013 |
| WO | WO 2013/130776 | 9/2013 |
| WO | WO 2013/149185 | 10/2013 |
| WO | WO 2013/170272 | 11/2013 |
| WO | WO 2013/173392 | 11/2013 |
| WO | WO 2013/173393 | 11/2013 |
| WO | WO 2014/009774 | 1/2014 |
| WO | WO 2014/040752 | 3/2014 |
| WO | WO 2014/062697 | 4/2014 |
| WO | WO2014/078484 | 5/2014 |
| WO | WO 2014/080251 | 5/2014 |
| WO | WO2014/134543 | 9/2014 |
| WO | WO2015/106599 | 7/2015 |

OTHER PUBLICATIONS

Wang, Zhiyong, et al. "Structure—activity and High-content Imaging Analyses of Novel Tubulysins," Chemical Biology & Drug Design 70(2): 75-86, (2007).

Patterson, Andrew W., et al. "Design, synthesis, and biological properties of highly potent tubulysin D analogues," Chemistry—A European Journal 13(34): 9534-9541, (2007).

Steinmetz, Heinrich, et al. "Isolation, crystal and solution structure determination, and biosynthesis of tubulysins—powerful inhibitors of tubulin polymerization from myxobacteria," Angewandte Chemie International Edition 43(37): 4888-4892, (2004).

March, Jerry. Advanced organic chemistry: reactions, mechanisms, and structure. vol. 4. New York: McGraw-Hill, 1968, p. 362-363, 816, 885, 896.

Lopes, Francisca, Rui Moreira, and Jim Iley. "Acyloxymethyl as a drug protecting group. Part 5.1 Kinetics and mechanism of the hydrolysis of tertiary N-acyloxymethylsulfonamides," J. Chem. Soc., Perkin Trans. 2, vol. 3: 431-440, (1999).

Churlaud, Carine, et al., "Novel 4-(Trimethylsilyl)aminoalkanes and 4-(Trimethylsilyl)aminoalk-2-enes, via a 1,5-Hydride Shift, in the Reaction of r-Unsaturated Silanes with Aminomethylbenzotriazoles," Organometallics, 18(21): 4270-4274.

Peltier, Hillary M., et al. "The total synthesis of tubulysin D," Journal of the American Chemical Society 128(50): 16018-16019 (2006).

Wu, Shih Hsiung, Zhi Wei Guo, and Charles J. Sih "Enhancing the enantioselectivity of Candida lipase-catalyzed ester hydrolysis via noncovalent enzyme modification," Journal of the American Chemical Society 112(5) (1990).

Sasse, F., et al. "Tubulysins, new cytostatic peptides from myxobacteria acting on microtubuli. Production, isolation, physicochemical and biological properties," J Antibiot 53:879-885 (2000).

Kaur, G., et al., "Biological evaluation of tubulysin A: a potential anticancer and antiangiogenic natural product," Biochem. J. 396, 235-242, (2006).

Domling, A., et al., "Myxobacterial epothilones and tubulysins as promising anticancer agents," Mol. Diversity, 9:141-147, (2005).

Pando, O., et al, "First Total Synthesis of Tubulysin B." Org. Lett., 11(24): 5567-5569, (2009).

G. Hofle, G., et al., "Semisynthesis and degradation of the tubulin inhibitors epothilone and tubulysin," Pure Appi. Chem. 75:167-178, (2003).

(56) References Cited

OTHER PUBLICATIONS

Rose, "Taxol-based combination chemotherapy and other in vivo preclinical antitumor studies," J Natl Cancer Inst Monogr, 15:47-53 (1993).
Lee et al., "BMS-247550: a novel epothilone analog with a mode of action similar to paclitaxel but possessing superior antitumor efficacy," Clin Cancer Res 7:1429-1437 (2001).
PCT Search Report and Written Opinion for PCT/US2011/046797, completed Dec. 23, 2011.
Khalil, M., et al., "Mechanism of Action of Tubulysin, an Antimitotic Peptide from Myxobacteria," ChemBioChem. 7(4):678-683 (2006).
Speckamp, et al., "New Developments in the Chemistry of N-Acyliminium Ions and Related Intermediates," Tetrahedron 56(24):3817-3856 (2000).
Raghavan, Bhooma, et al. "Cytotoxic Simplified Tubulysin Analogues," J. Med. Chem. 51:1530-1533 (2008).
PCT Search Report and Written Opinion for PCT/EP2003/011603, completed Feb. 11, 2011.
Patterson, Andrew W., Hillary M. Peltier, and Jonathan A. Ellman. "Expedient synthesis of N-methyl tubulysin analogues with high cytotoxicity," The Journal of Organic Chemistry, 73(12): 4362-4369 (2008).
Pathak, et al. "Enzymatic protecting group techniques in organic synthesis," Stereosel. Biocatal. 2000, pp. 775-797.
Remington: The Science and Practice of Pharmacy, 21st ed., (2005).
Agoston E.S. et al., "Vitamin D Analogs as Anti-Carcinogenic Agents," *Anti-Cancer Agents in Medicinal Chemistry*, 2006; 6(1): 53-71.
Anderson et al., "Potocytosis: Sequestration and transport of small molecules by caveolae," *Science*, 1992; 255: 410-411.
Antony A.C., "Folate receptors," *Annu Rev Nutr*, 1996; 16: 501-21.
Antony A.C., "The biological chemistry of folate receptors," *Blood*, 1992; 79(11):2807-2820.
Antony A.C. et al., "Studies of the Role of a Particulate Folate-binding Protein in the Uptake of 5-Methyltetrahydrofolate by Cultured Human KB Cells," *J. Biological Chem.*, 1985; 260(28):14911-7.
Archer M.C. et al., "Separation of Folic Acid Derivatives and Pterins by High-Performance Liquid Chromatography," *Methods in Enzymology*, 1980; 66: pp. 452-459.
Arya et al., "Design and Synthesis of Analogs of Vitamin E: Antiproliferative Activity Against Human Breast Adenocarcinoma Cells," *Bioorganic & Medicinal Chemistry Letters*, 1998; vol. 8, pp. 2433-2438.
Ayers W.A., "Effect of Vitamin B12 and Analogs on the Respiration of a Marine Bacterium," *Archives of Biochemistry and Biophysics*, 1962, vol. 96, pp. 210-215.
Barnett C.J. et al., "Structure-Activity Relationships of Dimeric Catharanthus Alkaloids. 1. Deacetylvinblastine Amide (Vindesine) Sulfate," *J. Med. Chem.* 21: 88-96 (1978).
Bavetsias, V. et al., "Design and synthesis of Cyclopenta[g]quinazoline-based antifolates as inhibitors of thymidylate synthase and potential antitumor agents," J Med Chem, 2000; 43(10): 1910-1921.
Bavetsias, V., et al., "The design and synthesis of water-soluble analogues of CB30865, a quinazolin-4-one-based antitumor agent," J Med Chem, 2002; 45(17): 3692-3702.
Birinberg E. M. et al., "Synthesis and antimetabolic activity of pyrimidine analogs of folic and pteroic acids," *Pharmaceutical Chemistry Journal*, 1969; 3(6): pp. 331-333.
Bock et al., "Sulfonamide structure-activity relationships in a cell-free system. 2. Proof for the formation of a sulfonamide-containing folate analog," *Journal of Medical Chemistry*, 17: 23-28 (1974).
Boger, D.L. et al., "An improved synthesis of 1,2,9,9a-tetrahydrocyclopropa[c]benz[e]indol-4-one (CBI): a simplified analog of the CC-1065 alkylation subunit," *J. Org. Chem.*, 1992; 57: 2873-2876.
Campbell et al., "Folate-binding protein is a marker for ovarian cancer," *Cancer Res.*, 1991; 51: 5329-5338.

Cho et al., "Single-chain Fv/folate conjugates mediate efficient lysis of folate-receptor-positive tumor cells," *Bioconjug. Chem.* 8(3): 338-346 (1997).
Christensen et al., "Membrane receptors for endocytosis in the renal proximal tubule," *Int. Rev. Cytol.*, 1998; 180: 237-284.
Churlaud C. et al., "Novel 4-(Trimethylsilyl)aminoalkanes and 4-(Trimethylsilyl)aminoalk-2-enes, via a 1,5-Hydride Shift, in the Reaction of α-Unsaturated Silanes with Aminomethylbenzotriazoles," *Organomettalics*, 1999; 18(21): 4270-4274.
Citro G. et al., "Inhibition of leukemia cell proliferation by folic acid—polylysine-mediated introduction of c-*myb* antisense oligodeoxynucelotides into HL-60 cells," *Br. J. Cancer*, 1994; 69: 463-467.
Cope A.C. et al., "Thermal Rearrangement of Allyl-type Sulfoxides, Sulfones and Sulfinates," *J. Am. Chem. Soc.*, 1950; 72; 59-67.
Cosulich D.B. et al., "Analogs of Pteroylglutamic Acid. I. N10-Alkylpteroic Acid and Derivatives," *JACS*, 1948, 70 (5), pp. 1922-1926.
DeVita, Jr., Vincent et al (eds); *Biologic Therapy of Cancer*; 2nd ed., J.B. Lippincott Company; 1995.
Domling A. et al., "Myxobacterial Epothilones and Tubulysins as Promising Anticancer Agents," *Molecular Diversity*, 2005; 9: 141-147.
Douglas J.T. et al., "Targeted Gene Delivery by Tropism-Modified Adenoviral Vectors," *Nat. Biotechnol.*, 1996, vol. 14, pp. 1574-1578.
Eichman, J.D. et al., "The Use of PAMAM Dendrimers in the Efficient Transfer of Genetic Material Into Cells", Jul. 2000, *PSTT*, vol. 3, No. 7, pp. 232-245.
Foong, L.Y. et al., "Development of a Novel Thiol Reagent for Probing Ion Channel Structure: Studies in a Model System," Biochemistry, 1997, vol. 36, pp. 1343-1348.
Frankel AE., "Immunotoxin therapy of cancer," *Oncology*, 1993; 7(5): 69-78.
Shealy Y.F., "Synthesis and Evaluation of Some New Retinoids for Cancer Chemoprevention," *Preventive Medicine*, 1989, vol. 18, pp. 624-645.
Gangjee et al., "The effect of 5-alkyl modification on the biological activity of pyrrolo[2,3-d]pyrimidine containing classical and non-classical antifolates as inhibitors of dihydrofolate reductase and as antitumor and/or antiopportunistic infection agents," *J Med Chem.*, 2008; 51(15):4589-4600.
Garin-Chesa et al., "Trophoblast and ovarian cancer antigen LK26. Sensitivity and specificity in immunopathology and molecular identification as a folate-binding protein," *Am. J. Pathol.* 142(2): 557-562 (1993).
GE Healthcare, Instructions 71-7104-00 AD.
Gibbs, DD et al., "BGC 945, a novel tumor-selective thymidylate synthase inhibitor targeted to alpha-folate receptor-overexpressing tumors," Cancer Res, 2005; 65(24): 11721-11728.
Gottschalk S. et al., "Folate receptor mediated DNA delivery into tumor cells: potosomal disruption results in enhanced gene expression," *Gene Therapy*, 1994; 1(3): 185-191.
Greene T.E. et al., "Protective Groups in Organic Synthesis," 2d edition, John Wiley & Sons, Inc. New York (1991).
Hanck A.B. et al., "Dexpanthenol (Ro 01-4709) in the treatment of constipation," *Acta Vitaminol Enzymol*, 1982; vol. 4 (1-2), pp. 87-97 (abstract only).
Harvison, P.J. et al., "Synthesis and Biological Activity of Novel Folic Acid Analogues: Pteroyl-S-alkylhomocysteine Sulfoximines," *Journal of Medicinal Chemistry*, 1992, vol. 35, pp. 1227-1233.
U.S. Appl. No. 60/946,092, filed Jun. 25, 2007, Vlahov et al.
U.S. Appl. No. 60/982,595, filed Nov. 25, 2007, Vlahov et al.
U.S. Appl. No. 61/036,176, filed Mar. 13, 2008, Vlahov et al.
U.S. Appl. No. 61/036,186, filed Mar. 13, 2008, Vlahov et al.
Henderson, E.A. et al., Targeting the alpha-folate receptor with cyclopenta[g]quinazoline-based inhibitors of thymidylate synthase, Bioorg Med Chem, 2006; 14(14): 5020-5042.
Ho R. I. et al., "A simple radioassay for dihydrofolate synthetase activity in *Escherichia coli* and its application to an inhibition study of new pteroate analogs," *Anal. Biochem.*, 1976, 73(2), pp. 493-500.

(56) References Cited

OTHER PUBLICATIONS

Hofland et al., "Folate-targeted gene transfer in vivo," *Mol Ther* 5(6): 739-744 (2002).
Hofle, G. et al., "Semisynthesis and Degradation of the Tubulin Inhibitors Epothilone and Tubulysin", 2003, *Pure Appl. Chem.*, vol. 75, Nos. 2-3, pp. 167-178.
Holladay et al., "Riboflavin-mediated delivery of a macromolecule into cultured human cells," *Biochim Biophys Acta*, 1426(1): 195-204 (1999).
Holm, J. et al., "Folate receptors in malignant and benign tissues of human female genital tract," *BioSci. Rep.*, 17(4): 415-427 (1997).
Holm, J. et al., "High-affinity folate binding in human choroid plexus. Characterization of radioligand binding, immunoreactivity, molecular heterogeneity and hydrophobic domain of the binding protein," *Biochem J.*, 280(1): 267-271 (1991).
Hosomi A. et al., "Affinity for a-tocopherol transfer protein as a determinant of the biological activities of vitamin E analogs," *Federation of European Biochemical Societies Letters*, 1997, vol. 409, pp. 105-108.
Houlihan, C. M. et al., "Preparation and Purification of Pteroic Acid from Folic Acid," *Analytical Biochemistry*, 1972, vol. 46, pp. 1-6.
Hynes et al., "Quinazolines as inhibitors of dihydrofolate reductase. 4. Classical analogues of folic and isofolic acids", *Journal of Medical Chemistry*, 1977; 20: 588-591.
Jackman, A. L. et al., "Antifolates targeted specifically to the folate receptor," *Adv Drug Deliv Rev*, 2004; 56(8): 1111-1125.
Jones T.R. et al., "A potent antitumour quinazoline inhibitor of thymidylate synthetase: synthesis, biological properties and therapeutic results in mice," *Eur J Cancer*, 1981; 17(1):11-9.
Jones T.R. et al., "Quinazoline antifolates inhibiting thymidylate synthase: variation of the amino acid," *J Med Chem*, 1986; 29(6):1114-8.
Jung K.H. et al., "Intramolecular o-glycoside bond formation," *Chem. Rev.*, 2000, 100, 4423-42.
Kagechika H et al., "Synthetic Retinoids: Recent Developments Concerning Structure and Clinical Utility," *Journal of Medicinal Chemistry*, 2005; vol. 48, No. 19, pp. 5875-5883.
Kamen et al., "Delivery of folates to the cytoplasm fo MA104 cells is mediated by a surface receptor that recycles," *J. Biol. Chem.*, 263: 13602-13609 (1988).
Kamen et al., "The folate receptor works in tandem with a probenecid-sensitive carrier in MA104 cells in vitro," *J. Clin. Invest.*, 87(4): 1442-1449 (1991).
Kamen, B. A. et al., "Receptor-mediated folate accumulation is regulated by the cellular folate content," *Proc. Natl. Acad. Sci. USA*, 83: 5983-5987 (1986).
Kandiko C.T. et al., "Inhibition of Rat Brain Pyruvate Dehydrogenase by Thiamine Analogs," *Biochemical Pharmacology*, 1988; vol. 37, No. 22, pp. 4375-4380.
Kane et al., "The influence of extracellular folate concentration on methotrexate uptake by human KB cells. Partial characterization of a membrane-associated methotrexate binding protein," *J. Biol. Chem.*, 261: 44-49 (1986).
Kim et al., "Synthesis and biological activity of 10-thia-10-deaza analogs of folic acid, pteroic acid, and related compounds", *Journal of Medical Chemistry*, 18: 776-780 (1975).
Kranz et al., "Conjugates of folate and anti-T-cell-receptor antibodies specifically target folate-receptor-positive tumor cells for lysis," *Proc. Natl. Acad. Sci. USA*, 1995; 92(20), pp. 9057-9061.
Kumar H.P. et al., "Folate transport in Lactobacillus salivarius. Characterization of the transport mechanism and purification and properties of the binding component," *J. Biol. Chem.*. 1987; 262(15):7171-7179.
Ladino et al., "Folate-maytansinoids: target-selective drugs of low molecular weight," *Int. J. Cancer*, 73(6): 859 864 (1997).
Lambooy J. P., "Riboflavin Analogs Utilized for Metabolism by a Lactobacillus Casei Mutant," *Int. J. Biochem.*, vol. 16, No. 2, 1984, pp. 231-234.

Landuer W. et al., "The Interaction in Teratogenic Activity of the Two Niacin Analogs 3-acetylpyridine and 6-aminonicotinamide," *J Exp Zool*, 151(3):253-258 (1962).
Langone, J.J., et al., "Radioimmunoassays for the Vinca Alkaloids, Vinblastine and Vincristine", 1979, *Analytical Biochemistry*, No. 95, pp. 214-221.
Larock R.C., "Comprehensive Organic Transformations, a guide to functional group preparations," VCH Publishers, Inc. New York (1989).
Leamon CP et al, "Cytotoxicity of folate-Pseudomonas exotoxin conjugates toward tumor cells. Contribution of translocation domain," *J. Biol. Chem.* 268(33): 24847-24854 (1993).
Leamon CP et al., "Comparative Preclinical Activity of the Folate-targeted Vinca Alkaloid Conjugates EC140 and EC145," *Int J Cancer*, 2007; 121(7):1585-92.
Leamon CP et al., "Cytotoxicity of momordin-folate conjugates in cultured human cells," *J. Biol. Chem.*, 1992; 267(35): 24966-24971.
Leamon CP et al., "Delivery of macromolecules into living cells: a method that exploits folate receptor endocytosis," *Proc. Natl. Acad. Sci. USA* 88(13): 5572-5573 (1991).
Leamon CP et al., "Folate-mediated targeting: from diagnostics to drug and gene delivery," *Drug Discovery Today* 6: 44-51 (2001).
Leamon CP et al., "Folate-targeted chemotherapy," *Adv Drug Deliv Rev*, 2004;56(8): 1127-41.
Leamon CP et al., "Membrane folate-binding proteins are responsible for folate-protein conjugate endocytosis into cultured cells," *Biochem. J.* 291: 855-860 (1993).
Leamon CP et al., "Selective targeting of malignant cells with cytotoxin-folate conjugates," *J. Drug Target*. 2(2): 101-112 (1994).
U.S. Appl. No. 60/590,580, filed Jul. 23, 2004, Vlahov et al.
Leamon CP et al., "Synthesis and biological evaluation of EC140: A novel folate-targeted vinca alkaloid conjugate," *Bioconjug Chem*, 2006;17(5):1226-32.
Leamon CP et al., "Synthesis and Biological Evaluation of EC20: A New Folate-Derived, (99m)Tc-Based Radiopharmaceutical," *Bioconjug. Chem.* 13(6): 1200-1210 (2002).
Leamon CP et al., "Synthesis and biological evaluation of EC72: a new folate-targeted chemotherapeutic," *Bioconjug Chem.*, 2005;16(4):803-11.
Leamon et al., "Folate-mediated drug delivery: effect of alternative conjugation chemistry," *J. Drug Target* 7(3): 157-169 (1999).
Lee et al, "Measurement of Endosome pH Following Folate Receptor-Mediated Endocytosis," *Biochim. Biophys. Acta* 1312(3): 237-242 (1996).
Lee W.W. et al., "Folic acid antagonists. Methotrexate analogs containing spurious amino acids. Dichlorohomofolic acid," *Journal of Medical Chemistry*, 17: 326-330 (1974).
Lee et al., "Synthesis and evaluation of taxol-folic acid conjugates as targeted antineoplastics," *Bioorg Med Chem*. 10(7): 2397-2414, (2002).
Lee, Francis Y. F., et al., "BMS-247550: A Novel Epothilone Analog With a Mode of Action Similar to Paclitaxel But Possessing Superior Antitumor Efficacy," *Clin Cancer Res*, 2001, No. 7, pp. 1429-1437.
Lee, R. J. and Huang, L., "Folate-Targeted, Anionic Liposome-Entrapped Polylysine-Condensed Dna For Tumor Cell-Specific Gene Transfer," *J. Biol. Chem.* 271(14): 8481-8487 (1996).
Lee, R. J. and Low, P. S, "Delivery of liposomes into cultured KB cells via folate receptor-mediated endocytosis," *J. Biol. Chem.* 269(5): 3198-3204 (1994).
Lee, R. J. and Low, P. S., "Folate-mediated tumor cell targeting of liposome-entrapped doxorubicin in vitro," *Biochim. Biophys. Acta* 1233: 134-144 (1995).
Lemon, Julia, et al., "Conversion of Pteroylglutamic Acid to Pteroic Acid by Bacterial Degradation," *Archives of Biochemistry*, 1948; vol. 19, pp. 311-316.
Levy, Carl C., et al. "The Enzymatic Hydrolysis of Methotrexate and Folic Acid", 1967, *The Journal of Biological Chemistry*, vol. 242, No. 12, pp. 2933-2938.
Lewis et al., "Receptor-mediated folate uptake is positively regulated by disruption of actin cytoskeleton," *Cancer Res.* 58(14): 2952-2956 (1998).

(56) References Cited

OTHER PUBLICATIONS

Li et al, "Targeted delivery of antisense oligodeoxynucleotides by LPDII," *J. Liposome Res.* 7(1): 63 (1997).

Liu et al., "Targeted Drug Delivery to Chemoresistant Cells: Folic Acid Derivatization of FdUMP[10] Enhances Cytotoxicity Toward 5-FU-Resistant Human Colorectal Tumor Cells," *J. Org. Chem.* 66: 5655-5663 (2001).

Lonsdale D, "A Review of the Biochemistry, Metabolism and Clinical Benefits of Thiamin(e) and Its Derivatives," publication, Advance Access Publication, vol. 3, Feb. 2006, pp. 49-59.

Lopes et al., "Acyloxymethyl as a drug protecting group. Part 5.1 Kinetics and mechanism of the hydrolysis of tertiary N-acyloxymethylsulfonamides," *J. Chem. Soc.*, Perkin Trans. 2, pp. 431-439 (1999).

Low P.S. et al., "Folate Receptor-Targeted Drugs for Cancer and Inflammatory Diseases," *Adv Drug Deliv Rev*, 2004;56(8):1055-1058.

Lu et al., "Folate-targeted enzyme prodrug cancer therapy utilizing penicillin-V amidase and a doxorubicin prodrug," *J. Drug Target*, 7(1): 43-53 (1999).

Lu, J. Y. and Low, P. S., "Folate targeting of haptens to cancer cell surfaces mediates immunotherapy of syngeneic murine tumors," *Cancer Immunol Immunother*, 51: 153-162 (2002).

Lu, J. Y. and Low, P. S., "Folate-mediated delivery of macromolecular anticancer therapeutic agents," *Adv. Drug Del Rev*, 2002; 54(5): 675-693.

Luo et al., "Efficient syntheses of pyrofolic acid and pteroyl azide, reagents for the production of carboxyl-differentiated derivatives of folic acid," *J. Am. Chem. Soc.*, 119: 10004-10013 (1997).

Mack D.O. et al., "The Carboxylation Activity of Vitamin K Analogs with Substitutions at Position 2, 3, or 5," *Journal of Biological Chemistry*, 1979; vol. 254, pp. 2656-2664.

Mancuso A.J. et al., "Activated Dimethyl Sulfoxide: Useful Reagents for Synthesis," *Synthesis*, 1981, pp. 165-184.

March, Advanced Organic Chemistry, 1992, John Wiley & Sons, 4th Ed., pp. 362-363, 816, 885, 896.

Mathais et al., "Receptor-mediated targeting of 67Ga-deferoxamine-folate to folate-receptor-positive human KB tumor xenografts," *Nucl Med Biol*, 26(1): 23-25 (1999).

Mathais et al., "Synthesis of [(99m)Tc]DTPA-folate and its evaluation as a folate-receptor-targeted radiopharmaceutical," *Bioconjug Chem*, 11(2): 253-257 (2000).

Mathias et al., "Indium-111-DTPA-Folate as a potential folate-receptor-targeted radiopharmaceutical," *J. Nucl. Med.*, 39(9): 1579-1585 (1998).

Mathias et al., "Tumor-Selective Radiopharmaceutical Targeting Via Receptor-Mediated Endocytosis of Gallium-67-Deferoxamine-Folate," *J. Nucl. Med*, 37(6): 1003-1008 (1996).

Mathias, C. J., "A kit formulation for preparation of [(111)In]In-DTPA-folate, a folate-receptor-targeted radiopharmaceutical," *Nucl. Med. Biol.*, 25(6): 585-587 (1998).

Matsui et al., "Studies on mitomycins. III. The synthesis and properties of mitomycin derivatives," *J Antibiot*, 21: 189-198 (1968).

Kamao M. et al., "Determination of Plasma Vitamin K by High Performance Liquid Chromatography with Fluorescence Detection Using Vitamin K Analogs as Internal Standards," *Journal of Chromatography B*, 2005; vol. 816, pp. 41-48.

McAlinden TP et al., "Synthesis and Biological Evaluation of a Fluorescent Analogue of Folic Acid," *Biochemistry*, 1991; 30: 5674-81.

McHugh M et al., "Demonstration of a High Affinity Folate Binder in Human Cell Membranes and Its Characterization in Cultured Human KB Cells," *J Biol Chem*, 1979; 254(22):11312-8.

Melani et al., "Targeting of interleukin 2 to human ovarian carcinoma by fusion with a single-chain Fv of antifolate receptor antibody," *Cancer Res.* 58(18): 4146-4154 (1998).

U.S. Appl. No. 60/808,367, filed May 25, 2006, Vite et al.

Melby, E.L. et al, "Entry of Protein Toxins in Polarized Epithelial Cells"; *Cancer Research*, 1993; 53: 1755-1760.

Mislick et al., "Transfection of folate-polylysine DNA complexes: evidence for lysosomal delivery," *Bioconjug. Chem.*, 6(5): 512-515 (1995).

Mock D.M. et al., "Urinary Biotin Analogs Increase In Humans During Chronic Supplementation: the Analogs are Biotin Metabolites," *Am J Physiol Endocrinol Metab*, 1997; 272: E83-E85.

Morshed et al., "Folate transport proteins mediate the bidirectional transport of 5-methyltetrahydrofolate in cultured human proximal tubule cells," *J. Nutr.*, 127(6): 1137-1147 (1997).

Nair et al., "Folate analogs altered in the C9-N10 bridge region. 14. 11-Oxahomofolic acid, a potential antitumor agent", *Journal of Medical Chemistry*, 23: 59-65 (1980).

Nair et al., "Folate analogs altered in the C9-N10 bridge region. 18. Synthesis and antitumor evaluation of 11-oxahomoaminopterin and related compounds," *Journal of Medical Chemistry*, 24: 1068-1073 (1981).

Nair et al., "Folate analogs altered in the C9-N10 bridge region: N10-tosylisohomofolic acid and N10-tosylisohomoaminopterin," *Journal of Medical Chemistry*, 21: 673-677 (1978).

Nair et al., "Folate analogs altered in the C9-N10 bridge region: 11-thiohomofolic acid," *Journal of Medical Chemistry*, 22: 850-855 (1979).

Nair et al., "Folate analogs. 20. Synthesis and antifolate activity of 1',2',3',4',5',6'-hexahydrohomofolic acid," *Journal of Medical Chemistry*, 26: 135-140 (1983).

Nair et al., "Folate analogs. 21. Synthesis and antifolate and antitumor activities of N10-(cyanomethyl)-5,8-dideazafolic acid," *Journal of Medical Chemistry*, 26: 605-607 (1983).

Nair et al., "Folate analogs. 22. Synthesis and biological evaluation of two analogs of dihydrofolic acid possessing a 7,8-dihydro-8-oxapterin ring system," *Journal of Medical Chemistry*, 26: 1164-1168 (1983).

Nair et al., "Folate analogues altered in the C9-N10 bridge region. 10-Oxafolic acid and 10-oxaaminopterin," *Journal of Medical Chemistry*, 19: 825-829 (1976).

Neuss, N. et al., "Vinca Alkaloids. XXX (1). Chemistry Of The Deoxyvinblastines (Deoxy-VLB), Leurosine (VLR), and Pleurosine, Dimeric Alkaloids From Vinca," *Tetrahedron Letters*, No. 7, pp. 783-787 (1968).

Neuzil J. et al., "Vitamin E Analogs: A New Class of Multiple Action Agents with Anti-Neoplastic and Anti-Atherogenic Activity," *Apoptosis*, 2002; vol. 7, pp. 179-187.

Nielsen P. et al., "Phosphates of Riboflavin and Riboflavin Analogs: A Reinvestigation by High-Performance Liquid Chromatography," *Analytical Biochemistry*, vol. 130, 1983, pp. 359-368.

Nimmo-Smith R.H. et al., "Some Effects of 2-deaminopteroylglutamic Acid upon Bacterial Growth," *J. Gen. Microbial.*, 1953; 9: 536-544.

Nishikawa, Yuji et al., "Growth Inhibition of Hepatoma Cells Induced by Vitamin K and Its Analogs," *Journal of Biological Chemistry*, 1995; vol. 270, No. 47, pp. 28304-28310.

Nomura, Makoto et al., "Development of an Efficient Intermediate α-[2-(Trimethylsilyl)ethoxy]-2-N-[2-(trimethylsilyl)ethoxycarbonyl]folic Acid, for the Synthesis of Folate (γ)-Conjugates, and Its Application to the Synthesis of Folate-Nucleoside Conjugates," *Journal of Organic Chemistry*, 2000, vol. 65, pp. 5016-5021.

Nosaka K.et al., "Separate Determination of Anticoccidial Thiamine Analogs by High-performance Liquid Chromatography," *ActaA Vitaminol. Et Enzymol*, 1984, vol. 6 (2), pp. 137-142.

Oatis et al., "Synthesis of quinazoline analogues of folic acid modified at position 10," *Journal of Medical Chemistry*, 20: 1393-1396 (1977).

Olsnes S. et al., "Immunotoxins-entry into cells and mechanisms of action," *Immunology Today*, 1989; vol. 10, No. 9, pp. 291-295.

Patrick et al., "Folate Receptors As Potential Therapeutic Targets in Choroid Plexus Tumors of Sv40 Transgenic Mice," *J. Neurooncol,.* 32(2): 111-123 (1997).

Patrick et al., "Intracerebral bispecific ligand-antibody conjugate increases survival of animals bearing endogenously arising brain tumors," *Int. J. Cancer*, 78(4): 470-79 (1998).

Peltier, Hillary M., et al., "The Total Synthesis of Tubulysin D," 2006, *J. Am. Chem. Soc.*, No. 128, pp. 16018-19.

(56) References Cited

OTHER PUBLICATIONS

Pizzorno G., et al., "Intracellular metabolism of 5,10-dideazatetrahydrofolic acid in human leukemia cell lines," *Molecular Pharmacology*, 1991, 39 (1), pp. 85-89.
Plante et al., "Polyglutamyl and polylysyl derivatives of the lysine analogues of folic acid and homofolic acid," *Journal of Medical Chemistry*, 19: 1295-1299 (1976).
Politis I. et al., "The Effect of Various Vitamin E Derivatives on the Urokinase-Plasminogen Activator System of Ovine Macrophages and Neutrophils," *British Journal of Nutrition*, vol. 89, 2003, pp. 259-265.
Prabhu V. et al., "Arabidopsis dihydropteroate synthase: general properties and inhibition by reaction product and sulfonamides," *Phytochem.*, 1997; 45(1): 23-27.
Prasad et al., "Functional coupling between a bafilomycin A1-sensitive proton pump and a probenecid-sensitive folate transporter in human placental choriocarcinoma cells," *Biochim. Biophys. Acta*, 1994; 1222(2): 309.
Pratt, A.G. et al. "The Hydrolysis of Mono-, Di, and Triglutamate Derivatives of Folic Acid With Bacterial Enzymes," *The Journal of Biological Chemistry*, 1968, vol. 243, No. 24, pp. 6367-6372.
Punj, V. et al., "Effect of Vitamin D Analog (1α Hydroxy D5) Immunoconjugated to Her-2 Antibody on Breast Cancer," *Int. J. Cancer*, 2004; 108: 922-929.
Raghavan B et al., "Cytotoxic Simplified Tubulysin Analogues," *J. Med. Chem.*, 2008; 51(6), pp. 1530-1533.
Ranasinghe, M. G. et al.; "A Facile Synthesis of Unsymmetrical Thiolsulfonates via Sulfonylation of Mercaptans," *Synthetic Communications*, 1988; 18(3), pp. 227-232.
Reddy et al., "Optimization of folate-conjugated liposomal vectors for folate receptor-mediated gene therapy," *J. Pharm. Sci*, 88(11): 1112-1118 (1999).
Reddy et al., "Preclinical evaluation of EC145, a folate-vinca alkaloid conjugate," *Cancer Res.*, 2007; 67:4434-42.
Reddy et al., "Retargeting of viral vectors to the folate receptor endocytic pathway," *J Control Release*, 74(1-3): 77-82 (2001).
Reddy, J. A., Low, P. S., "Folate-Mediated Targeting of Therapeutic and Imaging Agents to Cancers," *Crit. Rev. Ther. Drug Carrier Syst.*, vol. 15, No. 6, 1998, pp. 587-627.
Remington: The Science & Practice of Pharmacy, 21th Edition (Lippincott Williams & Wilkins, 2005).
Renz P. et al., "Synthesis of 4-Aza-5, 6-diethylbenzimidazole and Biosynthetic Preparation of 4- and 7-Aza-5, 6-dimethylbenzimidazolylcobamide," *Z Naturforsch*, 1997, vol. 52c, pp. 287-291.
Rijnboutt et al., "Endocytosis of GPI-linked membrane folate receptor-alpha," *J. Cell Biol.*, 132(1-2): 35-47 (1996).
Roberts et al., "Folic acid analogs. Modifications in the benzene-ring region. 3. Neohomofolic and neobishomofolic acids. An improved synthesis of folic acid and its analogs," *Journal of Medical Chemistry*, 16: 697-699 (1973).
Roberts et al., "Folic acid analogs. Modifications in the benzene-ring region. 2. Thiazole analogs," *Journal of Medical Chemistry*, 15: 1310-1312 (1972).
Roberts et al., "Folic acid analogs. Modifications in the benzene-ring region. 1. 2'- and 3'-Azafolic acids," *Journal of Medical Chemistry*, 14: 125-130 (1971).
Roberts et al., "Folic acid analogs. Modifications in the benzene-ring region. 4. 3'-Ethyl- and 3'-isopropylfolic acids," *Journal of Medical Chemistry*, 17: 219-222 (1974).
Rose W.C., "Taxol-Based Combination Chemotherapy and Other in Vivo Preclinical Antitumor Studies," *J Natl Cancer Inst Monogr*, 1993, No. 15, pp. 47-53.
Ross et al., "Differential regulation of folate receptor isoforms in normal and malignant tissues in vivo and in established cell lines. Physiologic and clinical implications," *Cancer*, 73(9): 2432-2443, (1994).
Rothberg et al, "Cholesterol controls the clustering of the glycophospholipid-anchored membrane receptor for 5-methyltetrahydrofolate," *J. Cell Biol.*, 111(6): 2931-2938 (1990).
Rothberg et al., "The glycophospholipid-linked folate receptor internalizes folate without entering the clathrin-coated pit endocytic pathway," *J. Cell Biol.*, 110(3): 637-649 (1990).
Roy et al., "Targeting T cells against brain tumors with a bispecific ligand-antibody conjugate," *Int. J. Cancer* 76(5): 761-66 (1998).
Sadasivan et al., "The complete amino acid sequence of a human folate binding protein from KB cells determined from the cDNA," *J. Biol. Chem.*, 1989; 264: 5806-5811.
Sargent D.R. et al., "Antimetabolites of Pantothenic Acid, Ureido- and Carbamoyl-Derivatives," *Texas Reports on Biology and Medicine*, 1975, vol. 33, No. 3, pp. 433-443.
Sasse F. et al., "Tubulysins, New Cytostatic Peptides from Myxobacteria Acting on Microtubuli Production, Isolation, Physico-Chemical and Biological Properties," *The Journal of Antibiotics*, 2000; vol. 53, No. 9, pp. 879-885.
Scott J.M, "Preparation and Purification of Pteroic Acid from Pteroylglutamic Acid (Folic Acid)," *Methods in Enzymology*, 1980, vol. 66, pp. 657-660.
Search Report for Taiwan Patent Application No. 093101735, dated Jul. 14, 2007, 1 page.
Semb J. et al., "Pteroic Acid Derivatives. V. Pteroyl-α-glutamyl-α-glutamylglutamic Acid, Pteroyl-γ-glutamyl-α-glutamylglutamic Acid, Pteroyl-α-glutamyl-γ-glutamylglutamic Acid," *JACS*, 1949; 71 (7): 2310-2315.
Senter et al., "Development of a Drug-Release Strategy Based on the Reductive Fragmentation of Benzyl Carbamate Disulfides," *J. Org. Chem.*, 55: 2975-2978 (1990).
Shimizu M. et al., "Synthesis and biological activities of new 1alpha, 25-dihydroxy-19-norvitamin D3 analogs with modifications in both the A-ring and the side chain," *Bioorganic & Medicinal Chemistry*, 2006; 14(12): 4277-94.
Shimizu, Kazui, et al., "Novel vitamin D3 antipsoriatic antedrugs: 16-En-22-oxa-1a,25-(OH)2D3 analogs," *Bioorganic & Medicinal Chemistry*, 2006;14: 1838-1850.
Shoup T.M. et al., "Synthesis of Fluorine-18-Labeled Biotin Derivatives: Biodistribution and Infection Localization," *J. Nucl. Med.*, 1994; 35: 1685-1690.
Skinner W.A. et al., "Structure-Activity Relations in the Vitamin E Series. II. Derivatives of α-Tocopherol Substituted at the 5-Methyl Group," *J. Med. Chem.*, 1969; 12 (1): 64-66.
Smart et al., "Clustered folate receptors deliver 5-methyltetrahydrofolate to cytoplasm of MA104 cells," *J. Cell Biol.*, 134(5): 1169-1177 (1996).
Smart et al., "Protein kinase C activators inhibit receptor-mediated potocytosis by preventing internalization of caveolae," *J. Cell Biol.*, 124(3): 307-313 (1994).
Spry C. et al., "A Class of Pantothenic Acid Analogs Inhibits Plasmodium Falciparum Pantothenate Kinase and Represses the Proliferation of Malaria Parasites," *Antimicrobial Agents and Chemotherapy*, 2005; 49(11): 4649-4657.
Steinberg, G. et al., "Synthesis and Evaluation of Pteroic Acid-Conjugated Nitroheterocyclic Phosphoramidates as Folate Receptor-Targeted Alkylating Agents," *J. Med. Chem.* 44: 69-73 (2001).
Steinmetz, H. et al., "Isolation, Crystal and Solution Structure Determination, and Biosynthesis of Tubulysins-Powerful Inhibitors of Tubulin Polymerization from Microbacteria", *Angew. Chem. Int. Ed.*, 2004, No. 43, pp. 4888-4892.
Takahata Y. et al., "Synthesis, Properties and Microbiological Activity of Hydrophobic Derivatives of Vitamin B12," *J. Nutr. Sci. Vitaminol.*, 1995, vol. 41, pp. 515-526.
Takasu, H. et al., "c-Fos protein as a target of anti-osteoclastogenic action of vitamin D, and synthesis of new analogs," *The Journal of Clinical Investigation*, 2006; vol. 116, No. 2, pp. 528-535.
Takeda, K. et al., "A Synthesis of a New Type of Alkoxycarbonylating Reagents from 1,1-Bis[6-(trifluoromethyl)benzotriazolyl] Carbonate (BTBC) and Their Reactions," *Sythesis*, 1987; 6: 557-560.
Temple et al., "Synthesis of pseudo cofactor analogs as potential inhibitors of the folate enzymes," *Journal of Medical Chemistry*, 25: 161-166 (1982).
Toffoli et al., "Overexpression of folate binding protein in ovarian cancers," *Int. J. Cancer* 74(2): 193-198 (1997).
Toraya T. et al , "Immobilized Derivatives of Vitamin B12 Coenzyme and Its Analogs," *Methods in Enzymology*, vol. 67, pp. 57-66.

(56) References Cited

OTHER PUBLICATIONS

Toraya T. et al., "The Synthesis of Several Immobilized Derivatives of Vitamin B12 Coenzyme and Their Use as Affinity Adsorbents for a Study of Interactions of Diol Dehydrase with the Coenzyme," *The Journal of Biological Chemistry*, 1990; vol. 255, No. 8, pp. 3520-3525.
Trachewsky D., "Antihypertensive Effect of Riboflavin Analogs in Rats with Mineralocorticoid-Induced Hypertension," *Hypertension*, 1981; vol. 3, No. 1, pp. 75-80.
Truneh A. et al., "Temperature-sensitive differential affinity of TRAIL for its receptors. DR5 is the highest affinity receptor," *J Biol Chem*, 2000; 275(30):23319-25.
Turek et al., "Endocytosis of folate-protein conjugates: ultrastructural localization in KB cells," *J. Cell Sci.* 106: 423-430 (1993).
Turk et al., "Characterization of a novel pH-sensitive peptide that enhances drug release from folate-targeted liposomes at endosomal pHs," *Biochim Biophys Acta*, 1559(1): 56-68 (2002).
Ueda M. et al., "Effect of Vitamin B12 Derivatives on Urinary Excretion of Methylmalonic Acid in Liver Diseases," *Acta Med. Okayama*, 1970; vol. 24, pp. 365-372.
Varma, R. et al., "GPI-anchored proteins are organized in submicron domains at the surface," *Nature*, 394(6695): 798-801 (1998).
Verwey, J., "Mitomycin C-Induced Renal Toxicity, a Dose-Dependent Side Effect?," *Eur J Cancer Clin Onco*, 1987; vol. 23, No. 2, pp. 195-199.
Vesely D.L. et al., "Biotin Analogs Activate Guanylate Cyclase," *Molecular and Cellular Biochemistry*, 1984; vol. 60, pp. 109-114.
Vlahov I.R. et al., "Design and regioselective synthesis of a new generation of targeted chemotherapeutics. Part 1: EC145, a folic acid conjugate of desacetylvinblastine monohydrazide," *Bioorg Med Chem Lett*, 2006; 16(19):5093-6.
Vogel et al., "Peptide-Mediated Release of Folate-Targeted Liposome Contents From Endosomal Compartments," *J. Am. Chem. Soc.*, 1996; 118(7): 1581-1586.
Vyas D. et al., "A practical synthesis of mitomycin A and its analogs," *J Org Chem*, 1986; 31:4307-4309.
Wang et al., "Delivery of antisense oligodeoxyribonucleotides against the human epidermal growth factor receptor into cultured KB cells with liposomes conjugated to folate via polyethylene glycol," *Proc. Natl. Acad. Sci.* USA, 92(8): 3318-3322 (1995).
Wang et al., "Design and synthesis of [111In]DTPA-folate for use as a tumor-targeted radiopharmaceutical," *Bioconjug Chem.*, 8(5): 673-679 (1997).
Wang et al., "Synthesis, purification, and tumor cell uptake of 67Ga-deferoxamine—folate, a potential radiopharmaceutical for tumor imaging," *Bioconj. Chem.*, 1996; 7(1): 56-62.
Wang S. et al., "Folate-mediated targeting of antineoplastic drugs, imaging agents, and nucleic acids to cancer cells," *J. Control Rel*, 1998; 53(1-3): 39-48.
Weinstock et al., "Folic acid analogs. II. p-{[(2,6-Diamino-8-purinyl)methyl]amino}-benzoyl-L-glutamic acid and related compounds," *Journal of Medical Chemistry*, 13: 995-997 (1970).
Weitman et al., "Cellular localization of the folate receptor: potential role in drug toxicity and folate homeostasis," *Cancer Res.*, 1992; 52(23): 6708-6711.
Weitman et al., "Distribution of the folate receptor GP38 in normal and malignant cell lines and tissues," *Cancer Res.*, 1992; 52(12): 3396-3401.
Westerhof G.R. et al., "Carrier-and Receptor-Mediated Transport of Folate Antagonists Targeting Folate-Dependent Enzymes: Correlates of Molecular-Structure and Biological Activity," *Molecular Pharmacology*, 1995, 48, pp. 459-471.
Westerhof GR et al., "A photoaffinity analogue of folic acid as a probe for the identification and function of a membrane folate binding protein (mFBP) in human CCRF-CEM leukemia cells," *Proccedings of the American Association for Cancer Research*, 1991; 32:328.

Wiener et al., "Targeting dendrimer-chelates to tumors and tumor cells expressing the high-affinity folate receptor," *Invest. Radiol.* 32(12): 748-54 (1997).
Wu M. et al., "Clustering of GPI-anchored folate receptor independent of both cross-linking and association with caveolin," *J. Membr. Biol.* 159(2): 137-147 (1997).
Wang, Xiu-Fang et al., "Vitamin E Analogs Trigger Apoptosis in HER2/erbB2-Overexpressing Breast Cancer Cells by Signaling Via the Mitochondrial Pathway," *Biochemical and Biophysical Research Communication*, 2005; vol. 326, pp. 282-289.
Zimmer H. et al., "Potential anticancer agents V., Synthesis of folic acid and pteroic acid analogs derived of caffeine and theophylline,"*Arzneimittelforschung*, 1966, 16(4), pp. 541-545.
Zimmerman, J., "Folic acid transport in organ-cultured mucosa of human intestine. Evidence for distinct carriers," *Gastroenterol.* 99(4): 964-972 (1990).
Angier, R. B., et al., "Pteroic Acid Analogs Containing Arsenic," J. American Chem. Soc., vol. 76, 1954, pp. 902-904.
Boothe, J. H., et al., "Pteroic Acid Derivatives. II. Pteroyl-γ-glutamylglutamic Acid and Pteroyl-γ-glutamyl-γ-glutamylglutamic Acid," J. American Chem. Soc., vol. 70, 1948, pp. 1099-1102.
Bartels R. et al., "Determination of pteroic acid by high-performance thin-layer chromatography: Contribution to the investigation of 7,8-dihydropteroate synthase," *Journal of Chromatography A*, 1994; vol. 659(1): 185-189.
Wikipedia, Derivative (Chemistry), http://en.wikipedia.org/wiki/Derivative_(chemistry), downloaded Dec. 16, 2009.
Wikipedia, Analog (Chemistry), http://en.wikipedia.org/wiki/Analog_(chemistry), downloaded Dec. 16, 2009.
Wikipedia, List of Purification Methods in Chemistry, http://en.wikipedia.org/wiki/List_of_purification_methods_in_chemistry, downloaded Dec. 16, 2009.
Wikipedia, Solution, http://en.wikipedia.org/wiki/Solution, downloaded Dec. 17, 2009.
Principles of Ion Exchange Chromatography, http://www.separations.us.tosohbioscience.com/ServiceSupport/TechSupport/ResourceCenter/PrinciplesofChromatography/IonExchange, downloaded Dec. 23, 2009.
Wikipedia, Conjugate, http://en.wikipedia.org/wiki/Conjugate, downloaded Dec. 17, 2009.
Wikipedia, Complex (Chemistry), http://en.wikipedia.org/wiki/Complex_(chemistry), downloaded Dec. 23, 2009.
Leamon Christopher P., "Aspects of Folate-Mediated Drug Delivery . . . Beyond Purdue" PowerPoint Presentation presented at Purdue University on May 4, 1999, (22 pages).
Achilefu et al. "A New Method for the Synthesis of Tri-tert-butyl Diethylenetriaminepentaacetic Acid Its Derivatives" *J. Org. Chem.* 2000; 65:1562-1565.
Carl et al. "A novel connector linkage applicable in prodrug design" J. Med. Chem. 1981;24(5):479-480.
Coney et al. "Cloning of a tumor-associated antigent: MOv18 and MOv19 antibodies recognize a folate-binding protein" Cancer Res. 1991;51(22):6125-32.
Crapatureanu et al. "Molecular necklaces. Cross-linking hemoglobin with reagents containing covalently attached ligands" Bioconjugate Chemistry, 1999;10(6):1058-67. Abstract Only.
Darnell, Ed. Molecular Cell Biology W. H. Freeman, San Francisco 1990;326-333.
DeNardo, Gerald. "When is Too Much Too Much and Yet Not Enough? Alas, a Plethora of Opportunities but Where's the Beef?" J. of Nuclear Medicine 2000; 41(3):470-3.
Dorwald, F. Z., "Side Reactions in Organic Synthesis: A Guide to Successful Synthesis Design," Wiley-VCH, Weinheim, 2005, p. ix of preface.
Forgac, "Structure and function of vacuolar class of ATP-driven pumps" Physiological Rev. 1989; 69(3), 765-795.
Garrett et al. "Synthesis and characterisation of polyamine-poly-(ethylene glycol) constructs for DNA binding and gene delivery" Bioorganic & Medicinal Chemistry, 2000; 8(7):1779-1797. Abstract Only.
Henderson et al. "Mediated uptake of folate by a high-affinity binding protein in sublines of L1210 cells adapted to nanomolar concentrations of folate" J. Membrane Biol., 1988;101:247-258.

(56) References Cited

OTHER PUBLICATIONS

Huang et al. "Design, syntheses and sequence selective DNA cleavage of functional models of bleomycin-II. 1,2 -trans-di substituted cyclopropane units as novel linkers" Bioorganic & Medicinal Chemistry, 1995;3(6):647-57. Abstract Only.

Jansen et al., "Identification of a Membrane-Associated Folate-Binding Protein in Human Leukemic CCRF-CEM Cells with Transport-Related Methotrexate Resistance"in Cancer Res., 1989, 49, 2455-2459.

Jansen, "Receptor- and Carrier-Mediated Transport Systems for Folates and Antifolates," Antifolate Drugs in Cancer Therapy, Jackman, Ed., Humana Press Inc, Totowa NJ (1999): 293-321.

Jansen et al. "The Reduced Folate/Methotrexate Carrier and a Membrane-Associated Folate Binding Protein as Transport Routes for Novel Antifolates: Structure-Activity Relationship" Chemistry and Biology of Pteridines and Folates New York, 1992;767-770.

Ke et al. "Targeting the Tumor-Associated Folate Receptor with a I" IN-DTPA Conjugate of Pteroic Acid Abstract No. 427. 48'h Annual Meeting of the Society of Nuclear Medicine Toronto, Canada, Jun. 26, 2001, available May 4, 2001; 1 pg.

Kemp et al. "New Protective Groups for Peptide Synthesis-I The Bic Group Base and Solvent Lability of the 5 -B enzi soxazolymethyl eneoxycarbonyl amino function" Tet. Lett. 1975;52:4625-4628.

Kutsky RJ. Handbook of Vitamins, Minerals, and Hormones, 2nd Edition. New York: Van Nostrand Reinhold: 1981;263-277.

Li et al. "Local concentration of folate binding protein GP38 in sections of human ovarian carcinoma by concentration of in vitro quantitative autoradiography." J. Nucl. Med. 1996; 37:665-672.

Linder et al., In vitro & in vivo studies with a-and y-isomers of 99'Tc-oxa folate show uptake of both isomers in folate receipt (+) KB Cell Lines J. Nuclear Med. 2000;41(5):470 Suppl.

Lee et al. "Prolonged circulating lives of single-chain Fv proteins conjugated with polyethylene glycol: a comparison of conjugation chemistries and compounds" Bioconjugate Chemistry, 1999;10(6):973-81. Abstract Only.

Mehvar R "Dextrans for targeted and sustained delivery of therapeutic and imaging agents" [Review] Journal of Controlled Release, 2000;69(1):1-25. Abstract Only.

Mezzanzanica et al. "Human T-lymphocytes targeted against an established human ovarian carcinoma with a bispecific F(ab')2 antibody prolong host survival in a murine xenograft model" Cancer Res. 1991; 51:5716-5721.

Miotti et al., "Characterization of Human Ovarian Carcinoma-Associated Antigens Defined by Novel Monoclonal Antibodies with Tumor—Restricted Specificity" Int. J. Cancer, 1987;39:297-303.

Pastan et al, eds. "The Pathways of Endocytosis" Endocytosis, Plenum Press, New York 1985;1-40.

Peterson et al. "Enzymatic cleavage of peptide-linked radiolabels from immunoconjugates" Bioconjugate Chemistry, 1999;10(4):553-7. Abstract Only.

Pizzorno et al. "5,10-Dideazatetrahydrofolic acid (DDATHF) transport in CCRFCEM and MA104 cell lines." J. Biol, Chem., 1993; 268(2):247-258.

Rothenberg et al. "Further observations on the folate-binding factor in some leukemic cells" J. Clin. Invest. 1971; 50(3):719-726.

Selhub et al. "The folate binding protein of rat kidney. Purification, properties, and cellular distribution" J. Biol. Chem. 1984;259(10):6601-6606.

Selhub et al. "Renal folate adsorption and the kidney folate binding protein I. Urinary Clearance studies" Am. J Physiol. 252:F750-F756.

Selhub et al. "Renal folate adsorption and the kidney folate binding protein II. Microinfusion studies" Am. J. Physiol. 252:F757-F760.

Sirotnak. "Obligate genetic expression in tumor cells of a fetal membrane property mediating "Folate" transport: biological significance and implications for improved therapy of human cancer" Cancer Res., 1985;45(9):3992-4000.

Stein et al. "Normal tissue reactivity of four anti-tumor monoclonal antibodies of clinical interest" Int. J. Cancer 1991;47(2):163-169.

Tanaka et al. "Preparation and characterization of a disulfide-linked bioconjugate of annexin V with the B-chain of urokinase: an improved fibrinolytic agent targeted to phospholipid-containing thrombi" Biochemistry, 1996;35(3):922-9. Abstract Only.

Toffoli et al. "Expression of folate binding protein as a prognostic factor for response to platinum-containing chemotherapy and survival in human ovarian cancer" Int. J. Cancer (Pred. Oncol) 1998; 79:121-126.

Weitman et al. "Distribution of the folate receptor GP38 in normal and malignant cell lines and tissues" Cancer Res. 1992;52(12):3396-3401.

Thaden et al. "Photoaffinity behavior of a conjugate of oligonucleoside methylphosphonate, rhodamine, and psoralen in the presence of complementary oligonucleotides" Bioconjugate Chemistry, 1993;4(5):386-94. Abstract Only.

Westerhof et al. "Membrane transport of natural folates and antifolate compounds in murine L1210 Leukemia cells: role of carrier-and receptor mediated transport systems" Cancer Res. 1991;51:5507-5513.

Williams et al. "Renal tubular transport of folic acid and methotrexate in the monkey" Am. J. Physiol 1982; 242(5):F484-490.

Weygand, et al., Chemishe. Berichte (1950) 83, 460-467.

Beevers, Christopher S., et al., "Curcumin Inhibits the Mammalian Target of Rapamycin-Mediated Signaling Pathways in Cancer Cells", 2006; Int. Journal Cancer; vol. 119; pp. 757-764.

Brown, Nicole E., et al., "Delayed Cystogenesis and Increased Ciliogenesis Associated with th Re-Expression of Polaris in Tg737 Mutant Mice", 2003, Kidney International, vol. 63, pp. 1220-1229.

Bukanov Nikolay, O. et al., "Long-Lasting Arrest of Murine Polycystic Kidney Disease With CDK Inhibitor Roscovitine", Dec. 14, 2006; Nature; vol. 444; pp. 949-952.

Hay, Nissim, et al., "Upstream and Downstream of mTOR", 2004, Genes & Development, vol. 18, No. 16, pp. 1926-1945.

Kennedy, Michael D., et al., "Evaluation of Folate Conjugate Uptake and Transport by the Choroid Plexus of Mice", (May 2003), vol. 20, No. 5, pp. 714-719.

Leamon, Christopher P., et al., "Folate-Liposome-Mediated Antisense Oligodeoxynucleotide Targeting to Cancer Cells: Evaluation in Vitro and in Vivo", 2003, Bioconjugate Chemistry, vol. 14, No. 4, pp. 738-747.

Nauta, Jeroen, et al., "Renal and Biliary Abnormalities in a New Murine Model of Autosomal Recessive Polycystic Kidney Disease", 1993, Pediatr. Nephrol. No. 7, pp. 163-172.

Piontek, Klaus B., et al. "A Functional Floxed Allele of Pkdl that Can Be Conditionally Inactivated in Vivo", J. Am. Soc. Nephrol. vol. 15, pp. 3035-3043.

Shillingford, Jonathan M., et al., "The mTOR Pathway is Regulated by Polycystin-1, and its Inhibition Reverses Renal Cystogenesis in Polycyctic Kidney Disease", Apr. 4, 2006, PNAS. vol. 103, No. 14, pp. 5466-5471.

Ke CY et al., "Folate-Receptor-Targeting of In-111 Using Pteroic Acid Conjugates of Benzyl-DTPA and Benzyl-DOTA," J. Nucl. Med., 2004; 45(5):457P.

Regueiro-Ren et al., "Synthesis and Biological Activity of Novel Epothilone Aziridines," Organic Letters, 2001; vol. 3, No. 17: 2693-96.

Kamen et al., "A review of folate receptor alpha cycling and 5-methyltetrahydrofolate accumulation with an emphasis on cell models in vitro," Advanced Drug Delivery Reviews, 2004; vol. 56:1085-97.

Elnakat et al., "Distribution, functionality and gene regulation of folate receptor isoforms: implications in targeted therapy," Advanced Drug Delivery Reviews, 2004; vol. 56:1067-84.

Sabharanjak et al., "Folate receptor endocytosis and trafficking," Advanced Drug Delivery Reviews, 2004; vol. 56: 1099-1109.

Paulos et al., "Folate receptor-mediated targeting of therapeutic and imaging agents to activated macrophages in rheumatoid arthritis," Advanced Drug Delivery Reviews, 2004; vol. 56: 1205-17.

Antony, "Folate receptors: reflections on a personal odysssey and a perspective on unfolding truth," Advanced Drug Delivery Reviews, 2004; vol. 56: 1059-66.

(56) References Cited

OTHER PUBLICATIONS

Lu et al., "Folate receptor-targeted immunotherapy of cancer: mechanism and therapeutic potential," Advanced Drug Delivery Reviews, 2004; vol. 56: 1161-76.
Roy et al., "Folate-mediated targeting of T cells to tumors," Advanced Drug Delivery Reviews, 2004; vol. 56: 1219-31.
Ke et al., "Folate-receptor-targeted radionuclide imaging agents," Advanced Drug Delivery Reviews, 2004; vol. 56: 1143-60.
Gabizon et al., "Tumor cell targeting of liposome-entrapped drugs with phospholipid-anchored folic acid-PEG Conjugates," Advanced Drug Delivery Reviews, 2004; vol. 56: 1177-92.
Zhao et al., "Tumor-selective targeted delivery of genes and antisense oligodeoxyribonucleotides via the folate receptor," Advanced Drug Delivery Reviews, 2004; vol. 56: 1193-1204.
Pantos CM et al., "Ligand Binding and Kinetics of Folate Receptor Recycling in Vivo: Impact on Receptor-Mediated Drug Delivery," Molecular Pharmacology, 2004; 66:1406-1414.
Griesser UJ, "The Importance of Solvents," in Polymorphism in the Pharmaceutical Industry, Hilfiker ed., 2006; p. 211-230.
Wikipedia, Structural analog, http://en.wikipedia.org/wiki/Structural_analog, downloaded Apr. 7, 2009.
Wikipedia, Functional analog, http://en.wikipedia.org/wiki/Functional_analog, downloaded Apr. 7, 2009.
Wikipedia, Folic acid, http://en.wikipedia.org/wiki/Folic_acid, downloaded Apr. 7, 2009.
Lee JW et al., "Reduction of azides to primary amines in substrates bearing labile ester functionality. Synthesis of a PEG-solubilized, "Y"-shaped iminodiacetic acid reagent for preparation of folate-tethered drugs," Organic Letters, 1999; 1(2):179-181.
Atkinson SF et al., "Conjugation of folate via gelonin carbohydrate residues retains ribosomal-inactivating properties of the toxin and permits targeting to folate receptor positive cells," Journal of Biological Chemistry, 2001; 276(30):27930-27935.
Matulic-Adamic J et al., "An efficient synthesis of the ribozyme-folate conjugate," Tetrahedron Letters, 2002;43(25):4439-4441.
Harrison JG et al., A convenient synthetic route to oligonucleotide conjugates,: Bioorganic & Medicinal Chemistry Letters, 1997; 7(8): 1041-1046.
Dyson G., May P. "The Chemistry of Synthetic Pharmaceutical Substances", translation from English M.:-"The World", 1964, pp. 12-19.
Mashkovskiy M.D. Drugs, Moscow, New wave, 2001, vol. I, p. 11.
Robert Laplanche, et al.,"Physiologically Based Pharmacokinetic (PBPK) Modeling of Everolimus (RAD001) in Rats Involving Non-Linear Tissue Uptake,"Journal of Pharmacokinetics and Pharmacodynamics, 2007, vol. 34, No. 3, 373-400.
Pathalk et al., Enzymic protecting group techniques in organic synthesis, Stereosel. Biocatal. 775-797 (2000).
Dube D et al., "Preparation and Tumor Cell Uptake of Poly(N-isopropylacrylamide) Folate Conjugates"; Bioconjugate Chem, 2002; 13: 685-692.
Evans et al., "Synthessis of biotin conjugates of the antifungal compound cymoxanil," Pest Manag Sci, 2002; 58: 392-396.
Rao et al., Journal of Medicinal Chemistry, 1985, 28:1079-1088.
Conrad et al, Journal of Medicinal Chemistry, 1979, 22(4): 391-400.
Theti, D. S. et al., "Selective delivery of CB300638, a cyclopenta[g]quinazoline-based thymidylate synthase inhibitor into human tumor cell lines overexpressing the alpha-isoform of the folate receptor," Cancer Res, 2003; 63(13): 3612-3618.
Golub, T.R., et al., "Molecular Classification of Cancer: Class Discovery and Class Prediction by Gene Expression Monitoring," Science, 1999, vol. 286, 531-537 (Oct. 15, 1999).
Speckamp, et al.; "New Developments in the Chemistry of N-Acyliminium Ions and Related Intermediates" Tetrahedron 2000 vol. 56(24) 3817-3856.
Angier et al., Science, 1946, 103: 667-669.
Wolf et al., Journal of the American Chemical Society, 1947, 69: 2753-2759.

Parker et al., "Folate receptor expression in carcinomas and normal tissues determined by a quantitative radioligand binding assay," Analytical Biochemistry, 2005; 335:284-293.
Remy et al., Proceedings of the National Academy of Sciences of the United States of America, 1999, vol. 96, No. 10, pp. 5394-5399.
Na, Wang, and Kohn, "7-N-(Mercaptoalkylmitomycins: Implications of Cyclization for Drug Function," J Am Chem Soc 124:4666-77 (2002).
Putnam et al., "Polymer conjugates with anticancer activity", Advances in Polymer Science 1995, 122, 55-123.
Umemoto et al., "Molecular design of methotrexate-antibody conjugates for targeted cancer treatment", Journal of Bioactive and Compatible Polymers, 1992, 7(2), 191-219.
Sanderson et al., "In vivo drug-linker stability of an anti-CD30 dipeptide-linked auristatin immunoconjugate," Clinical Cancer Research, 2005; 11:843-852.
Wu et al., "Enhancing the enantioselectivity of candida lipase catalyzed ester hydrolysis via noncovalent enzyme modification," Journal of American Chemical Society, 1990; 112:1990-1995.
Patterson et al., "Expedient synthesis of N-Methyl tubulysin analogues with high cytotoxicity," Journal of Organic Chemistry, 2008; 73:4365-4369.
Gabizon et al., Clin Cancer Res, 9:6551-59 (2003).
Pouvreau, Isabelle et al.: "Effect of macrophage depletion by liposomes containing dichloromethylene-diphosphonate on endotoxin induce uveitis." J. Neuroimmun (1998) 86 p. 171-181.
Lindstedt, E.W. et al.; "Anti-tnf-alpha therapy for sight threatening uveitis." Br. J. Opthalmol. (2005) 89 p. 533-536.
Mangel, Andreas: GMP news, 2002, www.gmp-compliance.ord/eca_news_159.html, downloaded Mar. 19, 2014.
Definition of derivative and analog, from http://cancerweb.ncl.ac.uk/cgi-omd?query=derivative and http://cancerweb.ncl.ac.uk/cgi-bin/omd?query=analog, pp. 1-5, accessed Jul. 7, 2005.
Kaneko, Takushi, "New Hydrazone Derivatives of Adiramycin and their Immunoconjugates-A Correlation between Acid Stability and Cytotoxicity", Bioconj. Chem., vol. 2, No. 3, pp. 131-141 (May 1, 1991).
PCT International Search Report/Written Opinion for PCT/US2009/061049, completed May 15, 2010.
Polyak et al., "Introduction of spacer peptides N-terminal to a cleavage recognition motif in recombinant fusion proteins can improve site-specific cleavage," Protein Eng., 1997; 10(6):615-9.
University of Maryland Medical Center (UMMC), Vitamin B9 (folic acid), 2014, http://umm.edu/health/medical/altmed/supplement/vitamin-b9-folic-acid, pp. 1-10.
Cerner Multum, Inc., Drugs.com, Folic Acid, http://www.drugs.com/folic_acid.htm?printable=1, 1996-2014, Version: 5.01, Revision Date Oct. 15, 2009, pp. 1-4.
PCT International Search Report/Written Opinion prepared for PCT/US2010/061897, mailed Mar. 11, 2011.
Water, from http://www.biology-ionline,org/dictionary/Water, pp. 103, accessed Apr. 24, 2014.
Niosh List of antineoplastic and Other Hazardous Drugs in Healthcare settings 2010, pp. 1-16, published Sep. 20, 2010.
Chae et al, Recombinant Expression, Isotope labeling and purification of the Vitamin D Receptor Binding Peptide, Bull. Korean Chem Soc. 2011, 32, pp. 4337-4340.
Rudinger, peptide Hormones, JA Parsons, Ed., 1976, pp. 1-7.
SIGMA, 2004, pp. 1-2.
Berendsen, A Glimpse of the Holy Grail?, Science, 1998, 282, pp. 642-643.
Voet et al, Biochemistry, John Wiley & Sons Inc., 1995, pp. 235-241.
Ngo et al, Computational Complexity, Protein Structure protection, and the Levinthal Paradox, 1994, pp. 491-497.
Bradley et al, Limits of Cooperativity in a Structurally Modular Protein: Response of the Notch Ankyrin Domain to Analogous Alanine Substitutions in Each Repeat, J. Mol. Bio , 2002, 324, pp. 373-386.
Definition of moiety, from http://dictionary.reference.com/browse/moiety, pp. 1-3, accessed Aug. 26, 2010.

(56) References Cited

OTHER PUBLICATIONS

Muller, Prodrug approaches for Enhancing the Bioavailability of Drugs with Low Solubility, Chemistry & Biodiversity, 2009, 6, pp. 2071-2083.
Beaumont et al, Design of ester prodrugs to enhance oral absorption of poorly permeable compounds: Challenges to the Discovery Scientist, Current Drug Metbolism, 2003, 4, 461-485.
Hyo-Kyung Han, Targeted prodrug design to optimize drug delivery, AAPS Pharmsci 2000, 2(10), article 6, p. 1-11.
Yashveer Singh et al, Recent trends in targeted anticancer prodrug and conjugate design, Curr Med Chem, 2008, 15(18): 1802-1826.
Testa B, Prodrug Research: Futile or Fertile?, Biochem Pharm, 2004, 68, pp. 2097-2106.
Ettmayer et al, Lessons learned from marketed and investigational prodrugs, J. Med Chem, 2004, 47(10), pp. 2393-2404.
Machine Translation of WO 2004/005326, Jan. 15, 2004, pp. 1-5.
European Search Report prepared for corresponding European Application Serial No. 08841521.1, mailed Jul. 18, 2011.
Paranjpe, et al., "Tumor-targeted bioconjugate based delivery of camptothecin: design, synthesis and in vitro evaluation," ScienceDirect Journal of Controlled Release 100 (2004) 275-292.
Yang, et al., "Characterization of the pH of Folate Receptor-Containing Endosomes and the Rate of Hydrolysis of Internalized Acid-Labile Folate-Drug Conjugates," JPET 321: 462-468, 2007.
Henne, et al., "Synthesis and activity of a folate peptide camptothecin prodrug," ScienceDirect, Bioorganic & Medical Chemistry Letters 16 (2006) 5350-5355.
PCT International Search Report/Written Opinion for PCT/US2008/056824, completed Jul. 24, 2009.
Vlahov I. et al., "An assembly concept for the consecutive introduction of unsymmetrical disulfide bonds: synthesis of a releasable multidrug conjugate of folic acid," 2007, J. Org Chem, 72, 5968-5972.
Wang, L. et al., "Synthesis, biological, and antitumor activity of a highly potent 6-substituted pyrrolo[2,3-d]pyrimidine thienoyl antifolate inhibitor with proton-coupled folate transporter and folate receptor selectivity over the reduced folate carrier that inhibits β-glycinamide ribonucleotide formyltransferase," 2011, J. Med. Chem., 54, 7150-7164.
Vlahov I. et al., "Design and regioselective synthesis of a new generation of targeted therapeutics. Part 3: Folate conjugates of aminopterin hydrazide for the treatment of inflammation," 2011, Bioorg. Med. Chem. Lett., 21, 1202-1205.
Vlahov, I. et al., "Design and regioselective synthesis of a new generation of targeted chemotherapeutics. Part II: Folic acid conjugates of tubulysins and their hydrazides," Bioorg. Med. Chem. Lett., 2008, 18(16), 4558-4561.
Endocyte: Endocyte Enrolls First Patient in Phase 1 Study for the Small Molecule Drug Conjugate EC1456, a Folate-Targeted Tubulysin Conjugate in Advanced Solid Tumors. Dec. 2013. [Retrieved on May 6, 2015).
Leamon, et al., "Patient selection and targeted treatment in the management of platinum-resistant ovarian cancer," Pharmacogenomics and Personalized Medicine, 6:113-125 (2013).
Kularatne, S., "Synthesis and Biological Analysis of Prostate-Specific Membrane Antigen-Targeted Anticancer Prodrugs," J. Med. Chem, 2010, 53(21), 7767-7777.
Friestad, G. et al., "Stereoselective Mn-Mediated Coupling of Functionalized Iodides and Hydrazones: A Synthetic Entry to the Tubulysin γ-Amino Acids," Org. Lett., 2004, 6, 3249-3252.
Wipf, P. et al., "Synthesis of the Tubuvaline-Tubuphenylalanine (Tuv-Tup) Fragment of Tubulysin," Org. Lett., 2004, 6, 4057-4060.
Wipf, P. et al., "Total Synthesis of $N^{14}$-Desacetoxytubulysin H," Org Lett., 2007, 9, 1605-1607.
Sani, M. et al., "Total Synthesis of Tubulysin U and V," Angew. Chem. Int. Ed., 2007, 46, 3526-3529.
Dömling, A. et al., "Total Synthesis of Tubulysins U and V," Angew. Chem. Int. Ed., 2007, 46, 7235-7239.
Dömling, A. et al., "Total Synthesis of Tubulysins U and V," Angew. Chem. Int. Ed., 2007, 46, 2337-2348.
Du, Z. et al., "Catalytic study on the transesterification of dimethyl carbonate and phenol to diphenyl carbonate," Catalysis Communications, 2008, 9, 239-243.
Otera, J. et al., "Novel template effects of distannoxane catalysts in highly efficient transesterification and esterification," J. Org. Chem., 1991, 56, 5307-5311.

PROCESSES FOR PREPARING TUBULYSIN DERIVATIVES AND CONJUGATES THEREOF

CROSS-REFERENCE TO RELATED APPLICATIONS

This present application is a U.S. national stage application under 35 U.S.C. 371(b) of International Application No. PCT/US2013/034672 filed Mar. 29, 2013, and claims the benefit under 35 U.S.C. §119(e) of U.S. Provisional Application No. 61/617,386, filed Mar. 29, 2012, U.S. Provisional Application No. 61/684,450, filed Aug. 17, 2012, U.S. Provisional Application No. 61/771,451, filed Mar. 1, 2013, and U.S. Provisional Application 61/794,720, filed Mar. 15, 2013, the entirety of each of the disclosures of which are hereby incorporated herein by reference.

TECHNICAL FIELD

The invention described herein pertains to processes for preparing tubulysin derivatives, conjugates of tubulysins, and intermediates therefore.

BACKGROUND AND SUMMARY OF THE INVENTION

The tubulysins are members of a new class of natural products isolated from myxobacterial species (F. Sasse, et al., *J. Antibiot.* 2000, 53, 879-885). As cytoskeleton interacting agents, the tubulysins are mitotic poisons that inhibit tubulin polymerization and lead to cell cycle arrest and apoptosis (H. Steinmetz, et al., *Chem. Int. Ed.* 2004, 43, 4888-4892; M. Khalil, et al., *ChemBioChem.* 2006, 7, 678-683; G. Kaur, et al., *Biochem. J.* 2006, 396, 235-242). Tubulysins are extremely potent cytotoxic molecules, and exceed the cell growth inhibition of many other clinically relevant traditional chemotherapeutics, including epothilones, paclitaxel, and vinblastine. Furthermore, they are potent against multidrug resistant cell lines (A. Domling, et al., *Mol. Diversity* 2005, 9, 141-147). These compounds show high cytotoxicity tested against a panel of cancer cell lines with $IC_{50}$ values in the low picomolar range; thus, they are of interest as potential anticancer therapeutics. However, tubulysins have been reported to exhibit a narrow, or in some cases nonexistent, therapeutic window such that disease treatment with tubulysins is hampered by toxicity and other unwanted side effects. Accordingly, tubulysins have been conjugated with targeting agents to improve their therapeutic window. A total synthesis of tubulysin D possessing C-terminal tubuphenylalanine ($R_A$=H) (H. Peltier, et al., J. Am. Chem. Soc. 2006, 128, 16018-16019) has been reported. Recently, a modified synthetic protocol toward the synthesis of tubulysin B ($R_A$=OH) (O. Pando, et al., Org. Lett. 2009, 11, 5567-5569) has been reported. However, attempts to follow the published procedures to provide larger quantities of tubulysins were unsuccessful, being hampered in part by low yields, difficult to remove impurities, the need for expensive chromatographic steps, and/or the lack of reproducibility of several steps. The interest in using tubulysins for anticancer therapeutics accents the need for reliable and efficient processes for preparing tubulysins, and analogs and derivatives thereof. Therefore, there is a need for tubulysin derivatives, tubulysin analogs, and other tubulysin conjugate intermediates that are useful for preparing such targeted conjugates.

Tubulysin derivatives useful for preparing vitamin receptor binding tubulysin conjugates (also referred to herein as tubulysin linker derivatives) are described herein. Structurally, tubulysin linker derivatives include linear tetrapeptoid backbones, including illustrative compounds having the following formula

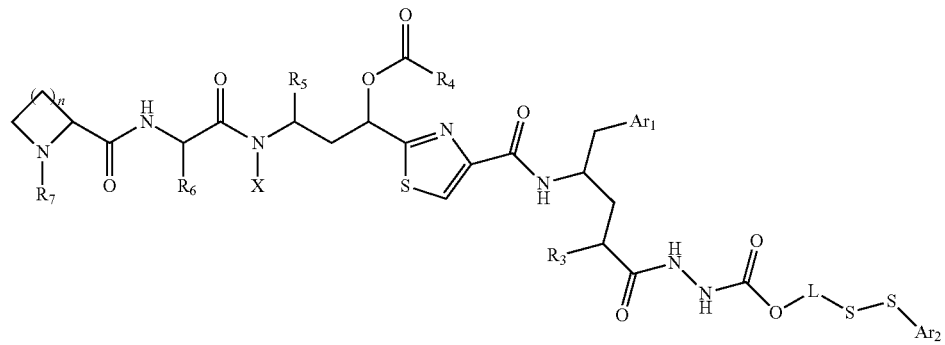

and salts thereof, wherein $Ar_1$ is optionally substituted aryl or optionally substituted heteroaryl;

$Ar_2$ is optionally substituted aryl or optionally substituted heteroaryl;

L is selected from the group consisting of

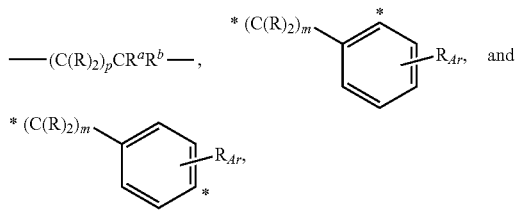

where p is an integer from about 1 to about 3, m is an integer from about 1 to about 4, and * indicates the points of attachment;

$R^a$, $R^b$, and R are each independently selected in each instance from the group consisting of hydrogen and alkyl; or any two of $R^a$, $R^b$, and R are taken together with the attached carbon atom(s) to form a carbocyclic ring; $R_{Ar}$ represents hydrogen, or 1 to 4 substituents each independently selected from the group consisting of amino or derivatives thereof, hydroxy or derivatives thereof, halo, thio or derivatives thereof, nitro, sulfonic acids and derivatives thereof, carboxylic acids and derivatives thereof, and alkyl, heteroalkyl, aryl, arylalkyl, arylheteroalkyl, heteroaryl, heteroarylalkyl, and heteroarylheteroalkyl, each of which is optionally substituted;

X is hydrogen; or X is alkyl or alkenyl, each of which is optionally substituted; or X is $R^{16}C(O)CH(R^{17})CH_2$; where $R^{17}$ is $C(O)R^{16}$, $C(O)OR^{16}$, or CN; where $R^{16}$ is independently in each instance alkyl, alkenyl, cycloalkyl, cycloalkenyl, heteroaryl, arylalkyl, or heteroarylalkyl, each of which is optionally substituted; or X is $CH_2QR^{18}$; where Q is N, O, or S; and $R^{18}$ is alkyl, alkenyl, cycloalkyl, cycloalkenyl, aryl, arylalkyl, heteroaryl, or heteroarylalkyl, each of which is optionally substituted, or $R^{18}$ is acyl, sulfonyl, or phosphonic acid or a derivative thereof;

$R_4$ is optionally substituted alkyl or optionally substituted cycloalkyl;

$R_3$ is optionally substituted alkyl;

$R_5$ and $R_6$ are each independently selected from the group consisting of optionally substituted alkyl and optionally substituted cycloalkyl;

$R_7$ is optionally substituted alkyl;

$R_{Ar}$ represents hydrogen, or 1 to 4 substituents each independently selected from the group consisting of amino or derivatives thereof, hydroxy or derivatives thereof, halo, thio or derivatives thereof, nitro, sulfonic acids and derivatives thereof, carboxylic acids and derivatives thereof, and alkyl, haloalkyl, heteroalkyl, aryl, arylalkyl, arylheteroalkyl, heteroaryl, heteroarylalkyl, and heteroarylheteroalkyl; and n is 1, 2, 3, or 4.

In another embodiment, X is Y—$CH_2$, where Y is $R_2C(O)O$ or $R_{12}O$; $R_2$ is selected from the group consisting of optionally substituted alkyl and optionally substituted cycloalkyl; and $R_{12}$ is alkyl, alkenyl, alkynyl, heteroalkyl, cycloalkyl, heterocycloalkyl, aryl, arylalkyl or heteroarylalkyl, each of which is optionally substituted.

In another embodiment, compounds of the formula

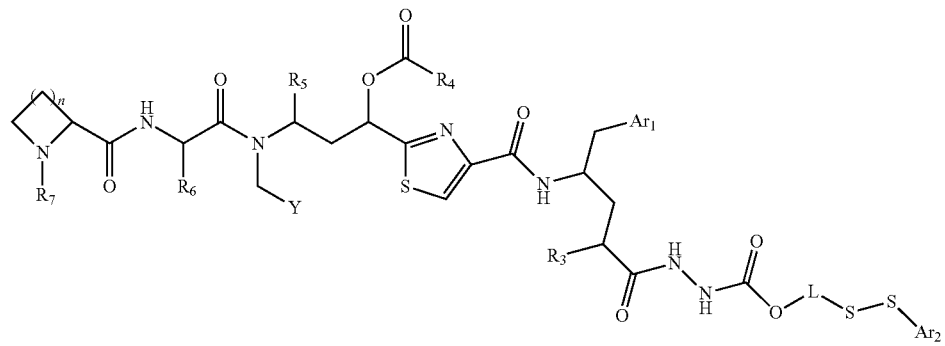

and salts thereof, are described. In another embodiment, the tubulysin linker derivative has formula T1

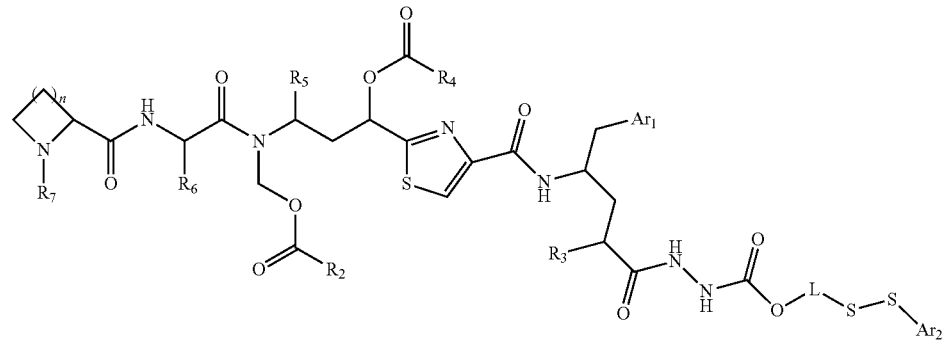

(T1)

or a salt thereof. In another embodiment, the tubulysin linker derivative has formula T2

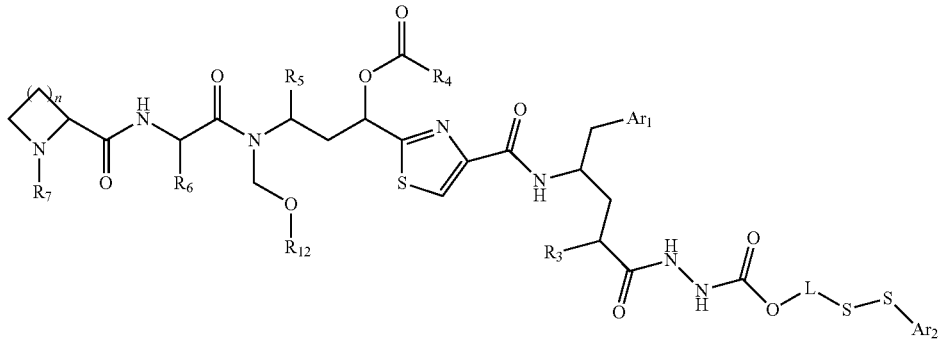

(T2)

or a salt thereof.

In another embodiment, in any of the embodiments described herein $Ar^2$ is optionally substituted aryl.

In another embodiment, in any of the embodiments described herein $Ar^2$ is optionally substituted heteroaryl.

Another illustrative group of tubulysins described herein are more particularly comprised of one or more non-naturally occurring or hydrophobic amino acid segments, such as N-methyl pipecolic acid (Mep), isoleucine (Ile),

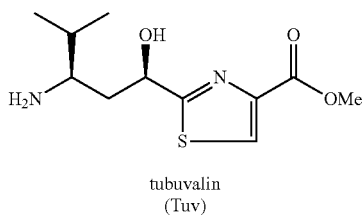

tubuvalin
(Tuv)

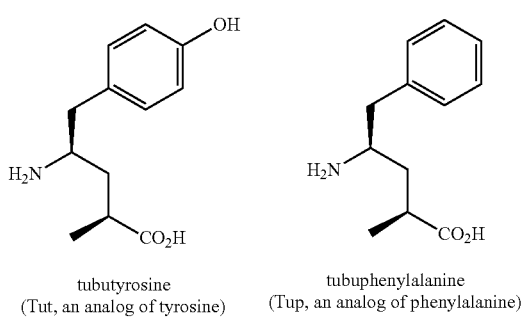

tubutyrosine
(Tut, an analog of tyrosine)

tubuphenylalanine
(Tup, an analog of phenylalanine)

and analogs and derivative of each of the foregoing. Derivatives and analogs of tubuvaline include compounds of the following formula,

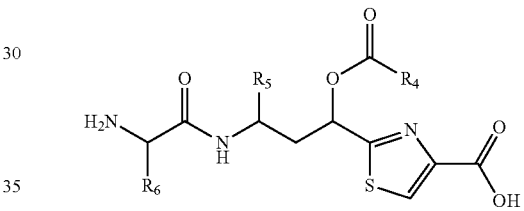

wherein $R_4$, $R_5$ and $R_6$ are as described in any of the embodiments described herein. Derivatives and analogs of tubutyrosine or tubuphenylalanine include compounds having formula,

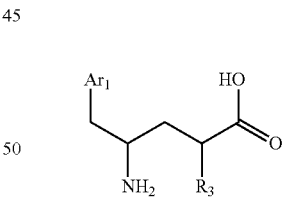

wherein $R_3$ and $Ar_1$ are as described in any of the embodiment described herein. A common feature in the molecular architecture of potent natural occurring tubulysins is the acid and/or base sensitive N-acyloxymethyl substituent (or a N,O-acetal of formaldehyde) represented by $R_2CO_2CH_2$ in the formula (T1).

In another embodiment, the compounds described herein are NHNH—C(O)O-L-SS—$Ar_2$ derivatives of naturally occurring tubulysins. An illustrative group of tubulysin derivatives described herein are those having formula 1.

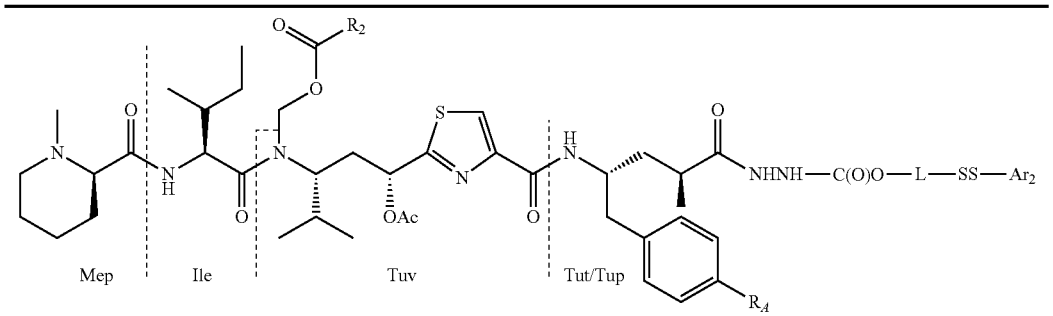

Formula 1, Structures of several tubulysin derivatives

| Tubulysin | $R_4$ | $R_2$ |
|---|---|---|
| A | OH | $CH_2CH(CH_3)_2$ |
| B | OH | $CH_2CH_2CH_3$ |
| C | OH | $CH_2CH_3$ |
| D | H | $CH_2CH(CH_3)_2$ |
| E | H | $CH_2CH_2CH_3$ |
| F | H | $CH_2CH_3$ |
| G | OH | $CH=C(CH_3)_2$ |
| H | H | $CH_3$ |
| I | OH | $CH_3$ |

Processes for preparing tubulysins, and analogs and derivatives thereof, are also described in WO 2012/019123, the disclosure of which is incorporated herein by reference in its entirety.

The formation of tubulysins conjugated to vitamin receptor binding moieties for targeted and/or selective delivery to cell populations expressing, overexpressing or selectively expressing cell surface vitamin receptors necessitates further modification of the highly toxic tubulysins. Described herein are improved processes for making natural tubulysins analogs or derivatives, which are useful for preparing vitamin receptor binding tubulysin conjugates including compounds of formula (T) and formula (I). Vitamin receptor binding conjugates of tubulysins are described in U.S. Patent Publication 2010/0048490, the disclosure of which is incorporated herein by reference in its entirety.

In one illustrative embodiment of the invention, processes for derivatives or analogs of natural tubulysins including compounds of formula (T). In another embodiment, vitamin receptor binding conjugates of tubulysins are described. The processes include one or more steps described herein. In another embodiment, a process is described for preparing a compound of formula B, wherein $R_5$ and $R_6$ are as described in the various embodiments herein, such as each being independently selected from optionally substituted alkyl or optionally substituted cycloalkyl; and $R_8$ is C1-C6 n-alkyl; wherein the process comprises the step of treating a compound of formula A with a silylating agent, such as triethylsilyl chloride, and a base, such as imidazole in an aprotic solvent.

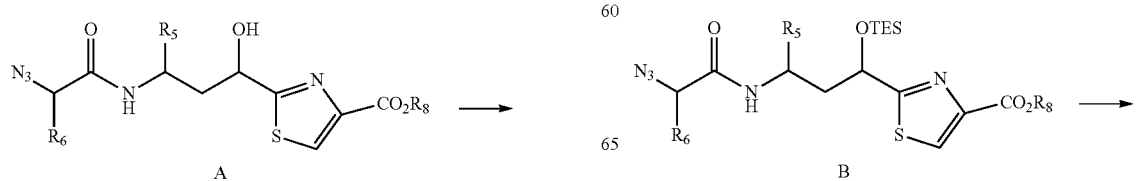

-continued

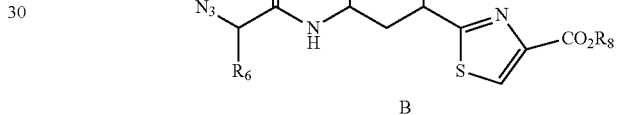

It is to be understood that $R_5$ and $R_6$ may each include conventional protection groups on the optional substituents.

In another embodiment, a process is described for preparing a compound of formula C, wherein $R_5$ and $R_6$ are as described in the various embodiments herein, such as each being independently selected from optionally substituted alkyl or optionally substituted cycloalkyl; $R_8$ is C1-C6 n-alkyl; and $R_2$ is as described in the various embodiments herein, such as being selected from optionally substituted alkyl or optionally substituted cycloalkyl; wherein the process comprises the step of treating a compound of formula B with a base and a compound of the formula $ClCH_2OC(O)R_2$ in an aprotic solvent at a temperature below ambient temperature, such as in the range from about $-78°$ C. to about $0°$ C.; wherein the molar ratio of the compound of the formula $ClCH_2C(O)R_2$ to the compound of formula B is from about 1 to about 1.5.

-continued

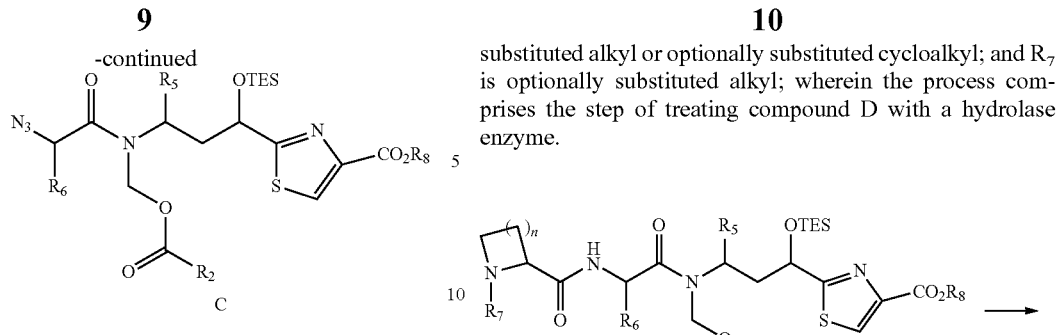

C

It is to be understood that $R_2$, $R_5$ and $R_6$ may each include conventional protection groups on the optional substituents.

In another embodiment, a process is described for preparing a compound of formula D, wherein $R_5$ and $R_6$ are as described in the various embodiments herein, such as being selected from optionally substituted alkyl or optionally substituted cycloalkyl; $R_8$ is C1-C6 n-alkyl; $R_2$ is as described in the various embodiments herein, such as being selected from optionally substituted alkyl or optionally substituted cycloalkyl; and $R_7$ is optionally substituted alkyl; wherein the process comprises the steps of a) preparing a compound of formula (E1) where $X_1$ is a leaving group from a compound of formula E; and b) treating a compound of formula C under reducing conditions in the presence of the compound of formula E1.

substituted alkyl or optionally substituted cycloalkyl; and $R_7$ is optionally substituted alkyl; wherein the process comprises the step of treating compound D with a hydrolase enzyme.

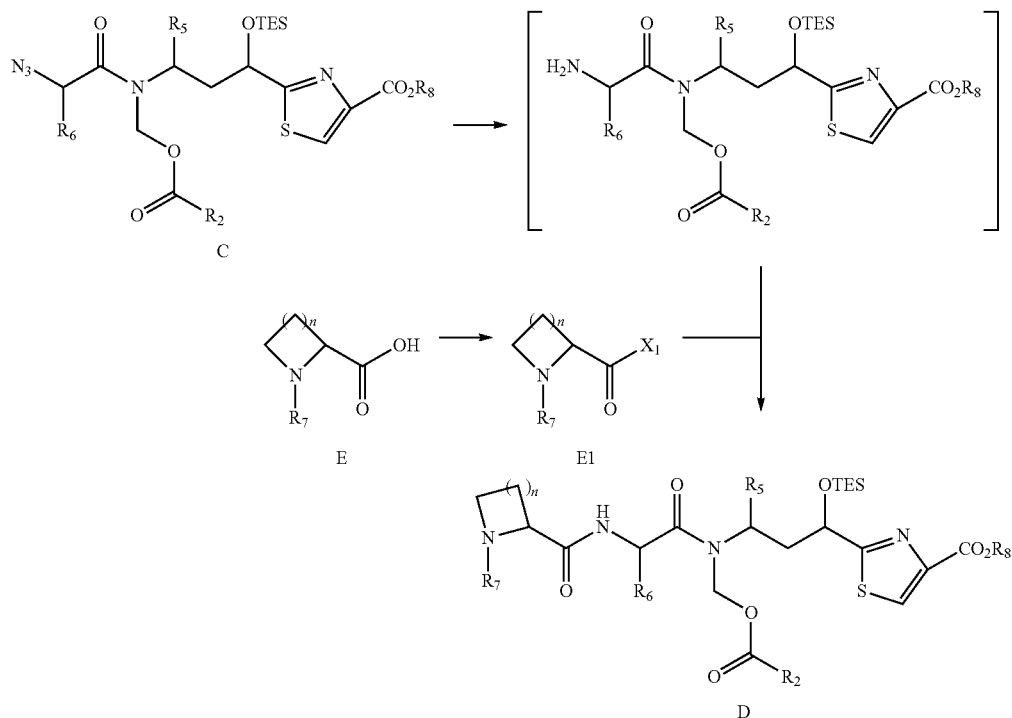

It is to be understood that $R_2$, $R_5$, $R_6$, and $R_7$ may each include conventional protection groups on the optional substituents.

In another embodiment, a process is described for preparing a compound of formula F, wherein $R_5$ and $R_6$ are as described in the various embodiments herein, such as being selected from optionally substituted alkyl or optionally substituted cycloalkyl; $R_2$ is as described in the various embodiments herein, such as being selected from optionally In another embodiment, a process is described for preparing a compound of formula F, wherein $R_5$ and $R_6$ are as described in the various embodiments herein, such as being selected from optionally substituted alkyl or optionally substituted cycloalkyl; $R_2$ is as described in the various embodiments herein, such as being selected from optionally substituted alkyl or optionally substituted cycloalkyl; and $R_7$ is optionally substituted alkyl; wherein the process comprises the step of treating compound D with a trialkyltin hydroxide (e.g. trimethyltin hydroxide). It is to be understood that $R_2$, $R_5$, $R_6$, and $R_7$ may each include conventional protection groups on the optional substituents.

In another embodiment, a process is described for preparing a compound of formula AF, wherein $R_5$ and $R_6$ are as described in the various embodiments herein, such as being selected from optionally substituted alkyl or optionally substituted cycloalkyl; $R_2$ is as described in the various embodiments herein, such as being selected from optionally substituted alkyl or optionally substituted cycloalkyl; and $R_7$ is optionally substituted alkyl; wherein the process comprises the step of contacting compound D with an alcohol, $R_{12}OH$, where $R_{12}$ is alkyl, alkenyl, alkynyl, heteroalkyl, cycloalkyl, heterocycloalkyl, aryl, arylalkyl or heteroarylalkyl, each of which is optionally substituted; and a transesterification catalyst. In one embodiment the transesterification catalyst is trifluoroacetic acid (TFA). In another embodiment, the transesterification catalyst is selected from the group consisting of $(R_{13})_8Sn_4O_2(NCS)_4$, $(R_{13})_2Sn(OAc)_2$, $(R_{13})_2SnO$, $(R_{13})_2SnCl_2$, $(R_{13})_2SnS$, $(R_{13})_3SnOH$, and $(R_{13})_3SnOSn(R_{13})_3$, where $R_{13}$ is independently selected from alkyl, arylalkyl, aryl, or cycloalkyl, each of which is optionally substituted. In another embodiment, the transesterification catalyst is $(R_{13})_2SnO$. Illustrative examples of $R_{13}$ include methyl, n-butyl. n-octyl, phenyl, o-MeO-phenyl, p-MeO phenyl, phenethyl, and benzyl.

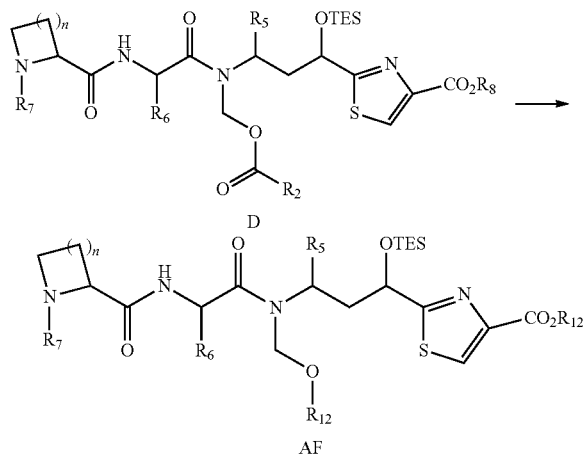

It is to be understood that $R_5$, $R_6$, $R_{12}$, and $R_7$ may each include conventional protection groups on the optional substituents.

In another embodiment, a process is described for preparing a transesterification product of each of the compounds of formula A and/or B, wherein $R_5$, $R_6$, and $R_8$ are as described in the various embodiments herein, and where $R_{12}$ is different from $R_9$; wherein the process comprises the step of contacting compound B with an alcohol, $R_{12}OH$, where $R_{12}$ is alkyl, alkenyl, alkynyl, heteroalkyl, cycloalkyl, heterocycloalkyl, aryl, arylalkyl or heteroarylalkyl, each of which is optionally substituted; and a transesterification catalyst. Illustratively, the transesterification catalyst is selected from the group consisting of $(R_{13})_8Sn_4O_2(NCS)_4$, $(R_{13})_2Sn(OAc)_2$, $(R_{13})_2SnO$, $(R_{13})_2SnCl_2$, $(R_{13})_2SnS$, $(R_{13})_3SnOH$, and $(R_{13})_3SnOSn(R_{13})_3$, where $R_{13}$ is independently selected from alkyl, arylalkyl, aryl, or cycloalkyl, each of which is optionally substituted. In another embodiment, the transesterification catalyst is $(R_{13})_2SnO$. Illustrative examples of $R_{13}$ include methyl, n-butyl. n-octyl, phenyl, o-MeO-phenyl, p-MeO phenyl, phenethyl, and benzyl.

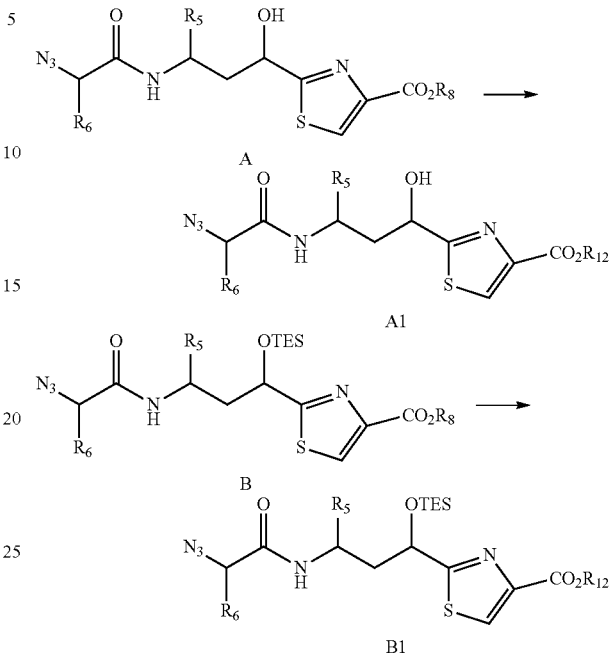

It is to be understood that $R_5$, $R_6$, and $R_{12}$ may each include conventional protection groups on the optional substituents.

In another embodiment, a process is described for preparing a compound of formula G, wherein $R_5$ and $R_6$ are as described in the various embodiments herein, such as being selected from optionally substituted alkyl or optionally substituted cycloalkyl; $R_2$ is as described in the various embodiments herein, such as being selected from optionally substituted alkyl or optionally substituted cycloalkyl; and $R_7$ is optionally substituted alkyl; wherein the process comprises the step of treating the silyl ether of compound F with a non-basic fluoride containing reagent.

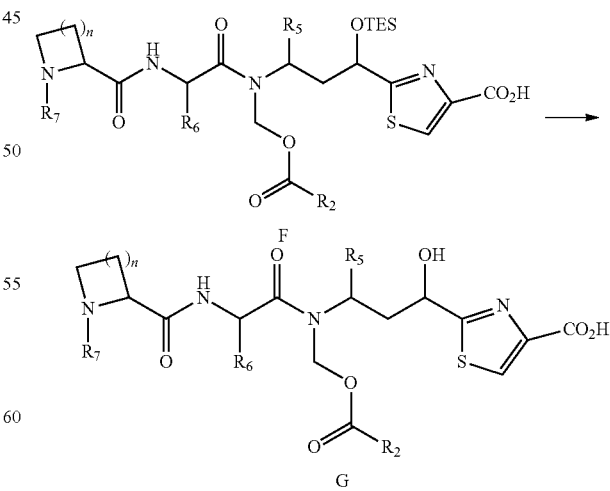

It is to be understood that $R_2$, $R_5$, $R_6$, and $R_7$ may each include conventional protection groups on the optional substituents.

In another embodiment, a process is described for preparing a compound of formula AG, wherein $R_5$ and $R_6$ are as described in the various embodiments herein, such as being selected from optionally substituted alkyl or optionally substituted cycloalkyl; $R_2$ is as described in the various embodiments herein, such as being selected from optionally substituted alkyl or optionally substituted cycloalkyl; and $R_7$ is optionally substituted alkyl; wherein the process comprises the step of contacting compound F with an alcohol, $R_{12}OH$, where $R_{12}$ is alkyl, alkenyl, alkynyl, heteroalkyl, cycloalkyl, heterocycloalkyl, aryl, arylalkyl or heteroarylalkyl, each of which is optionally substituted; and a transesterification catalyst. In one embodiment the transesterification catalyst is trifluoroacetic acid (TFA). In another embodiment, the transesterification catalyst is selected from the group consisting of $(R_{13})_8Sn_4O_2(NCS)_4$, $(R_{13})_2Sn(OAc)_2$, $(R_{13})_2SnO$, $(R_{13})_2SnCl_2$, $(R_{13})_2SnS$, $(R_{13})_3SnOH$, and $(R_{13})_3SnOSn(R_{13})_3$, where $R_{13}$ is independently selected from alkyl, arylalkyl, aryl, or cycloalkyl, each of which is optionally substituted. In another embodiment, the transesterification catalyst is $(R_{13})_2SnO$. Illustrative examples of $R_{13}$ are methyl, n-butyl. n-octyl, phenyl, o-MeO-phenyl, p-MeO phenyl, phenethyl, and benzyl.

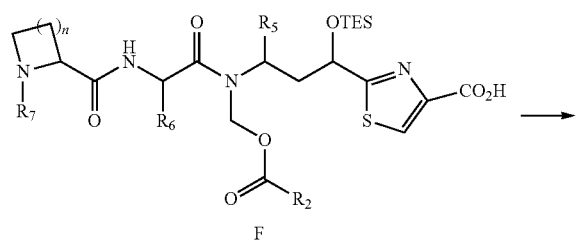

F

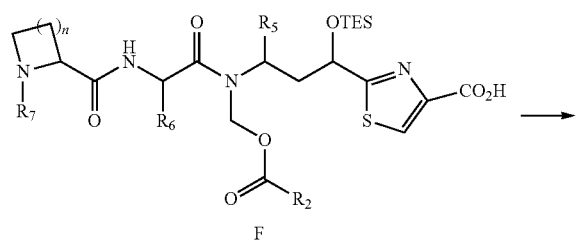

AG

It is to be understood that $R_2$, $R_5$, $R_6$, $R_7$, and $R_{12}$ may each include conventional protection groups on the optional substituents.

In another embodiment, a process is described for preparing a compound of formula BG, wherein $R_5$ and $R_6$ are as described in the various embodiments herein, such as being selected from optionally substituted alkyl or optionally substituted cycloalkyl; $R_2$ is as described in the various embodiments herein, such as being selected from optionally substituted alkyl or optionally substituted cycloalkyl; $R_{12}$ is as described in the various embodiments herein, such as being selected from alkyl, alkenyl, alkynyl, heteroalkyl, cycloalkyl, heterocycloalkyl, aryl, arylalkyl or heteroarylalkyl, each of which is optionally substituted; and $R_7$ is optionally substituted alkyl; wherein the process comprises the step of contacting compound AF with a metal hydroxide or carbonate. Illustrative examples of a metal hydroxide or carbonate include LiOH, $Li_2CO_3$, NaOH, $Na_2CO_3$, KOH, $K_2CO_3$, $Ca(OH)_2$, $CaCO_3$, $Mg(OH)_2$, $MgCO_3$, and the like.

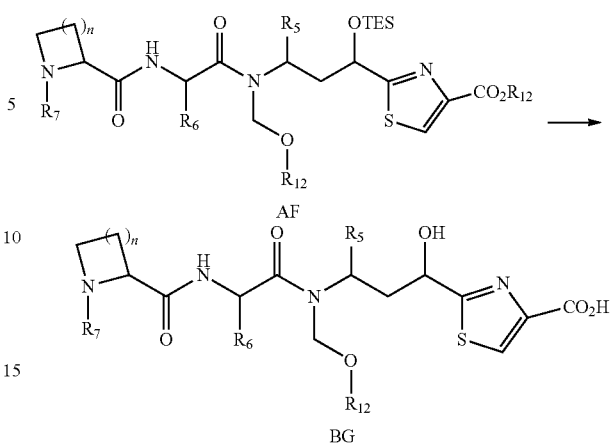

AF

BG

It is to be understood that $R_5$, $R_6$, $R_7$, and $R_{12}$ may each include conventional protection groups on the optional substituents.

In another embodiment, a process is described for preparing a compound of formula H, wherein $R_5$ and $R_6$ are as described in the various embodiments herein, such as being selected from optionally substituted alkyl or optionally substituted cycloalkyl; $R_2$ and $R_4$ are as described in the various embodiments herein, such as being selected from optionally substituted alkyl or optionally substituted cycloalkyl; and $R_7$ is optionally substituted alkyl; wherein the process comprises the step of treating a compound of formula G with an acylating agent of formula $R_4C(O)X_2$, where $X_2$ is a leaving group.

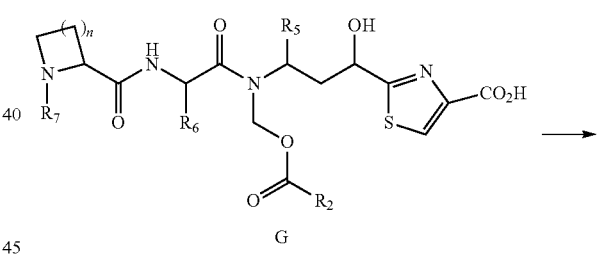

G

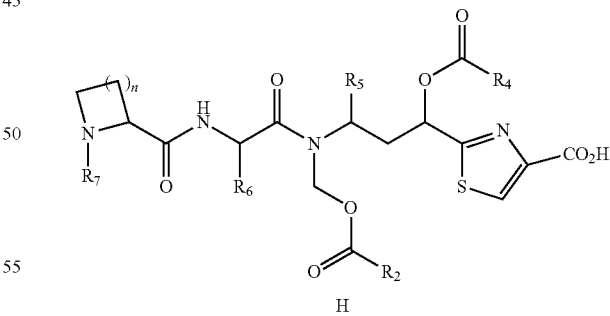

H

It is to be understood that $R_2$, $R_4$, $R_5$, $R_6$, and $R_7$ may each include conventional protection groups on the optional substituents.

In another embodiment, a process is described for preparing a compound of formula AH, wherein $R_5$ and $R_6$ are as described in the various embodiments herein, such as being selected from optionally substituted alkyl or optionally substituted cycloalkyl; $R_2$ and $R_4$ are as described in the various embodiments herein, such as being selected from optionally substituted alkyl or optionally substituted cycloalkyl; $R_{12}$ is as described in the various embodiments herein, such as being selected from alkyl, alkenyl, alkynyl, heteroalkyl, cycloalkyl, heterocycloalkyl, aryl, arylalkyl or heteroarylalkyl, each of which is optionally substituted; and $R_7$ is optionally substituted alkyl; wherein the process comprises the step of treating a compound of formula BG with an acylating agent of formula $R_4C(O)X_2$, where $X_2$ is a leaving group.

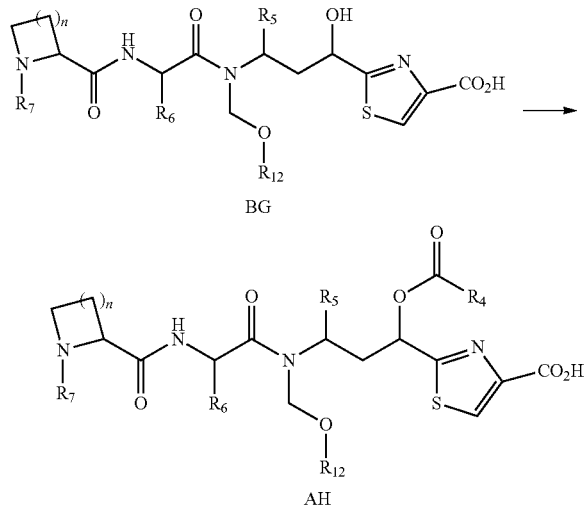

It is to be understood that $R_4$, $R_5$, $R_6$, and $R_7$ may each include conventional protection groups on the optional substituents.

In another embodiment, a process is described for preparing a tubulysin linker derivative of formula (T1), wherein $Ar_1$ is optionally substituted aryl; $Ar_2$ is optionally substituted aryl or optionally substituted heteroaryl; L is selected from the group consisting of

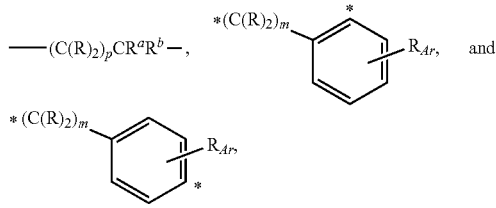

where p is an integer from about 1 to about 3, m is an integer from about 1 to about 4, and * indicates the points of attachment;

$R^a$, $R^b$, and R are each independently selected in each instance from the group consisting of hydrogen and alkyl; or any two of $R^a$, $R^b$, and R are taken together with the attached carbon atom(s) to form a carbocyclic ring;

$R_{Ar}$ represents 0 to 4 substituents selected from the group consisting of amino, or derivatives thereof, hydroxy or derivatives thereof, halo, thio or derivatives thereof, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof; $R_1$ is hydrogen, optionally substituted alkyl, optionally substituted arylalkyl or a pro-drug forming group; $R_5$ and $R_6$ are as described in the various embodiments herein, such as being selected from optionally substituted alkyl or optionally substituted cycloalkyl; $R_3$ is optionally substituted alkyl; $R_2$ and $R_4$ are as described in the various embodiments herein, such as being selected from optionally substituted alkyl or optionally substituted cycloalkyl; and $R_7$ is optionally substituted alkyl;

wherein the process comprises the step of forming an active ester intermediate from a compound of formula H; and reacting the active ester intermediate with a compound of the formula I to give a compound of the formula T.

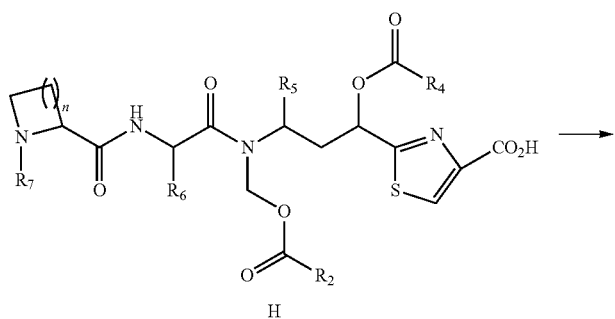

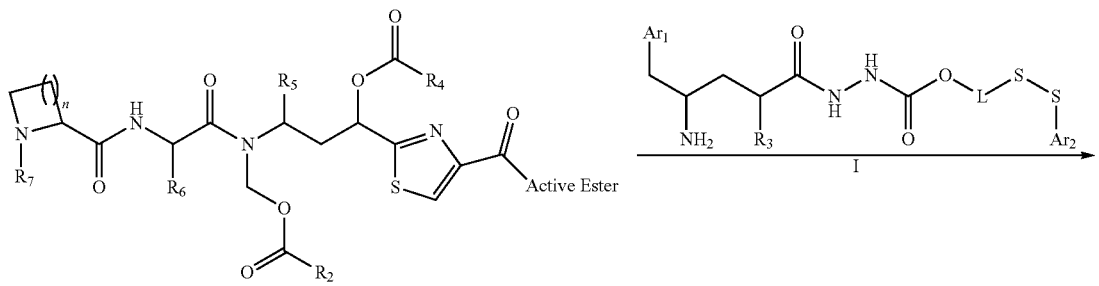

-continued

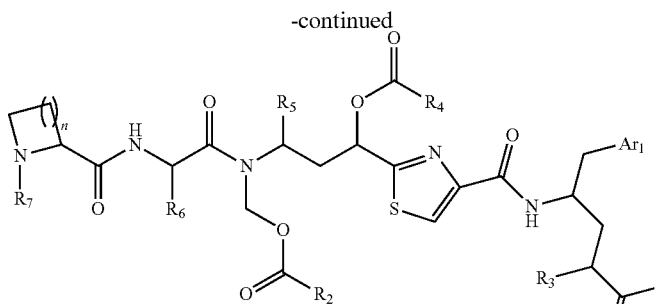

T1

It is to be understood that $Ar_1$, $Ar_2$, $R_1$, $R_2$, $R_4$, $R_5$, $R_6$, and $R_7$ may each include conventional protection groups on the optional substituents.

In another embodiment, a process is described for preparing a tubulysin linker derivative of formula (T2), wherein $Ar_1$ is optionally substituted aryl; $Ar_2$ is optionally substituted aryl or optionally substituted heteroaryl; L is selected from the group consisting of

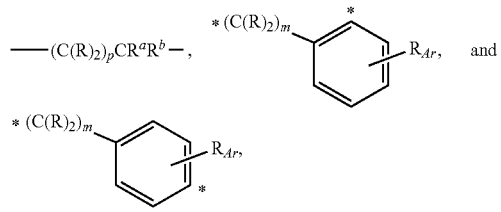

where p is an integer from about 1 to about 3, m is an integer from about 1 to about 4, and * indicates the points of attachment;

$R^a$, $R^b$, and R are each independently selected in each instance from the group consisting of hydrogen and alkyl; or any two of $R^a$, $R^b$, and R are taken together with the attached carbon atom(s) to form a carbocyclic ring;

$R_{Ar}$ represents 0 to 4 substituents selected from the group consisting of amino, or derivatives thereof, hydroxy or derivatives thereof, halo, thio or derivatives thereof, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof;

$R_1$ is hydrogen, optionally substituted alkyl, optionally substituted arylalkyl or a pro-drug forming group; $R_5$ and $R_6$ are as described in the various embodiments herein, such as being selected from optionally substituted alkyl or optionally substituted cycloalkyl; $R_3$ is optionally substituted alkyl; $R_2$ and $R_4$ are as described in the various embodiments herein, such as being selected from optionally substituted alkyl or optionally substituted cycloalkyl; and $R_7$ is optionally substituted alkyl;

wherein the process comprises the step of contacting compound T, with an alcohol, $R_{12}OH$, where $R_{12}$ is alkyl, alkenyl, alkynyl, heteroalkyl, cycloalkyl, heterocycloalkyl, aryl, arylalkyl or heteroarylalkyl, each of which is optionally substituted; and a transesterification catalyst.

In one embodiment the transesterification catalyst is trifluoroacetic acid (TFA). In another embodiment, the transesterification catalyst is selected from the group consisting of $(R_{13})_8Sn_4O_2(NCS)_4$, $(R_{13})_2Sn(OAc)_2$, $(R_{13})_2SnO$, $(R_{13})_2SnCl_2$, $(R_{13})_2SnS$, $(R_{13})_3SnOH$, and $(R_{13})_3SnOSn(R_{13})_3$, where $R_{13}$ is independently selected from alkyl, arylalkyl, aryl, or cycloalkyl, each of which is optionally substituted. In another embodiment, the transesterification catalyst is $(R_{13})_2SnO$. Illustrative examples of $R_{13}$ are methyl, n-butyl, n-octyl, phenyl, o-MeO-phenyl, p-MeO phenyl, phenethyl, and benzyl. It is to be understood that $Ar_1$, $Ar_2$, $R_1$, $R_2$, $R_4$, $R_5$, $R_6$, $R_7$, and $R_{12}$ may each include conventional protection groups on the optional substituents.

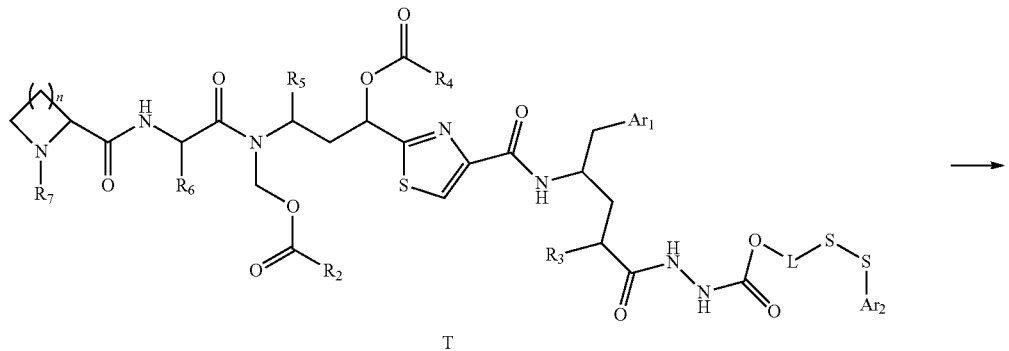

T

-continued

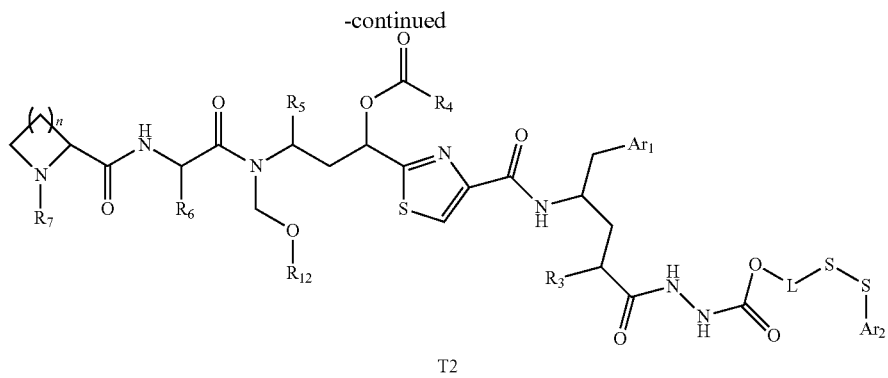

T2

In another embodiment, a process is described for preparing a tubulysin linker derivative of formula (T2), wherein $Ar_1$ is optionally substituted aryl; $Ar_2$ is optionally substituted aryl or optionally substituted heteroaryl; L is selected from the group consisting of

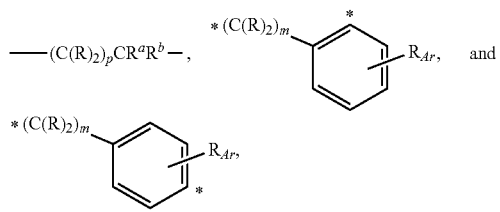

where p is an integer from about 1 to about 3, m is an integer from about 1 to about 4, and * indicates the points of attachment;

$R^a$, $R^b$, and R are each independently selected in each instance from the group consisting of hydrogen and alkyl; or any two of $R^a$, $R^b$, and R are taken together with the attached carbon atom(s) to form a carbocyclic ring;

$R_{Ar}$ represents 0 to 4 substituents selected from the group consisting of amino, or derivatives thereof, hydroxy or derivatives thereof, halo, thio or derivatives thereof, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof;

$R_1$ is hydrogen, optionally substituted alkyl, optionally substituted arylalkyl or a pro-drug forming group; $R_5$ and $R_6$ are as described in the various embodiments herein, such as being selected from optionally substituted alkyl or optionally substituted cycloalkyl; $R_3$ is optionally substituted alkyl; $R_2$ and $R_4$ are as described in the various embodiments herein, such as being selected from optionally substituted alkyl or optionally substituted cycloalkyl; and $R_7$ is optionally substituted alkyl;

wherein the process comprises the step of forming an active ester intermediate from a compound of formula AH; and reacting the active ester intermediate with a compound of the formula I to give a compound of the formula T2.

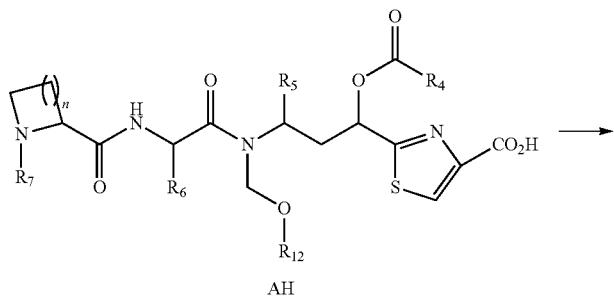

AH

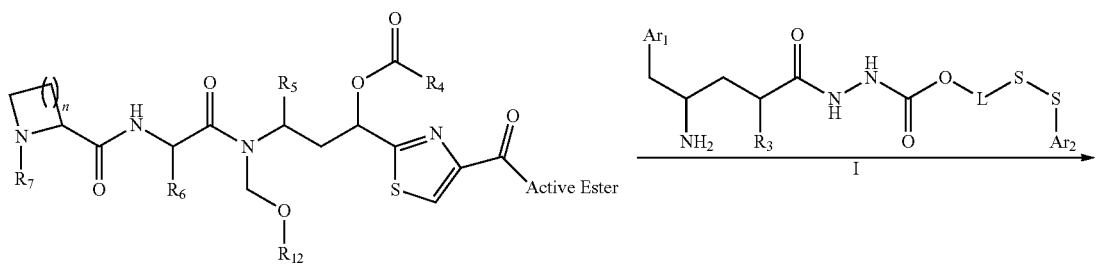

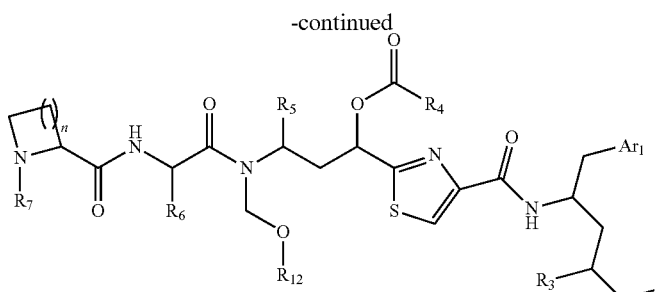

T2

It is to be understood that Ar$_1$, Ar$_2$, R$_1$, R$_{12}$, R$_3$, R$_4$, R$_5$, R$_6$, and R$_7$ may each include conventional protection groups on the optional substituents.

It is to be understood that the acyloxymethyl group (R$_2$—C(O)—CH$_2$) present on any of compounds C, D, F, G, H, and T1 may be converted into the corresponding ether group (R$_{12}$—O—CH$_2$), or other group (X or Y—CH$_2$) using the process of contacting the compound with trifluoroacetic acid (TFA), as described herein, and also as described in WO 2009/055562, the disclosure of which is incorporated herein by reference. Accordingly, the following compounds are also described herein

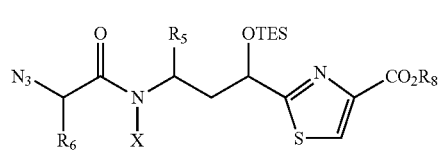

XC

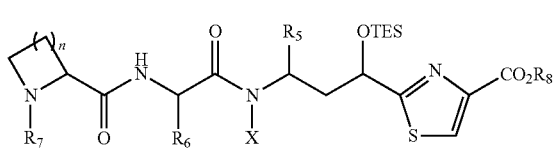

XD

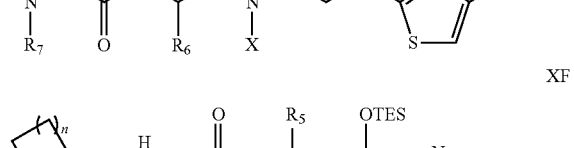

XF

XG

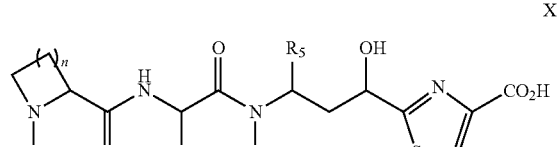

XH

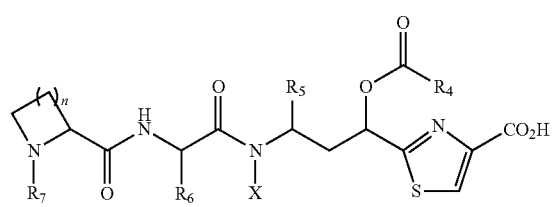

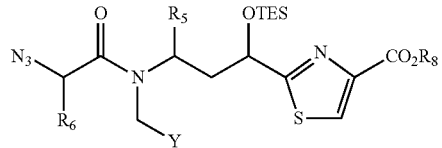

YC

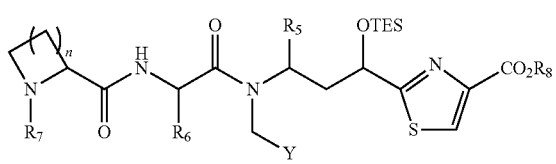

YD

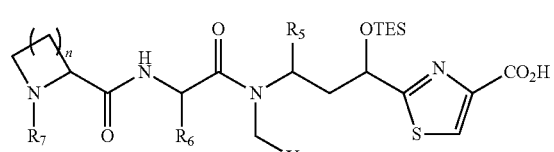

YF

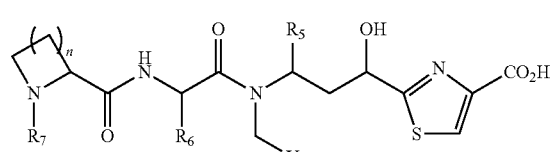

YG

YH

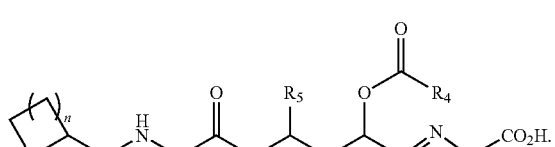

It is to be further understood that each of XC, XD, XF, XG, and XH can be used in the processes described herein in place of each of C, D, F, G, and H, respectively, to prepare the corresponding compound having an ether group (R$_{12}$—O—CH$_2$), or other group (X).

It is to be further understood that each of YC, YD, YF, YG, and YH can be used in the processes described herein in place of each of C, D, F, G, and H, respectively, to prepare the corresponding compound having an ether group (R$_{12}$—O—CH$_2$), or other group (Y—CH$_2$).

DETAILED DESCRIPTION

In one embodiment, a process is described for preparing a compound of formula B, wherein $R_5$ and $R_6$ are as described in the various embodiments herein, such as being selected from optionally substituted alkyl or optionally substituted cycloalkyl; and $R_8$ is C1-C6 n-alkyl; wherein the process comprises the step of treating a compound of formula A with triethylsilyl chloride and imidazole in an aprotic solvent.

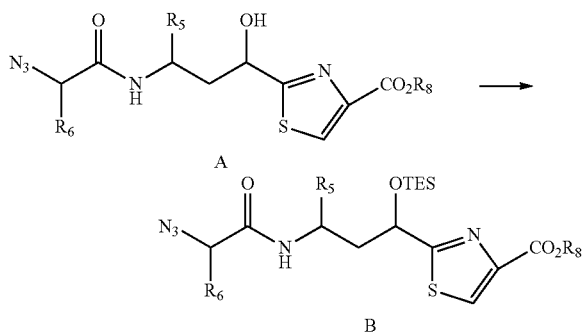

In the previously reported preparations of the intermediate silyl ether of formula 2, use of a large excess of triethylsilyl trifluoromethylsulfonate (TESOTf) and lutidine is described (see, for example, Peltier, et al., 2006). It was found that the reported process makes it necessary to submit the product of the reaction to a chromatographic purification step. Contrary to that reported, it has been surprisingly discovered herein that the less reactive reagent TESCl may be used. It has also been surprisingly discovered herein that although TESCl is a less reactive reagent, it may nonetheless be used in nearly stoichiometric amounts in the processes described herein. It is appreciated herein that the use of the less reactive TESCl may also be advantageous when the process is performed on larger scales, where higher reactivity reagents may represent a safety issue. It has also been discovered that the use of TESCl in nearly stoichiometric amounts renders the chromatographic purification step unnecessary. In an alternative of the embodiment, the process is performed without subsequent purification. In another alternative of the foregoing embodiments, and each additional embodiment described herein, $R_5$ is isopropyl. In another alternative of the foregoing embodiments, and each additional embodiment described herein, $R_6$ is sec-butyl. In another alternative of the foregoing embodiments, and each additional embodiment described herein, $R_8$ is methyl. In another alternative of the foregoing embodiments, and each additional embodiment described herein, the silyl ether is TES.

In an illustrative example of the processes described herein, a process for preparing the silyl ether 4 in high yield is described wherein compound 1 is treated with 1.05 equivalent of TESCl and 1.1 equivalent of imidazole.

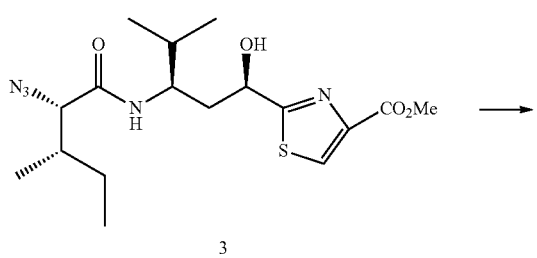

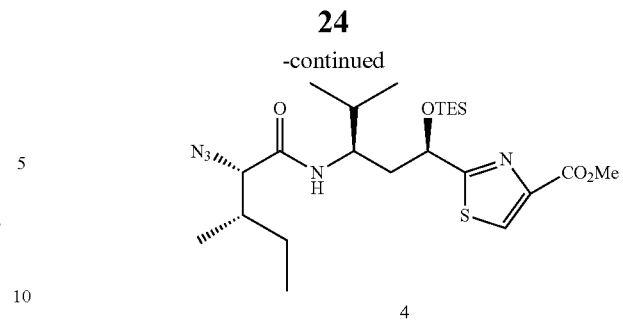

In one alternative of the foregoing example, the compound 4 is not purified by chromatography.

In another embodiment, a process is described for preparing a compound of formula C, wherein $R_5$ and $R_6$ are each independently selected from the group consisting of optionally substituted alkyl and optionally substituted cycloalkyl; $R_8$ is C1-C6 n-alkyl; and $R_2$ is selected from the group consisting of optionally substituted alkyl and optionally substituted cycloalkyl; wherein the process comprises the step of treating a compound of formula B with from about 1 equivalent to about 1.5 equivalent of base and from about 1 equivalent to about 1.5 equivalent of a compound of the formula $ClCH_2C(O)R_2$ in an aprotic solvent at a temperature from about $-78°$ C. to about $0°$ C.

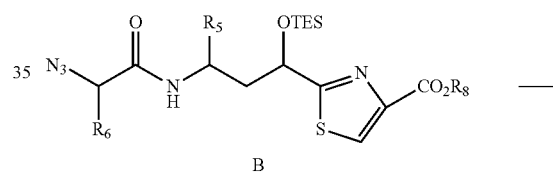

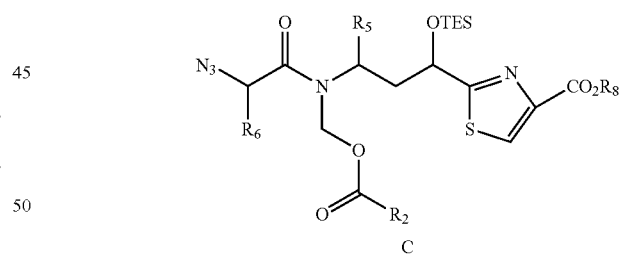

In another embodiment, the process of the preceding embodiment is described wherein the compounds of formulae B and C have the stereochemistry shown in the following scheme for B' and C'.

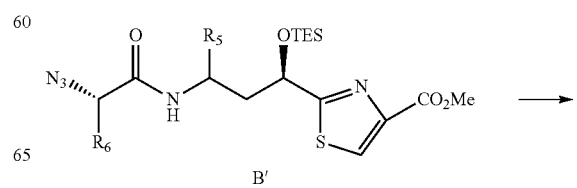

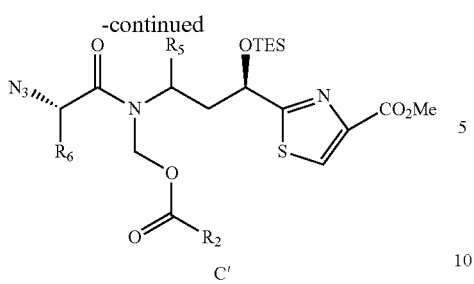

C'

In another illustrative embodiment, the ether analog of C' can be used to prepare the tubulysins, the tubulysin conjugates, and the tubulysin linker compounds described herein.

In another illustrative embodiment, the process of any one of the preceding embodiments is described wherein about 1 equivalent to about 1.3 equivalent of a compound of the formula $ClCH_2C(O)R_2$ is used. In another illustrative example, the process of any one of the preceding embodiments is described, wherein about 1.2 equivalent of a compound of the formula $ClCH_2C(O)R_2$ is used. In another illustrative example, the process of any one of the preceding embodiments is described wherein $R_2$ is n-propyl. In another alternative of the foregoing embodiments, and each additional embodiment described herein, $R_2$ is $CH_2CH(CH_3)_2$, $CH_2CH_2CH_3$, $CH_2CH_3$, $CH—C(CH_3)_2$, or $CH_3$.

In an illustrative example of the processes described herein, a process for preparing the N,O-acetal 5 is described. In another illustrative example, compound 2 is treated with 1.1 equivalent of potassium hexamethyldisilazane (KHMDS) and 1.2 equivalent of chloromethyl butanoate in a nonprotic solvent at about −45° C. In another illustrative example, the product formed by any of the preceding examples may be used without chromatographic purification.

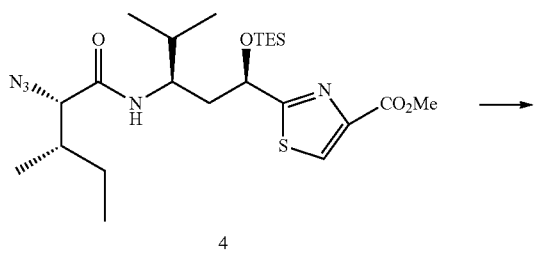

4

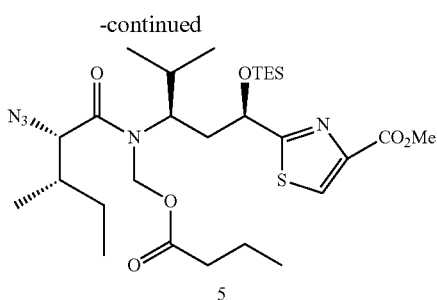

5

The ether analogs of compound 5 can also be used to prepare the tubulysins, tubulysin linker compounds

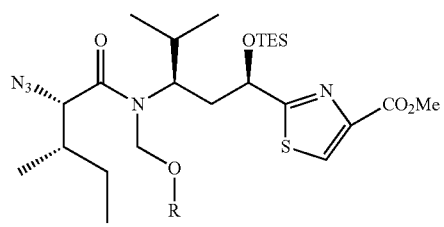

In another embodiment, a process is described for preparing a compound of formula D, wherein $R_5$ and $R_6$ are each independently selected from the group consisting of optionally substituted alkyl and cycloalkyl; $R_8$ is C1-C6 n-alkyl; $R_2$ is selected from the group consisting of optionally substituted alkyl and cycloalkyl; and $R_7$ is optionally substituted alkyl; wherein the process comprises the steps of a) preparing a compound of formula (E1) where $X_1$ is a leaving group from a compound of formula E; and b) treating a compound of formula C under reducing conditions with the compound of formula E1.

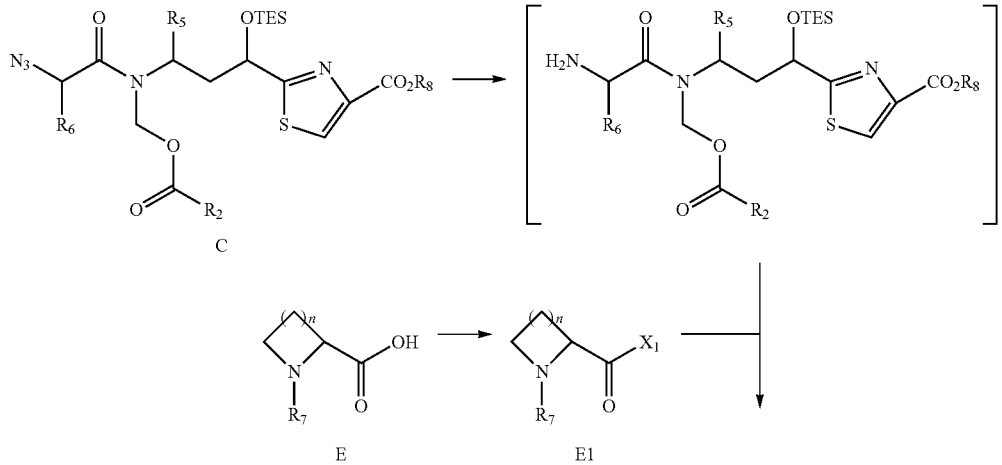

-continued

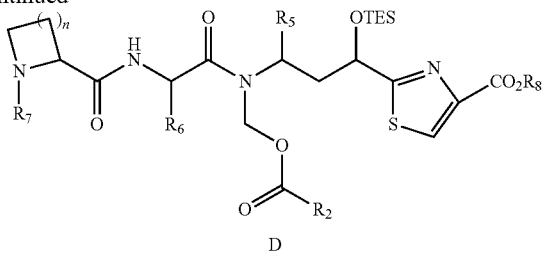

D

In one illustrative example, a mixture of compound 5 and the pentafluorophenyl ester of D-N-methyl-pipecolic acid is reduced using $H_2$ and a palladium-on-charcoal catalyst (Pd/C) to yield compound 6. It has been discovered herein that epimerization of the active ester of pipecolic acid can occur during reaction or during its preparation or during the reduction under the previously reported reaction conditions. For example, contrary to prior reports indicating that epimerization does not occur (see, for example, Peltier, 2006), upon repeating those reported processes on a larger scale it was found here that substantial amounts of epimerized compounds were formed. In addition, it was discovered herein that substantial amounts of rearrangement products formed by the rearrangement of the butyryl group to compound 8a were formed using the reported processes. Finally, it was discovered herein that the typical yields of the desired products using the previously reported processes were only about half of that reported. It has been discovered herein that using diisopropylcarbodiimide (DIC) and short reaction times lessens that amount of both the unwanted by-product resulting from the epimerization reaction and the by-product resulting from the rearrangement reaction. In another alternative of the foregoing embodiments, and each additional embodiment described herein, n is 3. In another alternative of the foregoing embodiments, and each additional embodiment described herein, $R_7$ is methyl.

In one illustrative example, it was found that limiting the reaction time for the preparation of pentafluorophenyl D-N-methyl-pipecolate to about 1 hour lessened the formation of the diastereomeric tripeptide 9a. It has also been discovered that using dry 10% Pd/C as catalyst, rather than a more typically used wet or moist catalyst, lessens the amount of epimer 9 formed during the reduction. It has also been discovered that using dry 10% P/C and/or shorter reaction times also lessens the formation of rearranged amide 8.

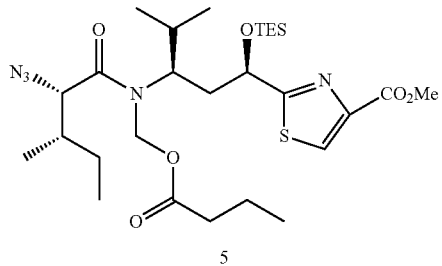

5

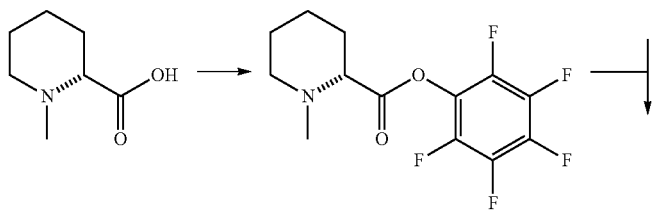

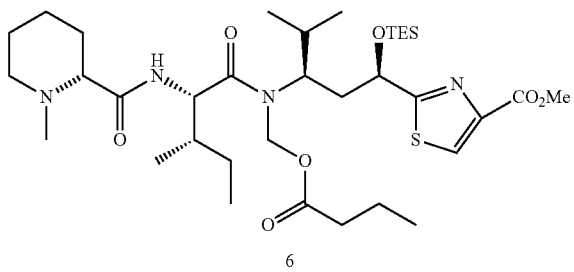

6

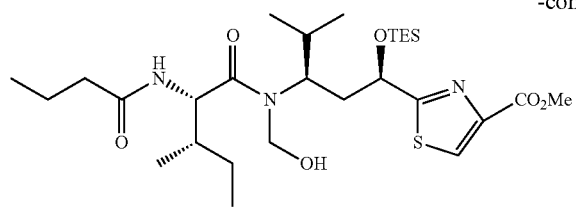

8a

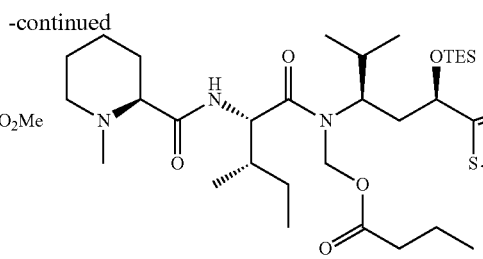

9a

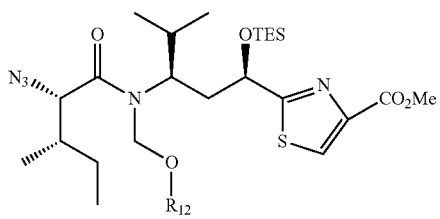

5-e

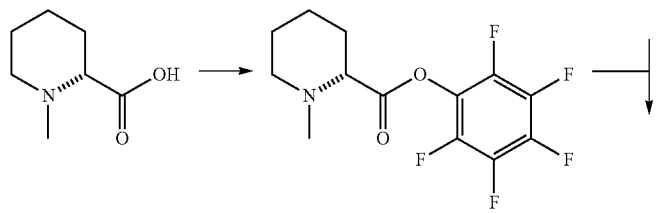

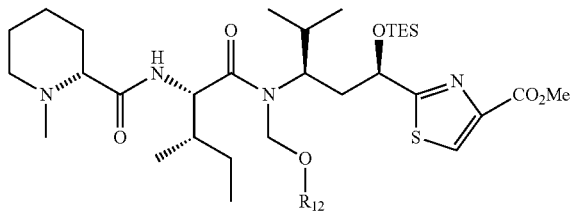

6-e

In another embodiment the ether analogs of 5 and 6 can be used to prepare the tubulysins, tubulysin conjugates, and tubulysin linker compounds described herein. It has been previously reported that removal of the protecting group from the secondary hydroxyl group leads to an inseparable mixture of the desired product 5a and a cyclic O,N-acetal side-product, 5b, as shown in the following scheme.

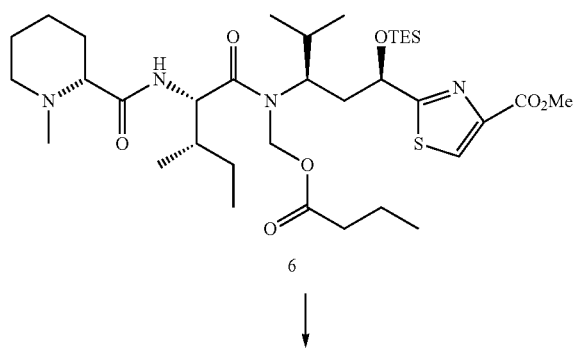

6

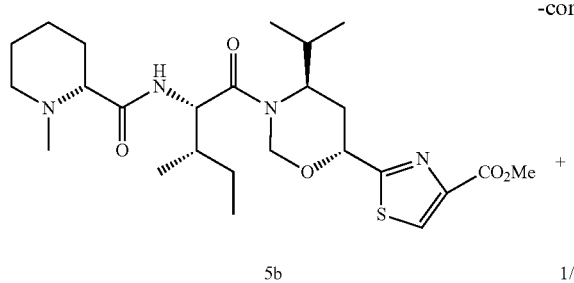

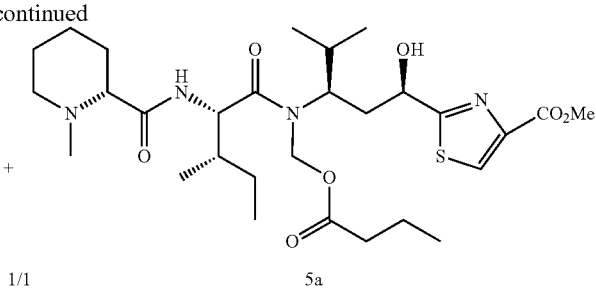

5b          5a

Further, upon repeating the reported process, it has been discovered herein that removal of the methyl ester using basic conditions, followed by acetylation of the hydroxyl group leads to an additional previously unreported side-product, iso-7a. That additional side-product is difficult to detect and difficult to separate from the desired compound 7a. Without being bound by theory, it is believed herein that iso-7a results from rearrangement of the butyrate group from the N-hydroxymethyl group to the secondary hydroxyl group, as shown below.

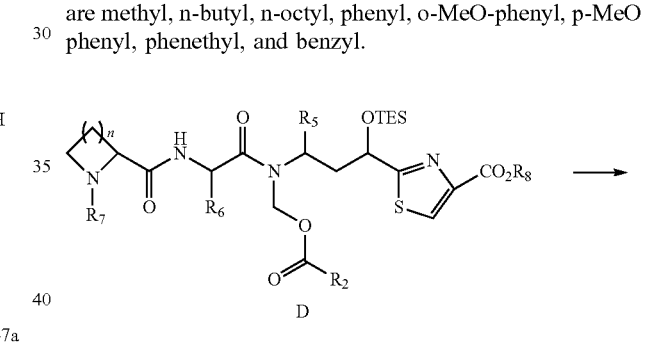

iso-7a

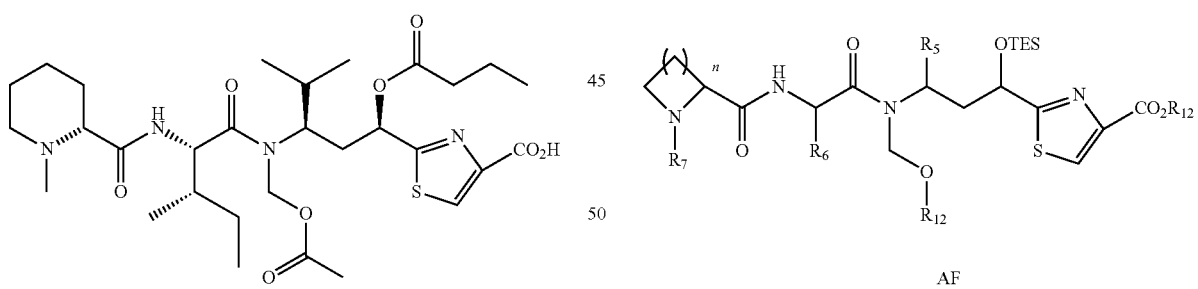

It has been discovered that reordering the two deprotection steps and using different conditions for each deprotection reaction results in improved yields of compounds of formula H, such as compound 7a, after introduction of the $R_4CO$ group on the secondary hydroxyl group, as further described below.

In another embodiment, a process is described for preparing a compound of formula AF, wherein $R_5$ and $R_6$ are as described in the various embodiments herein, such as being selected from optionally substituted alkyl or optionally substituted cycloalkyl; $R_2$ is as described in the various embodiments herein, such as being selected from optionally substituted alkyl or optionally substituted cycloalkyl; and $R_7$ is optionally substituted alkyl; wherein the process comprises the step of contacting compound D with an alcohol, $R_{12}OH$, where $R_{12}$ is alkyl, alkenyl, alkynyl, heteroalkyl, cycloalkyl, heterocycloalkyl, aryl, arylalkyl or heteroarylalkyl, each of which is optionally substituted; and a transesterification catalyst. In one embodiment the transesterification catalyst is trifluoroacetic acid (TFA). In another embodiment, the transesterification catalyst is selected from the group consisting of $(R_{13})_8Sn_4O_2(NCS)_4$, $(R_{13})_2Sn(OAc)_2$, $(R_{13})_2SnO$, $(R_{13})_2SnCl_2$, $(R_{13})_2SnS$, $(R_{13})_3SnOH$, and $(R_{13})_3SnOSn(R_{13})_3$, where $R_{13}$ is independently selected from alkyl, arylalkyl, aryl, or cycloalkyl, each of which is optionally substituted. In another embodiment, the catalyst is $(R_{13})_2SnO$. Illustrative examples of $R_{13}$ are methyl, n-butyl, n-octyl, phenyl, o-MeO-phenyl, p-MeO phenyl, phenethyl, and benzyl.

It is to be understood that $R_5$, $R_6$, $R_{12}$, and $R_7$ may each include conventional protection groups on the optional substituents.

In another embodiment, a process is described for preparing a compound of formula F, wherein $R_5$ and $R_6$ are each independently selected from the group consisting of optionally substituted alkyl and optionally substituted cycloalkyl; $R_2$ is selected from the group consisting of optionally substituted alkyl and optionally substituted cycloalkyl; and $R_7$ is optionally substituted alkyl; wherein the process comprises the step of treating compound D with a hydrolase enzyme.

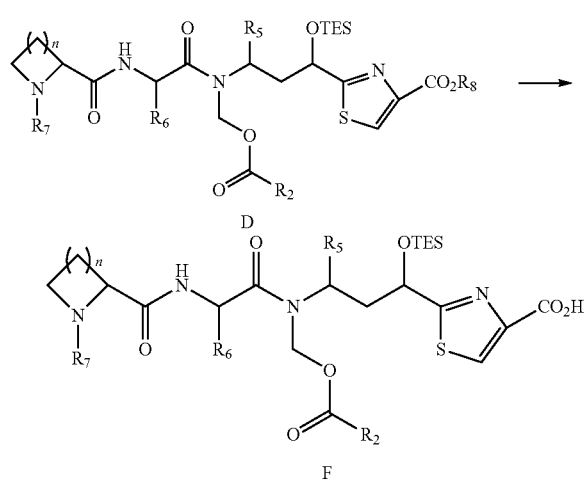

In another embodiment, the preceding process wherein the treating step comprises adding a solution of compound D in a water miscible solvent to a buffered solution containing the hydrolase enzyme at a rate which minimizes precipitation of the ester. In another embodiment the ester is added over a period of from about 24 hours to about 100 hours. In another embodiment the ester is added over a period of from about 48 hours to about 100 hours. In another alternative of the foregoing embodiments, and each additional embodiment described herein, $R_8$ is methyl. In another embodiment, the embodiment of any one of the preceding embodiments wherein the hydrolase enzyme is an esterase is described. In another embodiment, the embodiment of any of the preceding embodiments wherein the esterase is a pig liver esterase is described.

In another embodiment, a process is described for preparing a compound of formula F, wherein $R_5$ and $R_6$ are each independently selected from the group consisting of optionally substituted alkyl and optionally substituted cycloalkyl; $R_2$ is selected from the group consisting of optionally substituted alkyl and optionally substituted cycloalkyl; and $R_7$ is optionally substituted alkyl; wherein the process comprises the step of treating compound D with a trialkyltin hydroxide. In one illustrative embodiment, the trialkyltin hydroxide is trimethyltin hydroxide.

In an illustrative example, a solution of compound 4 in dimethyl sulfoxide (DMSO) is added over a period of 90 hours, to a buffered solution of pig liver esterase. In another illustrative example, the buffer is a phosphate buffer. In another illustrative example, the solution of the enzyme has a pH of 6.5 to 8.5. In another illustrative, example the solution of the enzyme has a pH of 7.4 to 7.8. It is appreciated that the buffering material used can be any buffer compatible with the hydrolase enzyme used to remove the ester.

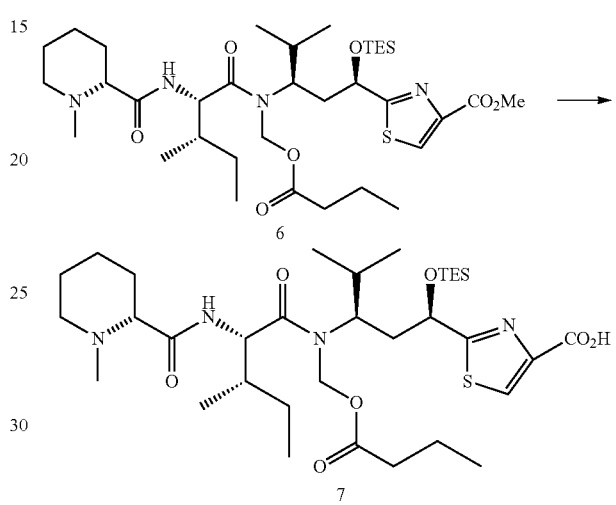

In another illustrative example, a solution of methyl ester 6 and trimethyltin hydroxide in 1,2-dichloroethane was heated to yield acid 7.

Tripeptide methyl ester 6 (reported in an earlier patent application [1]) was treated with trimethyltin hydroxide to yield corresponding acid 7. The triethylsilyl group was removed by treatment with hydrogen fluoride-triethyl amine complex, and acetylated, resulting in acetyl-tripeptide acid 8.

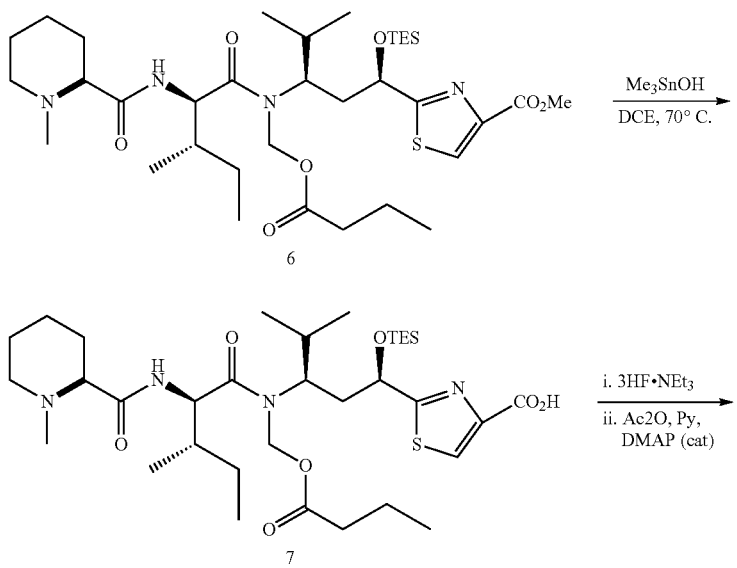

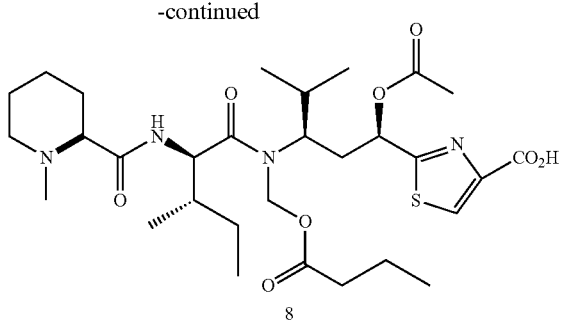

8

In another embodiment, a process is described for preparing a compound of formula G, wherein $R_5$ and $R_6$ are each independently selected from the group consisting of optionally substituted alkyl and optionally substituted cycloalkyl; $R_2$ is selected from the group consisting of optionally substituted alkyl and optionally substituted cycloalkyl; and $R_7$ is optionally substituted alkyl; wherein the process comprises the step of treating the silyl ether of compound F with a non-basic fluoride reagent. It has been discovered herein that use of basic conditions can lead to the production of a by-product arising from the rearrangement of the ester group to give compound G'.

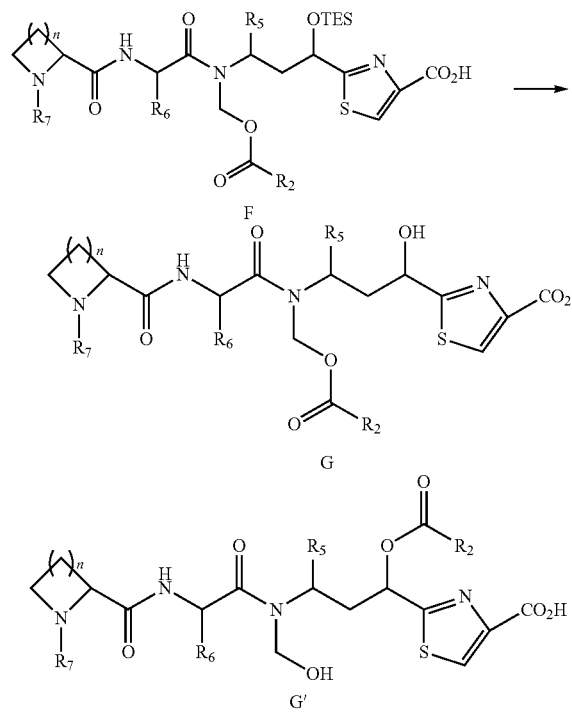

In an illustrative example, compound 7 is treated with $Et_3N.3HF$ to cleave the TES-ether in the preparation of the corresponding alcohol 6'. It is to be understood that other non-basic fluoride reagents to cleave the silyl ether of compounds F may be used in the methods and processes described herein, including but not limited to pyridine.HF, and the like to cleave the TES-ether.

In another embodiment, a process is described for preparing a compound of formula AG, wherein $R_5$ and $R_6$ are as described in the various embodiments herein, such as being selected from optionally substituted alkyl or optionally substituted cycloalkyl; $R_2$ is as described in the various embodiments herein, such as being selected from optionally substituted alkyl or optionally substituted cycloalkyl; and $R_7$ is optionally substituted alkyl; wherein the process comprises the step of contacting compound F with an alcohol, $R_{12}OH$, where $R_{12}$ is alkyl, alkenyl, alkynyl, heteroalkyl, cycloalkyl, heterocycloalkyl, aryl, arylalkyl or heteroarylalkyl, each of which is optionally substituted; and a transesterification catalyst. In one embodiment the transesterification catalyst is trifluoroacetic acid (TFA). In another embodiment, the transesterification catalyst is selected from the group consisting of $(R_{13})_8Sn_4O_2(NCS)_4$, $(R_{13})_2Sn(OAc)_2$, $(R_{13})_2SnO$, $(R_{13})_2SnCl_2$, $(R_{13})_2SnS$, $(R_{13})_3SnOH$, and $(R_{13})_3SnOSn(R_{13})_3$, where $R_{13}$ is independently selected from alkyl, arylalkyl, aryl, or cycloalkyl, each of which is optionally substituted. In another embodiment, the catalyst is $(R_{13})_2SnO$. Illustrative examples of $R_{13}$ are methyl, n-butyl. n-octyl, phenyl, o-MeO-phenyl, p-MeO phenyl, phenethyl, and benzyl.

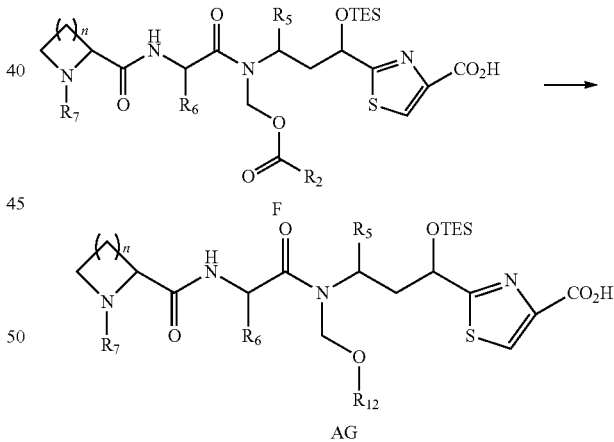

It is to be understood that $R_2$, $R_5$, $R_6$, $R_7$, and $R_{12}$ may each include conventional protection groups on the optional substituents.

In another embodiment, a process is described for preparing a compound of formula BG, wherein $R_5$ and $R_6$ are as described in the various embodiments herein, such as being selected from optionally substituted alkyl or optionally substituted cycloalkyl; $R_2$ is as described in the various embodiments herein, such as being selected from optionally substituted alkyl or optionally substituted cycloalkyl; $R_{12}$ is as described in the various embodiments herein, such as being selected from alkyl, alkenyl, alkynyl, heteroalkyl, cycloalkyl, heterocycloalkyl, aryl, arylalkyl or heteroarylalkyl, each of which is optionally substituted; and $R_7$ is optionally substituted alkyl; wherein the process comprises the step of contacting compound AF with a metal hydroxide or carbonate. Illustrative examples of a metal hydroxide or carbonate include LiOH, $Li_2CO_3$, NaOH, $Na_2CO_3$, KOH, $K_2CO_3$, $Ca(OH)_2$, $CaCO_3$, $Mg(OH)_2$, $MgCO_3$, and the like.

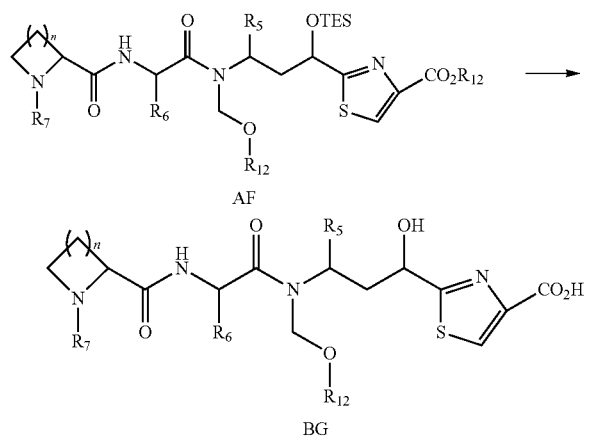

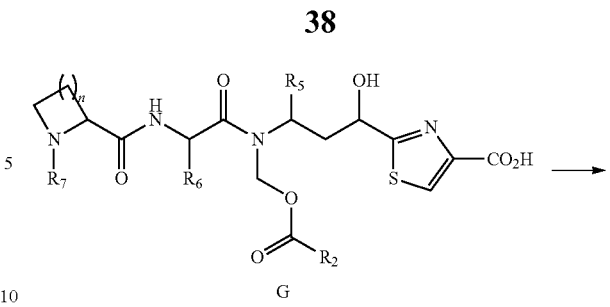

G

It is to be understood that $R_5$, $R_6$, $R_7$, and $R_{12}$ may each include conventional protection groups on the optional substituents.

In another embodiment, a process is described for preparing a compound of formula H, wherein $R_5$ and $R_6$ are each independently selected from the group consisting of optionally substituted alkyl and optionally substituted cycloalkyl; $R_2$ and $R_4$ are independently selected from the group consisting of optionally substituted alkyl and optionally substituted cycloalkyl; and $R_7$ is optionally substituted alkyl; wherein the process comprises the step of treating a compound of formula G with an acylating agent of formula $R_4C(O)X_2$, where $X_2$ is a leaving group. It is appreciated that the resulting product may contain varying amounts of the mixed anhydride of compound H and $R_4CO_2H$. In another embodiment, the process described in the preceding embodiment further comprises the step of treating the reaction product with water to prepare H, free of or substantially free of anhydride. In another embodiment, the process of the preceding embodiments wherein $X_2$ is $R_4CO_2$, is described. In another embodiment, the process of any one of the preceding embodiments wherein $R_4$ is C1-C4 alkyl is described. In another alternative of the foregoing embodiments, and each additional embodiment described herein, $R_4$ is methyl. In another embodiment, the process of any one of the preceding embodiments wherein $R_6$ is sec-butyl is described. In another embodiment, the process of any one of the preceding embodiments wherein $R_7$ is methyl is described. In another embodiment, the process of any one of the preceding embodiments wherein $R_5$ is iso-propyl is described.

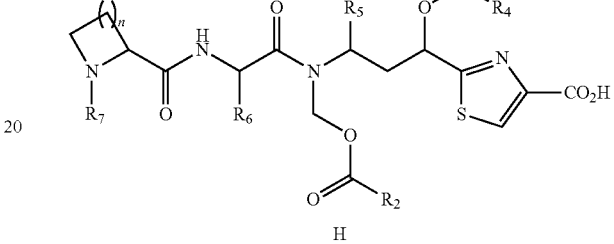

H

In an illustrative example, compound 6' is treated with acetic anhydride in pyridine. It has been discovered herein that shortening the time for this step of the process improves the yield of compound H by limiting the amount of the previously undescribed alternative acylation side products, such as formula 7a that are formed. It is appreciated that the resulting product may contain varying amounts of the mixed anhydride of 8 and acetic acid. In another embodiment, treatment of the reaction product resulting from the preceding step with water in dioxane yields compound 8, free of or substantially free of anhydride. It is to be understood that other solvents can be substituted for dioxane in the hydrolysis of the intermediate mixed anhydride. Alternatively, the step may be performed without solvent.

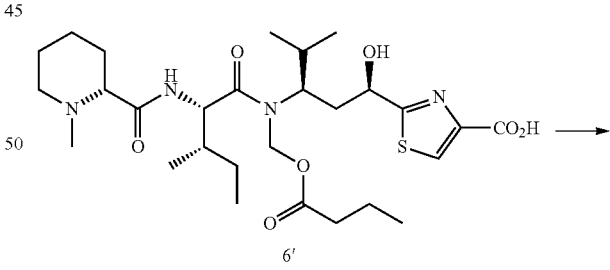

6'

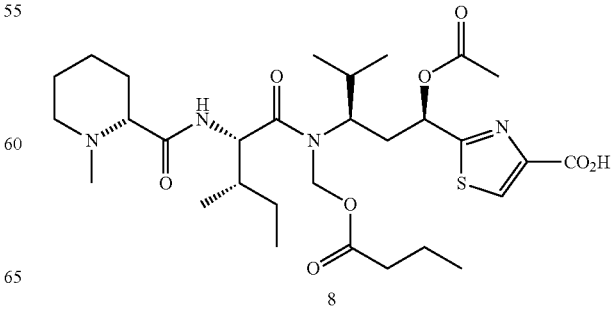

8

-continued

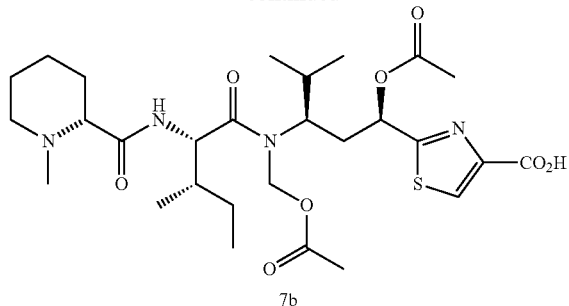

7b

In another embodiment, a process is described for preparing a compound of formula AH, wherein $R_5$ and $R_6$ are as described in the various embodiments herein, such as being selected from optionally substituted alkyl or option- -continued

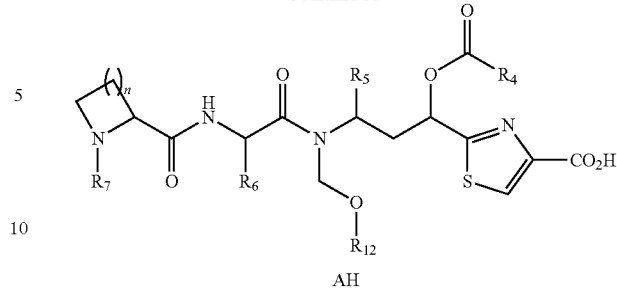

AH

It is to be understood that $R_4$, $R_5$, $R_6$, and $R_7$ may each include conventional protection groups on the optional substituents.

In another embodiment, a process for preparing compound I is described.

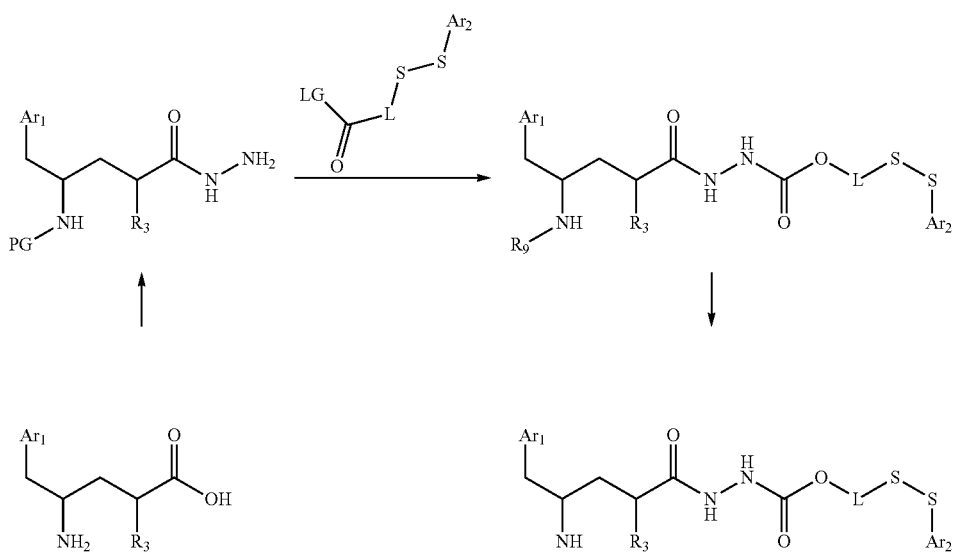

ally substituted cycloalkyl; $R_2$ and $R_4$ are as described in the various embodiments herein, such as being selected from optionally substituted alkyl or optionally substituted cycloalkyl; $R_{12}$ is as described in the various embodiments herein, such as being selected from alkyl, alkenyl, alkynyl, heteroalkyl, cycloalkyl, heterocycloalkyl, aryl, arylalkyl or heteroarylalkyl, each of which is optionally substituted; and $R_7$ is optionally substituted alkyl; wherein the process comprises the step of treating a compound of formula BG with an acylating agent of formula $R_4C(O)X_2$, where $X_2$ is a leaving group.

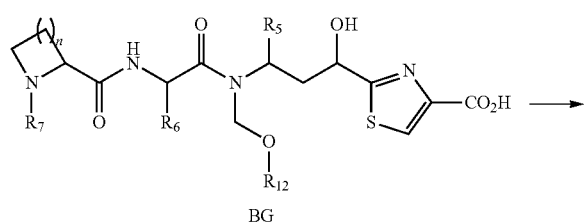

BG where PG is a protecting group, LG is a leaving group, and $Ar_1$, $Ar_2$, L, and $R_3$ are as described in any of the embodiments described herein.

In one illustrative example, mixed carbonate 11 was prepared from 4-nitropyridyldisulfide ethanol 12 and 4-nitrophenyl chloroformate as shown. Boc-Tut-hydrazide 13 was prepared from corresponding acid 10 and coupled with mixed carbonate 11 to yield activated Boc-Tut fragment 14.

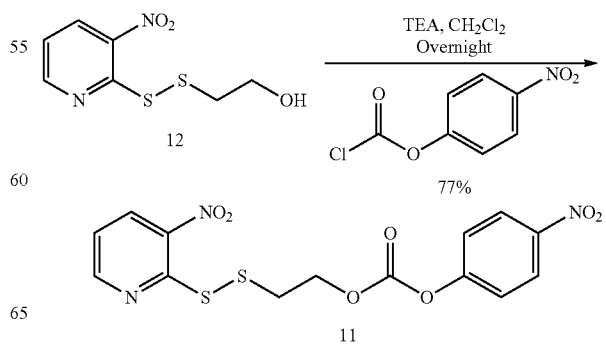

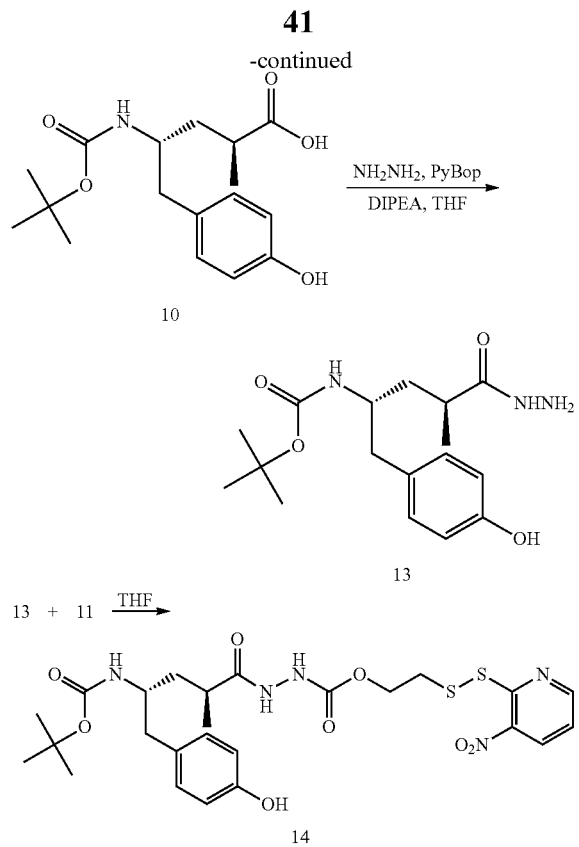

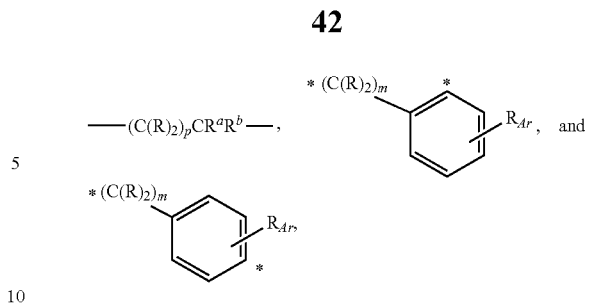

where p is an integer from about 1 to about 3, m is an integer from about 1 to about 4, and * indicates the points of attachment;

$R^a$, $R^b$, and R are each independently selected in each instance from the group consisting of hydrogen and alkyl; or any two of $R^a$, $R^b$, and R are taken together with the attached carbon atom(s) to form a carbocyclic ring;

$R_{Ar}$ represents 0 to 4 substituents selected from the group consisting of amino, or derivatives thereof, hydroxy or derivatives thereof, halo, thio or derivatives thereof, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof;

$R_5$ and $R_6$ are each independently selected from the group consisting of optionally substituted alkyl and optionally substituted cycloalkyl; $R_3$ is optionally substituted alkyl; $R_2$ and $R_4$ are independently selected from the group consisting of optionally substituted alkyl and optionally substituted cycloalkyl; and $R_7$ is optionally substituted alkyl;

wherein the process comprises the steps of c) forming an active ester intermediate from a compound of formula H; and d) reacting the active ester intermediate with a compound of the formula I.

In another embodiment, a process is described for preparing a tubulysin linker derivative T, wherein $Ar_1$ is optionally substituted aryl; $Ar_2$ is optionally substituted aryl or optionally substituted heteroaryl; L is selected from the group consisting of

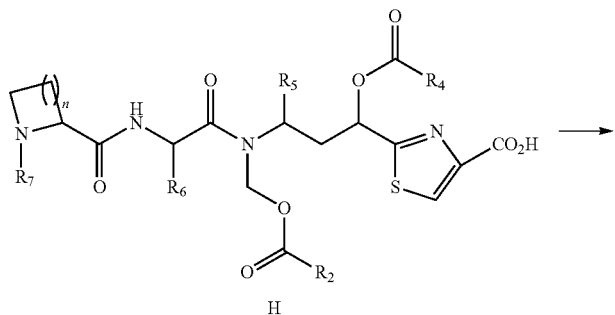

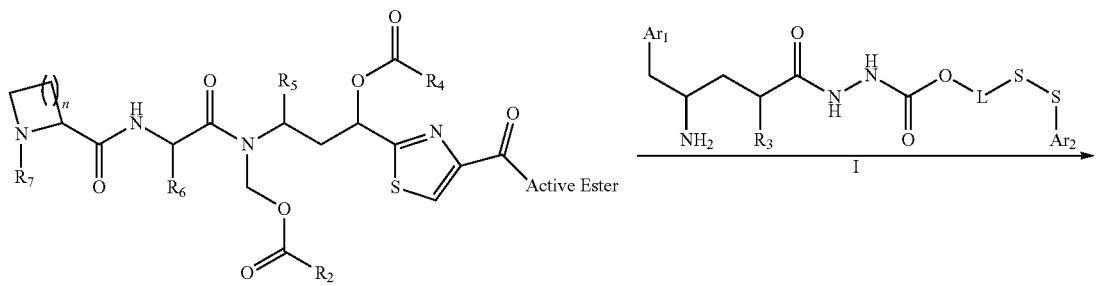

-continued

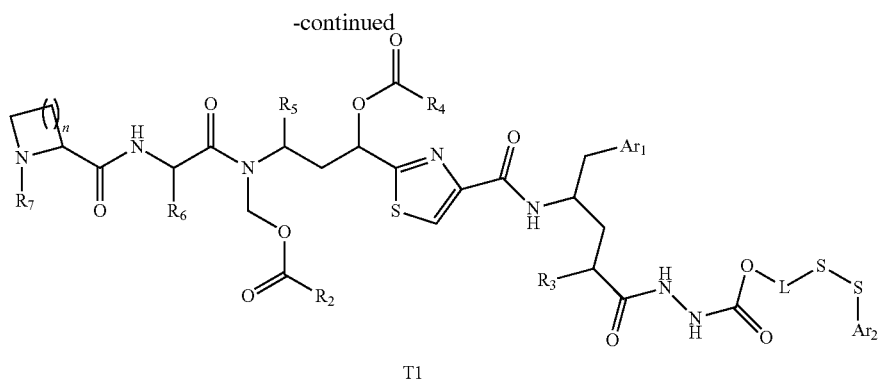

T1

In one embodiment, compound H is treated with an excess amount of active ester forming agent and pentafluorophenol to form the pentafluorophenol ester of compound H, followed by removal of the excess active ester forming agent prior to the addition of compound I. In another alternative of the foregoing embodiments, and each additional embodiment described herein, $Ar_1$ is phenyl. In another alternative of the foregoing embodiments, and each additional embodiment described herein, $Ar_1$ is substituted phenyl. In another alternative of the foregoing embodiments, and each additional embodiment described herein, $Ar_1$ is 4-substituted phenyl. In another alternative of the foregoing embodiments, and each additional embodiment described herein, $Ar_1$ is $R_4$-substituted phenyl. In another alternative of the foregoing embodiments, and each additional embodiment described herein, $Ar_1$ is 4-hydroxyphenyl, or a hydroxyl protected form thereof. In another alternative of the foregoing embodiments, and each additional embodiment described herein, $Ar_2$ is substituted pyridyl. In another alternative of the foregoing embodiments, and each additional embodiment described herein, $Ar_2$ is substituted 2-pyridyl. In another alternative of the foregoing embodiments, and each additional embodiment described herein, $Ar_2$ is 3-nitro-2-pyridyl. In another alternative of the foregoing embodiments, and each additional embodiment described herein, $R_3$ is methyl.

In an illustrative example, compound 8 is treated with an excess amount of a polymeric version of a carbodiimide and pentafluorophenol to form the pentafluorophenyl ester of 8, the polymeric carbodiimide is removed by filtration; and compound 9 is added to the solution to yield tubulysin B linker derivative 2. In another embodiment, the process of any one of the preceding embodiments wherein the polymeric carbodiimide is polystyrene-$CH_2$—N=C=N-cyclohexane (PS-DCC) is described.

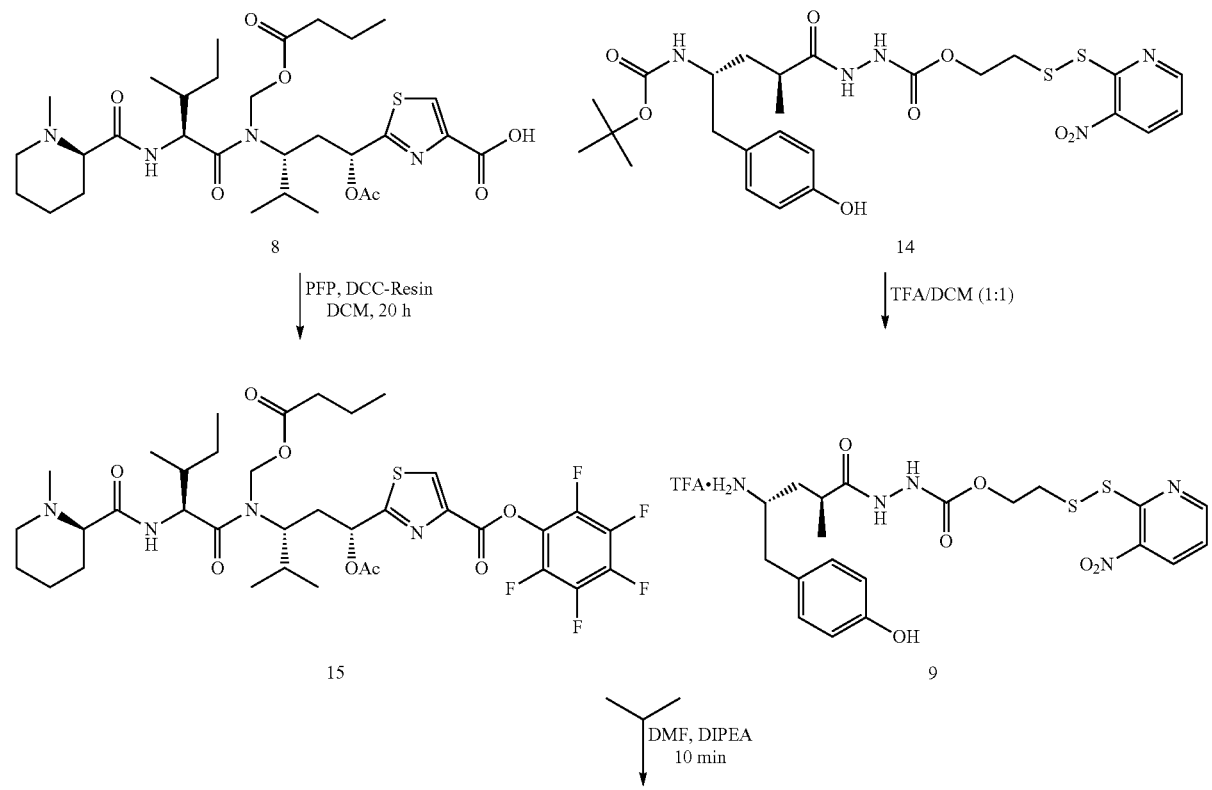

-continued
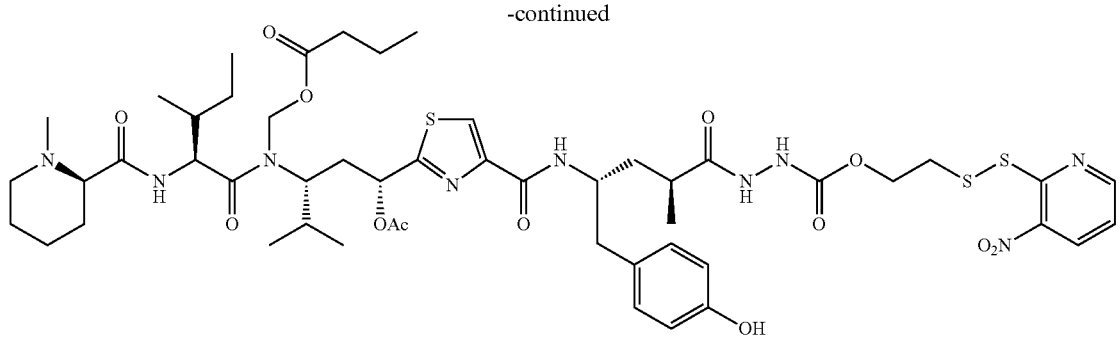
2
In another embodiment, the ether analog of compound 8 can be converted to the ether analog of compound 2, via the ether analog of compound 15, where R is allyl, or $CH_2(CH_2)_nCH_3$, and n is 1, 2, 3, 4, 5, or 6.
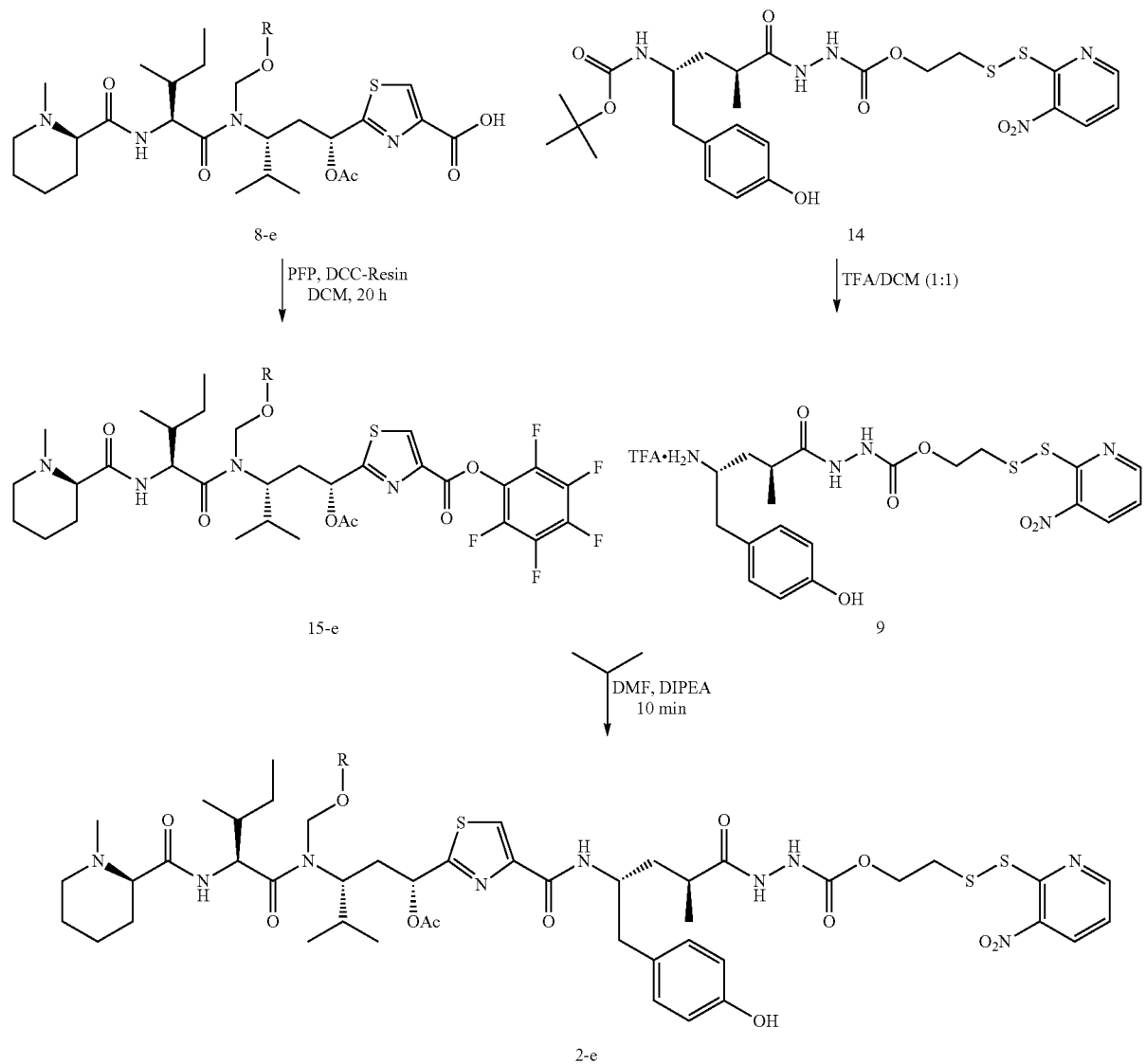

In another embodiment, a process is described for preparing a tubulysin linker derivative of formula (T2), wherein Ar₁ is optionally substituted aryl; Ar₂ is optionally substituted aryl or optionally substituted heteroaryl; L is selected from the group consisting of

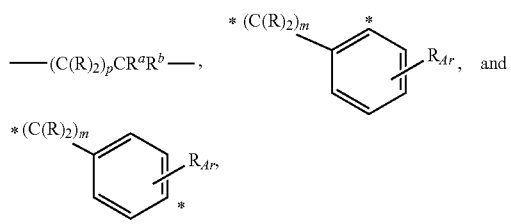

where p is an integer from about 1 to about 3, m is an integer from about 1 to about 4, and * indicates the points of attachment;

Ra, Rb, and R are each independently selected in each instance from the group consisting of hydrogen and alkyl; or any two of $R^a$, $R^b$, and R are taken together with the attached carbon atom(s) to form a carbocyclic ring;

$R_{Ar}$ represents 0 to 4 substituents selected from the group consisting of amino, or derivatives thereof, hydroxy or derivatives thereof, halo, thio or derivatives thereof, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof;

$R_1$ is hydrogen, optionally substituted alkyl, optionally substituted arylalkyl or a pro-drug forming group; $R_5$ and $R_6$ are as described in the various embodiments herein, such as being selected from optionally substituted alkyl or optionally substituted cycloalkyl; $R_3$ is optionally substituted alkyl; $R_2$ and $R_4$ are as described in the various embodiments herein, such as being selected from optionally substituted alkyl or optionally substituted cycloalkyl; and $R_7$ is optionally substituted alkyl;

wherein the process comprises the step of contacting compound T, with an alcohol, $R_{12}OH$, where $R_{12}$ is alkyl, alkenyl, alkynyl, heteroalkyl, cycloalkyl, heterocycloalkyl, aryl, arylalkyl or heteroarylalkyl, each of which is optionally substituted; and a transesterification catalyst.

In one embodiment the transesterification catalyst is trifluoroacetic acid (TFA). In another embodiment, the transesterification catalyst is selected from the group consisting of $(R_{13})_8Sn_4O_2(NCS)_4$, $(R_{13})_2Sn(OAc)_2$, $(R_{13})_2SnO$, $(R_{13})_2SnCl_2$, $(R_{13})_2SnS$, $(R_{13})_3SnOH$, and $(R_{13})_3SnOSn(R_{13})_3$, where $R_{13}$ is independently selected from alkyl, arylalkyl, aryl, or cycloalkyl, each of which is optionally substituted. In another embodiment, the catalyst is $(R_{13})_2SnO$. Illustrative examples of $R_{13}$ are methyl, n-butyl, n-octyl, phenyl, o-MeO-phenyl, p-MeO-phenyl, phenethyl, and benzyl. It is to be understood that $Ar_1$, $Ar_2$, $R_1$, $R_2$, $R_4$, $R_5$, $R_6$, $R_7$, and $R_{12}$ may each include conventional protection groups on the optional substituents.

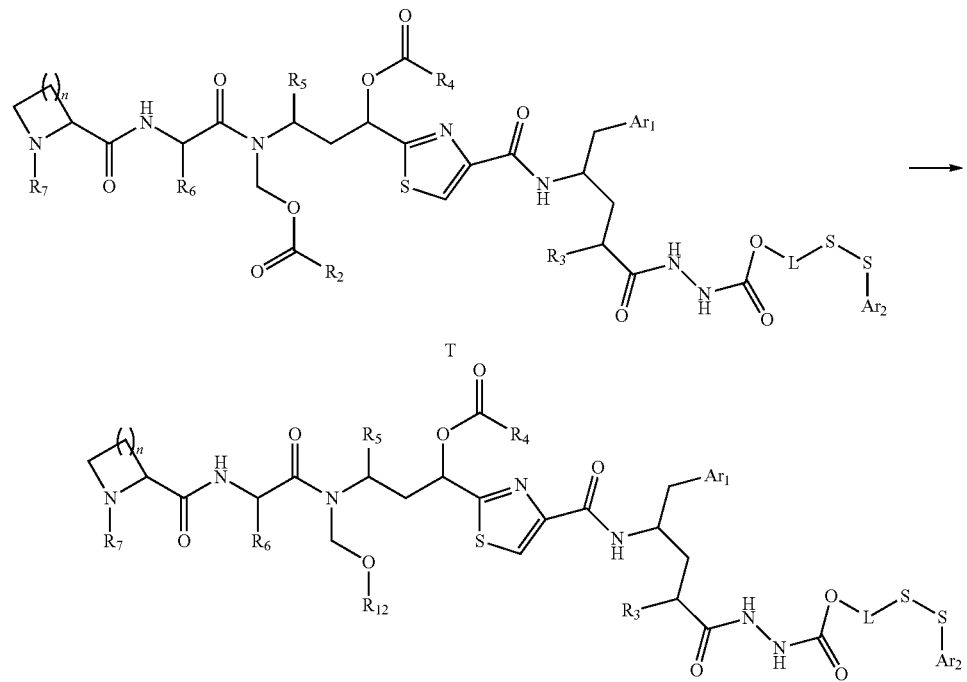

In another embodiment, a process is described for preparing a tubulysin linker derivative of formula (T2), wherein Ar₁ is optionally substituted aryl; Ar₂ is optionally substituted heteroaryl; L is selected from the group consisting of

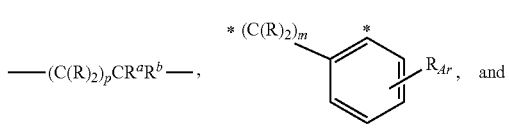

-continued

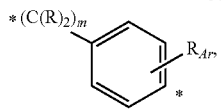

where p is an integer from about 1 to about 3, m is an integer from about 1 to about 4, and * indicates the points of attachment;

$R_1$ is hydrogen, optionally substituted alkyl, optionally substituted arylalkyl or a pro-drug forming group; $R_5$ and $R_6$ are as described in the various embodiments herein, such as being selected from optionally substituted alkyl or optionally substituted cycloalkyl; $R_3$ is optionally substituted alkyl; $R_2$ and $R_4$ are as described in the various embodiments herein, such as being selected from optionally substituted alkyl or optionally substituted cycloalkyl; and $R_7$ is optionally substituted alkyl;

wherein the process comprises the step of forming an active ester intermediate from a compound of formula AH; and reacting the active ester intermediate with a compound of the formula I to give a compound of the formula T2.

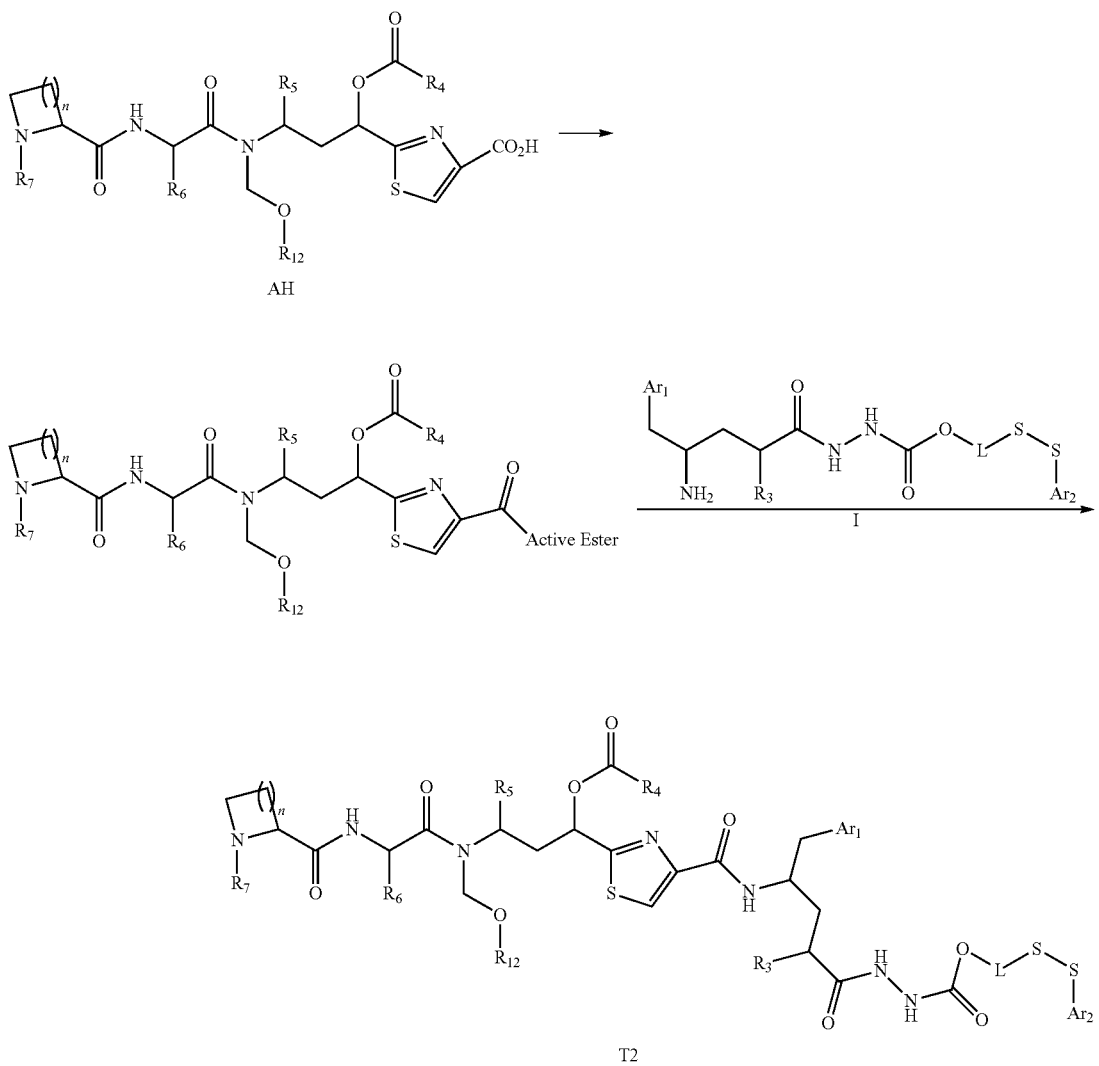

Ra, Rb, and R are each independently selected in each instance from the group consisting of hydrogen and alkyl; or any two of $R^a$, $R^b$, and R are taken together with the attached carbon atom(s) to form a carbocyclic ring;

$R_{Ar}$ represents 0 to 4 substituents selected from the group consisting of amino, or derivatives thereof, hydroxy or derivatives thereof, halo, thio or derivatives thereof, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof;

It is to be understood that $Ar_1$, $Ar_2$, $R_1$, $R_{12}$, $R_3$, $R_4$, $R_5$, $R_6$, and $R_7$ may each include conventional protection groups on the optional substituents.

In another embodiment, a compound having formula D, wherein the compound is free of or substantially free of a compound having formula C-1 is described, where in $R_2$, $R_5$, $R_6$, $R_7$, and $R_8$ are as described in any of the embodiments described herein. Without being bound by theory, it is believed herein that compounds C-1 are formed from the corresponding compounds C via an acyl transfer.

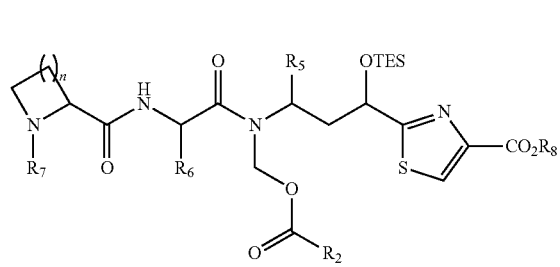

D

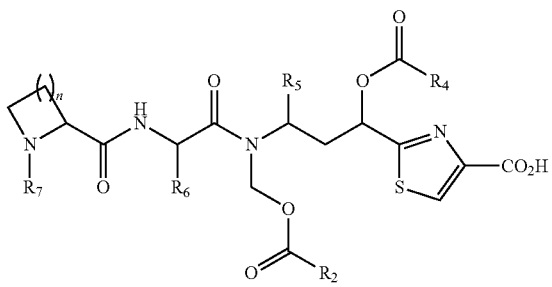

H

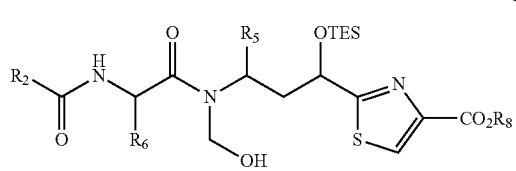

C-1

In another embodiment, compound 4, free of or substantially free of compound 8a and/or compound iso-6 is described. In another embodiment, an optically pure form of compound 6 is formed.

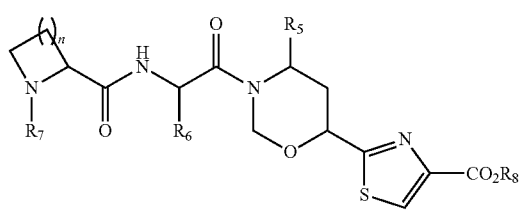

Oxazine-2

In another embodiment, a compound F is described wherein $R_2$, $R_5$, $R_6$, $R_7$ and $R_8$ are as described in the any of the embodiments described herein.

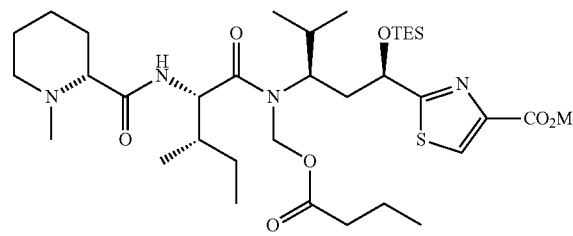

6

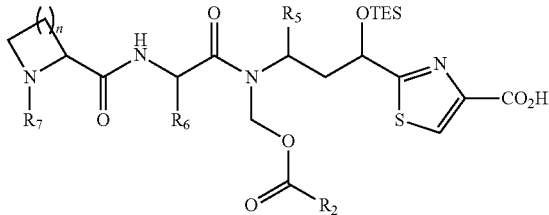

F

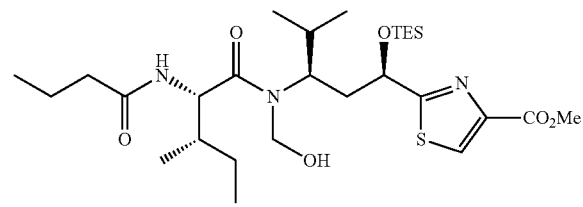

8a

In another embodiment, the compound having formula 7 is described.

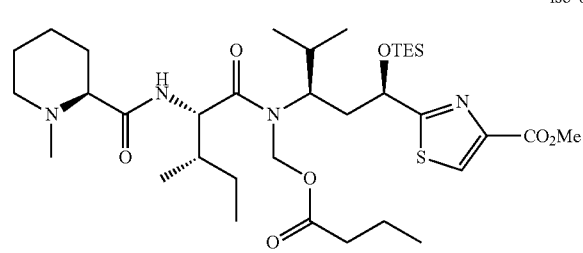

iso-6

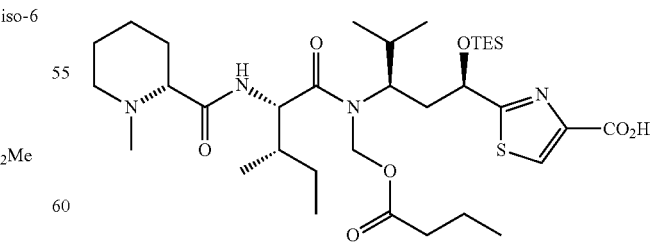

7

In another embodiment, a compound H, wherein the compound H is free of or substantially free, of a compound having the formula Oxazine-2 is described.

In another embodiment a compound G, where the compound is free of or substantially free of a compound G' is described, wherein $R_2$, $R_5$, $R_6$, and $R_7$ are as described in any of the embodiments described herein.

G

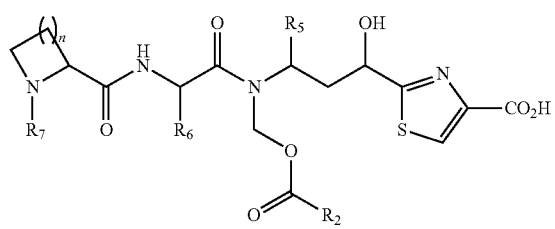

G'

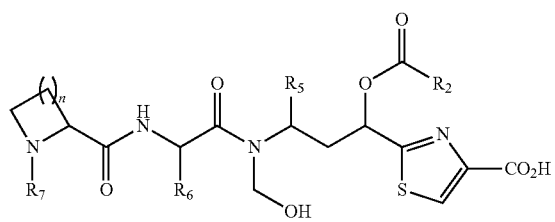

In another embodiment, compound 6' is described, wherein compound 6' is free of or substantially free of the isomer of G' shown below

6'

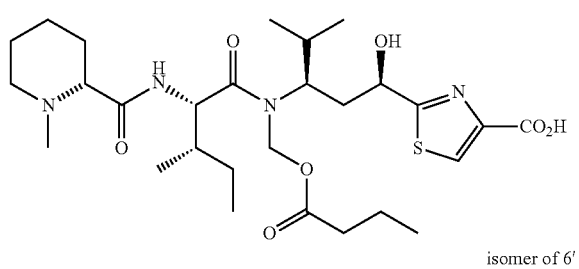

isomer of 6'

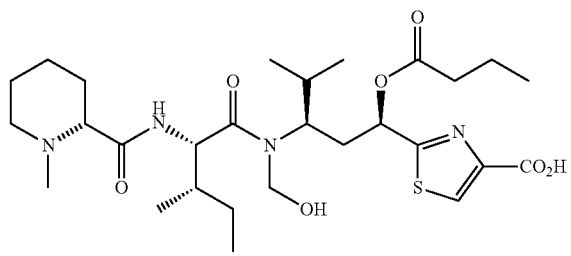

In another embodiment, compound 8 is described, wherein compound 8 is free of or substantially free of compound 8b is described

8

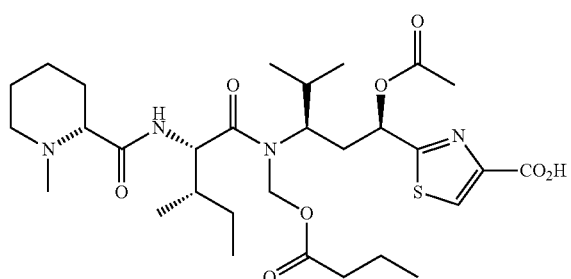

8b

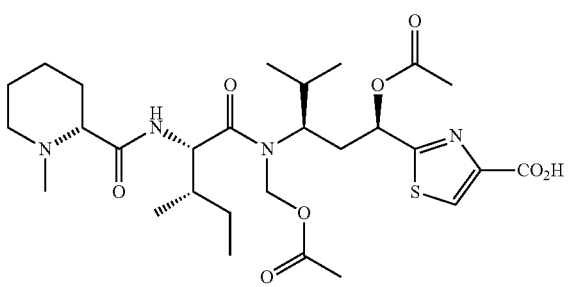

In another embodiment, a compound I is described wherein $Ar_1$, $Ar_2$, $R_3$ and L are as described in any of the embodiments described herein.

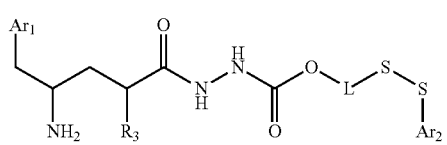

In another alternative of the foregoing embodiments, and each additional embodiment described herein, L is

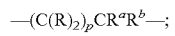

—$(C(R)_2)_p CR^a R^b$—;

where p is an integer from about 1 to about 3, m is an integer from about 1 to about 4, ** indicates the attachment point to the carbonyl group, and * indicates the point of attachment to $SAr_2$; $R^a$, $R^b$, and R are each independently selected from the group consisting of hydrogen and alkyl; or any two of $R^a$, $R^b$, and R are taken together with the attached carbon atom(s) to form a carbocyclic ring. In another embodiment of each of the embodiments described herein, $R^a$ and $R^b$ are hydrogen. In another embodiment of each of the embodiments described p is 1. In another embodiment of the foregoing embodiments and each additional embodiment described herein $R^a$ and $R^b$ are hydrogen and p is 1.

In another embodiment, a compound H is described wherein $R_4$ is Me and $R_2$, $R_5$, $R_6$, and $R_7$ are as described in any of the embodiments described herein; and the compound H is free of or substantially free of the compound H wherein $R_4$ and $R_2$ are both Me.

H

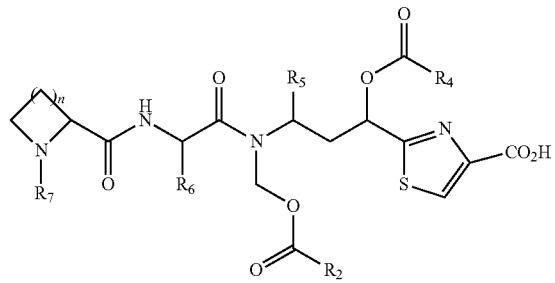

In another alternative of the foregoing embodiments, and each additional embodiment described herein, $R_5$ is isopropyl.

In another alternative of the foregoing embodiments, and each additional embodiment described herein, $R_6$ is sec-butyl.

In another alternative of the foregoing embodiments, and each additional embodiment described herein, $R_8$ is methyl.

In another alternative of the foregoing embodiments, and each additional embodiment described herein, $R_2$ is $CH_2CH(CH_3)_2$, $CH_2CH_2CH_3$, $CH_2CH_3$, $CH=C(CH_3)_2$, or $CH_3$.

In another alternative of the foregoing embodiments, and each additional embodiment described herein, n is 3.

In another alternative of the foregoing embodiments, and each additional embodiment described herein, $R_7$ is methyl.

In another alternative of the foregoing embodiments, and each additional embodiment described herein, $R_8$ is methyl.

In another alternative of the foregoing embodiments, and each additional embodiment described herein, $R_4$ is methyl.

In another alternative of the foregoing embodiments, and each additional embodiment described herein, $Ar_1$ is phenyl. In another alternative of the foregoing embodiments, and each additional embodiment described herein, $Ar_1$ is substituted phenyl. In another alternative of the foregoing embodiments, and each additional embodiment described herein, $Ar_1$ is 4-substituted phenyl. In another alternative of the foregoing embodiments, and each additional embodiment described herein, $Ar_1$ is $R_4$-substituted phenyl. In another alternative of the foregoing embodiments, and each additional embodiment described herein, $Ar_1$ is 4-hydroxyphenyl, or a hydroxyl protected form thereof.

In another alternative of the foregoing embodiments, and each additional embodiment described herein, $R_3$ is methyl.

Illustrative embodiments of the invention are further described by the following enumerated clauses:

1. A process for preparing a compound of the formula

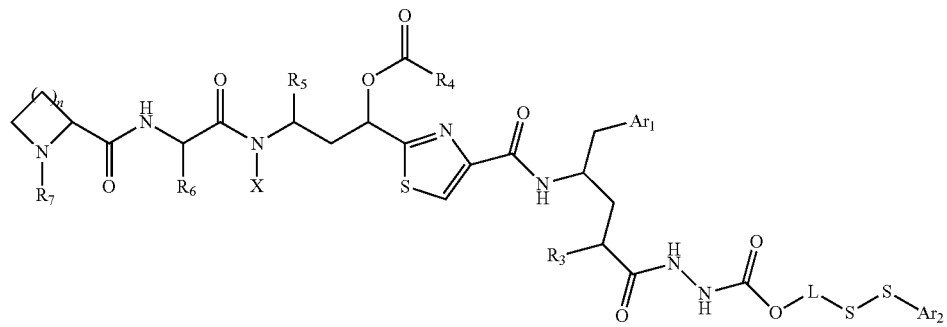

or a salt or solvate thereof; wherein $Ar_1$ is optionally substituted aryl or optionally substituted heteroaryl;

$Ar_2$ is optionally substituted aryl or optionally substituted heteroaryl;

L is selected from the group consisting of

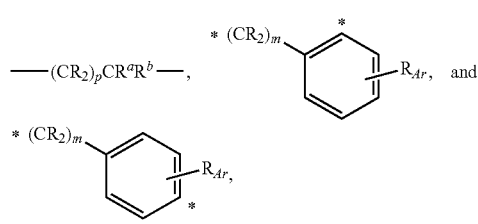

where p is an integer from about 1 to about 3, m is an integer from about 1 to about 4, and * indicates the points of attachment;

$R^a$, $R^b$, and R are each independently selected in each instance from the group consisting of hydrogen and alkyl; or any two of $R^a$, $R^b$, and R are taken together with the attached carbon atom(s) to form a carbocyclic ring;

$R_{Ar}$ represents 0 to 4 substituents selected from the group consisting of amino, or derivatives thereof, hydroxy or derivatives thereof, halo, thio or derivatives thereof, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof;

X is hydrogen; or X is alkyl or alkenyl, each of which is optionally substituted; or X is $R^{16}C(O)CH(R^{17})CH_2$; where $R^{17}$ is $C(O)R^{16}$, $C(O)OR^{16}$, or CN; where $R^{16}$ is independently in each instance alkyl, alkenyl, cycloalkyl, cycloalkenyl, heteroaryl, arylalkyl, or heteroarylalkyl, each of which is optionally substituted; or X is $CH_2QR^{18}$; where Q is N, O, or S; and $R^{18}$ is alkyl, alkenyl, cycloalkyl, cycloalkenyl, aryl, arylalkyl, heteroaryl, or heteroarylalkyl, each of which is optionally substituted, or $R^{18}$ is acyl, sulfonyl, or phosphonic acid or a derivative thereof;

$R_3$ is optionally substituted alkyl;

$R_4$ is optionally substituted alkyl or optionally substituted cycloalkyl;

$R_5$ and $R_6$ are each independently selected from the group consisting of optionally substituted alkyl and optionally substituted cycloalkyl;

$R_7$ is optionally substituted alkyl;

$R_{12}$ is alkyl, alkenyl, alkynyl, heteroalkyl, cycloalkyl, heterocycloalkyl, aryl, arylalkyl or heteroarylalkyl, each of which is optionally substituted;

and n is 1, 2, 3, or 4;

wherein the process comprises the step of treating a compound of formula A with triethylsilyl chloride and imidazole in an aprotic solvent, where $R_8$ is C1-C6 unbranched alkyl or the step of treating a compound of formula B with a base and a compound of the formula $ClCH_2C(O)R_2$ in an aprotic solvent at a temperature from about −78° C. to about 0° C.; wherein the molar ratio of the compound of the formula $ClCH_2C(O)R_2$ to the compound of formula B from about 1 to about 1.5, where $R_8$ is C1-C6 unbranched alkyl

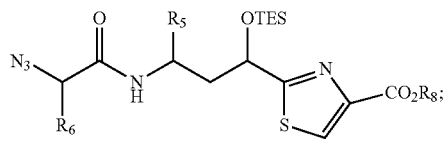
B or the steps of a) preparing a compound of formula (E1) from a compound of formula (E), where $X_1$ is a leaving group

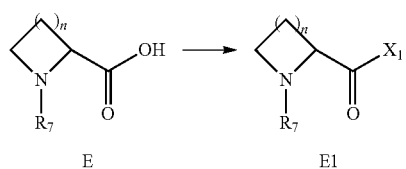

and b) treating a compound of formula XC under reducing conditions in the presence of the compound of formula E1, where $R_8$ is C1-C6 unbranched alkyl

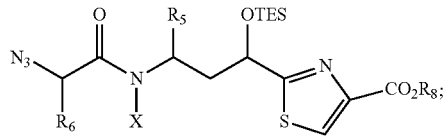
XC or the step of treating compound of formula XD with a hydrolase enzyme or with a trialkyltin hydroxide, where $R_8$ is C1-C6 unbranched alkyl

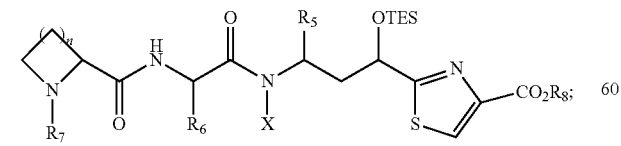
XD or the step of treating a compound of formula XF with a non-basic fluoride reagent

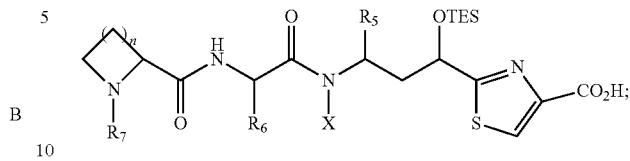
XF or the step of treating a compound of formula XG with an acylating agent of formula $R_4C(O)X_2$, where $X_2$ is a leaving group

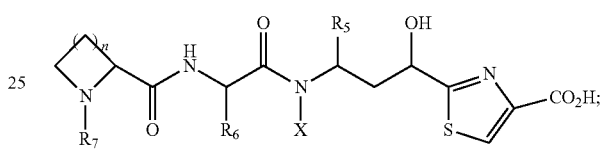
XG or the steps of c) forming an active ester intermediate from a compound of formula XH

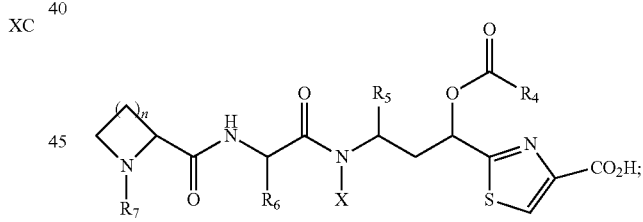
XH and d) reacting the active ester intermediate with a compound of the formula I

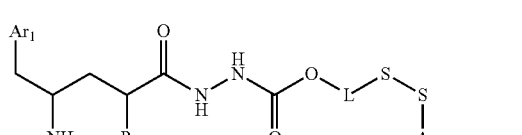
I or combinations thereof.

1A. A process for preparing a compound of the formula

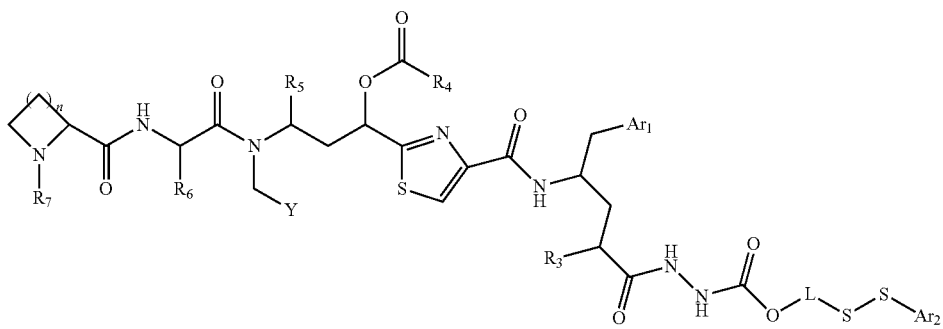

or a salt or solvate thereof; wherein $Ar_1$ is optionally substituted aryl or optionally substituted heteroaryl;

$Ar_2$ is optionally substituted aryl or optionally substituted heteroaryl;

L is selected from the group consisting of

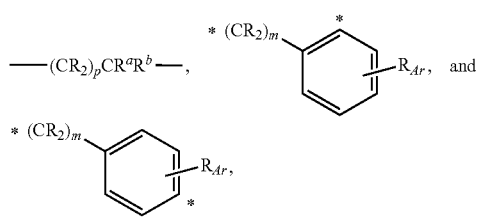

where p is an integer from about 1 to about 3, m is an integer from about 1 to about 4, and * indicates the points of attachment;

$R^a$, $R^b$, and R are each independently selected in each instance from the group consisting of hydrogen and alkyl; or any two of $R^a$, $R^b$, and R are taken together with the attached carbon atom(s) to form a carbocyclic ring;

$R_{Ar}$ represents 0 to 4 substituents selected from the group consisting of amino, or derivatives thereof, hydroxy or derivatives thereof, halo, thio or derivatives thereof, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof;

Y is acyloxy or $R_{12}O$;

$R_3$ is optionally substituted alkyl;

$R_4$ is optionally substituted alkyl or optionally substituted cycloalkyl;

$R_5$ and $R_6$ are each independently selected from the group consisting of optionally substituted alkyl and optionally substituted cycloalkyl;

$R_7$ is optionally substituted alkyl;

$R_{12}$ is alkyl, alkenyl, alkynyl, heteroalkyl, cycloalkyl, heterocycloalkyl, aryl, arylalkyl or heteroarylalkyl, each of which is optionally substituted;

and n is 1, 2, 3, or 4;

wherein the process comprises the step of treating a compound of formula A with triethylsilyl chloride and imidazole in an aprotic solvent, where $R_8$ is C1-C6 unbranched alkyl

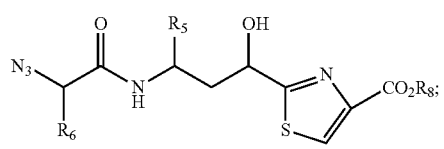

or the step of treating a compound of formula B with a base and a compound of the formula $ClCH_2C(O)R_2$ in an aprotic solvent at a temperature from about −78° C. to about 0° C.; wherein the molar ratio of the compound of the formula $ClCH_2C(O)R_2$ to the compound of formula B from about 1 to about 1.5, where $R_8$ is C1-C6 unbranched alkyl

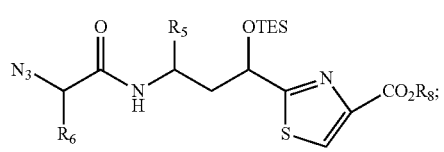

or the steps of a) preparing a compound of formula (E1) from a compound of formula (E), where $X_1$ is a leaving group

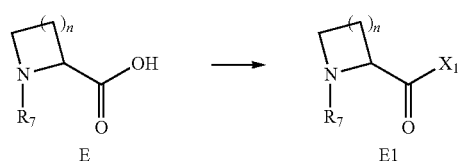

and b) treating a compound of formula C under reducing conditions in the presence of the compound of formula E1, where $R_8$ is C1-C6 unbranched alkyl

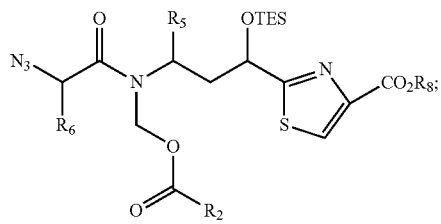

C or the step of treating compound of formula D with a hydrolase enzyme or with a trialkyltin hydroxide, where $R_8$ is C1-C6 unbranched alkyl

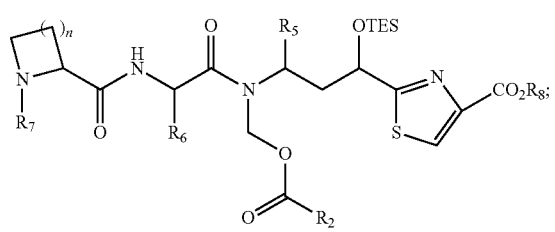

D or the step of treating a compound of formula F1 with a non-basic fluoride reagent

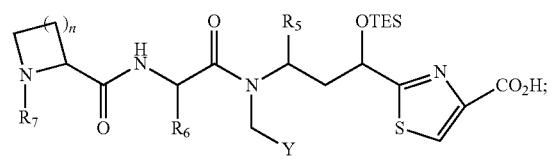

F1 the step of treating a compound of formula G1 with an acylating agent of formula $R_4C(O)X_2$, where $X_2$ is a leaving group

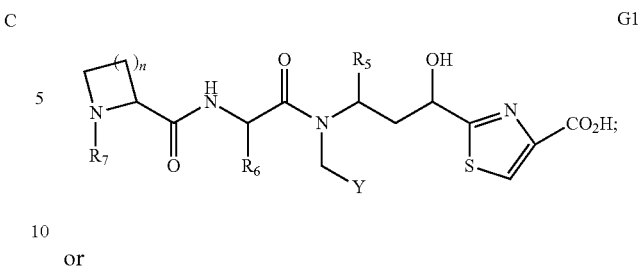

G1 or the steps of c) forming an active ester intermediate from a compound of formula H1

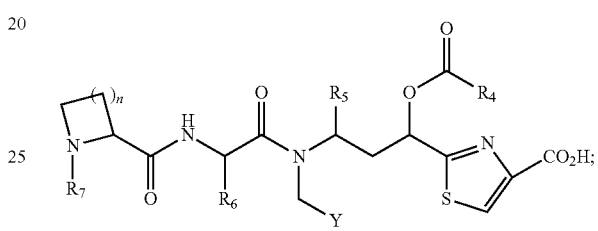

H1 and d) reacting the active ester intermediate with a compound of the formula I

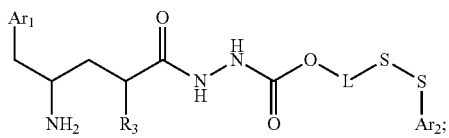

I or combinations thereof.

1B. A process for preparing a compound of the formula

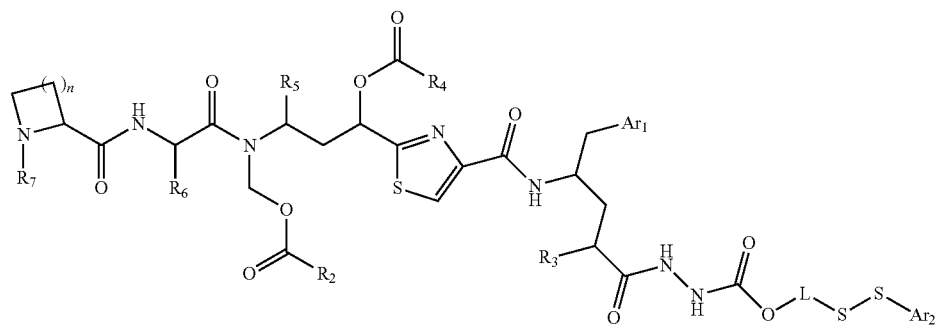

or a salt thereof, wherein $Ar_1$ is optionally substituted aryl or optionally substituted heteroaryl;

$Ar_2$ is optionally substituted aryl or optionally substituted heteroaryl;

L is selected from the group consisting of

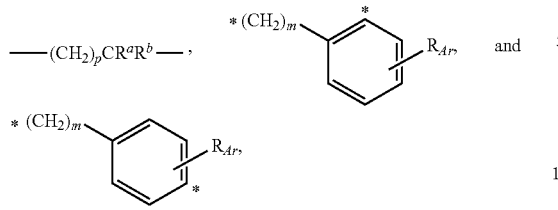

where p is an integer from about 1 to about 3, m is an integer from about 1 to about 4, and * indicates the points of attachment;

$R^a$, $R^b$, and R are each independently selected in each instance from the group consisting of hydrogen and alkyl; or any two of $R^a$, $R^b$, and R are taken together with the attached carbon atom(s) to form a carbocyclic ring;

$R_{Ar}$ represents 0 to 4 substituents selected from the group consisting of amino, or derivatives thereof, hydroxy or derivatives thereof, halo, thio or derivatives thereof, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof;

$R_2$ is selected from the group consisting of optionally substituted alkyl and optionally substituted cycloalkyl;

$R_3$ is optionally substituted alkyl;

$R_4$ is optionally substituted alkyl or optionally substituted cycloalkyl;

$R_5$ and $R_6$ are each independently selected from the group consisting of optionally substituted alkyl and optionally substituted cycloalkyl;

$R_7$ is optionally substituted alkyl; and n is 1, 2, 3, or 4;

wherein the process comprises the step of treating a compound of formula A with triethylsilyl chloride and imidazole in an aprotic solvent, where $R_8$ is C1-C6 unbranched alkyl

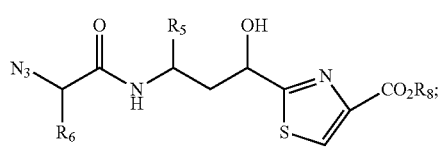

or the step of treating a compound of formula B with a base and a compound of the formula $ClCH_2C(O)R_2$ in an aprotic solvent at a temperature from about −78° C. to about 0° C.; wherein the molar ratio of the compound of the formula $ClCH_2C(O)R_2$ to the compound of formula B from about 1 to about 1.5, where $R_8$ is C1-C6 unbranched alkyl

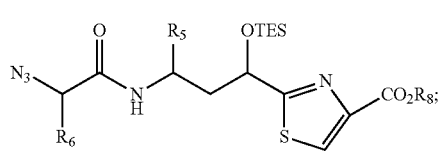

or the steps of a) preparing a compound of formula (E1) where $X_1$ is a leaving group from a compound of formula E

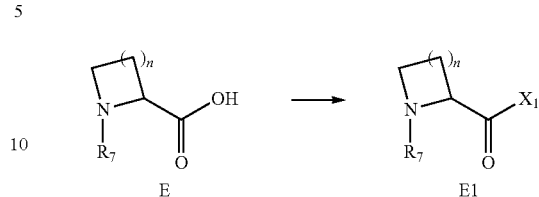

and b) treating a compound of formula C under reducing conditions in the presence of the compound of formula E1, where $R_8$ is C1-C6 unbranched alkyl

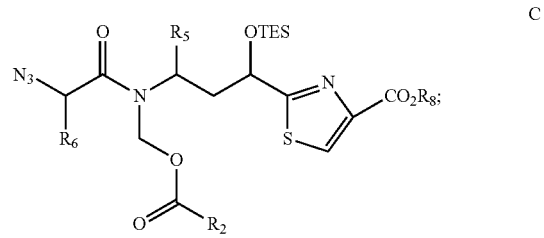

or the step of treating compound D with a hydrolase enzyme or with a trialkyltin hydroxide, where $R_8$ is C1-C6 unbranched alkyl

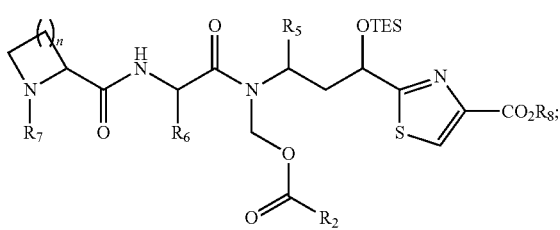

or the step of treating the silyl ether of compound F with a non-basic fluoride reagent

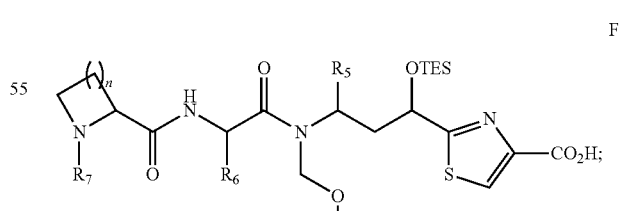

or the step of treating a compound of formula G with an acylating agent of formula $R_4C(O)X_2$, where $X_2$ is a leaving group

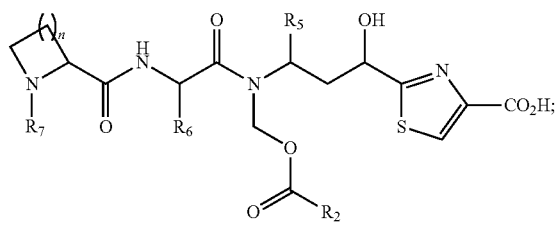

G or the steps of c) forming an active ester intermediate from a compound of formula H

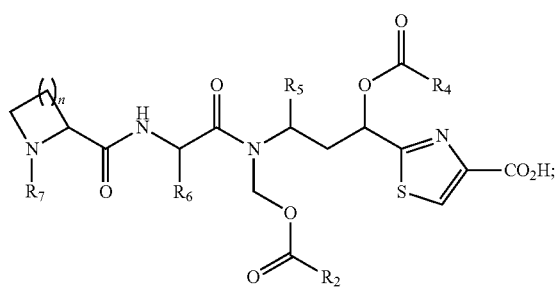

H and d) reacting the active ester intermediate with a compound of the formula I

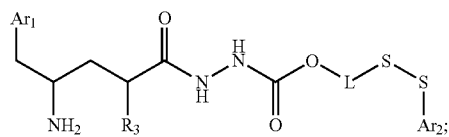

or combinations thereof.

1C. A process for preparing a compound of the formula

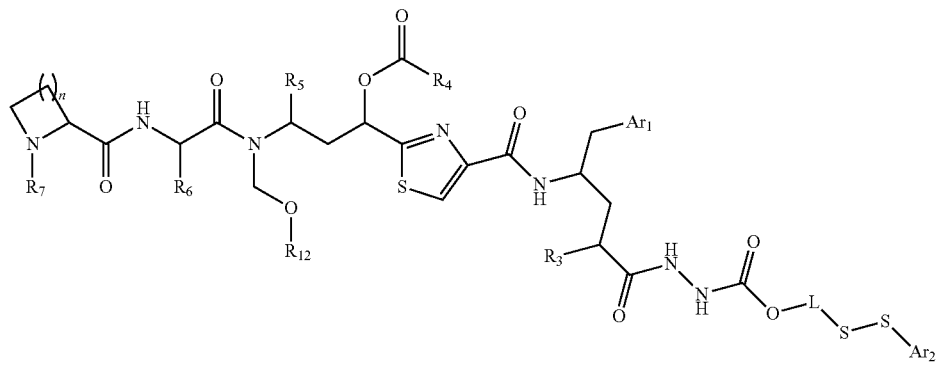

or a salt thereof, wherein $Ar_1$ is optionally substituted aryl;

$Ar_2$ is optionally substituted aryl or optionally substituted heteroaryl;

L is selected from the group consisting of

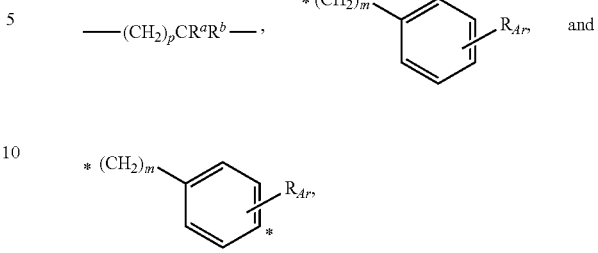

where p is an integer from about 1 to about 3, m is an integer from about 1 to about 4, and * indicates the points of attachment;

$R^a$, $R^b$, and R are each independently selected in each instance from the group consisting of hydrogen and alkyl; or any two of $R^a$, $R^b$, and R are taken together with the attached carbon atom(s) to form a carbocyclic ring;

$R_{Ar}$ represents 0 to 4 substituents selected from the group consisting of amino, or derivatives thereof, hydroxy or derivatives thereof, halo, thio or derivatives thereof, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof;

$R_2$ is selected from the group consisting of optionally substituted alkyl and optionally substituted cycloalkyl;

$R_{12}$ is alkyl, alkenyl, alkynyl, heteroalkyl, cycloalkyl, heterocycloalkyl, aryl, arylalkyl or heteroarylalkyl, each of which is optionally substituted;

$R_3$ is optionally substituted alkyl;

$R_4$ is optionally substituted alkyl or optionally substituted cycloalkyl;

$R_5$ and $R_6$ are each independently selected from the group consisting of optionally substituted alkyl and optionally substituted cycloalkyl;

$R_7$ is optionally substituted alkyl; and n is 1, 2, 3, or 4;

wherein the process comprises the step of treating a compound of formula A with triethylsilyl chloride and imidazole in an aprotic solvent, where $R_8$ is C1-C6 unbranched alkyl

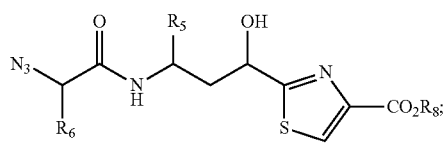

A or the step of treating a compound of formula B with a base and a compound of the formula $ClCH_2C(O)R_2$ in an aprotic solvent at a temperature from about $-78°$ C. to about $0°$ C.; wherein the molar ratio of the compound of the formula $ClCH_2C(O)R_2$ to the compound of formula B from about 1 to about 1.5, where $R_8$ is C1-C6 unbranched alkyl

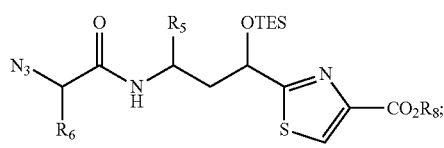

B or the steps of a) preparing a compound of formula (E1) where $X_1$ is a leaving group from a compound of formula E

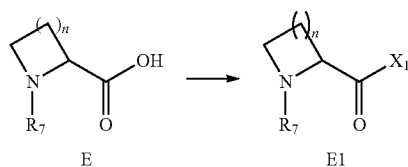

and b) treating a compound of formula C under reducing conditions in the presence of the compound of formula E1, where $R_8$ is C1-C6 unbranched alkyl

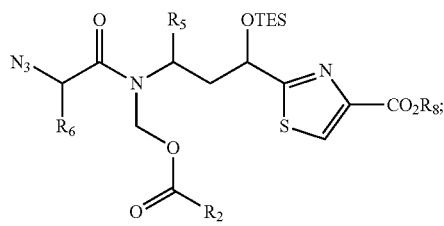

C or the step of treating compound D with a hydrolase enzyme or with a trialkyltin hydroxide, where $R_8$ is C1-C6 unbranched alkyl

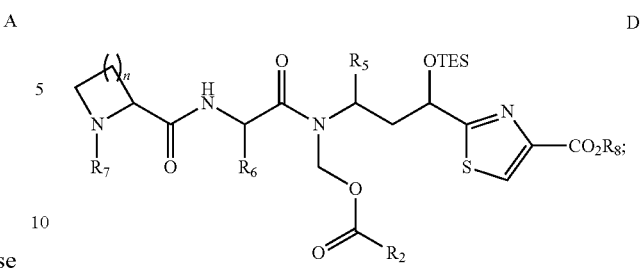

D or the step of contacting compound D with an alcohol $R_{12}OH$; and a transesterification reagent selected from TFA or $(R_{13})_8Sn_4O_2(NCS)_4$, $(R_{13})_2Sn(OAc)_2$, $(R_{13})_2SnO$, $(R_{13})_2SnCl_2$, $(R_{13})_2SnS$, $(R_{13})_3SnOH$, or $(R_{13})_3SnOSn(R_{13})_3$, where $R_{13}$ is independently selected from alkyl, arylalkyl, aryl, or cycloalkyl, each of which is optionally substituted or the step of contacting compound AF with water and an alkaline salt;

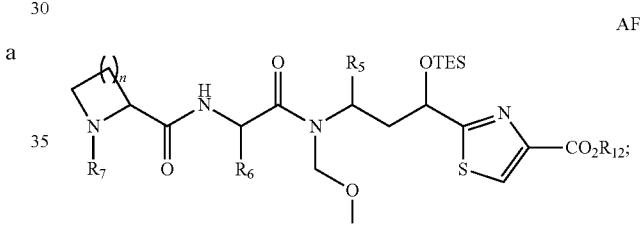

AF or the step of treating a compound of formula BG with an acylating agent of formula $R_4C(O)X_2$, where $X_2$ is a leaving group

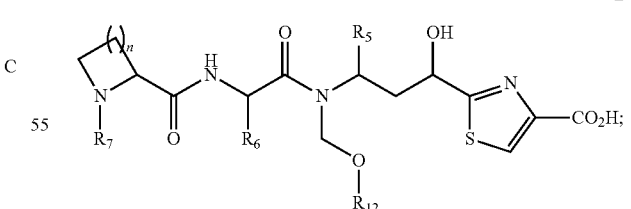

BG or the steps of c1) forming an active ester intermediate from a compound of formula AH

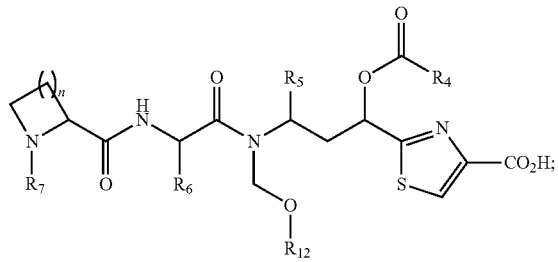

AH and d1) reacting the active ester intermediate with a compound of the formula I

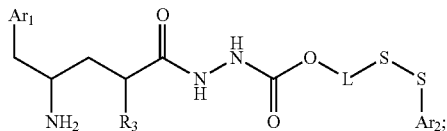

or combinations thereof.

1D. A compound of the formula

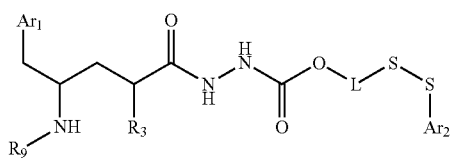

or a salt or solvate thereof;

wherein $Ar_1$ is optionally substituted aryl or optionally substituted heteroaryl;

$Ar_2$ is optionally substituted aryl or optionally substituted heteroaryl;

L is selected from the group consisting of $$—(CR_2)_p CR^a R^b —,$$

 and

where p is an integer from about 1 to about 3, m is an integer from about 1 to about 4, and * indicates the points of attachment;

$R^a$, $R^b$, and R are each independently selected in each instance from the group consisting of hydrogen and alkyl; or any two of $R^a$, $R^b$, and R are taken together with the attached carbon atom(s) to form a carbocyclic ring;

$R_{Ar}$ represents 0 to 4 substituents selected from the group consisting of amino, or derivatives thereof, hydroxy or derivatives thereof, halo, thio or derivatives thereof, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof;

$R_3$ is optionally substituted alkyl; and $R_9$ is hydrogen or an amine protecting group.

1E. A compound of the formula

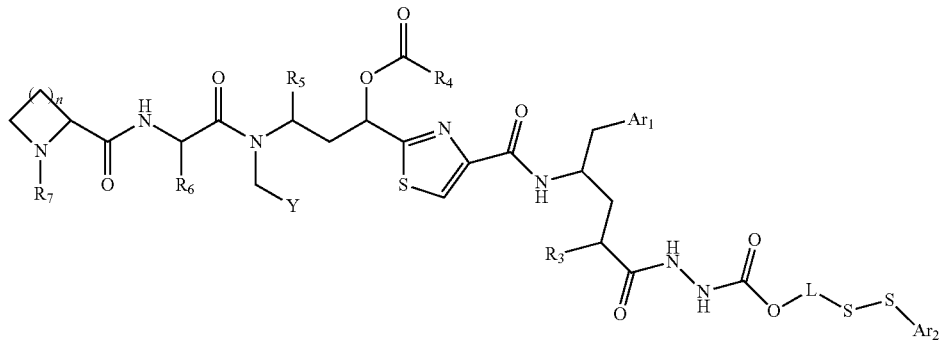

or a salt thereof, wherein $Ar_1$ is optionally substituted aryl or optionally substituted heteroaryl;

$Ar_2$ is optionally substituted aryl or optionally substituted heteroaryl;

L is selected from the group consisting of $$—(CR_2)_p CR^a R^b —,$$

 and

where p is an integer from about 1 to about 3, m is an integer from about 1 to about 4, and * indicates the points of attachment;

$R^a$, $R^b$, and R are each independently selected in each instance from the group consisting of hydrogen and alkyl; or any two of $R^a$, $R^b$, and R are taken together with the attached carbon atom(s) to form a carbocyclic ring; $R_{4r}$ represents hydrogen, or 1 to 4 substituents each independently selected from the group consisting of amino or derivatives thereof, hydroxy or derivatives thereof, halo, thio or derivatives thereof, nitro, sulfonic acids and derivatives thereof, carboxylic acids and derivatives thereof, and alkyl, heteroalkyl, aryl, arylalkyl, arylheteroalkyl, heteroaryl, heteroarylalkyl, and heteroarylheteroalkyl, each of which is optionally substituted;

Y is $R_2C(O)O$ or $R_{12}O$;

$R_2$ is selected from the group consisting of optionally substituted alkyl and optionally substituted cycloalkyl;

$R_4$ is optionally substituted alkyl or optionally substituted cycloalkyl;

$R_3$ is optionally substituted alkyl;

$R_5$ and $R_6$ are each independently selected from the group consisting of optionally substituted alkyl and optionally substituted cycloalkyl;

$R_7$ is optionally substituted alkyl;

$R_{12}$ is alkyl, alkenyl, alkynyl, heteroalkyl, cycloalkyl, heterocycloalkyl, aryl, arylalkyl or heteroarylalkyl, each of which is optionally substituted;

$R_{4r}$ represents hydrogen, or 1 to 4 substituents each independently selected from the group consisting of amino or derivatives thereof, hydroxy or derivatives thereof, halo, thio or derivatives thereof, nitro, sulfonic acids and derivatives thereof, carboxylic acids and derivatives thereof, and alkyl, haloalkyl, heteroalkyl, aryl, arylalkyl, arylheteroalkyl, heteroaryl, heteroarylalkyl, and heteroarylheteroalkyl; and n is 1, 2, 3, or 4.

1F. The process or compound of any one of the previous clauses wherein Y is acyloxy.

1G. The process or compound of any one of the previous clauses wherein Y is $R_2C(O)O$, where $R_2$ is selected from the group consisting of optionally substituted alkyl and optionally substituted cycloalkyl.

1H. The process or compound of any one of the previous clauses wherein Y is $R_{12}O$, where $R_{12}$ is alkyl, alkenyl, alkynyl, heteroalkyl, cycloalkyl, heterocycloalkyl, aryl, arylalkyl or heteroarylalkyl, each of which is optionally substituted.

2. The process of any one of the previous clauses comprising the step of treating a compound of formula A with triethylsilyl chloride and imidazole in an aprotic solvent, where $R_8$ is C1-C6 unbranched alkyl

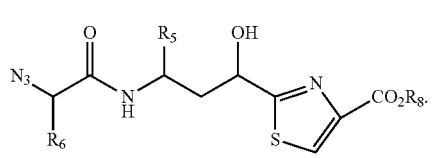

A

3. The process of any one of the previous clauses comprising the step of treating a compound of formula B with a base and a compound of the formula $ClCH_2C(O)R_2$ in an aprotic solvent at a temperature from about −78° C. to about 0° C.; wherein the molar ratio of the compound of the formula $ClCH_2C(O)R_2$ to the compound of formula B from about 1 to about 1.5, where $R_8$ is C1-C6 unbranched alkyl

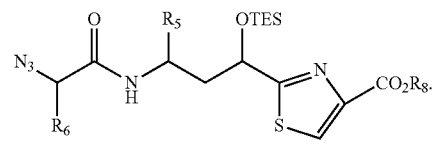

B

4. The process of any one of the previous clauses comprising the steps of
a) preparing a compound of formula (E1) from a compound of formula E, where $X_1$ is a leaving group

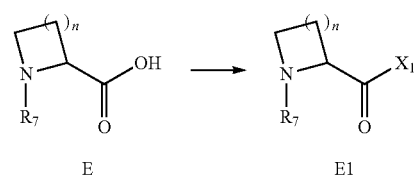

and
b) treating a compound of formula C under reducing conditions in the presence of the compound of formula E1, where $R_8$ is C1-C6 unbranched alkyl

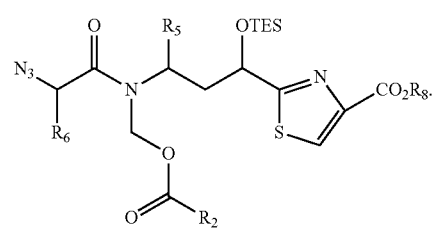

C

5. The process of any one of the previous clauses comprising the step of treating compound D with a hydrolase enzyme or a trialkyltin hydroxide, where $R_8$ is C1-C6 unbranched alkyl

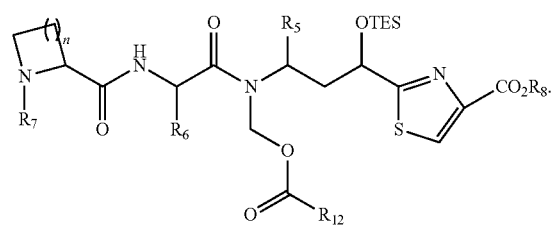

D

5A The process of any one of the previous clauses comprising the step of contacting compound D with an alcohol $R_{12}OH$; and a transesterification reagent selected from $(R_{13})_8Sn_4O_2(NCS)_4$, $(R_{13})_2Sn(OAc)_2$, $(R_{13})_2SnO$, $(R_{13})_2SnCl_2$, $(R_{13})_2SnS$, $(R_{13})_3SnOH$, $(R_{13})_3SnOSn(R_{13})_3$, or a combination thereof, where $R_{13}$ is independently selected from alkyl, arylalkyl, aryl, or cycloalkyl, each of which is optionally substituted.

5B. The process of any one of the previous clauses comprising the step of contacting compound AF with water and an alkaline salt;

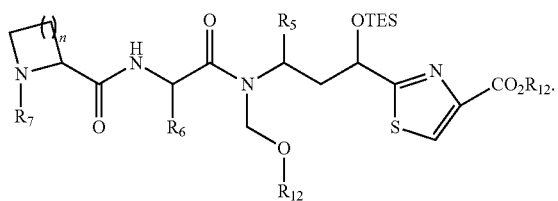

AF

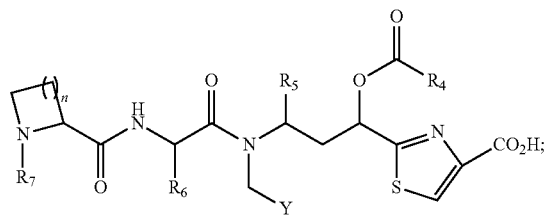

H1

6. The process of any one of the previous clauses comprising the step of treating a compound of formula G1 with an acylating agent of formula $R_4C(O)X_2$, where $X_2$ is a leaving group and d) reacting the active ester intermediate with a compound of the formula I

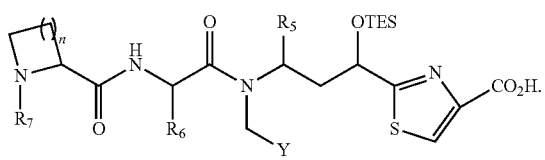

G1

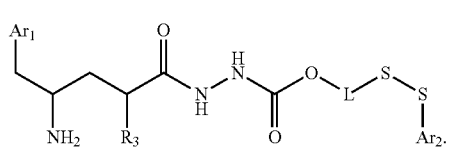

I

6A. The process of any one of the previous clauses comprising the step of treating a compound of formula G with an acylating agent of formula $R_4C(O)X_2$, where $X_2$ is a leaving group 7A. The process of any one of the previous clauses comprising the steps of c) forming an active ester intermediate from a compound of formula H

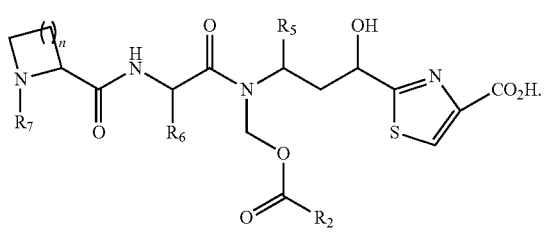

G

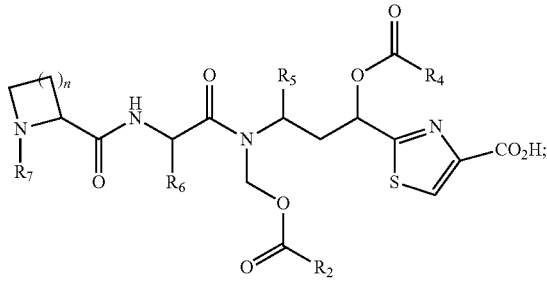

H

6B. The process of any one of the previous clauses comprising the step treating a compound of formula BG with an acylating agent of formula $R_4C(O)X_2$, where $X_2$ is a leaving group and d) reacting the active ester intermediate with a compound of the formula I

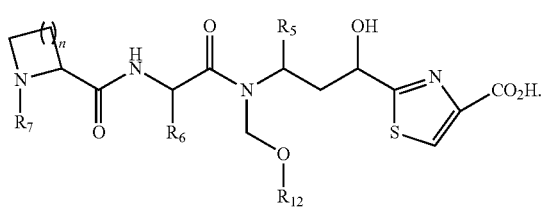

BG

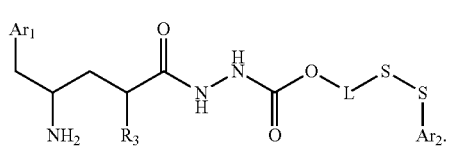

7. The process of any one of the previous clauses comprising the steps of c) forming an active ester intermediate from a compound of formula H1

7B. The process of any one of the previous clauses comprising the steps of c) forming an active ester intermediate from a compound of formula AH

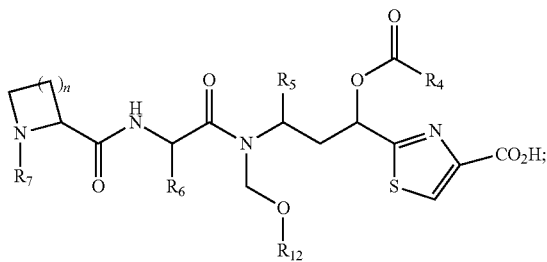

and d) reacting the active ester intermediate with a compound of the formula I

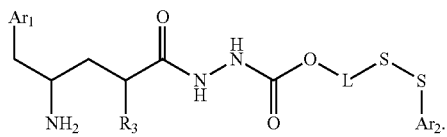

8. The process or compound of any one of the preceding clauses wherein $R_2$ is C1-C8 alkyl or C3-C8 cycloalkyl.

9. The process or compound of any one of the preceding clauses wherein $R_2$ is n-butyl.

10. The process or compound of any one of the preceding clauses wherein $R_3$ is C1-C4 alkyl.

11. The process or compound of any one of the preceding clauses wherein $R_3$ is methyl.

12. The process or compound of any one of the preceding clauses wherein $Ar_1$ is optionally substituted aryl.

12A. The process or compound of any one of the preceding clauses wherein $Ar_1$ is phenyl or hydroxyphenyl.

13. The process or compound of any one of the preceding clauses wherein $Ar_1$ is 4-hydroxyphenyl.

14. The process or compound of any one of the preceding clauses wherein $R_4$ is C1-C8 alkyl or C3-C8 cycloalkyl.

15. The process or compound of any one of the preceding clauses wherein $R_4$ is methyl.

16. The process or compound of any one of the preceding clauses wherein $R_5$ is branched C3-C6 or C3-C8 cycloalkyl.

17. The process or compound of any one of the preceding clauses wherein $R_5$ is iso-propyl.

18. The process or compound of any one of the preceding clauses wherein $R_6$ is branched C3-C6 or C3-C8 cycloalkyl.

19. The process or compound of any one of the preceding clauses wherein $R_5$ is sec-butyl.

20. The process or compound of any one of the preceding clauses wherein $R_7$ is C1-C6 alkyl.

21. The process or compound of any one of the preceding clauses wherein $R_7$ is methyl.

22. The process or compound of any one of the preceding clauses wherein $Ar_2$ is optionally substituted heteroaryl.

22A. The process or compound of any one of the preceding clauses wherein $Ar_2$ is substituted pyridyl.

23. The process or compound of any one of the preceding clauses wherein $Ar_2$ is substituted 2-pyridyl.

24. The process or compound of any one of the preceding clauses wherein $Ar_2$ is 3-nitro-2-pyridyl.

25. The process or compound of any one of the preceding clauses wherein $R_2$ is $CH_2CH(CH_3)_2$, $CH_2CH_2CH_3$, $CH_2CH_3$, $CH=C(CH_3)_2$, or $CH_3$.

26. The process or compound of any one of the preceding clauses wherein $Ar_1$ is substituted phenyl.

27. The process or compound of any one of the preceding clauses wherein $Ar_1$ is 4-substituted phenyl.

28. The process or compound of any one of the preceding clauses wherein $Ar_1$ is $R_4$-substituted phenyl.

29. The process or compound of any one of the preceding clauses wherein $Ar_1$ is 4-hydroxyphenyl, or a hydroxyl protected form thereof.

30. The process or compound of any one of the preceding clauses wherein L is $—(C(R)_2)_pCR^aR^b—$.

30. The process or compound of any one of the preceding clauses wherein L is $—(C(R)_2)_pCR^aR^b—$, p is 1, and each of $R^a$ and $R^b$ is methyl.

31. The process or compound of any one of the preceding clauses wherein L is

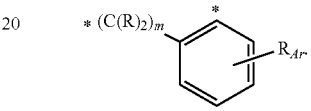

32. The process or compound of any one of the preceding clauses wherein L is

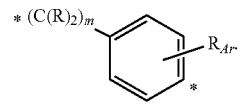

32A. The process or compound of any one of clauses 1 to 7 wherein O-L-S is $O—(C(R)_2)_pCR^aR^b—S$.

32B. The process or compound of any one of clauses 1 to 7 wherein O-L-S is

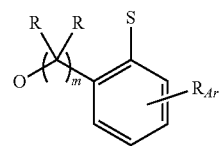

32C. The process or compound of any one of clauses 1 to 7 wherein O-L-S is

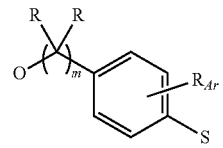

33. The process or compound of any one of the preceding clauses wherein $R^a$ and $R^b$ are each hydrogen.

34. The process or compound of any one of the preceding clauses wherein p is 1.

35. The process or compound of any one of the preceding clauses wherein m is 1.

35A. The process or compound of any one of the preceding clauses wherein the transesterification catalyst is selected from $(R_{13})_8Sn_4O_2(NCS)_4$, $(R_{13})_2Sn(OAc)_2$, $(R_{13})_2SnO$, $(R_{13})_2SnCl_2$, $(R_{13})_2SnS$, $(R_{13})_3SnOH$, and $(R_{13})_3SnOSn(R_{13})_3$, where $R_{13}$ is independently selected from alkyl, arylalkyl, aryl, or cycloalkyl, each of which is optionally substituted.

35B. The process or compound of any one of the preceding clauses wherein the transesterification catalyst is $(R_{13})_2SnO$.

35C. The process or compound of any one of the preceding clauses wherein the transesterification catalyst is $(n\text{-}Bu)_2SnO$.

35D. The process or compound of any one of the preceding clauses wherein the transesterification catalyst is TFA.

35E. The process or compound of any one of the preceding clauses wherein the alkaline salt is a metal hydroxide or a metal carbonate.

35F. The process or compound of any one of the preceding clauses wherein the alkaline salt is selected from LiOH, $Li_2CO_3$, NaOH, $Na_2CO_3$, KOH, $K_2CO_3$, $Ca(OH)_2$, $CaCO_3$, $Mg(OH)_2$, or $MgCO_3$.

36. The process or compound of any one of the preceding clauses wherein the alkaline salt is LiOH.

37. The process or compound of any one of the preceding clauses wherein $Ar_2$ is substituted pyridyl.

38. The process or compound of any one of the preceding clauses wherein $Ar_2$ is substituted 2-pyridyl.

39. The process or compound of any one of the preceding clauses wherein $Ar_2$ is 3-nitro-2-pyridyl.

40. The process or compound of any one of the preceding clauses wherein $R_2$ is $CH_2CH(CH_3)_2$, $CH_2CH_2CH_3$, $CH_2CH_3$, $CH=C(CH_3)_2$, or $CH_3$.

41. The process or compound of any one of the preceding clauses wherein $Ar_1$ is substituted phenyl.

42. The process or compound of any one of the preceding clauses wherein $Ar_1$ is 4-substituted phenyl.

43. The process or compound of any one of the preceding clauses wherein $Ar_1$ is $R_A$-substituted phenyl.

44. The process or compound of any one of the preceding clauses wherein $Ar_1$ is 4-hydroxyphenyl, or a hydroxyl protected form thereof.

45. The process or compound of any one of the preceding clauses wherein L is $-(C(R)_2)_pCR^aR^b-$.

46. The process or compound of any one of the preceding clauses wherein L is

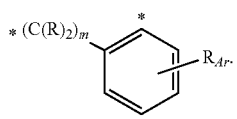

47. The process or compound of any one of the preceding clauses wherein L is

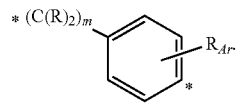

47A. The process or compound of any one of the preceding clauses wherein O-L-S is $O-(C(R)_2)_pCR^aR^b-S$.

47B. The process or compound of any one of the preceding clauses wherein O-L-S is

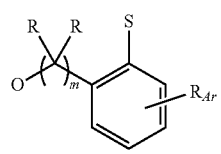

47C. The process or compound of any one of the preceding clauses wherein O-L-S is

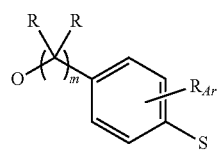

48. The process or compound of any one of the preceding clauses wherein $R^a$ and $R^b$ are each hydrogen.

49. The process or compound of any one of the preceding clauses wherein p is 1.

50. The process or compound of any one of the preceding clauses wherein m is 1.

50A. The process or compound of any one of the preceding clauses wherein each R is hydrogen.

51. The process or compound of any one of the preceding clauses wherein $R_2$ is $CH_2CH(CH_3)_2$, $CH_2CH_2CH_3$, $CH_2CH_3$, $CH=C(CH_3)_2$, or $CH_3$.

52. The process or compound of any one of the preceding clauses wherein $R^a$ is hydrogen and $R^b$ is methyl.

52A. The process or compound of any one of the preceding clauses wherein R is hydrogen.

53. The process or compound of any one of the preceding clauses wherein $R^a$ and $R^b$ are each methyl.

54. The process or compound of any one of the preceding clauses wherein $R^a$ and $R^b$ are taken together with the attached carbon to form cyclopropyl.

55. The process or compound of any one of the preceding clauses wherein $R^a$ is hydrogen and $R^b$ is methyl.

55A. The process or compound of any one of the preceding clauses wherein $R^a$ and $R^b$ are each methyl.

55B. The process or compound of any one of the preceding clauses wherein $R^a$ and $R^b$ are taken together with the attached carbon to form cyclopropyl.

56. A process for preparing a compound of the formula

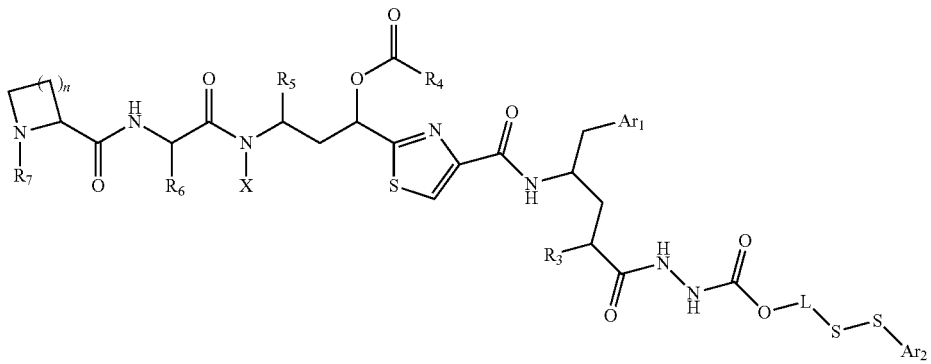

wherein

Ar$_1$ is optionally substituted aryl;

Ar$_2$ is optionally substituted aryl or optionally substituted heteroaryl;

L is selected from the group consisting of

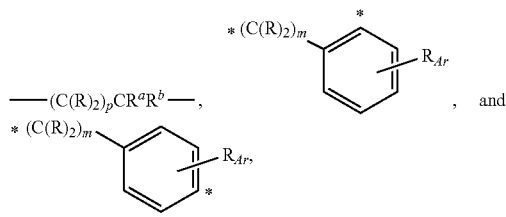

where p is an integer from about 1 to about 3, m is an integer from about 1 to about 4, and * indicates the points of attachment;

R$^a$, R$^b$, and R are each independently selected in each instance from the group consisting of hydrogen and alkyl; or any two of R$^a$, R$^b$, and R are taken together with the attached carbon atom(s) to form a carbocyclic ring;

R$_{Ar}$ represents 0 to 4 substituents selected from the group consisting of amino, or derivatives thereof, hydroxy or derivatives thereof, halo, thio or derivatives thereof, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, carboxylic acids and derivatives thereof;

where X is hydrogen or alkyl, including C$_{1-6}$ alkyl and C$_{1-4}$ alkyl, alkenyl, including C$_{2-6}$ alkenyl and C$_{2-4}$ alkenyl, cycloalkyl, aryl, heteroaryl, arylalkyl, or heteroarylalkyl, each of which is optionally substituted; or CH$_2$QR$^9$; where Q is NH, O, or S; or; and R$^9$ is alkyl, including C$_{1-6}$ alkyl and C$_{1-4}$ alkyl, alkenyl, including C$_{2-6}$ alkenyl and C$_{2-4}$ alkenyl, cycloalkyl, aryl, heteroaryl, arylalkyl, or heteroarylalkyl, each of which is optionally substituted; or R$^9$ is hydrogen or C(O)R$^{10}$, where R$^{10}$ is C$_{1-6}$ alkyl, C$_{2-6}$ alkenyl, aryl, heteroaryl, arylalkyl, or heteroarylalkyl, each of which is optionally substituted; or R$^9$ is C(O)R$^{20}$, S(O)$_2$R$^{20}$, or P(O)(OR$^{20}$)$_2$; where R$^{20}$ is independently selected in each instance from the group consisting of H, alkyl, including C$_{1-6}$ alkyl and C$_{1-4}$ alkyl, alkenyl, including C$_{2-6}$ alkenyl and C$_{2-4}$ alkenyl, cycloalkyl, aryl, heteroaryl, arylalkyl, or heteroarylalkyl, each of which is optionally substituted; or R$^{20}$ is a metal cation;

R$_3$ is optionally substituted alkyl;

R$_4$ is optionally substituted alkyl or optionally substituted cycloalkyl;

R$_5$ and R$_6$ are each independently selected from the group consisting of optionally substituted alkyl and optionally substituted cycloalkyl;

R$_7$ is optionally substituted alkyl; and n is 1, 2, 3, or 4;

wherein the process comprises the step of treating a compound of formula A with triethylsilyl chloride and imidazole in an aprotic solvent, where R$_8$ is C1-C6 unbranched alkyl

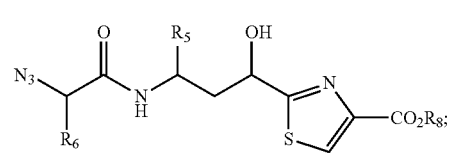

or the step of treating a compound of formula B with a base and a compound of the formula ClCH$_2$C(O)R$_2$ in an aprotic solvent at a temperature from about −78° C. to about 0° C.; wherein the molar ratio of the compound of the formula ClCH$_2$C(O)R$_2$ to the compound of formula B from about 1 to about 1.5, where R$_8$ is C1-C6 unbranched alkyl

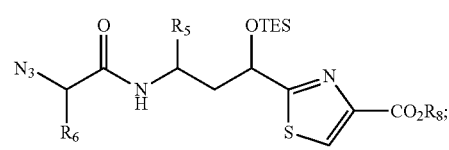

or the steps of a) preparing a compound of formula (E1) where X$_1$ is a leaving group from a compound of formula E

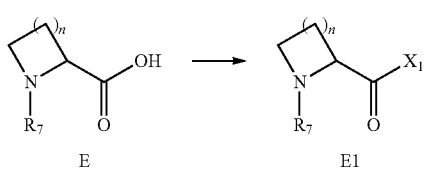

and b) treating a compound of formula C under reducing conditions in the presence of the compound of formula E1, where $R_8$ is C1-C6 unbranched alkyl

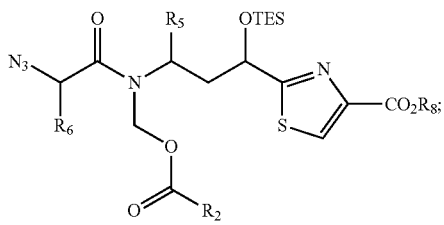

or the step of treating compound D with a hydrolase enzyme or with a trialkyltin hydroxide, where $R_8$ is C1-C6 unbranched alkyl

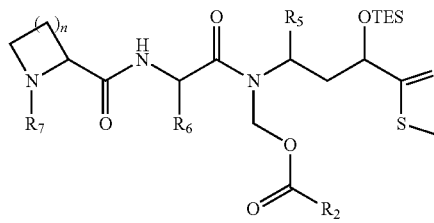

or the step of treating the silyl ether of compound F with a non-basic fluoride reagent

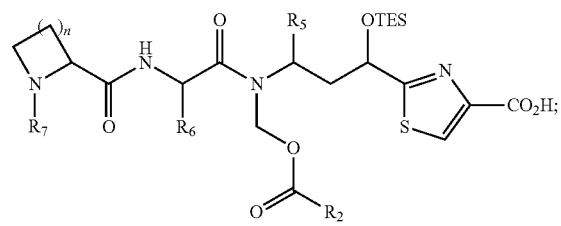

or the step of treating a compound of formula G with an acylating agent of formula $R_4C(O)X_2$, where $X_2$ is a leaving group

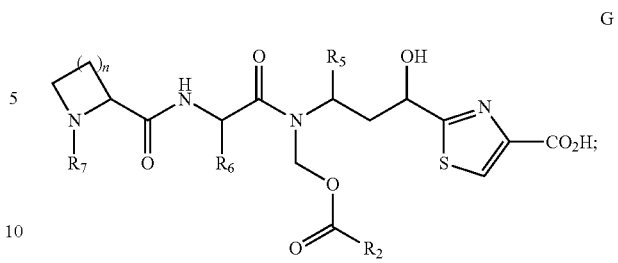

or the steps of c) forming an active ester intermediate from a compound of formula H

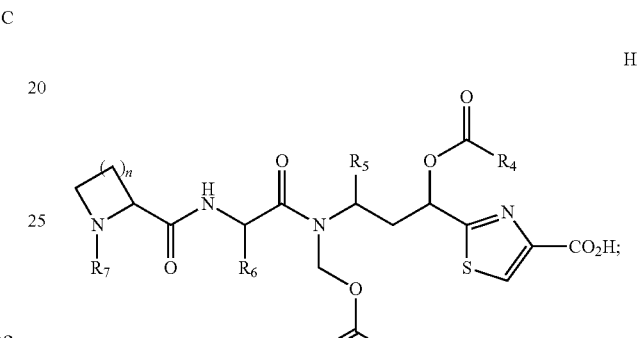

and d) reacting the active ester intermediate with a compound of the formula I

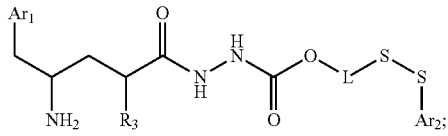

or combinations thereof.

57. The process of clause 56 wherein X is $CH_2QR^{9A}$; where Q is NH, O, or S; and $R^{9A}$ is alkyl, including $C_{1-6}$ alkyl and $C_{1-4}$ alkyl, alkenyl, including $C_{2-6}$ alkenyl and $C_{2-4}$ alkenyl, cycloalkyl, aryl, heteroaryl, arylalkyl, or heteroarylalkyl, each of which is optionally substituted; or $R^{9A}$ is H or $C(O)R^{10}$, where $R^{10}$ is $C_{1-6}$ alkyl, $C_{2-6}$ alkenyl, aryl, heteroaryl, arylalkyl, or heteroarylalkyl, each of which is optionally substituted.

58. The process of clause 56 wherein X is $CH_2QR^{9A}$; where Q is O; and $R^{9A}$ is alkyl, including $C_{1-6}$ alkyl and $C_{1-4}$ alkyl, alkenyl, including $C_{2-6}$ alkenyl and $C_{2-4}$ alkenyl, cycloalkyl, aryl, heteroaryl, arylalkyl, or heteroarylalkyl, each of which is optionally substituted; or $R^{9A}$ is H or $C(O)R^{10}$, where $R^{10}$ is $C_{1-6}$ alkyl, $C_{2-6}$ alkenyl, aryl, heteroaryl, arylalkyl, or heteroarylalkyl, each of which is optionally substituted.

59. The process of clause 56 wherein X is $CH_2QR^{9B}$; where Q is NH, O, or S; and $R^{9B}$ is $C(O)R^{20}$, $S(O)_2R^{20}$, or $P(O)(OR^{20})_2$; where $R^{20}$ is independently selected in each instance from the group consisting of H, alkyl, including $C_{1-6}$ alkyl and $C_{1-4}$ alkyl, alkenyl, including $C_{2-6}$ alkenyl and $C_{2-4}$ alkenyl, cycloalkyl, aryl, heteroaryl, arylalkyl, or heteroarylalkyl, each of which is optionally substituted; or $R^{20}$ is a metal cation.

60. The process of clause 56 wherein X is $CH_2QR^{9B}$; where Q is O; and $R^{9B}$ is $C(O)R^{20}$, $S(O)_2R^{20}$, or $P(O)(OR^{20})_2$; where $R^{20}$ is independently selected in each instance from the group consisting of H, alkyl, including $C_{1-6}$ alkyl and $C_{1-4}$ alkyl, alkenyl, including $C_{2-6}$ alkenyl and $C_{2-4}$ alkenyl, cycloalkyl, aryl, heteroaryl, arylalkyl, or heteroarylalkyl, each of which is optionally substituted; or $R^{20}$ is a metal cation.

61. The process of clause 56 wherein X is $CH_2QR^{9B}$; where Q is NH; and $R^{9B}$ is $C(O)R^{20}$, where $R^{20}$ is alkyl, alkenyl, cycloalkyl, aryl, or arylalkyl, each of which is optionally substituted.

62. The process of clause 56 wherein X is $CH_2CH=CHR^{22}$ or $CH_2C(R^{22})=CH_2$, where $R^{22}$ is $C(O)R^{20}$, where $R^{20}$ is wherein $R^{22}$ is alkyl, alkenyl, cycloalkyl, aryl, or arylalkyl, each of which is optionally substituted.

63. The process of clause 56 wherein X is $CH_2CH(R^a)C(O)R^{23}$, where $R^{23}$ is H, or alkyl, alkenyl, cycloalkyl, aryl, or arylalkyl, each of which is optionally substituted; $R^a$ is $C(O)R^9$, $C(O)OR^9$ or CN;

64. The process of clause 56 wherein X is $CH_2OR^{25}$; where $R^{25}$ is H, and alkyl, alkenyl, cycloalkyl, aryl, and arylalkyl, each of which is optionally substituted; or $R^{25}$ is alkyl, alkenyl, cycloalkyl, aryl, and arylalkyl, each of which is optionally substituted; or $R^{25}$ is alkyl.

65. The process of clause 56 wherein X is $CH_2OH$.

66. The process of clause 56 wherein X is $CH_2X^3$; where $X^3$ is halogen, including bromo or iodo, $OS(O)_2R^{24}$, $OP(O)(OR^{24})R^{24}$, or $OP(O)(OR^{24})_2$; where $R^{24}$ is independently selected in each instance from the group consisting of H, and alkyl, alkenyl, cycloalkyl, aryl, and arylalkyl, each of which is optionally substituted, and metal cations.

In one embodiment, one or more of the following intermediates can be used to prepare a tubulysin, tubulysin conjugate, and/or a tubulysin linker compound.

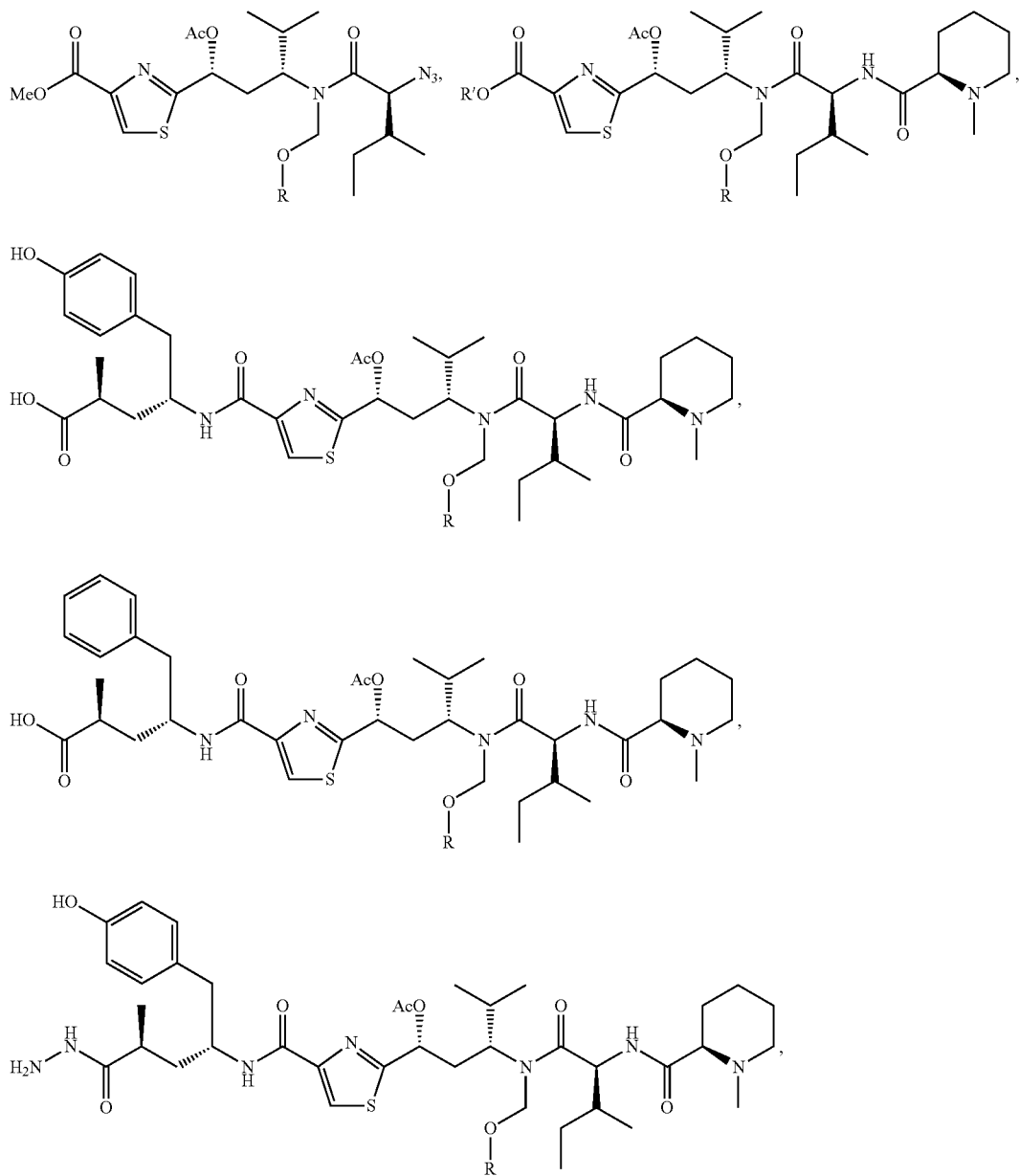

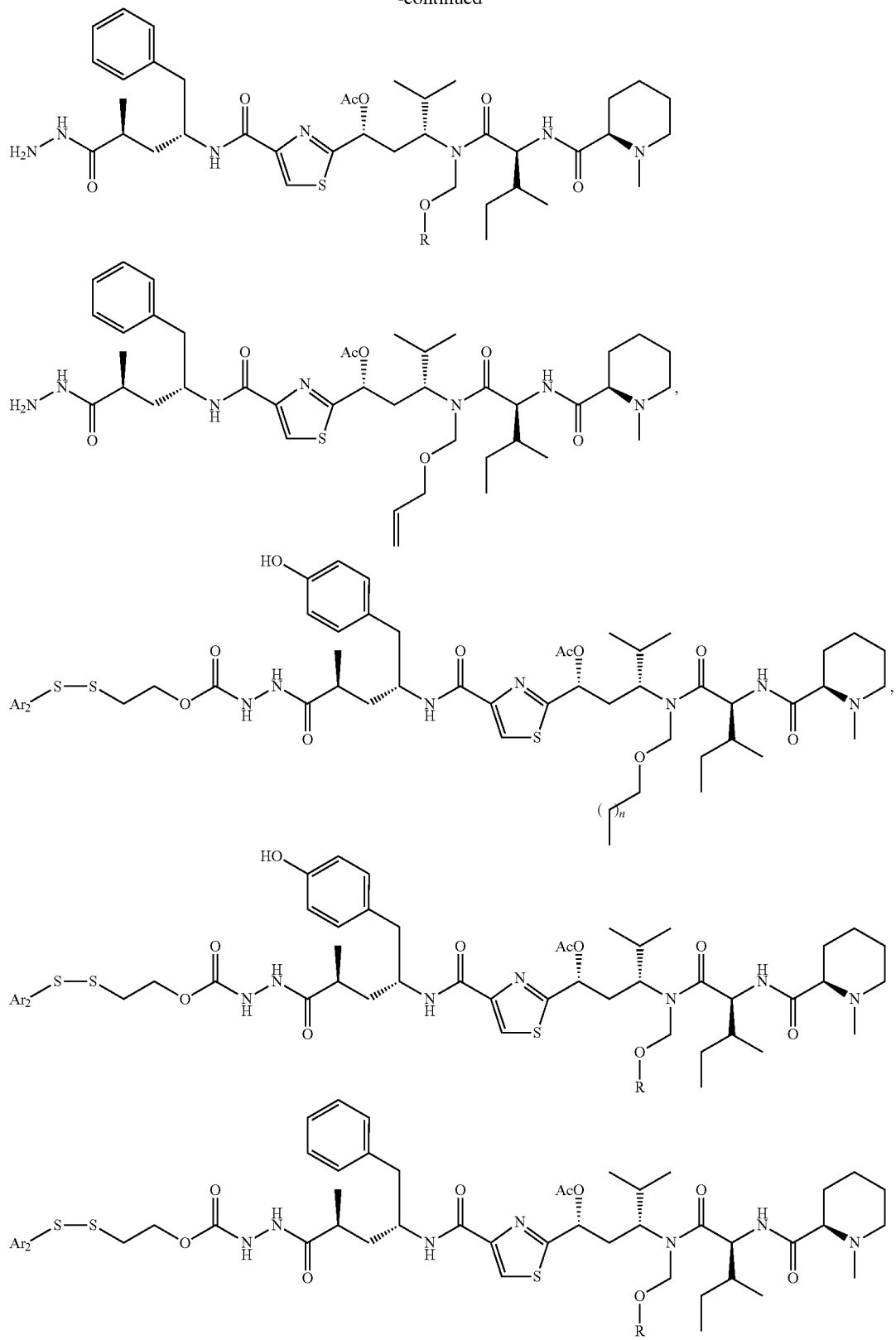
where R' is Me or R, and R is allyl, or $CH_2(CH_2)_2CH_3$, where n=1, 2, 3, 4, 5, or 6 and $Ar_2$ is as described in various embodiments described herein.
In another embodiment, processes for preparing tubulysin conjugates are described herein. In one aspect, the processes include the step of reacting compounds (2) and the corresponding tubulysins described herein that include a 3-nitropyridin-2-ylthio activating group (Ar$_2$), such as compounds of the formulae

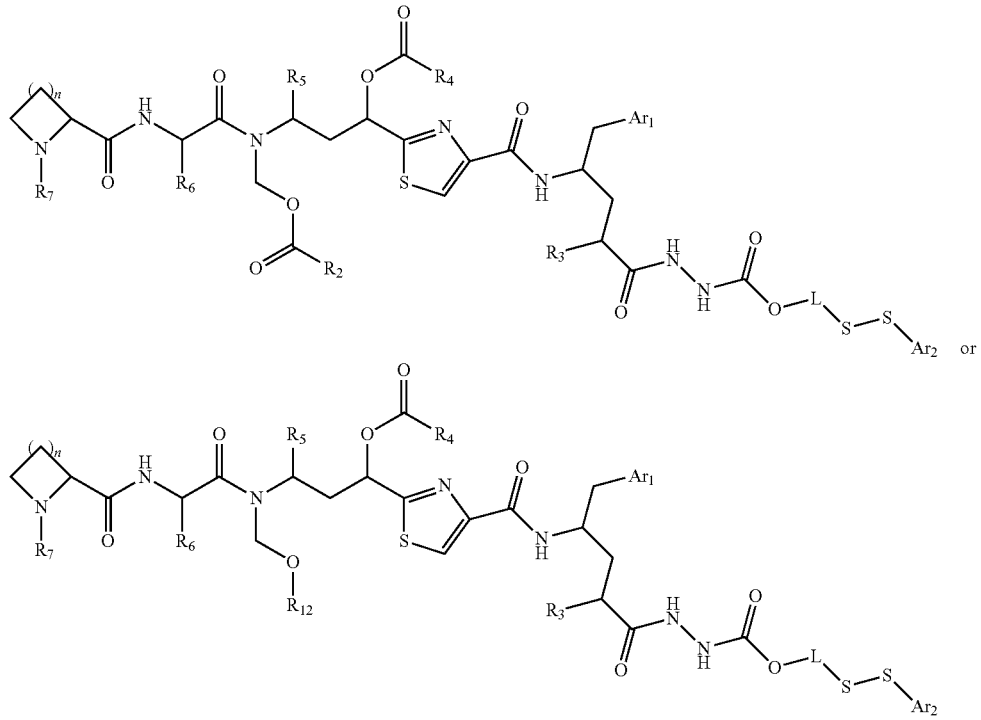

or salt and/or solvates thereof, as described herein, with a binding ligand-linker intermediate, such as are described in WO 2008/112873, the disclosure of which is incorporated herein by reference. In another aspect, the processes include acetonitrile as a reaction solvent. In another aspect, the processes include aqueous phosphate as a reaction medium buffer. Without being bound by theory, it is believed herein that the use of acetonitrile as a solvent leads to a more rapid homogenous reaction solution. In addition, though without being bound by theory, it is believed herein that a more rapidly formed homogenous reaction medium may improve the yield and rate at which tubulysin conjugates described herein are formed. In addition, though without being bound by theory, it is believed herein that the use of 3-nitropyridin-2-ylthio activating groups may lead to faster reaction times. In addition, though without being bound by theory, it is believed herein that the use of 3-nitropyridin-2-ylthio activating groups may provide better chromatographic separation between the product tubulysin conjugates and the by-product 3-nitropyridin-2-ylthiol compared to conventional pyridin-2-ylthio activating groups. In addition, such better chromatographic separation may allow the use of alternative purification methods. For example, in addition to preparative HPLC, the tubulysin conjugates described herein may be purified by rapid pass-through chromatography methods, such as flash C$_{18}$ chromatography, Biotage™ C$_{18}$ chromatography systems, and the like.

Additional methods and processes useful for performing the above processes are found in U.S. patent application Ser. No. 12/739,579, published as U.S. Application Publication No. 2010/0240701, the disclosure of which is incorporated herein by reference in its entirety.

It is to be understood that as used herein, the term tubulysin refers both collectively and individually to the naturally occurring tubulysins, and the analogs and derivatives of tubulysins. Illustrative examples of a tubulysin are shown in Table 1.

As used herein, the term tubulysin linker derivatives generally refers to the compounds described herein and analogs and derivatives thereof. It is also to be understood that in each of the foregoing, any corresponding pharmaceutically acceptable salt is also included in the illustrative embodiments described herein.

It is to be understood that such derivatives may include prodrugs of the compounds described herein, compounds described herein that include one or more protection or protecting groups, including compounds that are used in the preparation of other compounds described herein.

In addition, as used herein the term tubulysin linker derivatives also refers to prodrug derivatives of the compounds described herein, and including prodrugs of the various analogs and derivatives thereof. In addition, as used herein, the term tubulysin linker derivatives refers to both the amorphous as well as any and all morphological forms of each of the compounds described herein. In addition, as used herein, the term tubulysin linker derivatives refers to any and all hydrates, or other solvates, of the compounds described herein.

It is to be understood that each of the foregoing embodiments may be combined in chemically relevant ways to generate subsets of the embodiments described herein. Accordingly, it is to be further understood that all such subsets are also illustrative embodiments of the invention described herein.

The compounds described herein may contain one or more chiral centers, or may otherwise be capable of existing as multiple stereoisomers. It is to be understood that in one embodiment, the invention described herein is not limited to any particular stereochemical requirement, and that the compounds, and compositions, methods, uses, and medicaments that include them may be optically pure, or may be any of a variety of stereoisomeric mixtures, including racemic and other mixtures of enantiomers, other mixtures of diastereomers, and the like. It is also to be understood that such mixtures of stereoisomers may include a single stereochemical configuration at one or more chiral centers, while including mixtures of stereochemical configuration at one or more other chiral centers.

Similarly, the compounds described herein may include geometric centers, such as cis, trans, (E)-, and (Z)-double bonds. It is to be understood that in another embodiment, the invention described herein is not limited to any particular geometric isomer requirement, and that the compounds, and compositions, methods, uses, and medicaments that include them may be pure, or may be any of a variety of geometric isomer mixtures. It is also to be understood that such mixtures of geometric isomers may include a single configuration at one or more double bonds, while including mixtures of geometry at one or more other double bonds.

As used herein, the term aprotic solvent refers to a solvent which does not yield a proton to the solute(s) under reaction conditions. Illustrative examples of nonprotic solvents are tetrahydrofuran (THF), 2,5-dimethyl-tetrahydrofuran, 2-methyl-tetrahydrofuran, tetrahydropyran, diethyl ether, t-butyl methyl ether, dimethyl formamide, N-methylpyrrolidinone (NMP), and the like. It is appreciated that mixtures of these solvents may also be used in the processes described herein.

As used herein, an equivalent amount of a reagent refers to the theoretical amount of the reagent necessary to transform a starting material into a desired product, i.e. if 1 mole of reagent is theoretically required to transform 1 mole of the starting material into 1 mole of product, then 1 equivalent of the reagent represents 1 mole of the reagent; if X moles of reagent are theoretically required to convert 1 mole of the starting material into 1 mole of product, then 1 equivalent of reagent represents X moles of reagent.

As used herein, the term active ester forming agent generally refers to any reagent or combinations of reagents that may be used to convert a carboxylic acid into an active ester.

As used herein, the term active ester generally refers to a carboxylic acid ester compound wherein the divalent oxygen portion of the ester is a leaving group resulting in an ester that is activated for reacting with compounds containing functional groups, such as amines, alcohols or sulfhydryl groups. Illustrative examples of active ester-forming compounds are N-hydroxysuccinimide, N-hydroxyphthalimide, phenols substituted with electron withdrawing groups, such as but not limited to 4-nitrophenol, pentafluorophenol, N,N'-disubstituted isoureas, substituted hydroxyheteroaryls, such as but not limited to 2-pyridinols, 1-hydroxybenzotriazoles, 1-hydroxy-7-aza-benzotriazoles, cyanomethanol, and the like. Illustratively, the reaction conditions for displacing the active ester with a compound having an amino, hydroxy or thiol group are mild. Illustratively, the reaction conditions for displacing the active ester with a compound having an amino, hydroxy or thiol group are performed at ambient or below ambient temperatures. Illustratively, the reaction conditions for displacing the active ester with a compound having an amino, hydroxy or thiol group are performed without the addition of a strong base. Illustratively, the reaction conditions for displacing the active ester with a compound having an amino, hydroxy or thiol group are performed with the addition of a tertiary amine base, such as a tertiary amine base having a conjugate acid pKa of about 11 or less, about 10.5 or less, and the like.

As used herein, the term "alkyl" includes a chain of carbon atoms, which is optionally branched. As used herein, the term "alkenyl" and "alkynyl" includes a chain of carbon atoms, which is optionally branched, and includes at least one double bond or triple bond, respectively. It is to be understood that alkynyl may also include one or more double bonds. It is to be further understood that in certain embodiments, alkyl is advantageously of limited length, including $C_1$-$C_{24}$, $C_1$-$C_{12}$, $C_1$-$C_8$, $C_1$-$C_6$, and $C_1$-$C_4$. It is to be further understood that in certain embodiments alkenyl and/or alkynyl may each be advantageously of limited length, including $C_2$-$C_{24}$, $C_2$-$C_{12}$, $C_2$-$C_8$, $C_2$-$C_6$, and $C_2$-$C_4$. It is appreciated herein that shorter alkyl, alkenyl, and/or alkynyl groups may add less lipophilicity to the compound and accordingly will have different pharmacokinetic behavior. Illustrative alkyl groups are, but not limited to, methyl, ethyl, n-propyl, isopropyl, n-butyl, isobutyl, sec-butyl, tert-butyl, pentyl, 2-pentyl, 3-pentyl, neopentyl, hexyl, heptyl, octyl and the like.

As used herein, the term "cycloalkyl" includes a chain of carbon atoms, which is optionally branched, where at least a portion of the chain in cyclic. It is to be understood that cycloalkylalkyl is a subset of cycloalkyl. It is to be understood that cycloalkyl may be polycyclic. Illustrative cycloalkyl include, but are not limited to, cyclopropyl, cyclopentyl, cyclohexyl, 2-methylcyclopropyl, cyclopentyleth-2-yl, adamantyl, and the like. As used herein, the term "cycloalkenyl" includes a chain of carbon atoms, which is optionally branched, and includes at least one double bond, where at least a portion of the chain in cyclic. It is to be understood that the one or more double bonds may be in the cyclic portion of cycloalkenyl and/or the non-cyclic portion of cycloalkenyl. It is to be understood that cycloalkenylalkyl and cycloalkylalkenyl are each subsets of cycloalkenyl. It is to be understood that cycloalkyl may be polycyclic. Illustrative cycloalkenyl include, but are not limited to, cyclopentenyl, cyclohexylethen-2-yl, cycloheptenylpropenyl, and the like. It is to be further understood that chain forming cycloalkyl and/or cycloalkenyl is advantageously of limited length, including $C_3$-$C_{24}$, $C_3$-$C_{12}$, $C_3$-$C_8$, $C_3$-$C_6$, and $C_5$-$C_6$. It is appreciated herein that shorter alkyl and/or alkenyl chains forming cycloalkyl and/or cycloalkenyl, respectively, may add less lipophilicity to the compound and accordingly will have different pharmacokinetic behavior.

As used herein, the term "heteroalkyl" includes a chain of atoms that includes both carbon and at least one heteroatom, and is optionally branched. Illustrative heteroatoms include nitrogen, oxygen, and sulfur. In certain variations, illustrative heteroatoms also include phosphorus, and selenium. As used herein, the term "cycloheteroalkyl" including heterocyclyl and heterocycle, includes a chain of atoms that includes both carbon and at least one heteroatom, such as heteroalkyl, and is optionally branched, where at least a portion of the chain is cyclic. Illustrative heteroatoms include nitrogen, oxygen, and sulfur. In certain variations, illustrative heteroatoms also include phosphorus, and selenium. Illustrative cycloheteroalkyl include, but are not limited to, tetrahydrofuryl, pyrrolidinyl, tetrahydropyranyl, piperidinyl, morpholinyl, piperazinyl, homopiperazinyl, quinuclidinyl, and the like.

As used herein, the term "aryl" includes monocyclic and polycyclic aromatic groups, including aromatic carbocyclic and aromatic heterocyclic groups, each of which may be optionally substituted. As used herein, the term "carbaryl"

includes aromatic carbocyclic groups, each of which may be optionally substituted. Illustrative aromatic carbocyclic groups described herein include, but are not limited to, phenyl, naphthyl, and the like. As used herein, the term "heteroaryl" includes aromatic heterocyclic groups, each of which may be optionally substituted. Illustrative aromatic heterocyclic groups include, but are not limited to, pyridinyl, pyrimidinyl, pyrazinyl, triazinyl, tetrazinyl, quinolinyl, quinazolinyl, quinoxalinyl, thienyl, pyrazolyl, imidazolyl, oxazolyl, thiazolyl, isoxazolyl, isothiazolyl, oxadiazolyl, thiadiazolyl, triazolyl, benzimidazolyl, benzoxazolyl, benzthiazolyl, benzisoxazolyl, benzisothiazolyl, and the like.

As used herein, the term "amino" includes the group $NH_2$, alkylamino, and dialkylamino, where the two alkyl groups in dialkylamino may be the same or different, i.e. alkylalkylamino. Illustratively, amino includes methylamino, ethylamino, dimethylamino, methylethylamino, and the like. In addition, it is to be understood that when amino modifies or is modified by another term, such as aminoalkyl, or acylamino, the above variations of the term amino are included therein. Illustratively, aminoalkyl includes $H_2N$-alkyl, methylaminoalkyl, ethylaminoalkyl, dimethylaminoalkyl, methylethylaminoalkyl, and the like. Illustratively, acylamino includes acylmethylamino, acylethylamino, and the like.

As used herein, the term "amino and derivatives thereof" includes amino as described herein, and alkylamino, alkenylamino, alkynylamino, heteroalkylamino, heteroalkenylamino, heteroalkynylamino, cycloalkylamino, cycloalkenylamino, cycloheteroalkylamino, cycloheteroalkenylamino, arylamino, arylalkylamino, arylalkenylamino, arylalkynylamino, acylamino, and the like, each of which is optionally substituted. The term "amino derivative" also includes urea, carbamate, and the like.

As used herein, the term "hydroxy and derivatives thereof" includes OH, and alkyloxy, alkenyloxy, alkynyloxy, heteroalkyloxy, heteroalkenyloxy, heteroalkynyloxy, cycloalkyloxy, cycloalkenyloxy, cycloheteroalkyloxy, cycloheteroalkenyloxy, aryloxy, arylalkyloxy, arylalkenyloxy, arylalkynyloxy, acyloxy, and the like, each of which is optionally substituted. The term "hydroxy derivative" also includes carbamate, and the like.

As used herein, the term "thio and derivatives thereof" includes SH, and alkylthio, alkenylthio, alkynylthio, heteroalkylthio, heteroalkenylthio, heteroalkynylthio, cycloalkylthio, cycloalkenylthio, cycloheteroalkylthio, cycloheteroalkenylthio, arylthio, arylalkylthio, arylalkenylthio, arylalkynylthio, acylthio, and the like, each of which is optionally substituted. The term "thio derivative" also includes thiocarbamate, and the like.

As used herein, the term "acyl" includes formyl, and alkylcarbonyl, alkenylcarbonyl, alkynylcarbonyl, heteroalkylcarbonyl, heteroalkenylcarbonyl, heteroalkynylcarbonyl, cycloalkylcarbonyl, cycloalkenylcarbonyl, cycloheteroalkylcarbonyl, cycloheteroalkenylcarbonyl, arylcarbonyl, arylalkylcarbonyl, arylalkenylcarbonyl, arylalkynylcarbonyl, acylcarbonyl, and the like, each of which is optionally substituted.

As used herein, the term "sulfonyl" includes alkylsulfonyl, alkenylsulfonyl, alkynylsulfonyl, heteroalkylsulfonyl, heteroalkenylsulfonyl, heteroalkynylsulfonyl, cycloalkylsulfonyl, cycloalkenylsulfonyl, cycloheteroalkylsulfonyl, cycloheteroalkenylsulfonyl, arylsulfonyl, arylalkylsulfonyl, arylalkenylsulfonyl, arylalkynylsulfonyl, heteroarylsulfonyl, heteroarylalkylsulfonyl, heteroarylalkenylsulfonyl, heteroarylalkynylsulfonyl, acylsulfonyl, and the like, each of which is optionally substituted.

As used herein, the term "phosphonic acid or a derivative thereof" includes $PO_3H_2$ and salts thereof, and esters and amides thereof.

As used herein, the term "carboxylate and derivatives thereof" includes the group $CO_2H$ and salts thereof, and esters and amides thereof, and CN.

The term "optionally substituted" as used herein includes the replacement of hydrogen atoms with other functional groups on the radical that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

As used herein, the term "optionally substituted aryl" includes the replacement of hydrogen atoms with other functional groups on the aryl that is optionally substituted. Such other functional groups illustratively include, but are not limited to, amino, hydroxyl, halo, thiol, alkyl, haloalkyl, heteroalkyl, aryl, arylalkyl, arylheteroalkyl, nitro, sulfonic acids and derivatives thereof, carboxylic acids and derivatives thereof, and the like. Illustratively, any of amino, hydroxyl, thiol, alkyl, haloalkyl, heteroalkyl, aryl, arylalkyl, arylheteroalkyl, and/or sulfonic acid is optionally substituted.

Illustrative substituents include, but are not limited to, a radical $-(CH_2)_x Z^X$, where x is an integer from 0-6 and $Z^X$ is selected from halogen, hydroxy, alkanoyloxy, including $C_1$-$C_6$ alkanoyloxy, optionally substituted aroyloxy, alkyl, including $C_1$-$C_6$ alkyl, alkoxy, including $C_1$-$C_6$ alkoxy, cycloalkyl, including $C_3$-$C_8$ cycloalkyl, cycloalkoxy, including $C_3$-$C_8$ cycloalkoxy, alkenyl, including $C_2$-$C_6$ alkenyl, alkynyl, including $C_2$-$C_6$ alkynyl, haloalkyl, including $C_1$-$C_6$ haloalkyl, haloalkoxy, including $C_1$-$C_6$ haloalkoxy, halocycloalkyl, including $C_3$-$C_8$ halocycloalkyl, halocycloalkoxy, including $C_3$-$C_8$ halocycloalkoxy, amino, $C_1$-$C_6$ alkylamino, ($C_1$-$C_6$ alkyl)($C_1$-$C_6$ alkyl)amino, alkylcarbonylamino, N—($C_1$-$C_6$ alkyl)alkylcarbonylamino, aminoalkyl, $C_1$-$C_6$ alkylaminoalkyl, ($C_1$-$C_6$ alkyl)($C_1$-$C_6$ alkyl)aminoalkyl, alkylcarbonylaminoalkyl, N—($C_1$-$C_6$ alkyl) alkylcarbonylaminoalkyl, cyano, and nitro; or $Z^X$ is selected from $-CO_2R^4$ and $-CONR^5R^6$, where $R^4$, $R^5$, and $R^6$ are each independently selected in each occurrence from hydrogen, $C_1$-$C_6$ alkyl, and aryl-$C_1$-$C_6$ alkyl.

The term protecting group generally refers to chemical functional groups that can be selectively appended to and removed from functionality, such as amine groups, present in a chemical compound to render such functionality inert to chemical reaction conditions to which the compound is exposed. See. e.g., Greene and Wuts, Protective Groups in Organic Synthesis, 2d edition, John Wiley & Sons, New York, 1991. Numerous amine protecting groups are known in the art. Illustrative examples include the benzyloxycarbonyl (CBz), chlorobenzyloxycarbonyl, t-butyloxycarbonyl (Boc), fluorenylmethoxycarbonyl (Fmoc), isonicotinyloxycarbonyl (i-Noc) groups.

The term "prodrug" as used herein generally refers to any compound that when administered to a biological system generates a biologically active compound as a result of one or more spontaneous chemical reaction(s), enzyme-catalyzed chemical reaction(s), and/or metabolic chemical reaction(s), or a combination thereof. In vivo, the prodrug is typically acted upon by an enzyme (such as esterases, amidases, phosphatases, and the like), simple biological chemistry, or other process in vivo to liberate or regenerate the more pharmacologically active drug. This activation may occur through the action of an endogenous host enzyme or a non-endogenous enzyme that is administered to the host preceding, following, or during administration of the prodrug. Additional details of prodrug use are described in U.S. Pat. No. 5,627,165; and Pathalk et al., Enzymic protecting group techniques in organic synthesis, Stereosel. Biocatal. 775-797 (2000). It is appreciated that the prodrug is advantageously converted to the original drug as soon as the goal, such as targeted delivery, safety, stability, and the like is achieved, followed by the subsequent rapid elimination of the released remains of the group forming the prodrug.

Prodrugs may be prepared from the compounds described herein by attaching groups that ultimately cleave in vivo to one or more functional groups present on the compound, such as —OH—, —SH, —CO$_2$H, —N(R)$_2$. Illustrative prodrugs include but are not limited to carboxylate esters where the group is alkyl, aryl, aralkyl, acyloxyalkyl, alkoxycarbonyloxyalkyl as well as esters of hydroxyl, thiol and amines where the group attached is an acyl group, an alkoxycarbonyl, aminocarbonyl, phosphate or sulfate. Illustrative esters, also referred to as active esters, include but are not limited to 1-indanyl, N-oxysuccinimide; acyloxyalkyl groups such as acetoxymethyl, pivaloyloxymethyl, β-acetoxyethyl, β-pivaloyloxyethyl, 1-(cyclohexylcarbonyloxy) prop-1-yl, (1-aminoethyl)carbonyloxymethyl, and the like; alkoxycarbonyloxyalkyl groups, such as ethoxycarbonyloxymethyl, α-ethoxycarbonyloxyethyl, β-ethoxycarbonyloxyethyl, and the like; dialkylaminoalkyl groups, including di-lower alkylamino alkyl groups, such as dimethylaminomethyl, dimethylaminoethyl, diethylaminomethyl, diethylaminoethyl, and the like; 2-(alkoxycarbonyl)-2-alkenyl groups such as 2-(isobutoxycarbonyl)pent-2-enyl, 2-(ethoxycarbonyl)but-2-enyl, and the like; and lactone groups such as phthalidyl, dimethoxyphthalidyl, and the like.

Further illustrative prodrugs contain a chemical moiety, such as an amide or phosphorus group functioning to increase solubility and/or stability of the compounds described herein. Further illustrative prodrugs for amino groups include, but are not limited to, (C$_3$-C$_{20}$)alkanoyl; halo-(C$_3$-C$_{20}$)alkanoyl; (C$_3$-C$_{20}$)alkenoyl; (C$_4$-C$_7$)cycloalkanoyl; (C$_3$-C$_6$)-cycloalkyl(C$_2$-C$_{16}$)alkanoyl; optionally substituted aroyl, such as unsubstituted aroyl or aroyl substituted by 1 to 3 substituents selected from the group consisting of halogen, cyano, trifluoromethanesulphonyloxy, (C$_1$-C$_3$)alkyl and (C$_1$-C$_3$)alkoxy, each of which is optionally further substituted with one or more of 1 to 3 halogen atoms; optionally substituted aryl(C$_2$-C$_{16}$)alkanoyl, such as the aryl radical being unsubstituted or substituted by 1 to 3 substituents selected from the group consisting of halogen, (C$_1$-C$_3$)alkyl and (C$_1$-C$_3$)alkoxy, each of which is optionally further substituted with 1 to 3 halogen atoms; and optionally substituted heteroarylalkanoyl having one to three heteroatoms selected from O, S and N in the heteroaryl moiety and 2 to 10 carbon atoms in the alkanoyl moiety, such as the heteroaryl radical being unsubstituted or substituted by 1 to 3 substituents selected from the group consisting of halogen, cyano, trifluoromethanesulphonyloxy, (C$_1$-C$_3$)alkyl, and (C$_1$-C$_3$)alkoxy, each of which is optionally further substituted with 1 to 3 halogen atoms. The groups illustrated are exemplary, not exhaustive, and may be prepared by conventional processes.

It is understood that the prodrugs themselves may not possess significant biological activity, but instead undergo one or more spontaneous chemical reaction(s), enzyme-catalyzed chemical reaction(s), and/or metabolic chemical reaction(s), or a combination thereof after administration in vivo to produce the compound described herein that is biologically active or is a precursor of the biologically active compound. However, it is appreciated that in some cases, the prodrug is biologically active. It is also appreciated that prodrugs may often serves to improve drug efficacy or safety through improved oral bioavailability, pharmacodynamic half-life, and the like. Prodrugs also refer to derivatives of the compounds described herein that include groups that simply mask undesirable drug properties or improve drug delivery. For example, one or more compounds described herein may exhibit an undesirable property that is advantageously blocked or minimized may become pharmacological, pharmaceutical, or pharmacokinetic barriers in clinical drug application, such as low oral drug absorption, lack of site specificity, chemical instability, toxicity, and poor patient acceptance (bad taste, odor, pain at injection site, and the like), and others. It is appreciated herein that a prodrug, or other strategy using reversible derivatives, can be useful in the optimization of the clinical application of a drug.

As used herein, the term "treating", "contacting" or "reacting" when referring to a chemical reaction means to add or mix two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the term "composition" generally refers to any product comprising the specified ingredients in the specified amounts, as well as any product which results, directly or indirectly, from combinations of the specified ingredients in the specified amounts. It is to be understood that the compositions described herein may be prepared from isolated compounds described herein or from salts, solutions, hydrates, solvates, and other forms of the compounds described herein. It is also to be understood that the compositions may be prepared from various amorphous, non-amorphous, partially crystalline, crystalline, and/or other morphological forms of the compounds described herein. It is also to be understood that the compositions may be prepared from various hydrates and/or solvates of the compounds described herein. Accordingly, such pharmaceutical compositions that recite compounds described herein are to be understood to include each of, or any combination of, the various morphological forms and/or solvate or hydrate forms of the compounds described herein. Illustratively, compositions may include one or more carriers, diluents, and/or excipients. The compounds described herein, or compositions containing them, may be formulated in a therapeutically effective amount in any conventional dosage forms appropriate for the methods described herein. The compounds described herein, or compositions containing them, including such formulations, may be administered by a wide variety of conventional routes for the methods described herein, and in a wide variety of dosage formats, utilizing known procedures (see generally, Remington: The Science and Practice of Pharmacy, (21$^{st}$ ed., 2005)).

EXAMPLES

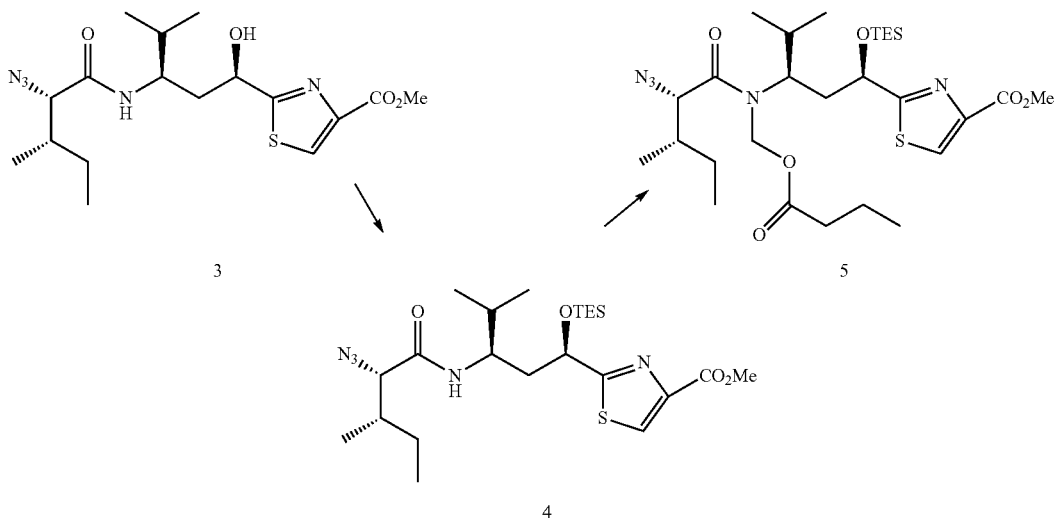

3

4

EXAMPLE. Synthesis of Dipeptide 5. 4.9 g of dipeptide 3 (11.6 mmol) was dissolved in 60 mL dichloromethane, imidazole (0.87 g, 12.7 mmol) was added to the resulting solution at 0° C. The reaction mixture was warmed slightly to dissolve all solids and re-cooled to 0° C. TESCl (2.02 mL, 12.1 mmol) was added drop-wise at 0° C., the reaction mixture was stirred under argon and warmed to room temperature over 2 h. TLC (3:1 hexanes/EtOAc) showed complete conversion. The reaction was filtered to remove the imidazole HCl salt, extracted with de-ionized water, and the aqueous phase was back-washed with dichloromethane, the combined organic phase was washed with brine, dried over $Na_2SO_4$, filtered to remove the $Na_2SO_4$, concentrated under reduced pressure, co-evaporated with toluene and dried under high-vacuum overnight to give 6.4 g of crude product 4 (vs 5.9 g of theoretical yield).

The crude product 4 was co-evaporated with toluene again and used without further purification. TES protected dipeptide was dissolved in 38 mL THF (anhydrous, inhibitor-free) and cooled to −45° C. and stirred for 15 minutes before adding KHMDS (0.5 M in toluene, 25.5 mL, 12.8 mmol, 1.1 equiv) drop-wise. After the addition of KHMDS was complete, the reaction mixture was stirred at −45° C. for 15 minutes, and chloromethyl butyrate (1.8 mL, 1.2 equiv, 14 mmol) was added. The reaction mixture changed from light yellow to a bluish color. TLC (20% EtOAc/petroleum ether) showed the majority of starting material was converted. LC-MS showed about 7% starting material left. The reaction was quenched by adding 3 mL MeOH, the mixture was warmed to room temperature and concentrated under reduced pressure to an oily residue. The residue was dissolved in petroleum ether and passed through short silica plug to remove the potassium salt. The plug was washed with 13% EtOAc/petroleum ether, and the collected eluates were combined and concentrated under reduced pressure. The crude alkylated product was passed through an additional silica plug (product/silica=1:50) and eluted with 13% EtOAc/petroleum ether to remove residual starting material to give 5.7 g of product 5 (two steps, yield 76%)

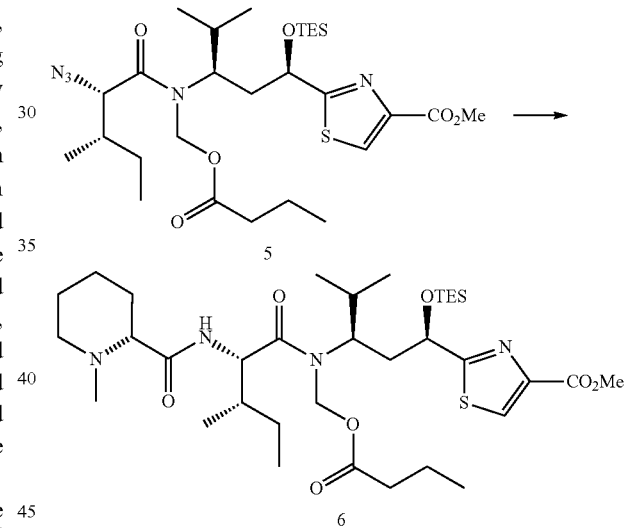

5

6

EXAMPLE. Synthesis of Tripeptide 6. Alkylated dipeptide 5 (4.3 g, 7.0 mmol), N-methyl pipecolinate (MEP) (4.0 g, 28.0 mmol, 4 equiv) and pentafluorophenol (5.7 g, 30.8 mmol. 4.4 equiv) were added to a flask. N-methylpyrrolidone (NMP, 86 mL) was added to the mixture. To the mixture was added diisopropylcarbodiimide (DIC, 4.77 mL, 30.8 mmol, 4.4 equiv) was added to the mixture. The mixture was stirred at room temperature for 1 h. Pd/C (10%, dry, 1.7 g) was added. The flask was shaken under hydrogen (30-35 psi) for 5 hours. The reaction mixture was analyzed by HPLC. The starting material was found to be less than 3%. The mixture was filtered through diatomaceous earth. The diatomaceous earth was extracted with 200 mL ethyl acetate. The filtrate and the ethyl acetate extract were combined and transferred to a separatory funnel and washed with 1% $NaHCO_3$/10% NaCl solution (200 mL×4). The organic layer was isolated and evaporated on a rotary evaporator under reduced pressure. The crude product was dissolved in 40 mL of MeOH/$H_2O$ (3:1). The crude product solution was loaded onto a Biotage C18 column (Flash 65i, 350 g, 450 mL, 65×200 mm) and eluted with buffer A [10 mM $NH_4OAc$/ACN (1:1)] and B (ACN, acetonitrile). The fractions were collected and organic solvent was removed by evaporating on a rotary evaporator. 100 mL of 10% NaCl solution and 100 mL of methyl tert-butyl ether (MTBE) were added to the flask and the mixture was transferred to a separatory funnel. The organic layer was isolated and dried over anhydrous Na₂SO₄, filtered and evaporated on a rotary evaporator to dryness. 2.5 g of tripeptide intermediate 6 was obtained (yield 50%).

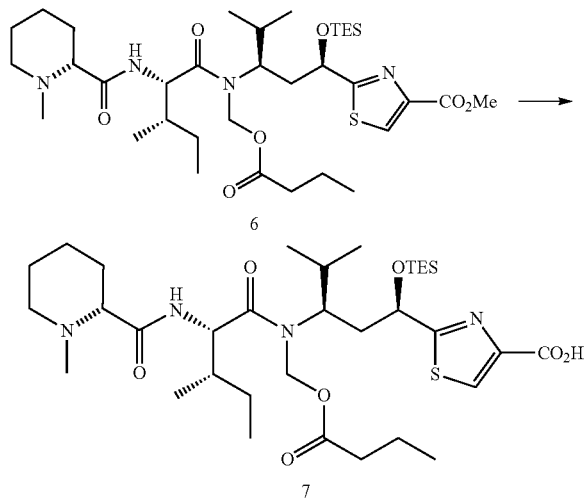

EXAMPLE. Synthesis of Tripeptide Acid 7. To 2 L of 0.05 M phosphate (pH=7.4) at 30° C. was added 3.6 g of porcine liver esterase (17 units/mg). 3.0 g of methyl ester 6 was dissolved in 100 mL of DMSO. The first 50 mL of this solution was added at a rate of 1.1 mL/h, and the second half was added at a rate of 1.2 mL/h via syringe pump. After the addition was complete, the reaction mixture was allowed to stir at 30° C. for several hours. HPLC of an EtOAc extract of the reaction mixture showed the reaction was complete. The reaction mixture was drained from the reactor in 1 L portions and extracted with EtOAc (3×1 L). The combined extracts were washed with brine, dried over Mg₂SO₄ and concentrated under reduced pressure. 2.8 g of product 7 was recovered (95%). The product appeared to be clean by UPLC analysis, except for pentafluorophenol carried over from the previous reaction.

Intermediate 7 spectral data: LCMS (ESI) [M+H]⁺ 697.3; ¹H NMR (CD3OD) 8.02 (s, 1H), 5.94 (d, J=12.3 Hz, 1H), 5.48 (d, J=12.3 Hz, 1H), 4.93 (d, J=8.2 Hz, 1H), 4.65 (d, J=8.5 Hz, 1H), 3.63 (s, br, 1H), 2.91 (br, 1H), 2.67 (s, 3H), 2.53-2.14 (m, 3H), 2.14-1.94 (m, 4H), 1.94-1.74 (m, 4H), 1.74-1.50 (m, 4H), 1.28-1.17 (m, 1H), 1.02-0.83 (m, 24H), 0.71-0.55 (m, 6H).

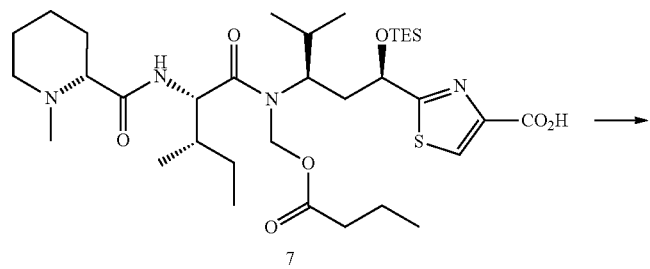

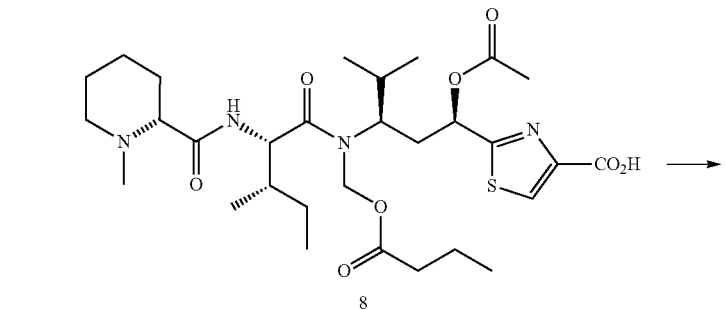

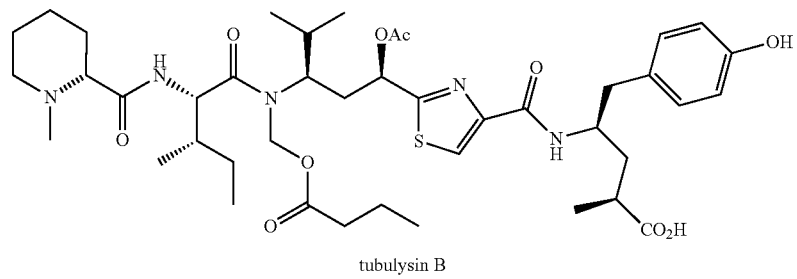

tubulysin B

EXAMPLE. Synthesis of Tubulysin B. 1.4 g (2.01 mmol) of tripeptide 7 was dissolved in 8.4 mL THF and 327.4 μL (2.01 mmol) of 3HF.NEt$_3$ was added and the reaction mixture stirred for 30 minutes. LC-MS analysis (10% to 100% acetonitrile, pH 7 buffer) confirmed complete deprotection of the TES group. THF was removed under reduced pressure. The residue was dried under high vacuum for 5 minutes. The crude product was dissolved in 8.4 mL dry pyridine. 2.85 mL (30.15 mmol, 15 equiv) of Ac$_2$O was added at 0° C. The resulting clear solution was stirred at room temperature for 3.5 hours. LC-MS analysis (10% to 100% acetonitrile, pH 7.0) indicated >98% conversion. 56 mL of dioxane/H$_2$O was added and the resulting mixture stirred at room temperature for 1 hour. The mixture was concentrated under reduced pressure. The residue was co-evaporated with toluene (3×) and dried under high vacuum overnight. Crude product 8 was used directly for the next reaction.

Intermediate 8 spectral data: LCMS (ESI) [M+H]$^+$ 625.2; $^1$H NMR (CD3OD) 8.00 (s, 1H), 6.00 (s, br, 1H), 5.84 (d, J=12.1 Hz, 1H), 5.40 (d, J=12.1 Hz, 1H), 4.63 (d, J=9.1 Hz, 1H), 3.09 (br, 1H), 2.60-2.20 (m, 7H), 2.12 (s, 3H), 2.09-1.86 (m, 3H), 1.80-1.63 (m, 3H), 1.59 (m, 5H), 1.19 (m, 1H), 1.03-0.81 (m, 15H); $^{13}$C NMR (CD3OD) 176.2, 174.2, 172.1, 169.1, 155.5, 125.2, 71.4, 69.6, 56.6, 55.5, 44.3, 37.7, 37.1, 36.4, 32.0, 31.2, 25.6, 23.7, 21.0, 20.9, 20.7, 19.3, 16.5, 14.2, 11.0 reduced pressure, extracted with EtOAc (3×), and dried over Na$_2$SO$_4$. The EtOAc was removed under reduced pressure and the residue was dried under high vacuum for 1 hour to yield 513 mg of the desired product (31% combined yield from 6).

Method B. Tripeptide 8 (229 mg, 0.367 mmol) was dissolved in EtOAc (anhydrous), 134.9 mg (0.733 mmol, 2.0 equiv) of pentafluorophenol was added, followed by 970 mg (1.84 mmol, 5.0 equiv) of DCC on the resin. The resulting reaction mixture was stirred at room temperature for 16 hours. LC-MS analysis indicated >96% conversion. The reaction mixture was filtered and concentrated to dryness, dried under high vacuum for 5 minutes. The residue was dissolved in 3.5 mL DMF, Tut-HCl (123.9 mg, 0.477 mmol, 1.3 equiv) was added, followed by DIPEA (0.42 mL, 2.386 mmole, 6.5 equiv). The resulting clear solution was stirred at room temperature for 10 minutes. The reaction mixture was diluted with DMSO, purified on prep-HPLC(X-bridge column, 10 mM NH$_4$OAc, 25% to 100%, two runs). The pure fractions were combined, the acetonitrile was removed under reduced pressure, the residue was extracted with EtOAc (2×) and the combined EtOAc extracts dried over Na$_2$SO$_4$. The EtOAc was removed under reduced pressure. The residue was dried under high vacuum for 1 hour to yield 175 mg of desired product (58% combined yield from 6).

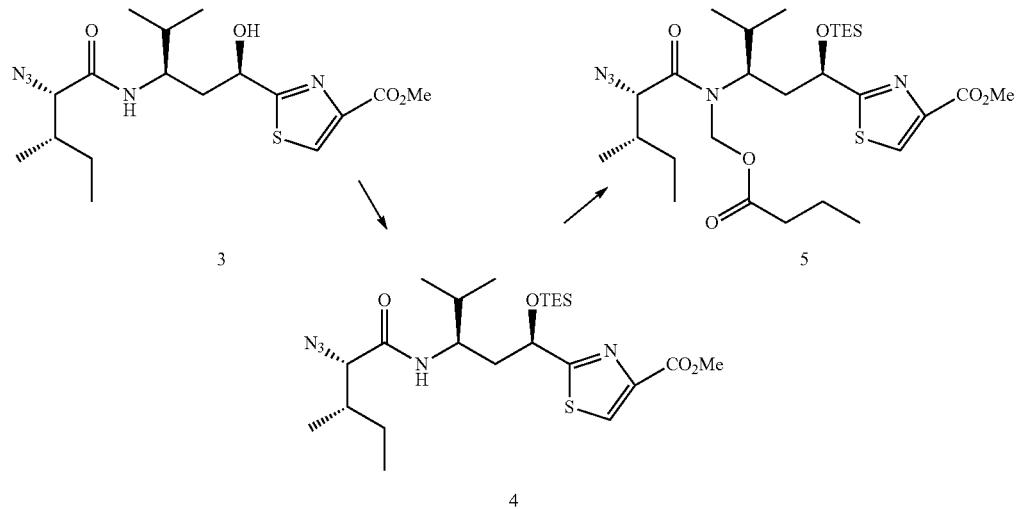

Method A. The crude tripeptide acid 8 was dissolved in 28 mL EtOAc (anhydrous) and 740 mg (4.02 mmol, 2.0 equiv) of pentafluorophenol was added, followed by 1.04 g (5.03 mmol, 2.5 equiv) of DCC. The resulting reaction mixture was stirred at room temperature for 1 hour. LC-MS (5% to 80% acetonitrile, pH=2.0, formic acid) analysis indicated >95% conversion. The urea by-product was filtered off, the EtOAc was removed under reduced pressure, and the residue was dried under high vacuum for 5 minutes. The residue was dissolved in 8.4 mL DMF, and tubutyrosine hydrochloride salt (Tut-HCl, 678.7 mg, 2.61 mmol, 1.3 equiv) was added, followed by DIPEA (2.28 mL, 13.07 mmol, 6.5 equiv). The resulting clear solution was stirred at room temperature for 10 minutes. The reaction mixture was diluted with DMSO and purified on prep-HPLC(X-bridge column, 10 mM NH$_4$OAc, pH=6.3, 25% to 100% acetonitrile). Pure fractions were combined, acetonitrile was removed under EXAMPLE. Large Scale Synthesis of Dipeptide 5. 10.2 g of dipeptide 3 (25.6 mmol) was dissolved in 130 mL dichloromethane, imidazole (1.9 g, 28.1 mmol) was added to the resulting solution at 0° C. The reaction mixture was warmed slightly to dissolve all solids and re-cooled to 0° C. TESCl (4.5 mL, 26.8 mmol) was added drop-wise at 0° C., the reaction mixture was stirred under argon and warmed to room temperature over 2 h. TLC (3:1 hexanes/EtOAc) showed complete conversion. The reaction was filtered to remove the imidazole HCl salt, extracted with de-ionized water, and the aqueous phase was back-washed with dichloromethane, the combined organic phase was washed with brine, dried over Na$_2$SO$_4$, filtered to remove the Na$_2$SO$_4$, concentrated under reduced pressure, co-evaporated with toluene and dried under high-vacuum overnight to give 12.2 g of product 4.

The crude product 4 was co-evaporated with toluene again and used without further purification. TES protected dipeptide was dissolved in 80 mL THF (anhydrous, inhibitor-free) and cooled to −45° C. and stirred for 15 minutes before adding KHMDS (0.5 M in toluene, 50 mL, 25.0 mmol, 1.05 equiv) drop-wise. After the addition of KHMDS was complete, the reaction mixture was stirred at −45° C. for 15 minutes, and chloromethyl butyrate (3.6 mL, 1.2 equiv, 28.3 mmol) was added. The reaction mixture changed from light yellow to a bluish color. TLC (20% EtOAc/petroleum ether) showed the reaction was complete. The reaction was quenched by adding 20 mL MeOH, the mixture was warmed to room temperature and concentrated under reduced pressure to an oily residue. The residue was dissolved in petroleum ether and passed through short silica plug to remove the potassium salt. The plug was washed with 13% EtOAc/petroleum ether, and the collected eluents were combined and concentrated under reduced pressure to give 12.1 g of product 5 (two steps, yield 76%)

ture was analyzed by HPLC. The reaction was complete. The mixture was filtered through celite. The celite was washed with 500 mL ethyl acetate. The solutions were combined and transferred to a separatory funnel and washed with 1% NaHCO$_3$/10% NaCl solution (250 mL×4). The organic layer was isolated and evaporated on a rotary evaporator under reduced pressure. The crude product was dissolved in dichloromethane and the urea was filtered. The crude product solution was loaded onto a Teledyne Redisep Silica Column (330 g) and purified with EtOAc/petroleum ether on CombiFlash flash chromatography system. The fractions were collected and organic solvent was removed by evaporating to give 5.0 g of the tripeptide (61%). NMR and mass spectral data were consistent with those measured for the Example

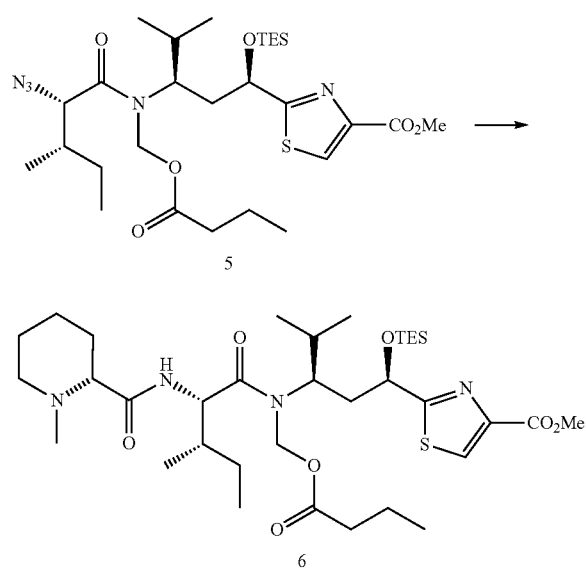

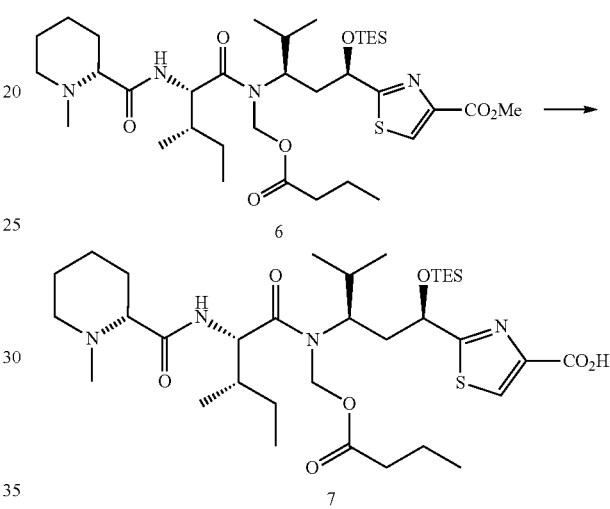

EXAMPLE. Large Scale Synthesis of Tripeptide 6. Alkylated dipeptide 5 (7.6 g, 12.4 mmol), N-methyl pipecolinate (MEP) (7.0 g, 48.9 mmol, 4 equiv) and pentafluorophenol (10.0 g, 54.3 mmol. 4.4 equiv) were added to a flask. N-methylpyrrolidone (NMP, 152 mL) was added to the mixture. To the mixture was added diisopropylcarbodiimide (DIC, 8.43 mL, 54.4 mmol, 4.4 equiv) was added to the mixture. The mixture was stirred at room temperature for 1 h. Pd/C (10%, dry, 3.0 g) was added. The flask was shaken under hydrogen (30-35 psi) for 5 hours. The reaction mix- EXAMPLE. Large Scale Synthesis of Tripeptide Acid 7. To 2 L of 0.05 M phosphate (pH=7.4) at 30° C. was added 3.6 g of porcine liver esterase (17 units/mg). 3.0 g of methyl ester 6 was dissolved in 100 mL of DMSO. The first 50 mL of this solution was added at a rate of 1.1 mL/h, and the second half was added at a rate of 1.2 mL/h via syringe pump. After the addition was complete, the reaction mixture was allowed to stir at 30° C. for several hours. HPLC of an EtOAc extract of the reaction mixture showed the reaction was complete. The reaction mixture was drained from the reactor in 1 L portions and extracted with 94% EtOAc-6% MeOH (vol./vol.) solution (3×1 L). The combined extracts were washed with brine, dried over Na$_2$SO$_4$ and concentrated under reduced pressure. 2.8 g of product 6 was recovered (95%). The product appeared to be clean by UPLC analysis, except for pentafluorophenol carried over from the previous reaction.

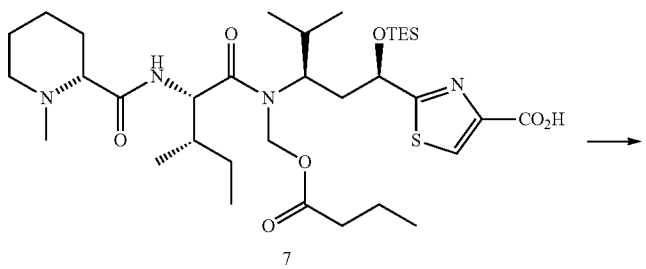

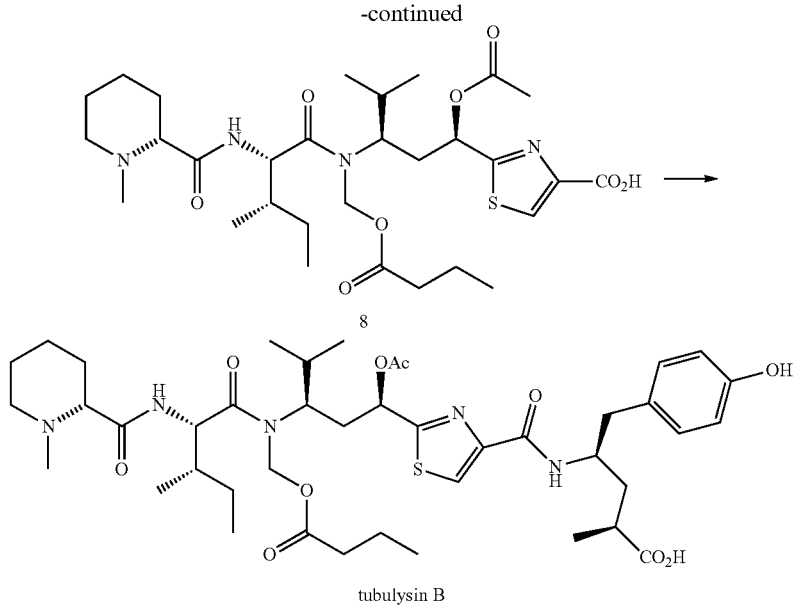

tubulysin B

EXAMPLE. Large Scale Synthesis of Tubulysin B. 3.0 g (4.30 mmol) of tripeptide 7 was dissolved in 18 mL THF and 0.70 mL (4.30 mmol) of 3HF.NEt$_3$ was added and the reaction mixture stirred for 30 minutes. LC-MS analysis (10% to 100% acetonitrile, pH 7 buffer) confirmed complete deprotection of the TES group. THF was removed under reduced pressure. The residue was dried under high vacuum for 5 minutes. The crude product was dissolved in 18 mL dry pyridine. 6.11 mL (64.50 mmol, 15 equiv) of Ac$_2$O was added at 0° C. The resulting clear solution was stirred at room temperature for 5 hours. LC-MS analysis (10% to 100% acetonitrile, pH 7.0) indicated >98% conversion. 117 mL of dioxane/H$_2$O was added and the resulting mixture stirred at room temperature for 1 hour. The mixture was concentrated under reduced pressure. The residue was co-evaporated with toluene (3×) and dried under high vacuum overnight. Crude product 8 was used directly for the next reaction. LCMS (ESI) [M+H]$^+$ 625.2; the NMR spectral data was consistent with structure 8.

Method B. The crude tripeptide acid 8 (2.67 g, 4.30 mmol) was dissolved in 43 mL of DCM (anhydrous), 1.59 g (8.6 mmol, 2.0 equiv) of pentafluorophenol was added, followed by 9.33 g (21.5 mmol, 5.0 equiv) of DCC on the resin. The resulting reaction mixture was stirred at room temperature for 16 hours. LC-MS analysis indicated >96% conversion. The reaction mixture was filtered and concentrated to dryness, dried under high vacuum for 5 minutes. The residue was dissolved in 16.5 mL DMF, Tut-HCl (1.45 g, 5.59 mmol, 1.3 equiv) was added, followed by DIPEA (4.88 mL, 27.95 mmol, 6.5 equiv). The resulting clear solution was stirred at room temperature for 10 minutes. The reaction mixture was purified on prep-HPLC(X-bridge column, 50 mM NH$_4$HCO$_3$, 25% to 100%, six runs). The pure fractions were combined, the acetonitrile was removed under reduced pressure, the residue was extracted with EtOAc (2×) and the combined EtOAc extracts dried over Na$_2$SO$_4$. The EtOAc was removed under reduced pressure. The residue was dried under high vacuum for 1 hour to yield 1.35 g of desired product (38% combined yield from 6). NMR spectral data was consistent with the tubulysin B.

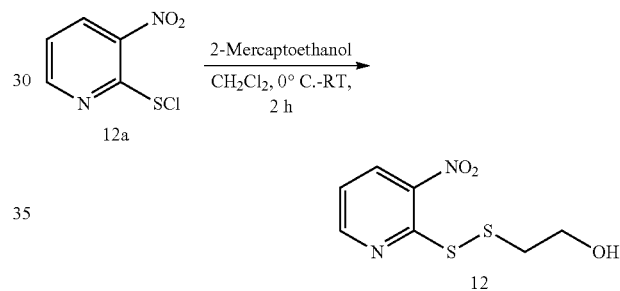

EXAMPLE. Synthesis of 3-nitro-2-disulfenylethanol 12. A three-necked 500 mL flask was dried and argon purged, then fitted with an addition funnel. 3-Nitro-2-sulfenyl chloride pyridine 12a (5.44 g, 27.11 mmol, 1.4 equiv) was added to the flask and dissolved in 200 mL of CH$_2$Cl$_2$. The solution was cooled to 0° C. Mercaptoethanol (1.33 mL, 18.98 mmol) was diluted with 50 mL of CH$_2$Cl$_2$ and placed in the addition funnel. The 2-mercaptoethanol solution was then added drop-wise slowly over the course of 15 minutes. The reaction progress was monitored by TLC (Rf 0.4 in 5% CH$_3$OH/CH$_2$Cl$_2$). Solvent was removed under reduced pressure and dried. The crude product was purified over silica gel (5% CH$_3$OH/CH$_2$Cl$_2$). The fractions were collected and solvent was removed by evaporating on a rotary evaporator and dried. 3.4 g of 3-nitro-2-disulfenylethanol 12 was obtained (77% yield).

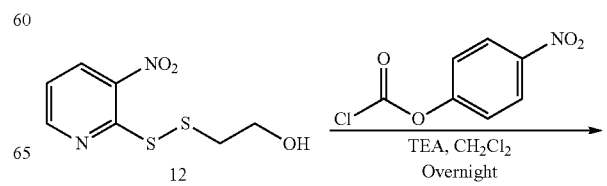

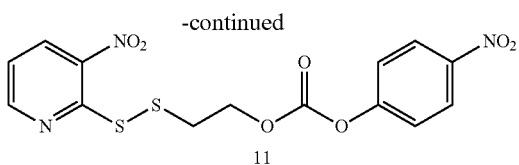

11

EXAMPLE. Synthesis of 4-nitrophenyl-(3'-nitropyridin-2'-yl)disulfenylethyl carbonate 11. A 250 mL Round-Bottomed Flask was dried and argon purged. 3-Nitro-2-disulfenylethanol 12 (3.413 g, 14.69 mmol) was added and dissolved in 45 mL of $CH_2Cl_2$. 4-Nitrophenylchloroformate (3.663 g, 17.63 mmol, 1.2 equiv) was added, along with triethylamine (2.9 mL, 20.57 mmol, 1.4 equiv), and the mixture stirred under argon overnight. The mixture was concentrated under reduced pressure and dried. The residue was purified by silica (30% EtOAc/petroleum ether) and the fractions were collected, solvent was removed under reduced pressure, and dried. 2.7 g of 4-nitrophenyl-(3'-nitropyridin-2'-yl)disulfenylethyl carbonate 11 was obtained (47% yield).

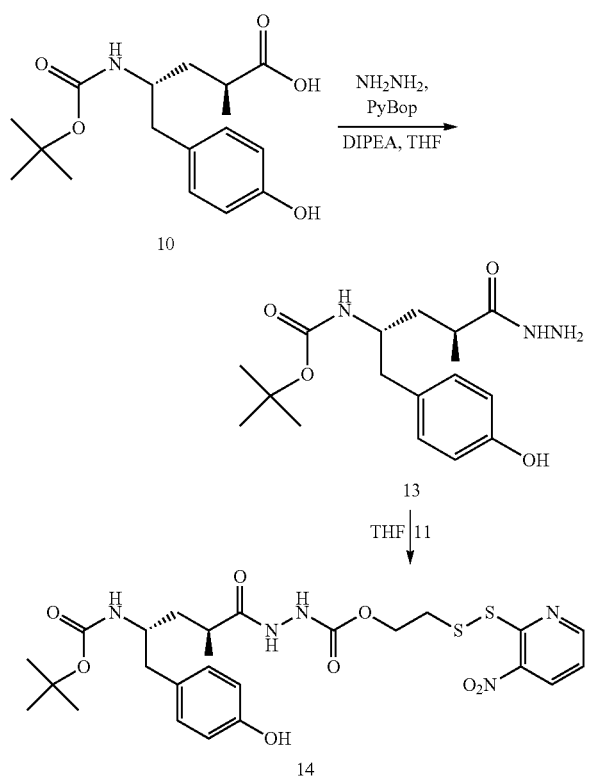

EXAMPLE. Synthesis of 2-(Boc-tubutyrosine (Tut))hydrazinecarboxylic acid (3' nitropyridyl-2'-yl)disulfanylethyl ester 14. 10.67 g (33 mmol) of Boc-Tut-acid 10 was dissolved in 100 mL anhydrous THF, 17.24 g (33 mmol) of PyBop, and 17.50 mL (99 mmol, 3.0 equiv) of DIPEA were added. The reaction mixture stirred for few minutes, 1.0 mL (31.68 mmol, 0.96 equiv) of hydrazine was added and stirred for 15 minutes. LC-MS analysis (X-Bridge shield RP18, 3.5 μm column; gradient 10% to 100% acetonitrile in 6 min, pH 7.4 buffer) confirmed the hydrazide 13 formation. 14.47 g (36.3 mmol, 1.1 equiv) of 4-nitrophenyl-(3'-nitropyridin-2'-yl)disulfenylethyl carbonate 11 was added. The resulting clear solution was stirred at room temperature for 24 hours. LC-MS analysis (X-Bridge shield RP18, 3.5 μm column; gradient 30% to 100% acetonitrile in 9 min, pH 7.4 buffer) indicated >98% conversion. The reaction mixture was diluted with EtOAc (~1.0 L), washed with sat. $NH_4Cl$ (400 mL), sat. $NaHCO_3$ solution (3×300 mL), and brine (300 mL). The organic layer was dried over $Na_2SO_4$ (100 g), and concentrated under reduced pressure. The crude product was loaded onto a Teledyne Redisep Gold Silica Column and eluted with $MeOH/CH_2Cl_2$ (330 g column; 0 to 10% gradient) using a CombiFlash chromatography system. The fractions were collected and solvent was removed under reduced pressure and dried. 16.10 g of 2-(Boc-Tut)hydrazinecarboxylic acid (3' nitropyridyl-2'-yl)disulfanylethyl ester 14 was obtained (82% yield).

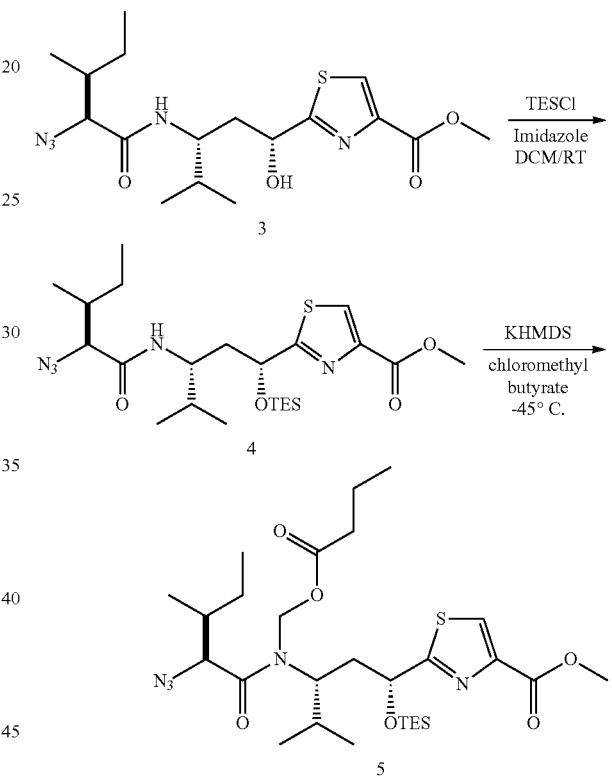

EXAMPLE. Synthesis of azido methylbutyrate dipeptide 5. 10.83 g of dipeptide 3 (27.25 mmol) was dissolved in 100 mL dichloromethane and imidazole (2.05 g, 1.1 eq.) was added. The reaction mixture was stirred at room temperature to dissolve all solids and cooled in the ice bath for 10 min. TESCl (4.8 mL, 1.05 eqiv.) was added drop-wise at 0° C., stirred under argon, and warmed to room temperature over 1.5 h. TLC (3:1 hexanes/EtOAc) showed complete conversion. The reaction was filtered to remove the imidazole HCl salt. 125 mL dichloromethane was added to the filtrate, and the resulting solution was extracted with 250 mL brine. The brine layer was extracted with 125 mL dichloromethane. The combined organic phase was washed with 250 mL brine, separated, dried over 45.2 g of $Na_2SO_4$, and filtered. The resulting solution was concentrated under reduced pressure, co-evaporated with toluene (2×5 mL) and dried over high-vacuum overnight to give 14.96 g of crude product 4.

The crude product 4 was used without further purification. TES protected dipeptide was dissolved in 100 mL THF (anhydrous, inhibitor-free), cooled to −45° C., and stirred at −45° C. for 15 minutes before adding KHMDS (0.5 M in toluene, 61 mL, 1.05 equiv.), drop-wise. After the addition of KHMDS was finished, the reaction was stirred at −45° C. for 20 minutes, and chloromethyl butyrate (4.4 mL, 1.1 equiv.) was added. The reaction mixture was stirred at −45° C. for another 20 minutes. The reaction was quenched with 25 mL MeOH and warmed to room temperature. 250 mL EtOAc and 250 mL brine were added to the reaction mixture, and the organic phase was separated. The solvent was evaporated to reduce the volume of solution. The solution was passed through 76.5 g silica in a 350 mL sintered glass funnel. The silica plug was washed with 500 mL EtOAc/petroleum ether (1:4). The filtrate and the wash were concentrated to oily residue and dried under high vacuum to give 16.5 g product 5 as a light yellow wax.

10 mL of dichloromethane, split into two portions, and purified with a 330 g Teledyne Redisep Silica Gold column. The combined fractions of two purifications were evaporated and dried under high vacuum to give 7.64 g of 6 as a pale yellow solid (overall yield: 39% over 3 steps from compound 3).

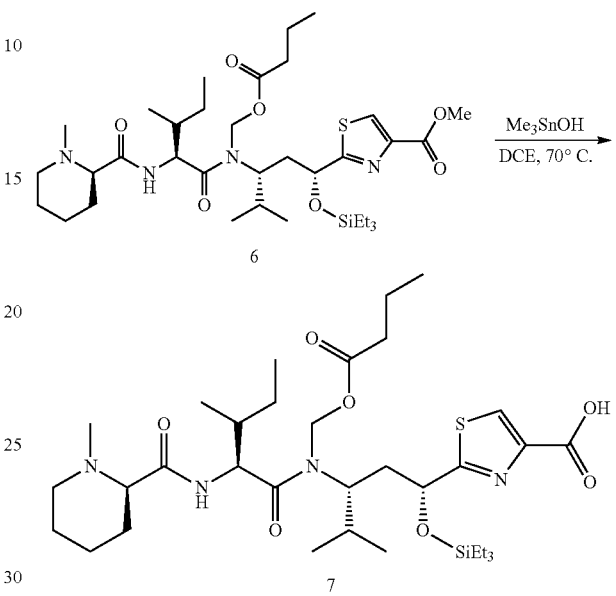

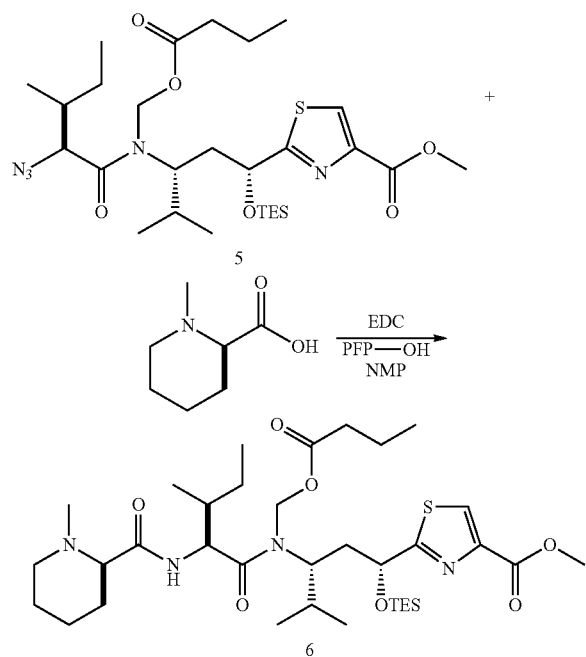

EXAMPLE. Synthesis of tripeptide methyl ester 6. Based on 16.5 g of alkylated dipeptide 5 (26.97 mmol.), N-methyl pipecolinate (MEP) (5.51 g, 1.4 equiv.) and pentafluorophenol (7.63 g, 1.5 equiv.) were added to a 300 mL hydrogenation flask. NMP (115 mL) was then added, followed by EDC (7.78 g, 1.5 equiv.). The mixture was stirred at room temperature for overnight. 16.5 g of alkylated dipeptide 5 was dissolved in 16.5 mL NMP, transferred the solution into the hydrogenation flask, washed the residual 5 with 8 mL NMP, and transferred into the hydrogenation flask. Dry 10% Pd/C (1.45, 0.05 eq.) was added. The reaction mixture was vacuumed/back filled with hydrogen 3 times, and the flask was shaken under hydrogen (~35 psi) for 3.5 hours. The reaction mixture was analyzed by HPLC. The reaction mixture was filtered through 40 g of celite in a 350 mL sintered glass funnel and washed with 250 mL of EtOAc. The filtrate and the wash were transferred to a separatory funnel and washed with a 1% NaHCO₃/10% NaCl solution (200 mL×3). The organic layer was isolated and dried over 45.2 g of Na₂SO₄. The solution was filtered and rotovaped under reduced pressure. A sticky amber residue was obtained and dried under high vacuum overnight to give 19.3 g of crude product. The crude product was dissolved in EXAMPLE. Alternative Synthesis of tripeptide acid 7. Methyl ester 6 (6.9 g, 9.7 mmol) was dissolved in 1,2-dichloroethane (193 mL) and added to a round bottomed flask, equipped with a stir bar and condenser. To this solution was added trimethyltin hydroxide (24.6 g, 14 eq.). The mixture was heated at 70° C. for 5 hours. LC-MS analysis indicated that the desired product had been formed and <15% of starting methyl ester 6 remained. The reaction was cooled in an ice bath for 30 minutes. The resulting precipitate was then removed by filtration. The filtrate was stored overnight at −20° C. The filtrate was then divided into two portions and each was subjected the chromatography procedure which follows.

Each portion was concentrated under reduced pressure and then placed under high vacuum for 30 min. The concentrate was then immediately dissolved in acetonitrile (95 mL). To this solution was then added an ammonium bicarbonate solution (95 mL; 50 mM, pH=7). This solution was loaded onto a Biotage SNAP C18 reverse phase cartridge (400 g, KP-C18-HS) and eluted with 50 mM ammonium bicarbonate and acetonitrile (1:1 to 100% ACN) using a Biotage chromatography system. Fractions were analyzed by LC-MS. Pure fractions were combined and ACN was removed under reduced pressure. The resulting aqueous suspension was extracted with EtOAc (3×). The combined organic layers were washed with brine, dried over anhydrous Na₂SO₄, and concentrated under reduced pressure. Purification of the two portions resulted in the recovery of 7 (4.6 g, 65%).

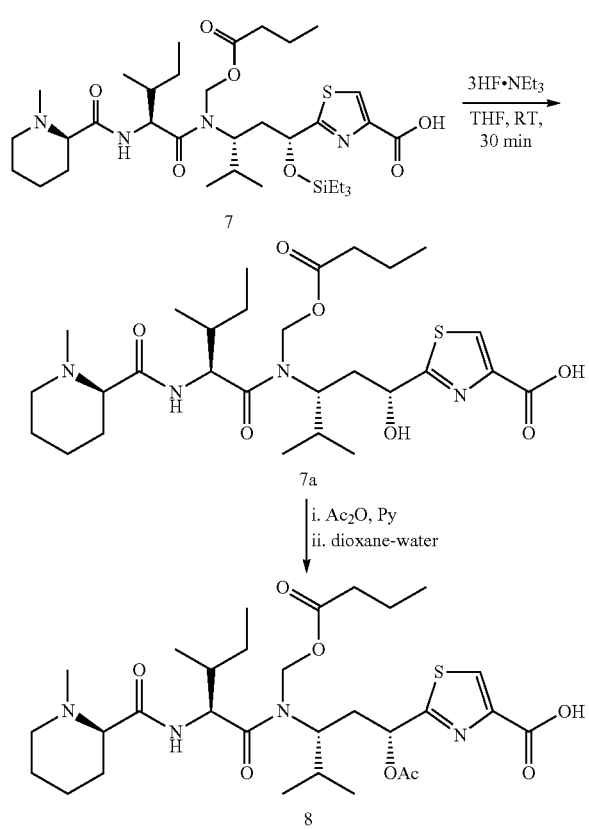

EXAMPLE. Synthesis of acetyl tripeptide acid 8. In a round bottomed flask, tripeptide acid 7 (3.9 g, 5.6 mmol) was dissolved in anhydrous THF (23 mL). To this solution was added 3 HF.TEA complex (1.8 mL, 2 eq.). The reaction was stirred at room temperature for 1 hour. LC-MS analysis indicated complete conversion to the desired des-TES product 7a. The solvent was removed under reduced pressure and the residue was placed on the high vacuum for 40 minutes. The resulting residue was then dissolved in pyridine (26 mL), and acetic anhydride (7.9 mL, 15 eq.) and DMAP (25 mg) were added. The reaction was stirred at room temperature for 1 hour. LC-MS analysis indicated complete conversion to the desired acetyl tripeptide acid 8. To the reaction mixture was then added a 1:1 solution of 1,4-dioxane/water (150 mL). The reaction was stirred for 1 hour at which point the solvents were removed under high vacuum rotovap. To the residue was added toluene and the solvent was removed under vacuum (80 mL, 3×). The resulting crude 8 was dried under high vacuum overnight. The crude material was then dissolved in ACN (72 mL). Sodium phosphate buffer (50 mM, pH=7.8, 288 mL) was then added, and the pH of the resulting suspension was adjusted to neutral using saturated sodium bicarbonate solution. This solution was loaded onto a Biotage SNAP C18 reverse phase cartridge (400 g, KP-C18-HS) and eluted with water and acetonitrile (20% ACN to 65% ACN) using a Biotage chromatography system. Fractions were analyzed by LC-MS. Clean fractions were combined, the ACN was removed, and the aqueous solution was placed on the freeze dryer, resulting in purified acetyl tripeptide 8 (2.5 g, 71%).

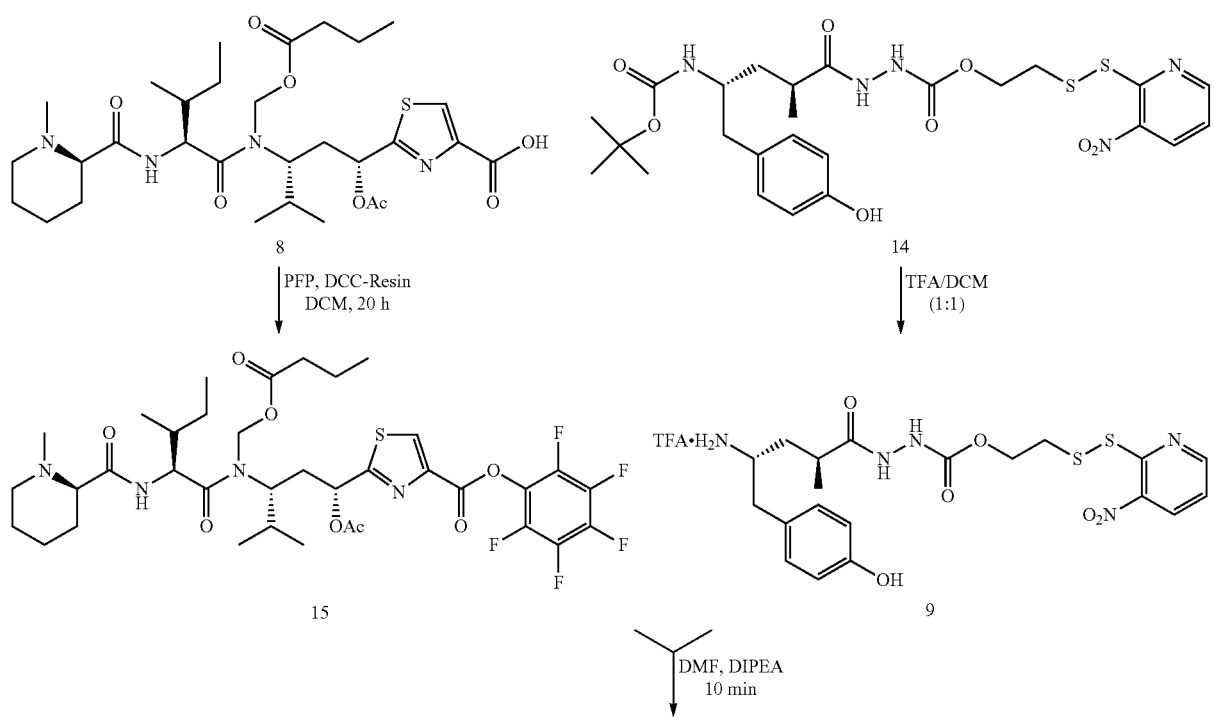

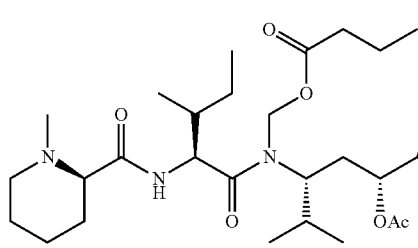
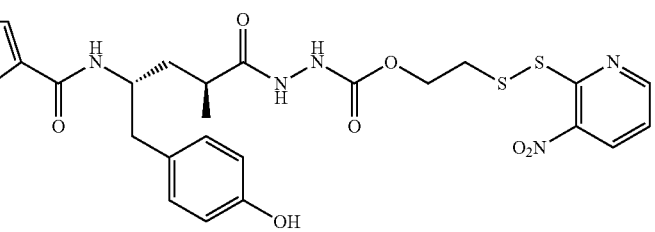

2

EXAMPLE. Synthesis of 2-(tubulysin B)hydrazinecarboxylic acid (3' nitropyridyl-2'-yl)disulfanylethyl ester 2. The activated Boc-Tut-fragment 14 (2.63 g, 4.42 mmol, 1.1 equiv) was treated with TFA/CH$_2$Cl$_2$ (42 mL; 1:1) and stirred for 30 minutes. LC-MS analysis (X-Bridge shield RP18, 3.5 µm column; gradient 10% to 100% acetonitrile in 6 min, pH 7.4 buffer) confirmed the product formation. TFA was removed under reduced pressure, co-evaporated with CH$_2$Cl$_2$ (3×30 mL) and activated Tut-derivative 9 was dried under high vacuum for 18 h. In another flask, the tripeptide acid 8 (2.51 g, 4.02 mmol) was dissolved in 70 mL CH$_2$Cl$_2$ (anhydrous) and 1.48 g (8.04 mmol, 2.0 equiv) of pentafluorophenol in 5 mL of CH$_2$Cl$_2$ was added, followed by 8.74 g (20.1 mmol, 5.0 equiv) of DCC-resin. The resulting reaction mixture was stirred at room temperature for 20 hours. LC-MS analysis (X-Bridge shield RP18, 3.5 µm column; gradient 10% to 100% acetonitrile in 6 min, pH 7.4 buffer) indicated >99% conversion. The DCC-resin was filtered off, the CH$_2$Cl$_2$ was removed under reduced pressure, and the pentafluorophenol activated product 15 was dried under high vacuum for 10 minutes. The residue was dissolved in 16.7 mL DMF, and DIPEA (12.6 mL, 72.36 mmol, 18.0 equiv) was added. Tut-fragment trifluoroacetic acid salt 9 in DMF (8.5 mL) was added slowly over 5 min. The resulting clear solution was stirred at room temperature for 1 h. LC-MS analysis (X-Bridge shield RP18, 3.5 µm column; gradient 10% to 100% acetonitrile in 6 min, pH 7.4 buffer) confirmed the product formation. The reaction mixture was diluted with EtOAc (700 mL), washed with brine (300 mL, 2×100 mL), dried over Na$_2$SO$_4$ (75 g), concentrated, and dried for 15 hours. The crude product was dissolved in CH$_2$Cl$_2$ (25 mL) and loaded onto a Teledyne Redisep Gold Silica Column and eluted with MeOH/CH$_2$Cl$_2$ (330 g column; 0 to 5% gradient) using Combiflash chromatographic system. The fractions were collected and solvent was removed by evaporating on a rotary evaporator and dried. 3.91 g of 2-(tubulysin B)hydrazinecarboxylic acid (3' nitropyridyl-2'-yl)disulfanylethyl ester 2 was obtained (89% yield).

EXAMPLE. General Synthesis of Disulfide Containing Tubulysin Conjugates. A binding ligand-linker intermediate containing a thiol group is taken in deionized water (ca. 20 mg/mL, bubbled with argon for 10 minutes prior to use) and the pH of the suspension was adjusted with aqueous phosphate (bubbled with argon for 10 minutes prior to use) to a pH of about 7.0 (the suspension may become a solution when the pH increased). Additional deionized water is added (ca. 20-25%) to the solution as needed, and to the aqueous solution is added immediately a solution of compound (2) in acetonitrile (ca. 20 mg/mL). The reaction mixture becomes homogenous quickly. After stirring under argon, e.g. for 45 minutes, the reaction mixture is diluted with 2.0 mM sodium phosphate buffer (pH 7.0, ca 150 volume percent) and the acetonitrile is removed under vacuum. The resulting suspension is filtered and the filtrate may be purified by preparative HPLC. Fractions are lyophilized to isolate the conjugates. The foregoing method is equally applicable for preparing other tubulysin conjugates by the appropriate selection of the tubulysin starting compound, including tubulysin starting compounds having a 3-nitropyridin-2-ylthio activating group.

Illustrative binding ligand-linker intermediates are described in WO 2008/112873, the disclosure of which is incorporated herein by reference.

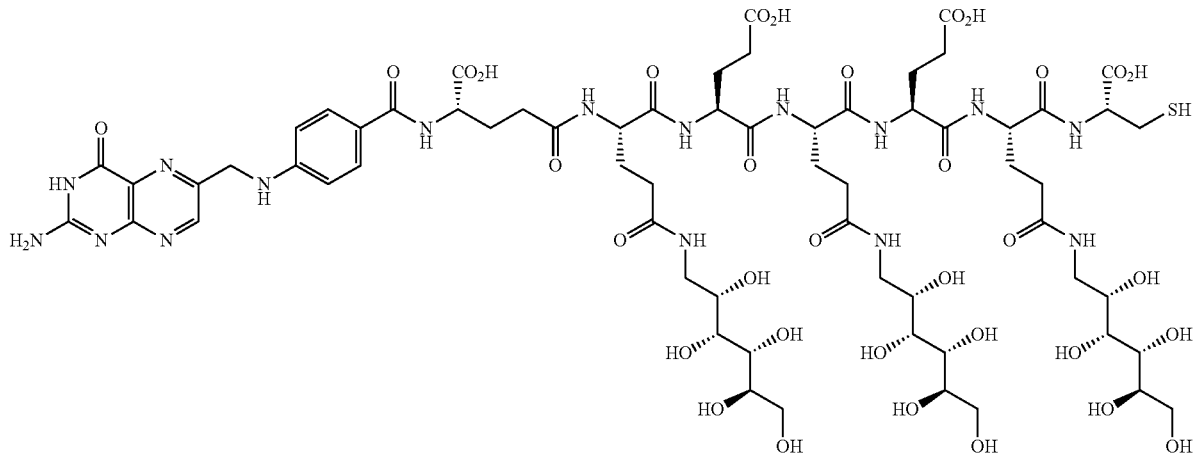 [SMILES: Nc1nc2ncc(CNc3ccc(C(=O)N[C@@H](CCC(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CCC(=O)O)C(=O)N[C@@H](CCC(=O)NC[C@H](O)[C@@H](O)[C@H](O)[C@H](O)CO)C(=O)N[C@@H](CS)C(=O)O)C(=O)O)cc3)nc2c(=O)[nH]1]

EC0488. This binding ligand-linker intermediate was prepared by SPPS according to the general peptide synthesis procedure described herein starting from H-Cys(4-methoxytrityl)-2-chlorotrityl-Resin, and the following SPPS reagents:

| Reagents | mmol | equivalent | MW | amount |
|---|---|---|---|---|
| H-Cys(4-methoxytrityl)-2-chlorotrityl-Resin (loading 0.6 mmol/g) | 0.10 | | | 0.17 g |
| EC0475 | 0.13 | 1.3 | 612.67 | 0.082 g |
| Fmoc-Glu(OtBu)—OH | 0.19 | 1.9 | 425.47 | 0.080 g |
| EC0475 | 0.13 | 1.3 | 612.67 | 0.082 g |
| Fmoc-Glu(OtBu)—OH | 0.19 | 1.9 | 425.47 | 0.080 g |
| EC0475 | 0.13 | 1.3 | 612.67 | 0.082 g |
| Fmoc-Glu-OtBu | 0.19 | 1.9 | 425.47 | 0.080 g |
| $N^{10}$TFA-Pteroic Acid (dissolve in 10 ml DMSO) | 0.16 | 1.6 | 408.29 | 0.066 g |
| DIPEA | | 2.0 eq of AA | | |
| PyBOP | | 1.0 eq of AA | | |

Coupling steps. In a peptide synthesis vessel add the resin, add the amino acid solution, DIPEA, and PyBOP. Bubble argon for 1 hr. and wash 3× with DMF and IPA. Use 20% piperidine in DMF for Fmoc deprotection, 3× (10 min), before each amino acid coupling. Continue to complete all 9 coupling steps. At the end treat the resin with 2% hydrazine in DMF 3× (5 min) to cleave TFA protecting group on Pteroic acid, wash the resin with DMF (3×), IPA (3×), MeOH (3×), and bubble the resin with argon for 30 min.

Cleavage step. Reagent: 92.5% TFA, 2.5% $H_2O$, 2.5% triisopropylsilane, 2.5% ethanedithiol. Treat the resin with cleavage reagent 3× (10 min, 5 min, 5 min) with argon bubbling, drain, wash the resin once with cleavage reagent, and combine the solution. Rotavap until 5 ml remains and precipitate in diethyl ether (35 mL). Centrifuge, wash with diethyl ether, and dry. About half of the crude solid (~100 mg) was purified by HPLC.

HPLC Purification step. Column: Waters Xterra Prep MS C18 10 μm 19×250 mm; Solvent A: 10 mM ammonium acetate, pH 5; Solvent B: ACN; Method: 5 min 0% B to 25 min 20% B 26 mL/min. Fractions containing the product was collected and freeze-dried to give 43 mg EC0488 (51% yield). $^1$H NMR and LC/MS (exact mass 1678.62) were consistent with the product.

EXAMPLE. Synthesis of EC0531.

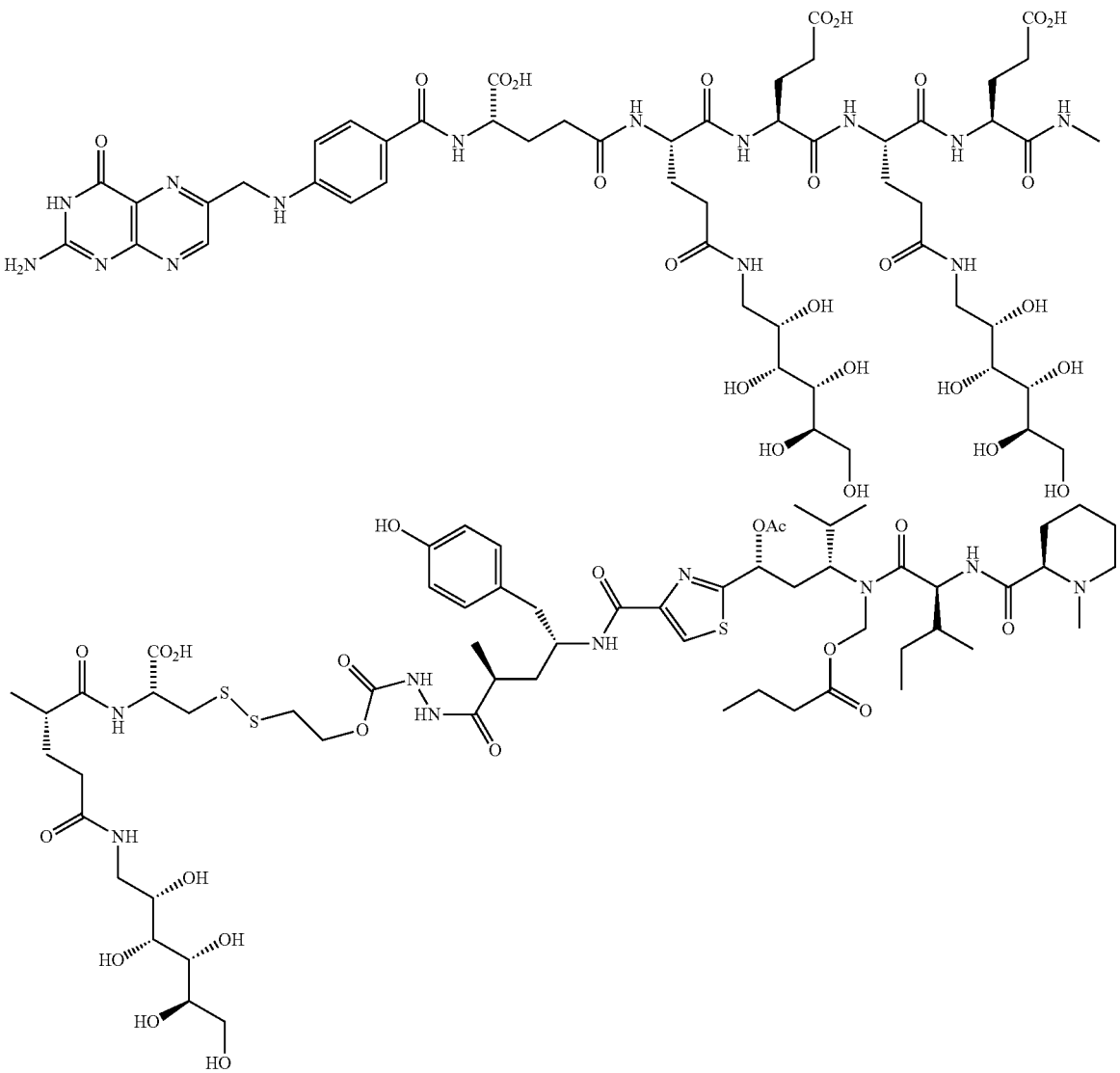

EC0531 is prepared according to the processes described herein from compound (2) and EC0488 in 73% yield.
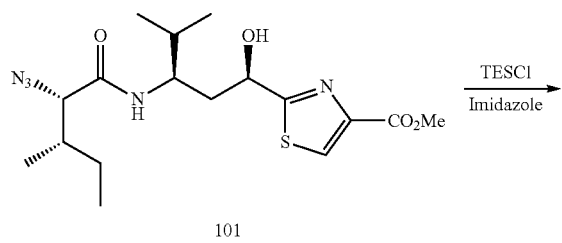
101
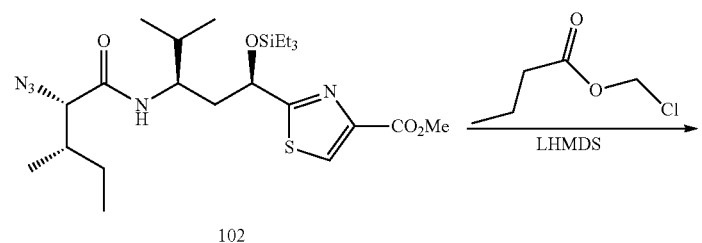
102
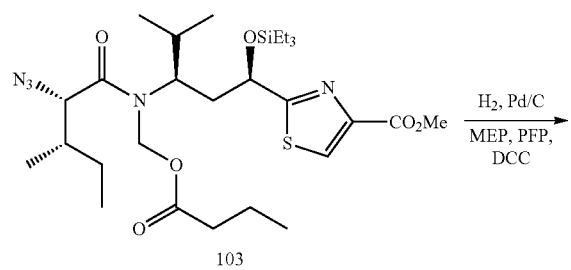
103
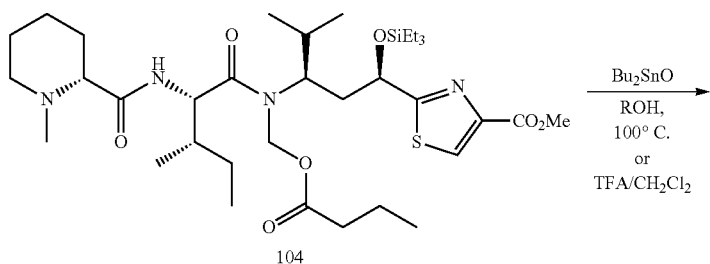
104
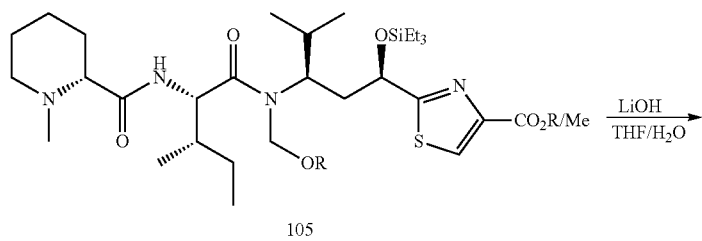
105
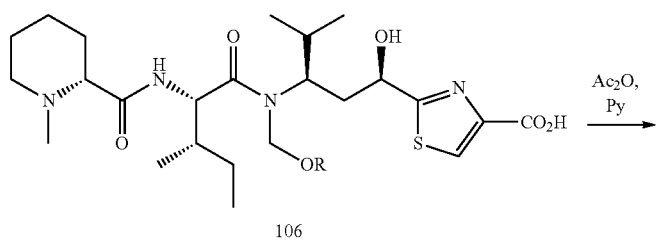
106

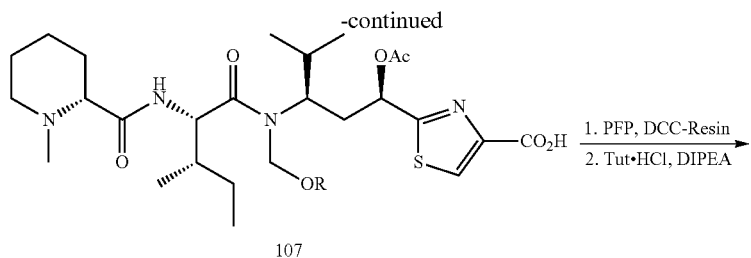

107

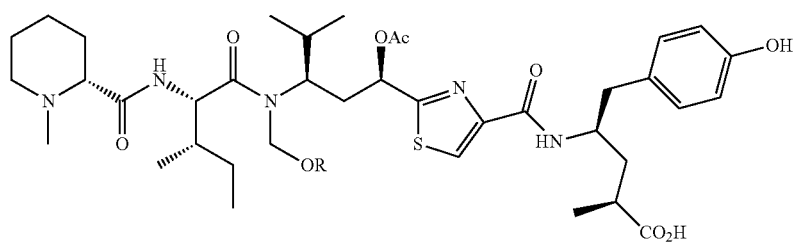

108

R: allyl, CH₂(CH₂)nCH₃, n = 1 2, 3, 4, 5, or 6I

The ether analog of compound 103 can also be prepared. Reductive condensation of that ether analog with MEP yields 105 directly.

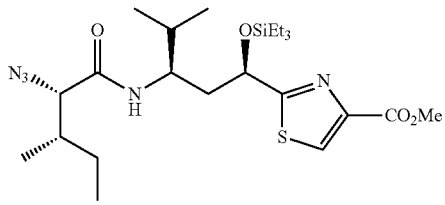

102

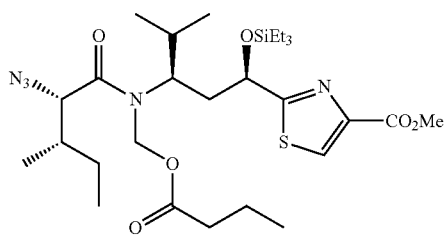

103

EXAMPLE. Compound 102. 4.9 g of dipeptide 101 (11.6 mmol) was dissolved in dichloromethane (60 mL) and imidazole (0.87 g, 12.7 mmol) was added to the resulting solution at 0° C. The reaction mixture was warmed slightly to dissolve all the solids and cooled back to 0° C. Triethylsilyl chloride (TESCl) (2.02 mL, 12.1 mmol) was added drop-wise at 0° C., stirred under argon, and warmed to room temperature over 2 h. TLC (3:1 hexanes/EtOAc) showed complete conversion. The reaction was filtered to remove the imidazole HCl salt, extracted with de-ionized water, and the aqueous phase was back-washed with dichloromethane. The combined organic phase was washed with brine, dried over Na₂SO₄, filtered, and concentrated under reduced pressure. The resulting residue was co-evaporated with toluene and dried over high-vacuum overnight to give 6.4 g of crude product 102 (5.9 g theoretical yield).

EXAMPLE. Compound 103. The crude product 102 was co-evaporated with toluene again and then dissolved in THF (38 mL, anhydrous, inhibitor-free), cooled to −45° C., and stirred for 15 minutes before adding potassium hexamethyldisilazide (KHMDS) (0.5 M in toluene, 25.5 mL, 12.8 mmol, 1.1 equiv), drop-wise. After the addition of KHMDS was finished, the reaction was stirred at −45° C. for 15 minutes, and chloromethyl butyrate (1.8 mL, 1.2 equiv, 14 mmol) was added. The reaction mixture changed from light yellow to a blueish color. TLC (20% EtOAc/petroleum ether) showed the majority of starting material converted. LC-MS showed about 7% starting material left. The reaction was quenched by adding MeOH (3 mL), warmed to room temperature, and concentrated to an oily residue. The residue was dissolved in petroleum ether and passed through short silica plug. The plug was washed with 13% EtOAc/petroleum ether, and the eluents was concentrated. The alkyated product was passed through silica plug (product/silica=1:50) and washed by 13% EtOAc/petroleum ether to remove residual starting material to give 5.7 g of product 103 (two steps with yield 76%).

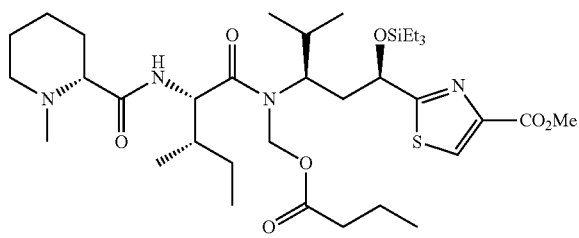

104

EXAMPLE. Compound 104. Alkylated dipeptide 103 (4.3 g, 7.0 mmol), N-methyl pipecolinate (MEP) (4.0 g, 28.0 mmol, 4 equiv), and pentafluorophenol (PFP) (5.7 g, 30.8 mmol. 4.4 equiv) were added to a flask. N-Methyl-2-pyrrolidone (NMP) (86 mL) was then added, followed by N,N'-diisopropylcarbodiimide (DIC) (4.77 mL, 30.8 mmol, 4.4 equiv). The mixture was stirred at room temperature for 1 h. Pd/C (10%, dry, 1.7 g) was added. The flask was shaken under hydrogen (30-35 psi) for 5 hours. The reaction mixture was analyzed by HPLC. The starting material was found to be less than 3%. The mixture was filtered through celite. The celite was washed with ethyl acetate (200 mL). The combined filtrate was transferred to separatory funnel and washed with 1% NaHCO$_3$/10% NaCl solution (200 mL×4). The organic layer was isolated and rotavaped under reduced pressure. The crude product was dissolved in 40 mL of MeOH/H$_2$O (3:1). The crude product solution was loaded onto a Biotage C18 column (Flash 65i, 350 g, 450 mL, 65×200 mm) and eluted with buffer A [10 mM NH$_4$OAc/ACN (1:1)] and B (ACN). The fractions were collected and organic solvent was removed under reduced pressure. A 10% NaCl solution (100 mL) and methyl t-buyl ether (MTBE) (100 mL) were added to the flask and the mixture was transferred to a separatory funnel. The organic layer was isolated and dried over anhydrous Na$_2$SO$_4$, filtered, and concentrated under reduced pressure. 2.5 g of tripeptide intermediate 104 was obtained (yield 50%).

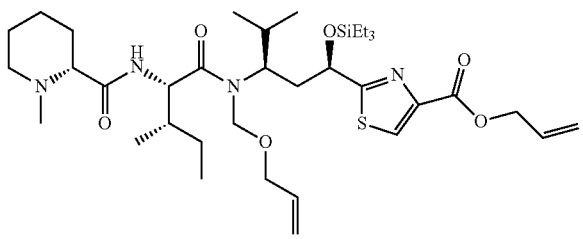

105a

EXAMPLE. Compound 105a. Compound 104 (50 mg, 0.07 mmol) in allyl alcohol (5 mL) was treated with di-n-butyltin oxide (1.75 mg, 0.007 mmol, 10% mol). The reaction mixture was heated to reflux for 22 hrs till the reaction was complete. The reaction was concentrated and purified with HPLC in 10-100% ACN/NH$_3$HCO$_3$ buffer (pH7.0) to give the title compound (32.4 mg, yield 65%). LCMS: [M+H]$^+$ m/z=707.73. $^1$H NMR (CD$_3$OD, δ in ppm): 8.35 (s, 1H), 6.01 (m, 2H); 5.2-5.5 (m, 3H), 5.14 (d, J=10.26 Hz, 1H), 5.04 (d, J=5.87 Hz, 1H), 4.88 (s, 3H), 4.82 (d, J=5.5 Hz, 2H), 4.70 (d, J=8.79 Hz, 1H), 4.50 (d, J=10.26 Hz, 1H), 4.42 (b, 1H), 4.06 (s, 2H), 2.92 (d, J=11.36 Hz, 1H), 2.55 (d, J=9.17 Hz, 1H), 1.95-2.20 (m, 7H), 1.45-1.82 (m, 7H), 1.22 (m, 2H), 0.82-1.00 (m, 17H), 0.77 (d, J=6.23 Hz, 3H), 0.59-0.70 (m, 6H); $^{13}$C NMR (CD$_3$OD, δ in ppm): 176.97, 175.08, 174.09, 160.95, 146.02, 134.13, 132.05, 127.94, 117.38, 116.37, 73.85, 70.32, 69.14, 68.40, 65.34, 56.89, 55.20, 53.55, 43.35, 40.37, 36.38, 31.59, 30.15, 24.80, 24.27, 22.93, 19.09, 18.71, 15.31, 9.52, 5.77, 4.41.

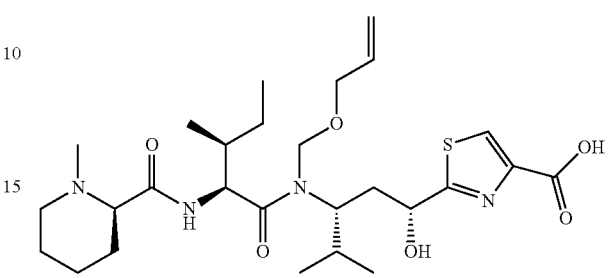

106a

EXAMPLE. Compound 106a. Compound 105a (15.3 mg, 0.02 mmol) was subjected to hydrolysis with LiOH.H$_2$O (0.99 mg, 0.024 mmol) in 4:1 THF/H$_2$O (2.5 mL) for 19 hrs at room temperature (rt). The reaction was purified with HPLC in 10-100% ACN/NH$_3$HCO$_3$ buffer (pH7.0) to provide compound 106a (9.2 mg, yield 83%). LCMS: [M+H]$^+$ m/z=553.55. $^1$H NMR (CD$_3$OD, δ in ppm): 7.94 (s, 1H), 6.00 (m, 1H), 5.1-5.4 (m, 3H), 4.68 (d, J=9.09 Hz, 2H), 4.10 (d, J=3.81 Hz, 2H), 2.80 (b, 1H), 2.56 (s, 2H), 1.4-2.2 (m, 1H), 1.20 (m, 1H), 0.80-0.99 (m, 13H); $^{13}$C NMR (CD$_3$OD, δ in ppm): 17.90, 167.53, 153.18, 134.05, 123.09, 116.53, 68.63, 67.25, 54.85, 54.44, 42.10, 37.75, 36.53, 30.60, 29.13, 24.26, 23.25, 21.37, 20.32, 19.53, 14.72, 9.51.

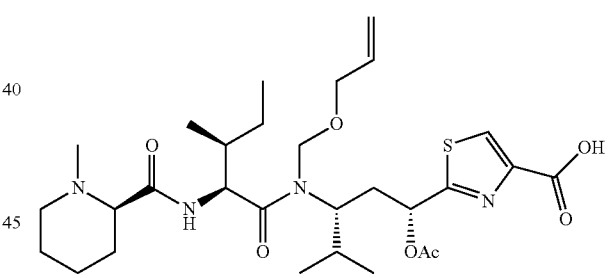

107a

EXAMPLE. Compound 107a. To compound 106a (9.2 mg, 0.017 mmol) in pyridine (1 mL) was added acetic anhydride (15.7 μL, 0.165 mmol) and a catalytic amount of 4-dimethylamino pyridine (0.053 M in pyridine, 5 μL) at rt under argon. The reaction was stirred for 24 hrs. To the reaction mixture was added 0.4 mL of dioxane/water (1:1) and stirred for 10 min, and then the solvent was removed in vacuo. The residue was purified with HPLC in 10-100% ACN/NH$_3$HCO$_3$ buffer (pH7.0) to provide the product 7a 10.4 mg (quantitative yield).

LCMS: [M+H]$^+$ m/z=595.59. $^1$H NMR (CD$_3$OD, δ in ppm): 7.96 (s, 1H), 5.8-6.0 (m, 2H), 5.33 (d, J=17.59 Hz, 1H), 5.19 (d, J=10.56 Hz, 1H), 4.71 (d, J=9.23 Hz, 2H), 4.05 (d, J=5.71 Hz, 2H), 3.30 (m, 6H), 2.50 (b, 4H), 2.10 (s, 3H), 1.40-2.00 (m, 7H), 1.20 (m, 1H), 0.80-1.02 (m, 11H); $^{13}$C NMR (CD$_3$OD, δ in ppm): 175.11, 170.44, 167.29, 153.45, 133.92, 123.40, 116.79, 116.55, 68.62, 67.82, 67.11, 54.75, 54.16, 42.39, 36.31, 36.12, 34.91, 30.55, 29.26, 24.09, 23.26, 21.25, 20.24, 19.48, 19.20, 14.78, 9.56.

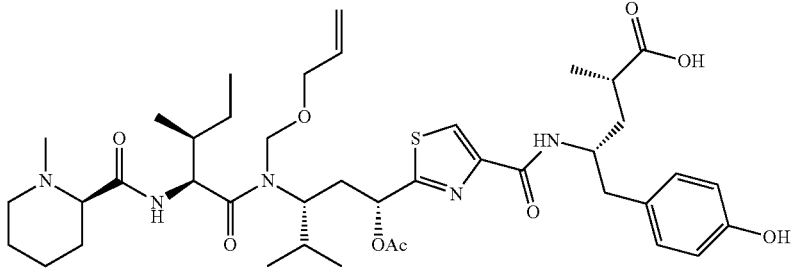

108a

EXAMPLE. Compound 107a (10.4 mg, 0.017 mmol) was dissolved in anhydrous methylene chloride (4 mL) and to this solution was added DCC-resin (2.3 mmol/g, 0.038 g, 0.087 mmol) and followed by pentafluorophenol (PFP, 6.26 mg, 0.034 mmol) at rt under argon. The reaction was stirred for 19 hrs at rt. The reaction mixture was filtered and the solution was concentrated. The residue was redissolved in dry DMF (4 mL). Then, (2S,4R)-4-amino-5-(4-hydroxyphenyl)-2-methylpentanoic acid (Tut acid) was added into the solution, followed by DIPEA (8.9 μL, 0.051 mmol). When completed, the reaction was concentrated in vacuo and the residue was purified with HPLC. Product 108a was obtained (13.1 mg, 96% yield). LCMS: [M+H]+ m/z=800.88. $^1$H NMR (CD$_3$OD, δ in ppm): 8.08 (s, 1H), 7.02 (d, J=8.43 Hz, 2H), 6.68 (d, J=8.06 Hz, 2H), 5.99 (d, J=10.99 Hz, 1H), 5.80 (m, 1H), 5.38 (d, J=9.53 Hz, 1H), 5.31 (d, J=17.23 Hz, 1H), 5.13 (d, J=10.63 Hz, 1H), 4.66 (d, J=8.79 Hz, 1H), 4.55 (d, J=10.28 Hz, 1H), 4.30 (b, 2H), 4.00 (b, 2H), 3.16 (b, 2H), 2.80 (d, J=5.86 Hz, 2H), 2.40 (b, 4H), 2.10-2.30 (b, 2H), 1.40-1.90 (b, 6H), 1.23 (s, 3H), 1.17 (d, J=6.96 Hz, 3H), 1.05 (d, J=6.23 Hz, 2H), 0.94 (d, J=6.97 Hz, 2H), 0.90 (d, J=7.70 Hz, 2H), 0.79 (d, J=6.6 Hz, 3H); $^{13}$C NMR (CD$_3$OD, δ in ppm): 179.24, 174.88, 170.97, 170.43, 170.20, 161.29, 155.62, 149.30, 133.70, 130.23, 128.44, 123.54, 116.41, 114.72, 69.92, 68.15, 67.87, 54.96, 53.92, 49.27, 42.40, 39.62, 37.72, 36.91, 36.08, 35.29, 31.01, 29.51, 29.33, 24.08, 23.72, 21.93, 19.40, 19.34, 18.89, 17.24, 15.00, 9.34.

EXAMPLE. Compound 114a. Compound 107a (26.4 mg, 0.044 mmol) was dissolved in anhydrous methylene chloride (5 mL) and to this solution was added DCC-resin (2.3 mmol/g, 0.096 g, 0.22 mmol), followed by pentafluorophenol (PFP, 16.4 mg, 0.089 mmol) at rt under argon. The reaction was stirred for 19 hrs at rt. The reaction was filtered and concentrated and the residue was redissolved in dry DMF (5 mL). 2-((3-nitropyridin-2-yl)disulfanyl)ethyl 2-((2S,4R)-4-((tert-butoxycarbonyl)amino)-5-(4-hydroxyphenyl)-2-methylpentanoyl)hydrazinecarboxylate (40.0 mg, 0.067 mmol) was deprotected with TFA/DCM (1:1, 5 mL, 1 drop of TIPS as scavenger) at rt for 1 hr. The solvent was removed under reduced pressure, 5 mL more of DCM was added, and then the solvent was co-evaporated to dryness. The residue was dissolved in dry DMF (2 mL) and was added to the solution of PFP ester intermediate in DMF made above after the addition of DIPEA (23.2 μL, 0.13 mmol) at rt under argon. The reaction was stirred for 19 hrs and diluted with EtOAc (20 mL). The organic phase was washed with water (5 mL×3) and brine. The organic layer was dried over anhydrous Na$_2$SO$_4$ and concentrated after filtration to give the crude product 114a (52.8 mg), which could be used for conjugation with folate. LCMS: [M+H]+ m/z=1072.92.

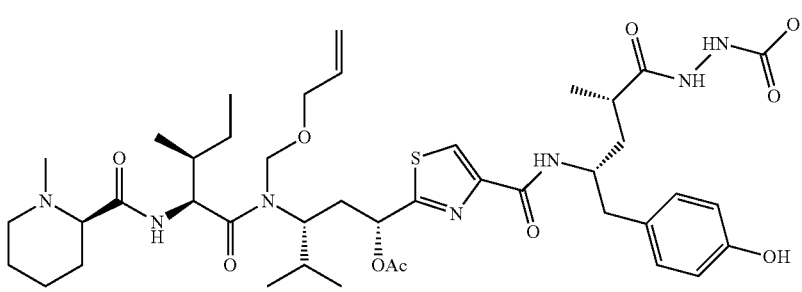

114a

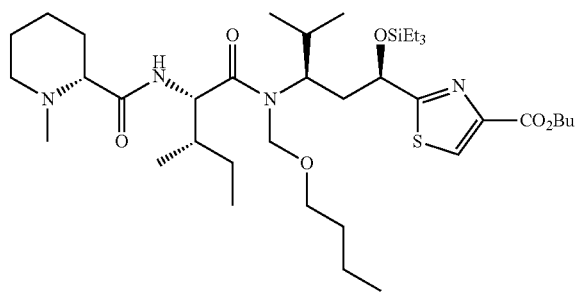

105b

EXAMPLE. Compound 105b. Compound 4 (75.9 mg, 0.11 mmol) in n-butanol (4 mL) was treated with n-Bu₂SnO (2.12 mg, 0.0085 mmol, 8.0 mol %) at rt and the reaction was heated to 100° C. for 2 days. The solvent was reduced to a minimum and the product was purified with CombiFlash (Teledyne Redisep Silica column, eluted with 0 to 15% of MeOH/DCM) to give 44.0 mg (56%) of intermediate 105b. LCMS: [M+H]$^+$ m/z=739.61. $^1$H NMR (CDCl$_3$, δ in ppm): 8.07 (s, 1H), 7.02 (d, J=9.68 Hz, 1H), 5.27 (d, J=9.67 Hz, 1H), 5.02 (dd, J=8.36, 2.64 Hz, 1H), 4.69 (t, J=9.23 Hz, 4.20-4.40 (m, 4H), 3.47 (td, J=6.6, 1.76 Hz, 2H), 2.88 (d, J=11.44 Hz, 1H), 2.46 (dd, J=10.55, 3.08 Hz, 2H), 1.90-2.24 (m, 8H), 1.10-1.79 (m, 18H), 0.80-1.00 (m, 19H), 0.58-0.78 (m, 6H).

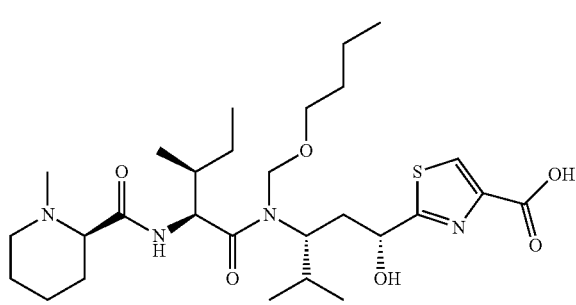

106b

EXAMPLE. Compound 106b. The same procedure as for compound 106a was followed. 106b (11.7 mg, 35%) was obtained from intermediate 105b (44.0 mg). LCMS: [M+H]$^+$ m/z=569.51. $^1$H NMR (CDCl$_3$ drops of CD$_3$OD, δ in ppm) 8.00 (s, 1H), 5.23 (b, 1H), 4.80 (b, 1H), 4.58 (d, J=8.80 Hz, 1H), 4.42 (b, 1H), 3.45 (t, J=6.38 Hz, 1H), 3.33 (b, 3H), 2.15-2.40 (m, 3H), 1.80-2.10 (m, 2H), 1.40-1.79 (m, 4H), 1.04-1.38 (m, 3H), 0.60-1.02 (m, 9H).

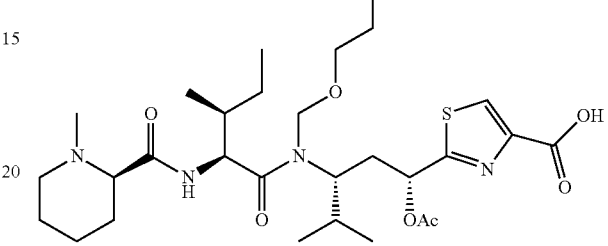

107b

EXAMPLE. Compound 107b. In a 10 mL round bottom flask, 106b (11.7 mg, 0.021 mmol) and acetic anhydride (20 µL, 0.212 mmol) were dissolved in pyridine (1 mL). To this solution was added a catalytic amount of dimethylaminopyridine (1 mg, 0.008 mmol). This solution was stirred at room temperature for 16 h under Argon. LCMS (10-100% ACN, 50 mM NH$_4$HCO$_3$ pH7) indicated all of the starting material had been consumed and product had been formed. To the flask was added a 1:1 mixture of 1,4-dioxane and water (0.4 mL) and the solution was stirred for 10 min to hydrolyze any potential diacetate side product. The reaction mixture was concentrated under reduced pressure, then purified by preparative HPLC (10-100% ACN, 50 mM NH$_4$HCO$_3$ pH7) to yield 107b (9.6 mg, 76%). LCMS: [M+H]$^+$=611.53. $^1$H NMR (CDCl$_3$ w/2 drops CD$_3$OD):
7.97 (s, 1H) 5.83 (d, J=9.9 Hz, 1H) 5.28 (s, 1H) 4.58 (d, J=9.0 Hz, 1H) 4.24 (d, J=9.3 Hz, 2H) 3.42 (m, 3H) 2.60-2.95 (br, 7H) 2.20-2.58 (br, 6H) 1.76-2.20 (br, 11H) 1.40-1.56 (br, 12H) 1.02-1.20 (br, 12H) 0.40-1.10 (br, 27H) 0.04 (s, 8H). $^{13}$C NMR: 175.04, 170.53, 67.78, 53.74, 44.33, 36.79, 35.64, 31.69, 29.89, 24.86, 20.96, 20.49, 19.52, 15.95, 13.99, 10.65, 1.21

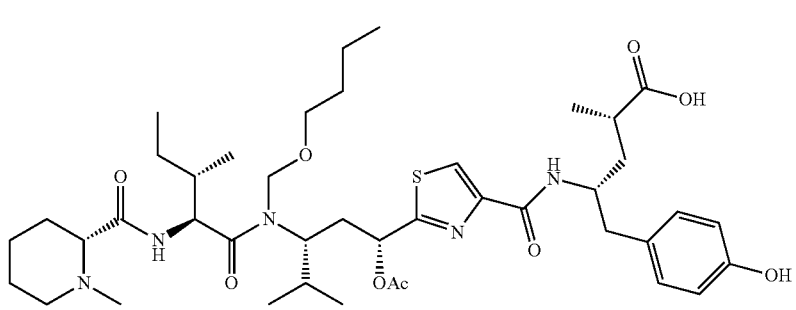

8b

EXAMPLE. Compound 108b. In a 25 mL round bottom flask, 107b (9.6 mg, 0.016 mmol) and pentafluorophenol (28.2 mg, 0.153 mmol) were dissolved in dry dichloromethane (5 mL). N-cyclohexylcarbodiimide, N'-methyl polystyrene (33.4 mg, 2.3 mmol/g, 0.077 mmol) was added and the reaction mixture was stirred at room temperature for 16 h under Argon. LCMS (10-100% ACN, 50 mM $NH_4HCO_3$ pH7) indicated all of the starting material had been consumed and activated intermediate had been formed. The reaction mixture was filtered and concentrated under reduced pressure, and the residue was dissolved in a solution of N,N-dimethylformamide (2 mL) and N,N-diisopropylethylamine (8 μL, 0.046 mmol). PFP ester intermediate (6.0 mg, 0.023 mmol) was added and the reaction mixture was stirred at room temperature for 2 h under argon. LCMS (10-100% ACN, 50 mM $NH_4HCO_3$ pH7) indicated all of the activated intermediate had been consumed and product had been formed. The reaction mixture was purified by preparative HPLC (10-100% ACN, 50 mM $NH_4HCO_3$ pH7) to yield 108b (4.7 mg, 37%). LCMS: $[M+H]^+$ m/z=816.71. $^1$H NMR ($CDCl_3$, δ in ppm): 8.04 (s, 1H) 7.05 (d, J=8.4 Hz, 2H) 6.80 (d, J=8.4 Hz, 2H) 5.90 (m, 1H) 5.38 (d, J=10.2 Hz, 1H) 4.63 (t, J=9.3 Hz, 1H) 4.38 (br, 1H) 4.27 (d, J=9.9 Hz, 1H) 3.48 (m, 1H) 3.34 (m, 2H) 2.86 (m, 6H) 2.56 (m, 3H) 2.23 (s, 3H) 2.16 (s, 3H) 1.22-2.10 (br, 16H) 1.12 (d, J=6.9 Hz, 3H) 1.03 (d, J=6.6 Hz, 3H) 0.88 (m, 14H). $^{13}$C NMR: 174.90, 170.44, 161.73, 155.52, 149.37, 130.77, 128.56, 124.33, 115.91, 70.40, 69.69, 67.62, 55.45, 53.70, 49.25, 44.61, 40.40, 36.94, 36.69, 35.93, 31.77, 31.16, 30.06, 24.94, 23.14, 21.08, 20.74, 20.20, 19.55, 17.78, 16.08, 14.05, 10.70

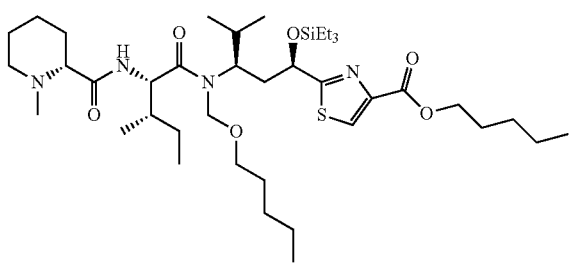

105c

EXAMPLE. Compound 105c. Compound 4 (73.9 mg, 0.10 mmol) in n-pentanol (4 mL) was treated with $n-Bu_2SnO$ (2.10 mg, 0.0083 mmol, 8.0 mol %) at rt and the reaction was heated to 100° C. for 2 days. The solvent was reduced to a minimum and the product was purified with CombiFlash (Teledyne Redisep Silica column, eluted with 0 to 15% of MeOH/DCM) to give 51.2 mg (64%) of intermediate 105c. LCMS: $[M+H]^+$ m/z=767.64. $^1$H NMR ($CDCl_3$, δ in ppm): 8.07 (m, 1H), 7.06 (t, J=9.23 Hz, 1H), 5.95 (d, J=12.3 Hz, 1H), 5.43 (d, J=12.32 Hz, 1H), 5.26 (d, J=9.68 Hz, 1H), 5.03 (dd, J=8.36, 2.64 Hz, 1H), 4.93 (dd, J=8.36, 6.24 Hz, 1H), 4.71 (dd, J=15.83, 8.80 Hz, 1H), 4.20-4.33 (m, 3H), 3.46 (m, 1H), 2.88 (d, J=11.43 Hz, 1H), 2.30-2.60 (m, 2H), 2.20 (s, 2H), 1.95-2.18 (m, 3H), 1.50-1.80 (m, 6H), 1.10-1.44 (m, 6H), 0.80-1.04 (m, 13H), 0.50-0.77 (m, 6H).

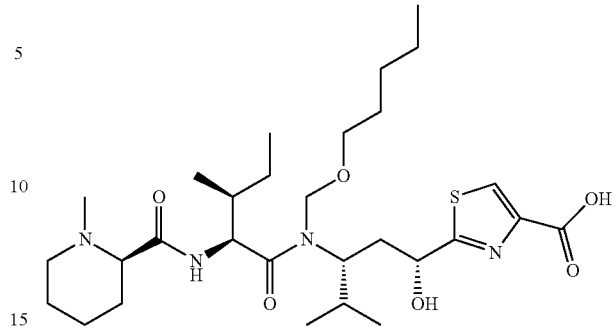

106c

EXAMPLE. Compound 106c. The same procedure as for compound 106a was followed, intermediate 106c (14.9 mg, 38%) was obtained from 105c (51.2 mg). LCMS: $[M+H]^+$ m/z=583.56. $^1$H NMR ($CD_3OD$, δ in ppm): 7.97 (s, 1H), 5.27 (d, J=9.67 Hz, 1H), 4.67 (d, J=9.23 Hz, 1H), 4.58 (d, J=9.68 Hz, 1H), 3.53 (m, 3H), 2.80 (b, 1H), 2.58 (b, 4H), 1.48-2.18 (m, 13H), 1.10-1.42 (m, 6H), 0.70-1.08 (m, 18H).

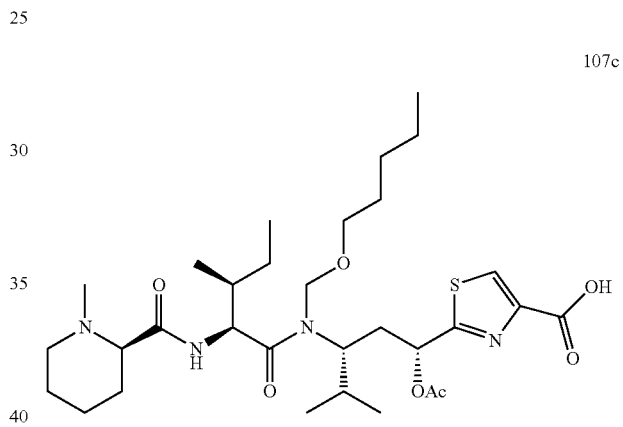

107c

EXAMPLE. Compound 107c. In a 10 mL round bottom flask, 106c (14.9 mg, 0.026 mmol) and acetic anhydride (20 μL, 0.212 mmol) were dissolved in pyridine (1 mL). This this solution was added a catalytic amount of dimethylaminopyridine (1 mg, 0.008 mmol). This solution was stirred at room temperature for 16 h under argon. LCMS (10-100% ACN, 50 mM $NH_4HCO_3$ pH7) indicated all of the starting material had been consumed and product had been formed. To the flask was added a 1:1 mixture of 1,4-dioxane and water (0.4 mL) and the solution was stirred for 10 min to hydrolyze any potential diacetate side product. The reaction mixture was concentrated under reduced pressure, then purified by preparative HPLC (10-100% ACN, 50 mM $NH_4HCO_3$ pH7) to yield 107c (4.8 mg, 30%). LCMS: $[M+H]^+$ m/z=625.58. $^1$H NMR ($CDCl_3$ w/2 drops $CD_3OD$) 7.98 (s, 1H) 5.82 (d, J=10.8 Hz, 1H) 5.26 (s, 1H) 4.57 (d, J=8.4 Hz, 1H) 4.23 (d, J=8.4 Hz, 2H) 3.42 (m, 3H) 2.60-2.92 (br, 8H) 2.15-2.40 (br, 4H) 1.90-2.12 (m, 7H) 1.38-1.90 (br, 14H) 1.00-1.38 (br, 13H) 0.50-1.00 (br, 22H), 0.03 (s, 13H). $^{13}$C NMR: 175.15, 150.56, 125.47, 69.55, 68.09, 55.33, 53.71, 44.59, 36.77, 35.74, 31.34, 30.19, 29.86, 29.32, 28.51, 24.84, 22.85, 22.55, 20.86, 20.40, 19.91, 15.94, 14.10, 10.63, 1.17

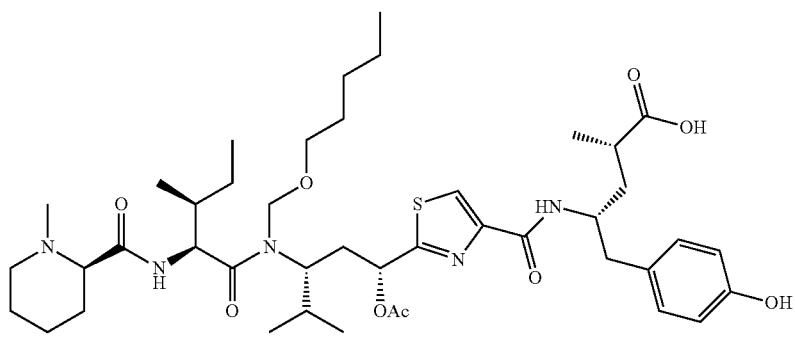

108c

EXAMPLE. Compound 108c. In a 25 mL round bottom flask, 107c (4.8 mg, 0.008 mmol) and pentafluorophenol (14.1 mg, 0.077 mmol) were dissolved in dry dichloromethane (5 mL). N-cyclohexylcarbodiimide, N-methyl polystyrene (16.7 mg, 2.3 mmol/g, 0.038 mmol) was added and the reaction mixture was stirred at room temperature for 16 h under Argon. LC-MS (10-100% ACN, 50 mM $NH_4HCO_3$ pH7) indicated all of the starting material had been consumed and activated intermediate had been formed. The reaction mixture was filtered and concentrated under reduced pressure, and the residue was dissolved in a solution of N,N-dimethylformamide (2 mL) and N,N-diisopropylethylamine (4 µL, 0.023 mmol). PFP ester intermediate (3.0 mg, 0.012 mmol) was added and the reaction mixture was stirred at room temperature for 2 h under Argon. LC-MS (10-100% ACN, 50 mM $NH_4HCO_3$ pH7) indicated all of the activated intermediate had been consumed and product had been formed. The reaction mixture was purified by preparative HPLC (10-100% ACN, 50 mM $NH_4HCO_3$ pH7) to yield 108c (1.1 mg, 17%). LCMS: [M+H]$^+$ m/z=830.76. $^1$H NMR (CDCl$_3$ w/2 drops CD$_3$OD): 8.00 (s, 1H) 7.01 (d, J=8.7 Hz, 2H) 6.74 (d, J=8.4 Hz, 2H) 5.89 (d, J=12.6 Hz, 1H) 5.25 (d, J=9.0 Hz, 1H) 4.55 (d, J=8.7 Hz, 1H) 4.30 (m, 3H) 3.39 (m, 3H) 3.21 (m, 2H) 2.81 (m, 3H) 2.04-2.60 (br, 45H) 1.76-2.04 (m, 5H) 1.34-1.76 (br, 9H) 1.20 (m, 6H) 1.12 (d, J=7.2 Hz, 4H) 1.01 (d, J=6.3 Hz, 3H) 0.89 (t, J=7.1 Hz, 6H) 0.78 (m, 6H)

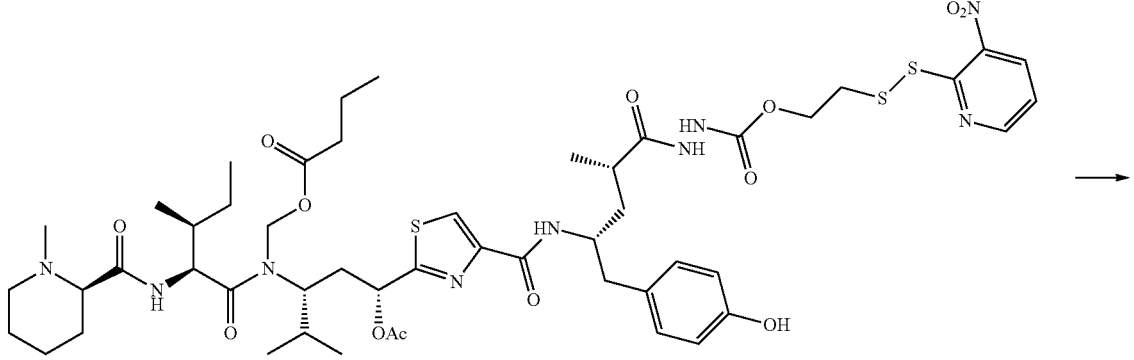

113

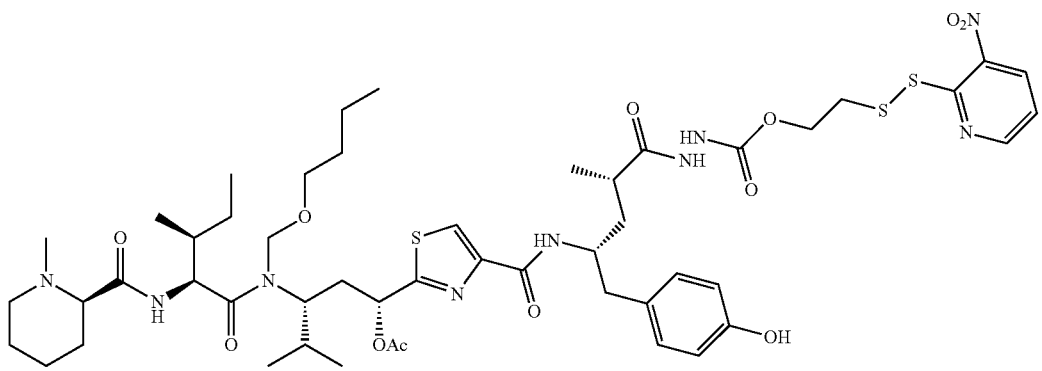

114b

EXAMPLE. Compound 114b. In a 5 mL round bottom flask, 113 (10.0 mg, 0.009 mmol) was dissolved in a solution of trifluoroacetic acid (125 μL, 1.632 mmol) and dichloromethane (0.5 mL) and stirred at room temperature for 1 hr under argon, then 1-butanol (200 μL, 2.186 mmol) added and reaction mixture stirred at room temperature for 30 min under argon. LCMS (10-100% ACN, 50 mM NH$_4$HCO$_3$ pH7) indicated all of the starting material had been consumed and product had been formed. The reaction mixture was purified by preparative HPLC (10-100% ACN, 50 mM NH$_4$HCO$_3$ pH7) to yield 114b (3.2 mg, 32%). LCMS: [M+H]$^+$ m/z=1088.79. $^1$H NMR (CDCl$_3$ w/2 drops CD$_3$OD): 8.86 (s, 1H) 8.47 (d, J=8.0 Hz, 1H) 7.99 (s, 1H) 7.31 (d, J=9.5 Hz, 2H) 7.01 (d, J=7.5 Hz, 2H) 6.73 (d, J=8.5 Hz, 2H) 5.94 (d, J=10.5 Hz, 1H) 5.34 (d, J=10.0 Hz, 1H) 4.58 (m, 3H) 4.38 (t, J=6.0 Hz, 4H), 4.27 (d, J=10.0 Hz, 2H) 3.37 (m, 2H) 3.18 (m, 2H) 3.09 (t, J=6.3 Hz, 3H) 2.70-2.90 (br, 6H) 2.43 (dd, J=11.0 Hz, 3.0 Hz, 2H) 2.26-2.36 (br, 4H) 2.12-2.22 (br, 10H) 2.02-2.12 (br, 2H) 1.86-2.02 (br, $^1$H) 1.69-1.80 (br, 6H) 1.54-1.69 (br, 10H) 1.34-1.52 (br, 12H) 1.09-1.34 (br, 16H) 1.047 (dd, J=15.0 Hz, 6.5 Hz, 19H) 0.88 (m, 19H) 0.75 (m, 17H). $^{13}$C NMR: 174.95, 174.59, 170.64, 170.23, 161.92, 156.91, 156.06, 153.88, 149.00, 133.77, 130.79, 123.92, 120.98, 115.53, 69.95, 69.61, 67.03, 63.82, 55.32, 53.21, 44.78, 41.42, 40.40, 36.84, 36.38, 35.62, 35.22, 31.54, 31.40, 30.37, 24.99, 24.66, 23.20, 20.68, 20.24, 19.56, 19.27, 17.69, 15.71, 13.72, 10.35

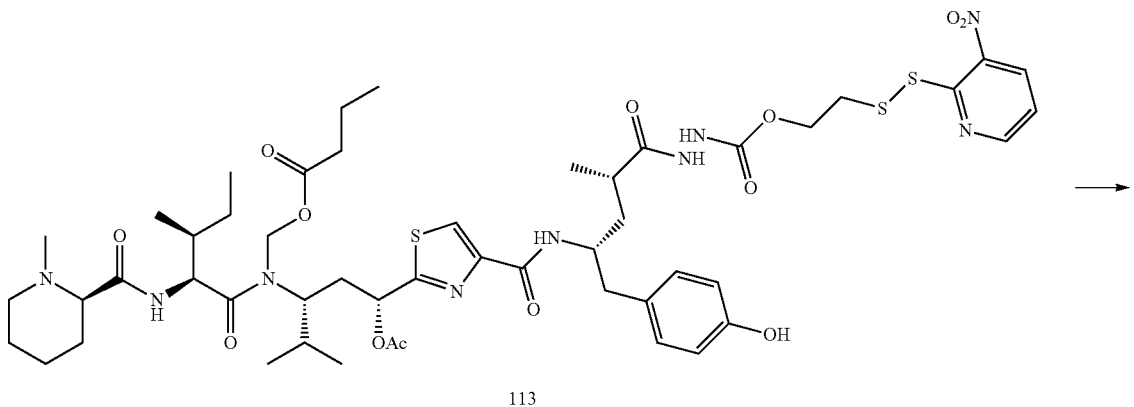

113

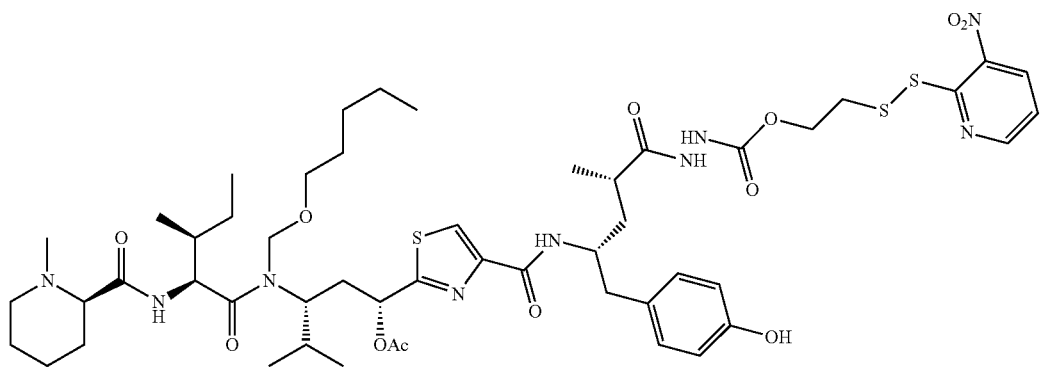

114c

EXAMPLE. Compound 114c. In a 5 mL round bottom flask, 113 (10.0 mg, 0.009 mmol) was dissolved in a solution of trifluoroacetic acid (125 μL, 1.632 mmol) and dichloromethane (0.5 mL) and stirred at room temperature for 1 hr under argon, then 1-pentanol (200 μL, 1.840 mmol) added and reaction mixture stirred at room temperature for 30 min under argon. LC-MS (10-100% ACN, 50 mM $NH_4HCO_3$ pH7) indicated all of the starting material had been consumed and product had been formed. The reaction mixture was purified by preparative HPLC (10-100% ACN, 50 mM $NH_4HCO_3$ pH7) to yield 114c (3.6 mg, 36%). LCMS: $[M+H]^+$ m/z=1102.77.

indicated all of the starting material had been consumed and product had been formed. The reaction mixture was purified by preparative HPLC (10-100% ACN, 50 mM $NH_4HCO_3$ pH7) to yield 117b (4.3 mg, 56%). LCMS: $[M+H]^+$ m/z=1306.82. $^1$H NMR (9:1 DMSO-d6:$D_2O$): 8.60 (s, 1H) 8.14 (s, 1H) 7.59 (d, J=8.5 Hz, 2H) 6.94 (d, J=7.5 Hz, 2H) 6.60 (dd, J=13.3 Hz, 8.8 Hz, 3H) 5.77 (d, J=11.5 Hz, 1H) 5.20 (d, J=9.5 Hz, 1H) 4.46 (m, 3H) 4.00-4.40 (br, 12H) 3.48-3.62 (br, 11H) 3.28-3.48 (br, 12H) 3.10-3.28 (br, 4H) 2.80-3.08 (br, 7H) 2.60-3.80 (br, 3H) 2.48 (s, 1H) 2.26-2.40 (br, 2H) 2.00-2.26 (br, 19H) 1.58-2.00 (br, 20H) 1.28-1.58 (br, 8H) 1.18 (q, J=7.5 Hz, 3H) 0.84-1.10 (br, 8H) 0.75 (m,

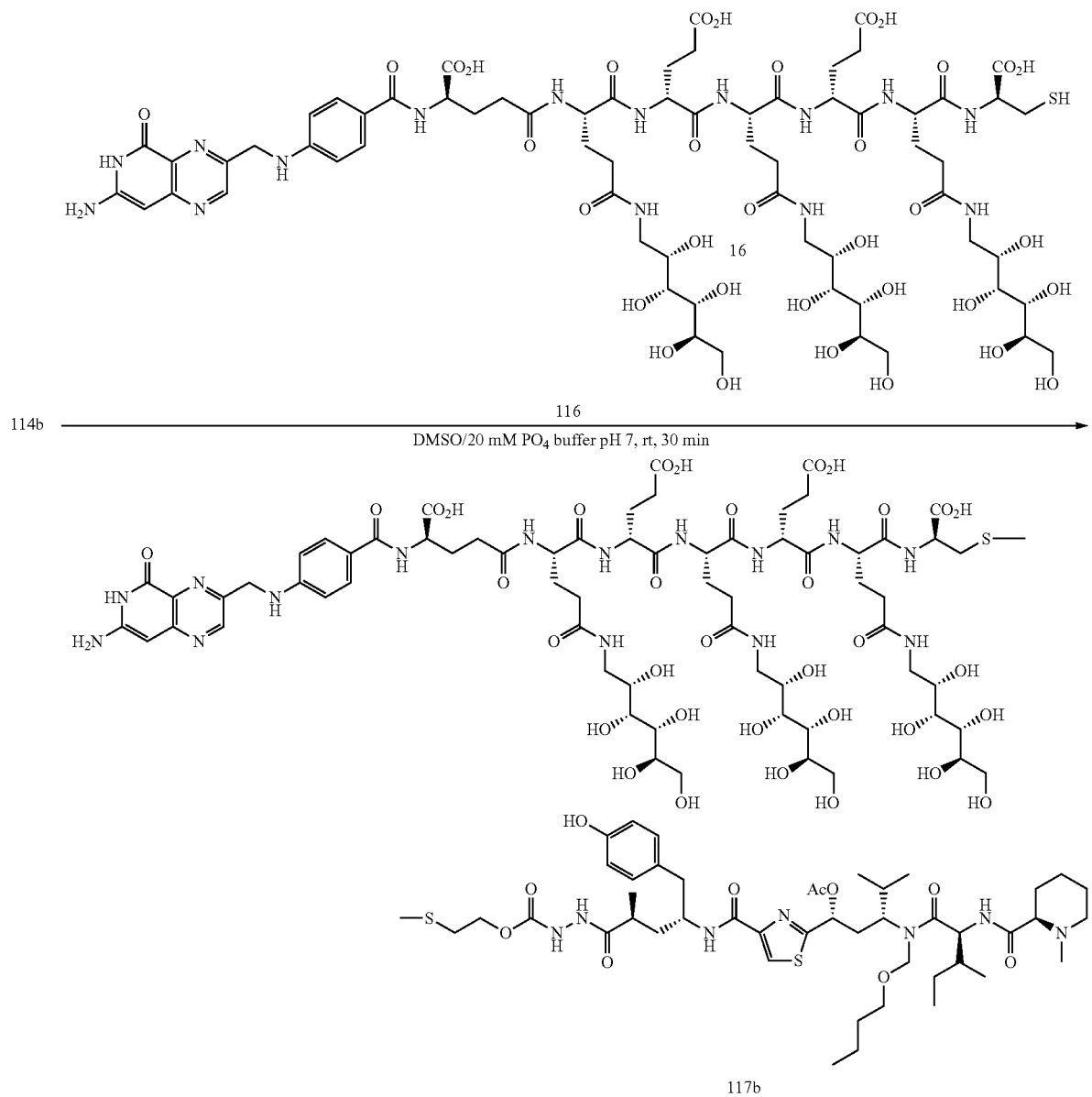

EXAMPLE. Compound 117b. In a 25 mL round bottom flask, 114b (3.2 mg, 0.003 mmol) was dissolved in dimethylsulfoxide (2 mL). A solution of 116 (4.9 mg, 0.003 mmol) in 20 mM, pH7, sodium phosphate buffer (2 mL) was added dropwise, stirring at room temperature with argon bubbling for 30 min. LCMS (10-100% ACN, 50 mM $NH_4HCO_3$ pH7)

9H) 0.60 (d, J=6.5 Hz, 3H). $^{13}$C NMR: 175.25, 174.93, 174.36, 173.59, 173.22, 172.76, 172.70, 172.02, 171.85, 171.67, 170.85, 170.34, 169.68, 166.48, 161.94, 160.67, 156.42, 155.80, 154.22, 150.98, 149.56, 149.21, 149.08, 130.64, 129.17, 128.69, 128.08, 124.89, 122.00, 115.31, 111.84, 72.31, 72.23, 71.82, 71.69, 69.84, 69.74, 68.21, 66.59, 63.52, 63.09, 55.04, 53.74, 53.56, 53.23, 52.96, 52.48, 46.11, 43.63, 42.39, 37.43, 35.69, 35.41, 35.19, 32.17,
EXAMPLE. Compound 109. 1.1 g of dipeptide 1 (2.77 mmole), was mixed with 53 mg (0.21 mmole, 0.08 eq) of n-Bu$_2$SnO in 15 mL of benzyl alcohol and heated to 130° C.
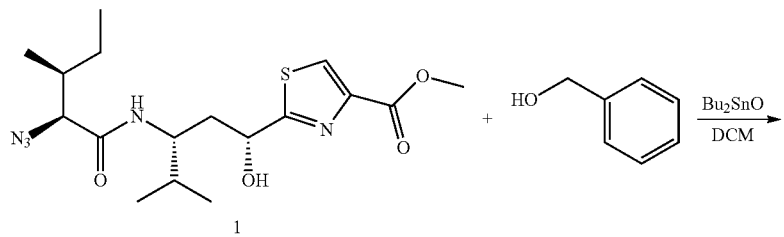
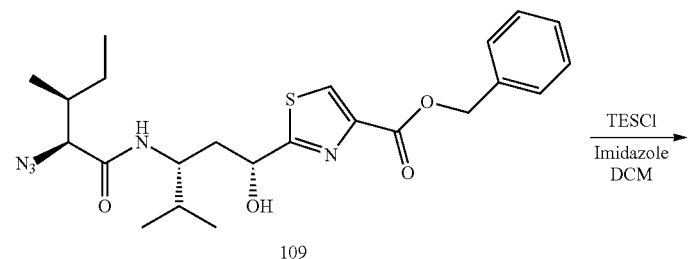
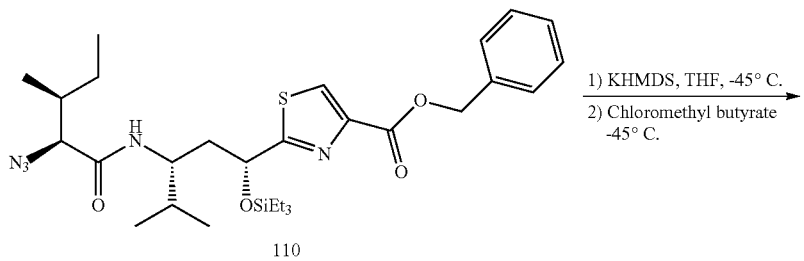
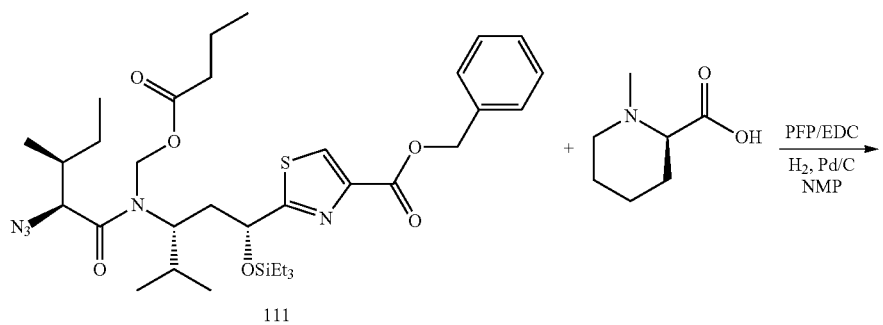
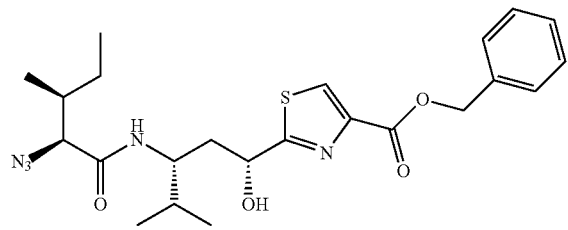

for 2½ hours, then 100° C. overnight. LC/MS showed no starting material left. The reaction mixture was loaded onto a 330 g of Combiflash column, purified with petroleum ether/EtOAc to give some clean fractions. Mixed fractions were repurified to give a combined yield of 0.67 g (51%) of pure benzyl ester 109. LCMS: [M+H]$^+$ m/z=474.46. $^1$H NMR (CDCl$_3$, δ in ppm): 8.12 (s, 1H), 7.46-7.43 (m, 2H), 7.40-7.32 (m, 3H), 6.68 (d, J=9.6 Hz, 1H), 5.41 (d, J=12.3 Hz, 1H), 5.36 (d, J=12.3 Hz, 1H), 5.24 (d, J=4.5 Hz, 1H), 4.87 (m, 1H), 4.02-3.90 (m, 2H), 2.24-2.13 (m, 2H), 1.88-1.78 (m, 2H), 1.42-1.30 (m, 2H), 1.07 (d, J=6.9 Hz, 3H), 0.97-0.90 (m, 9H). $^{13}$C NMR (CDCl$_3$, δ in ppm): 176.1, 170.2, 161.3, 146.5, 135.7, 128.6, 128.5, 128.4, 127.8, 69.6, 68.8, 66.9, 51.6, 41.1, 38.6, 31.8, 24.1, 19.7, 18.3, 16.0, 11.7.

110

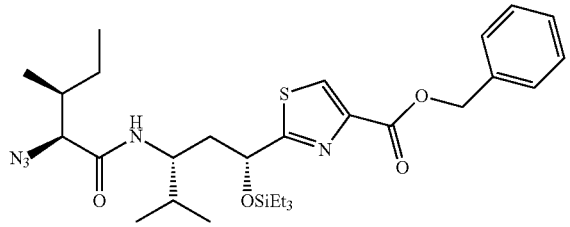

EXAMPLE. Compound 110. 0.67 g (1.42 mmole) of dipeptide benzyl ester 109 was dissolved in 5 mL dichloromethane. To this solution was added 263 μL of TESCl (236 mg, 1.56 mmole, 1.1 eq), and 117 mg (1.72 mmole, 1.2 eq) of imidazole. The reaction was stirred at 0° C. and solid formed. After 2 hours, the solid was filtered away and the filtrate was concentrated. The residue was on the Combiflash (24 g of silica column) with petroleum ether/EtOAC. After concentration, 763 mg (92%) of the desired product 110 was recovered. $^1$H NMR (CDCl$_3$, δ in ppm): 8.12 (s, 1H), 7.46-7.43 (m, 2H), 7.40-7.32 (m, 3H), 6.68 (d, J=8.4 Hz, 1H), 5.41 (d, J=12.3 Hz, 1H), 5.36 (d, J=12.3 Hz, 1H), 5.13 (t, J=5.7 Hz, 1H), 4.03-3.95 (m, 1H), 3.83 (d, 1H), 2.20-2.05 (m, 1H), 1.95-1.86 (m, 2H), 1.48-1.38 (m, 1H), 1.30-1.20 (m, 2H), 1.03 (d, 3H), 0.96-0.82 (m, 18H), 0.65 (t, 6H). $^{13}$C NMR (CDCl$_3$, δ in ppm): 178.2, 168.4, 161.1, 146.5, 135.7, 128.6, 128.5, 128.4, 127.7, 70.7, 70.1, 66.9, 51.3, 39.9, 38.3, 31.6, 24.2, 18.3, 17.6, 16.0, 11.5, 6.8, 4.6.

111

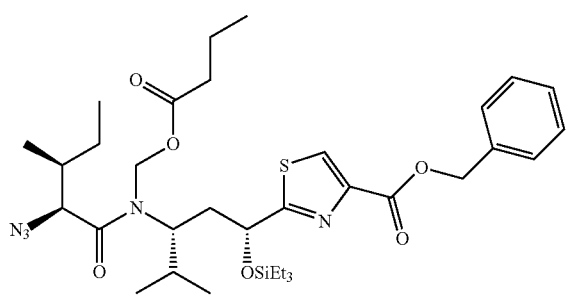

EXAMPLE. Compound 111. 746 mg (1.27 mmole) of TES protected dipeptide benzyl ester 110 was dissolved in 8 mL of THF (anhydrous, inhibitor-free) and cooled to −45° C. After 15 minutes of cooling, 2.8 mL of 0.5 M KHMDS (1.1 eq., 1.4 mmole) in toluene solution was added dropwise. After an additional 15 mins, 175 μL of chloromethyl butyrate (1.1 eq., 1.4 mmole) was added dropwise. After 30 mins, TLC showed only a trace amount of starting material left. After 2 hours, the reaction mixture was quenched 1 mL MeOH, and allowed to warm to room temperature. The reaction was extracted with EtOAc/brine. The organic layer was washed with brine and then concentrated to give 759 mg (87%) of crude product 111. LCMS: [M+Na]$^+$ m/z=710.57. $^1$H NMR (CDCl$_3$, δ in ppm) 8.10 (s, 1H), 7.44-7.40 (m, 2H), 7.39-7.30 (m, 3H), 5.43 (d, J=12.3 Hz, 1H), 5.37 (d, J=12.3 Hz, 1H), 5.35 (s, 2H), 4.98 (t, J=5.1 Hz, 1H), 4.40-4.20 (br, 1H), 3.52 (d, J=16.0 Hz, 1H), 2.42-2.38 (t, J=6.7 Hz, 2H), 2.25-2.05 (m, 2H), 1.78-1.72 (m, 2H), 1.68-1.55 (m, 3H), 1.30-1.20 (m, 1H), 1.00-0.85 (m, 24H), 0.65 (t, 6H). $^{13}$C NMR (CDCl$_3$, δ in ppm) 177.6, 173.0, 171.0, 161.1, 146.6, 135.7, 128.6, 128.42, 128.36, 127.6, 77.2, 70.8, 66.8, 63.5, 40.9, 35.9, 34.9, 31.1, 25.0, 20.1, 19.5, 18.1, 15.7, 13.6, 10.5, 6.8, 4.7.

112

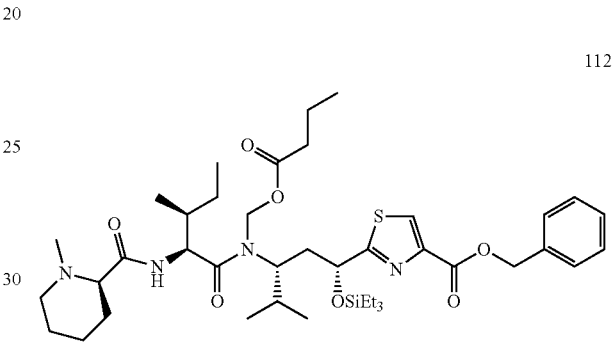

EXAMPLE. Compound 112. 239 mg of MEP (1.67 mmole, 1.5 eq), 316 mg of EDC (1.65 mmole, 1.5 eq), and 300 mg of pentafluorophenol (1.63 mmole, 1.5 eq) were dissolved in 8 mL of N-methyl-2-pyrrolidone. The reaction was stirred overnight. 759 mg (1.1 mmole) of the alkylated dipeptide 111 in 1 mL NMP was then added. An additional 0.8 mL of NMP was used to rinse the flask/syringe to transfer residue to the hydrogenation flask. 60 mg (0.05 eq) of 10% Pd/C was then added and the reaction mixture was hydrogenated at 35 PSI, overnight. LC/MS showed the major product is the benzyl ester, along with 10% free acid. The reaction was filtered through celite, and the filter cake was washed with EtOAc. The filtrate was extracted with brine, washed with brine, and concentrated. Combiflash purification with petroleum ether/EtOAc resulted in the recovery of 215 mg (25%) of pure benzyl ester 112. LCMS: [M+H]$^+$ m/z=787.66. $^1$H NMR (CDCl$_3$, δ in ppm): 8.09 (s, 1H), 7.44-7.40 (m, 2H), 7.39-7.30 (m, 3H), 7.07 (d, J=15.5 Hz, 1H), 5.93 (d, J=12.3 Hz, 1H), 5.42 (d, J=12.3 Hz, 1H), 5.34 (s, 2H), 4.93 (dd, J=8.4, 2.7 Hz, 1H), 4.70-4.60 (m, 1H), 4.50-4.30 (br, 1H), 2.88 (m, 1H), 2.60-2.28 (m, 4H), 2.21 (s, 3H), 2.08-1.89 (m, 4H), 1.80-1.40 (m, 8H), 1.36-1.1.07 (m, 3H), 1.00-0.80 (m, 21H), 0.77 (d, 3H), 0.65 (t, 6H). $^{13}$C NMR (CDCl$_3$, δ in ppm): 177.5, 175.1, 174.1, 173.0, 161.1, 146.5, 135.8, 128.6, 128.4, 128.3, 127.6, 77.2, 70.7, 69.5, 69.2, 66.7, 57.3, 55.4, 53.5, 53.4, 44.8, 41.3, 36.8, 35.9, 31.4, 30.3, 25.0, 24.7, 23.2, 20.2, 19.4, 18.1, 16.2, 13.6, 10.6, 6.8, 5.1, 4.7.

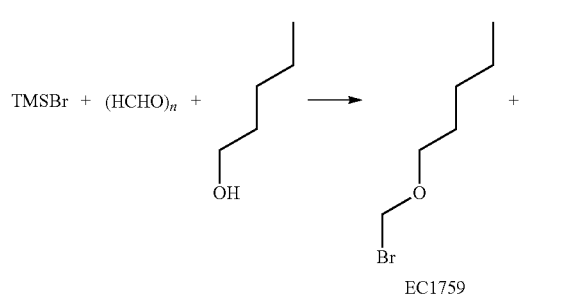

EC1759

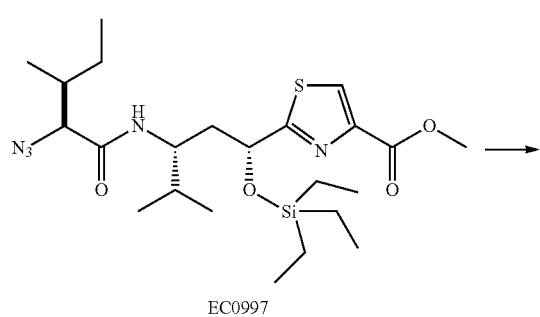

EC0997

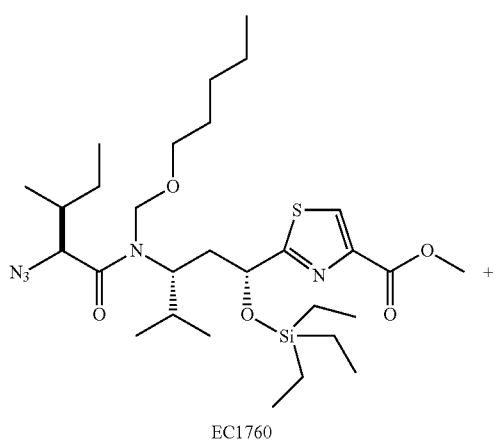

EC1760

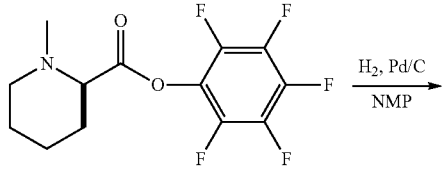

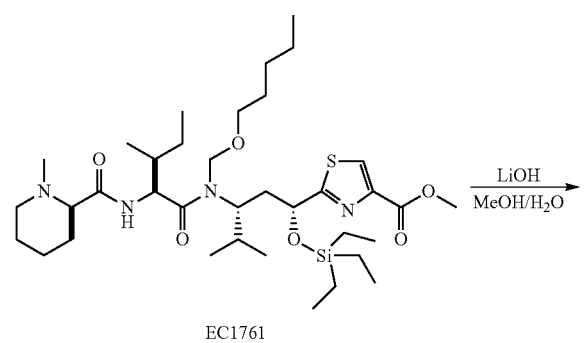

EC1761

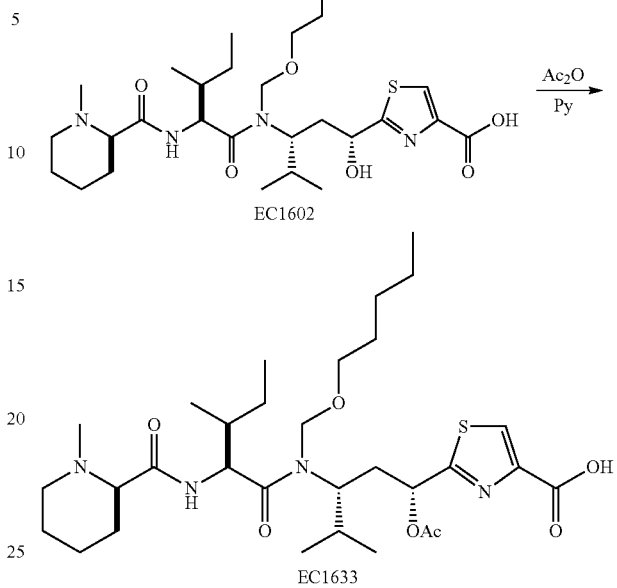

EC1602

EC1633

EXAMPLE. Synthesis of EC1759. Paraformaldehyde (1.5 g, 1.25 eq) was added to 16 mL of TMSBr. The resulted suspension was cooled to 0° C., and 1-pentanol (4.36 mL, 40 mmole, 1 equiv.) was added dropwise. The reaction was stirred at 0° C. and warmed up to room temperature. After overnight, TMSBr was evaporated under reduced pressure. Vacuum distillation of the residue was carried out at 7 mm Hg pressure, the fraction came out at 56° C. was the desired product EC1759 (4.3 g, 59%).

EXAMPLE. Synthesis of EC1760. 1.58 g (3.09 mmole) TES-dipeptide EC0997 was dissolved in 12 mL THF (anhydrous, inhibitor-free). The resulted solution was cooled to −45° C. To the solution, 6.5 mL of 0.5 M KHMDS in toluene (3.25 mmole, 1.05 equiv.) was added dropwise. After finishing the addition, the reaction mixture was stirred at −45° C. for 15 minutes. 600 µL of bromomethyl pentyl ether EC1759 (4.1 mmole, 1.33 equiv.) was added dropwise. The reaction mixture was warmed from −45° C. to −10° C. in 90 minutes, then quenched with 10% NaCl/1% NaHCO$_3$ aqueous solution, extracted with EtOAc. The organic phase was washed with 10% NaCl/1% NaHCO$_3$ aqueous solution three times, then brine. The separated organic phase was dried over Na$_2$SO$_4$. Na$_2$SO$_4$ was filtered off and the solvent was evaporated under vacuum to give 2.4 g of crude product. The crude product was purified with EtOAc/petroleum ether to give 1.47 g of product EC1760 (78%)

EXAMPLE. Synthesis of EC1761. 0.38 g of MEP (2.65 mmole, 1.4 equiv.) was suspended in 1.2 mL NMP, 0.53 g of PFP (2.88 mmole, 1.5 equiv.) and 0.55 g of EDC (2.87 mmole, 1.5 equiv.) were added. The reaction mixture was stirred overnight in a hydrogenation vessel.

1.17 g (1.91 mmole) of alkylated dipeptide EC1760 was dissolved in 0.3 mL NMP and transferred to the above hydrogenation vessel, and the residue of the dipeptide was rinsed with 0.3 mL NMP and transferred to the hydrogenation vessel. 154 mg of 10% Pd/C (dry, 0.05 equiv.) was added to the solution. The hydrogenation was carried out at 35 PSI. After 5 hrs, LC/MS showed there was no starting material. The reaction mixture was filtered through celite pad and the reaction vessel was washed with EtOAc and filtered through celite pad. The combined solution was washed with 10% NaCl/1% Na$_2$CO$_3$ solution to remove PFP, then with brine. The organic phase was dried over Na$_2$SO$_4$. Na$_2$SO$_4$ was filtered off and the solvent was evaporated under vacuum to give 1.20 g (88%) of crude product EC1761.

EXAMPLE. Synthesis of EC1602. 1.17 g (1.65 mmole) of tripeptide ester EC1761 was dissolved in 15 mL MeOH, the solution was cooled to 0° C. 300 mg of LiOH hydrate (7.15 mmole, 4.3 equiv.) dissolved in 5 mL H$_2$O was added to the ester solution, the resulted reaction mixture was stirred and warmed up to room temperature in 2 hours. LC/MS showed no starting material left. MeOH was removed using rotary evaporator, and the residual was worked up by extraction between EtOAc/brine. The organic phase was dried over Na$_2$SO$_4$. Na$_2$SO$_4$ was filtered off and the solvent was evaporated under vacuum to give 0.80 g (83%) of crude product EC1602.

EXAMPLE. Synthesis of EC1633. 0.80 g (1.37 mmole) of tripeptide acid EC1602 was dissolved in 6.4 mL of pyridine, the solution was cooled to 0° C. 6.0 mg (0.049 mmole, 0.035 equiv) DMAP was added and then 2 mL of acetic anhydride (21.2 mmole, 15.5 equiv) was added, the reaction mixture was warmed up to room temperature in 5 hours and stored in −20° C. for 2 days. 20 mL dioxane/20 mL H2O was added to the reaction mixture at 0° C. and stirred for 1 hour. The solvent was evaporated under reduced pressure. 20 mL of phosphate buffer (20 mM) and 5 mL acetonitrile were added to the residue, the pH of the resulted solution was adjusted to 5.4 using saturated NaHCO$_3$ solution. The solution was loaded on Biotage 120 g C18 column. The flask containing the crude product was rinsed with 1 mL acetonitrile/5 mL phosphate buffer and loaded on the column. The purification was done using a gradient from 20% ACN/80% water to 70% ACN/30%. The fractions containing the desired product were combined and ACN was evaporated under reduced pressure. There were white precipitate coming out from solution, brine was added to the suspension and EtOAc was used to extract the desired product. The organic phase was dried over Na$_2$SO$_4$. Na$_2$SO$_4$ was filtered off and the solvent was evaporated under vacuum to give 0.49 g (57%) of product EC1633.

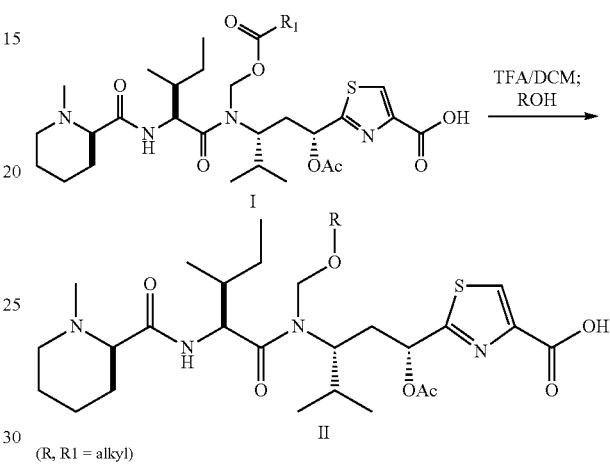

Scheme 2

(R, R1 = alkyl)

Scheme 3

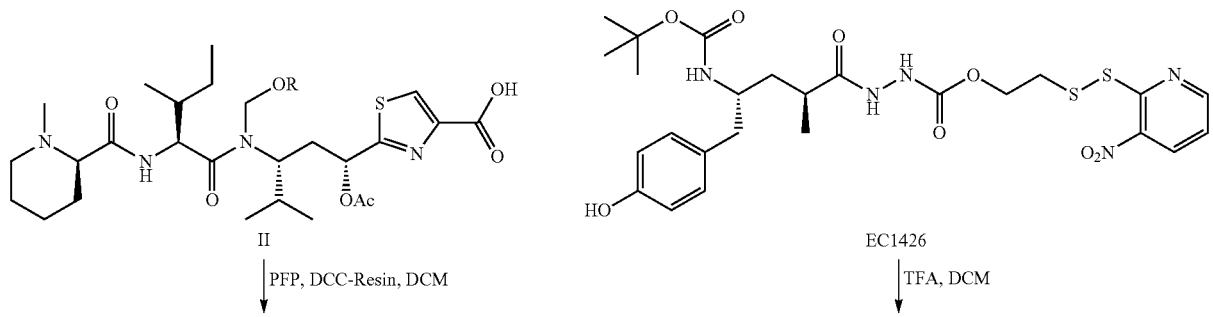

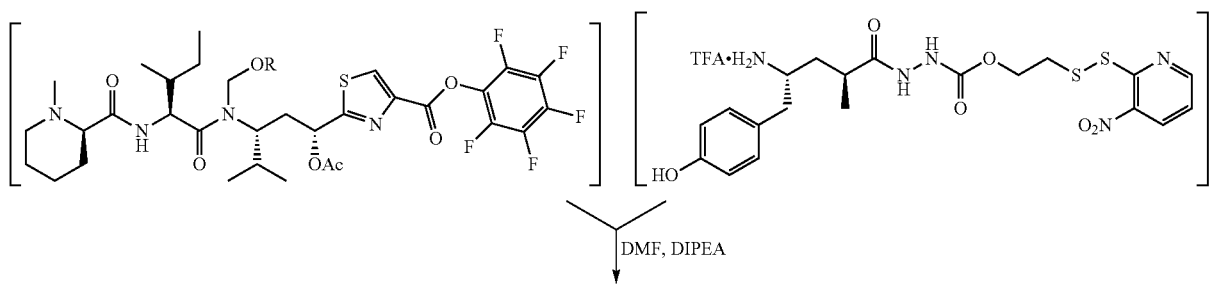

-continued

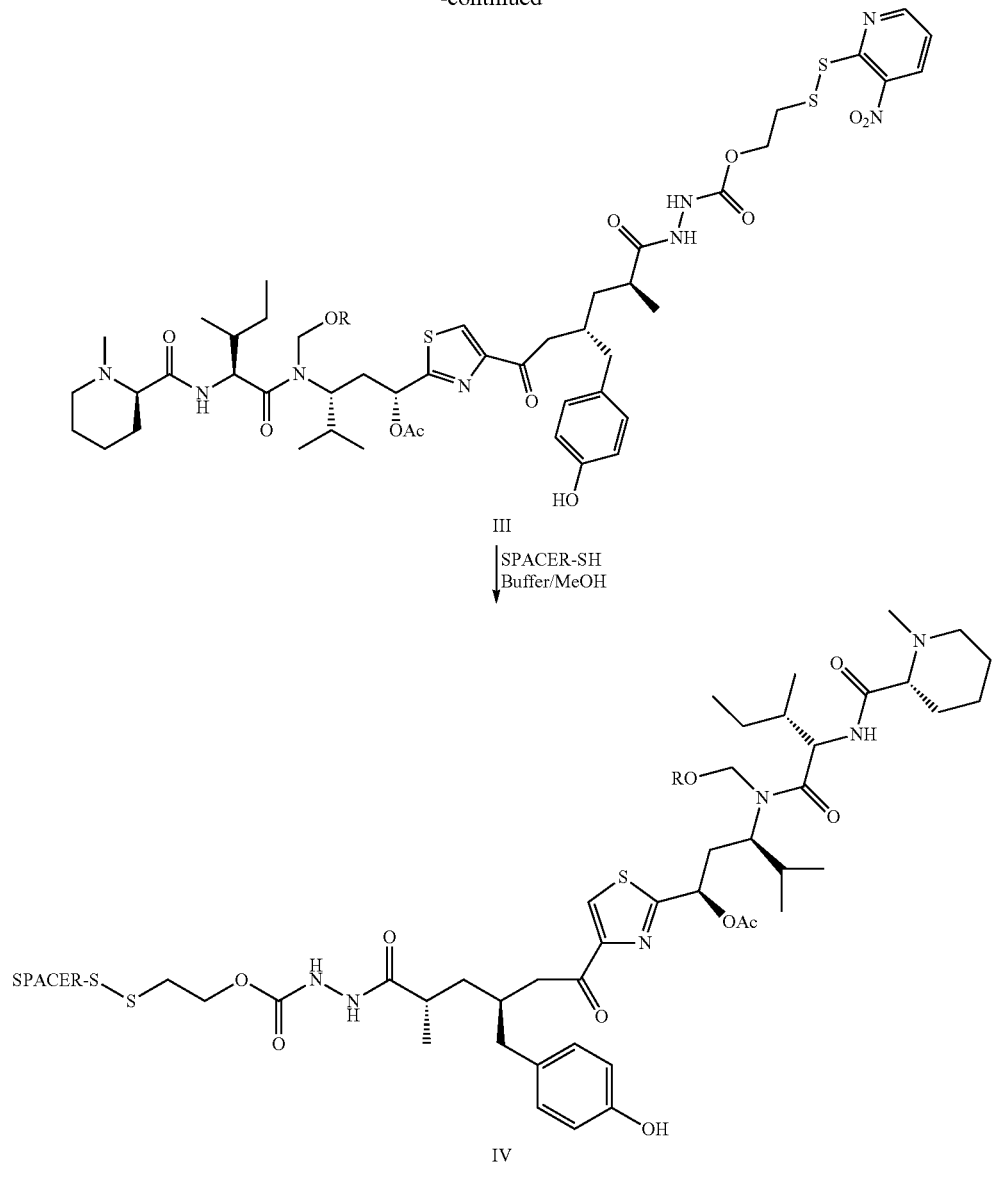

(R = alkyl)

Example. General Procedures:

Synthesis of EC1623 (Scheme 2). EC1008 (I: $R_1$=n-propyl. 103 mg) was dissolved in anhydrous dichloromethane (DCM, 2.0 mL) and to this solution was added trifluoroacetic acid (TFA, 0.50 mL). The resulting solution was stirred at ambient temperature under argon for 20 minutes, and to which was added 1-pentanol (0.72 mL). The reaction mixture was stirred at ambient temperature for 3 minutes, concentrated on a Buchi Rotavapor at 30° C. for 10 minutes, residue stirred at ambient temperature under high vacuum for 75 minutes, and to which was added saturated $NaHCO_3$ solution (10 mL) with vigorous stirring, followed by addition of acetonitrile (ACN, 3.0 mL). The resulting white suspension was stirred at ambient temperature for 3 minutes and let stand to settle. The top clear solution was loaded onto a Biotage SNAP 12 g KP-C18-HS column on a Biotage system. The white solid left in the reaction flask was dissolved in water (5.0 mL) and the solution was also loaded onto the Biotage column. The remaining solid stuck on the glass wall of the reaction flask was dissolved in ACN (2.0 mL). To this solution was added water (6.0 mL) and the resulting cloudy solution was loaded onto the same Biotage column. The reaction mixture was eluted following these parameters: Flow rate: 15 mL/min. A: water; B: CAN. Method: 25% B 2 CV (column volume), 25-50% B 3 CV, and 50% B 5 CV (1 CV=15 mL). Fractions containing the desired product was collected and freeze-dried to afford EC1623 (II: R=n-pentyl. 95.9 mg) as a white powder.

Synthesis of EC1662 (Scheme 3).

Step 1: Anhydrous DCM (5.0 mL) was added to a mixture of EC1623 (II: R=n-pentyl. 114 mg), pentafluorophenol (PFP, 67.3 mg), and DCC-resin (2.3 mmol/g, 396 mg) and the suspension was stirred at ambient temperature under argon for 23 hours. The resin was filtered off and washed with anhydrous DCM (3.0 mL) and the combined filtrates were concentrated under reduced pressure to give a residue, which was vacuumed at ambient temperature for 1 hour prior to use in Step 3.

Step 2: EC1426 (114 mg) was dissolved in anhydrous DCM (1.5 mL) and to which was added TFA (0.50 mL). The resulting solution was stirred at ambient temperature under argon for 70 minutes and concentrated under reduced pressure to give a residue, which was co-evaporated with anhydrous DCM (2.0 mL×3) and vacuumed at ambient temperature for 9 hours prior to use in Step 3.

Step 3: The residue from Step 1 was dissolved in anhydrous DCM (1.5 mL) and to this solution was added DIPEA (0.50 mL) followed by a solution of the residue from Step 2 dissolved in anhydrous dimethylformamide (DMF, 1.5 mL). The resulting solution was stirred at ambient temperature under argon for 1 hour, diluted with ethyl acetate (EtOAc, 60 mL), and washed with brine (20 mL×3). The organic layer was separated, dried ($Na_2SO_4$), and concentrated under reduced pressure to give a residue, which was vacuumed at ambient temperature for 2 hours, dissolved in DCM (3.5 mL), and loaded onto a 24 g silica gel column on a CombiFlash system for purification. The materials were eluted with 0-5% MeOH in DCM to afford EC1662 (III: R=n-pentyl. 171 mg) as a white solid.

EXAMPLE. Synthesis of EC1664 (Scheme 3). A solution of EC1454 (SPACER-SH; See Figure 1 for structure. 44.1 mg.) in 20 mM phosphate buffer (pH 7.0, 4.0 mL) was added to a solution of EC1662 (24.1 mg) in MeOH (4.8 mL), followed by addition of saturated $Na_2SO_4$ (0.30 mL). The reaction mixture was stirred at ambient temperature under argon for 30 minutes and the solution was injected onto a preparative HPLC (A: 50 M $NH_4HCO_3$ buffer, pH 7.0; B: CAN. Method: 10-80% B in 20 minutes.) for purification. Fractions containing the desired product were collected and freeze-dried to afford EC1664 (IV: R=n-pentyl. 42.8 mg) as a fluffy yellow solid.

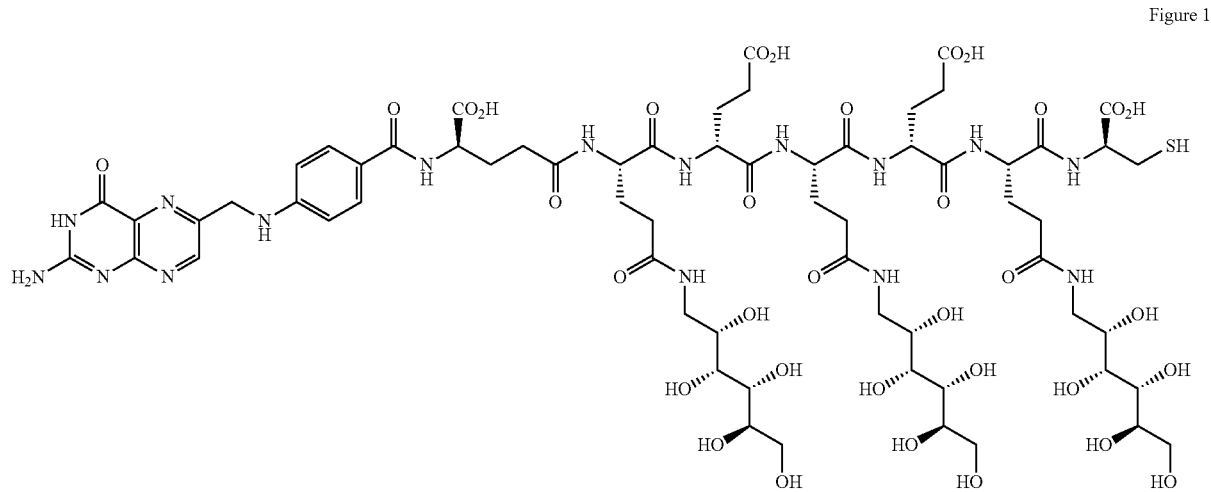

Figure 1

EC1454

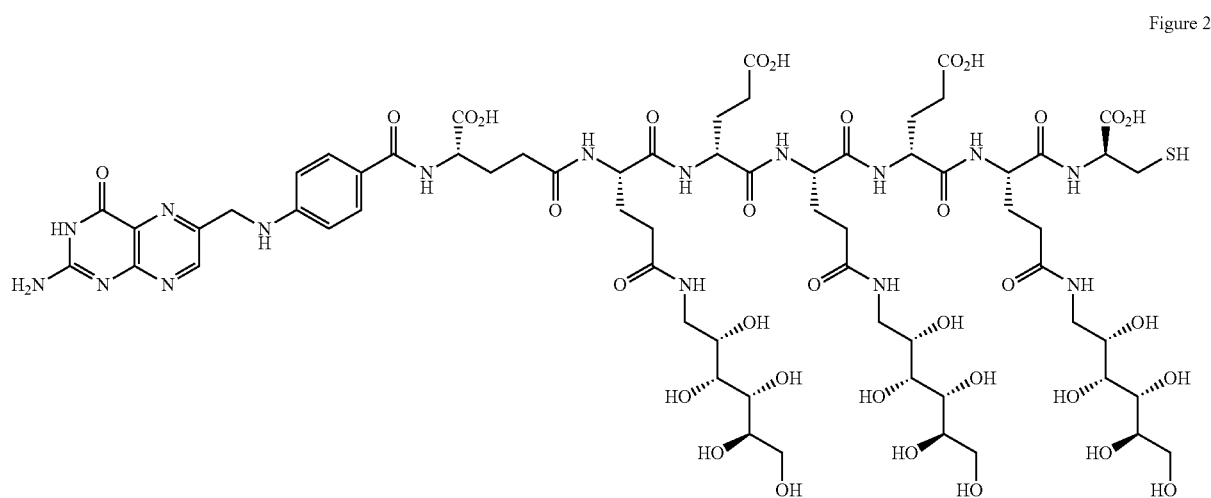

Figure 2

EC1759

The ether analogs of compounds 111 and 112 can be used to prepare the tubulysin intermediates described herein.

What is claimed is:
1. A process for preparing a compound of the formula

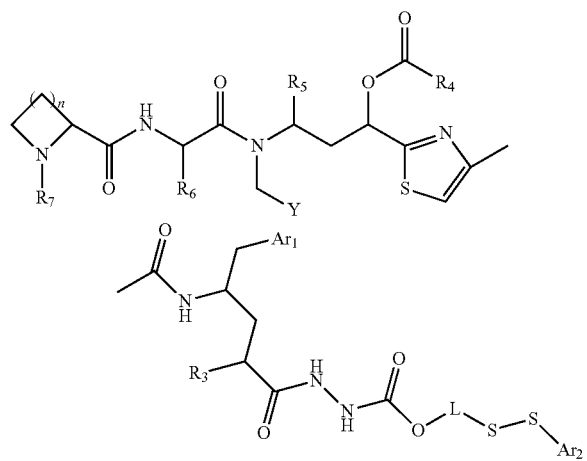

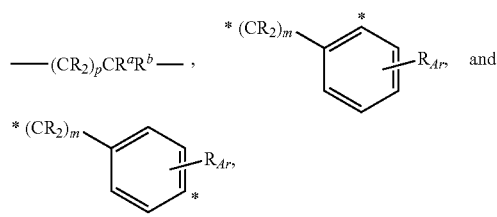

or a salt or solvate thereof; wherein
Ar₁ is optionally substituted aryl or optionally substituted heteroaryl;
Ar₂ is optionally substituted aryl or optionally substituted heteroaryl;
L is selected from the group consisting of —(CR₂)$_p$CR$^a$R$^b$—,   *(CR₂)$_m$—(phenyl)—R$_{Ar}$   and

*(CR₂)$_m$—(phenyl)—R$_{Ar}$, where p is an integer from about 1 to about 3, m is an integer from about 1 to about 4, and * indicates the points of attachment;
R$^a$, R$^b$, and R are each independently selected in each instance from the group consisting of hydrogen and alkyl; or any two of R$^a$, R$^b$, and R are taken together with the attached carbon atom(s) to form a carbocyclic ring;
R$_{Ar}$ represents 0 to 4 substituents selected from the group consisting of amino, or derivatives thereof, hydroxy or derivatives thereof, halo, thio or derivatives thereof, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, and carboxylic acids and derivatives thereof;
Y is acyloxy or R₁₂O;
R₃ is optionally substituted alkyl;
R₄ is optionally substituted alkyl or optionally substituted cycloalkyl;
R₅ and R₆ are each independently selected from the group consisting of optionally substituted alkyl and optionally substituted cycloalkyl;
R₇ is optionally substituted alkyl;
R₁₂ is alkyl, alkenyl, alkynyl, heteroalkyl, cycloalkyl, heterocycloalkyl, aryl, arylalkyl or heteroarylalkyl, each of which is optionally substituted; and
n is 1, 2, 3, or 4;
wherein the process comprises
the step of treating a compound of formula A with triethylsilyl chloride and imidazole in an aprotic solvent, where R₈ is C1-C6 unbranched alkyl

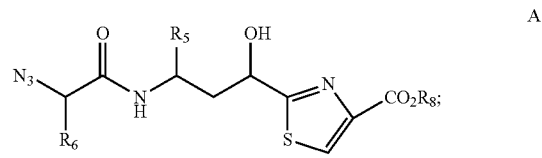

or
the step of treating a compound of formula B with a base and a compound of the formula ClCH₂OC(O)R₂ in an aprotic solvent at a temperature from about −78° C. to about 0° C.; wherein the molar ratio of the compound of the formula ClCH₂OC(O)R₂ to the compound of formula B is from about 1 to about 1.5, where R₂ is selected from the group consisting of optionally substituted alkyl and optionally substituted cycloalkyl and R₈ is C1-C6 unbranched alkyl

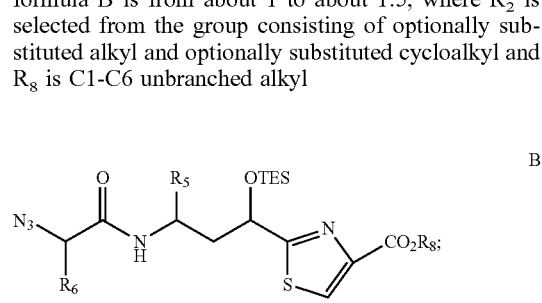

or
the steps of
a) preparing a compound of formula (E1) from a compound of formula (E), where X₁ is a leaving group

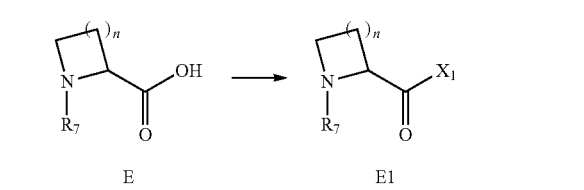

and
b) treating a compound of formula C under reducing conditions in the presence of the compound of formula E1, where R₈ is C1-C6 unbranched alkyl

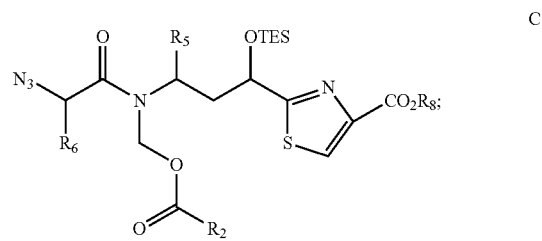

where R₂ is selected from the group consisting of optionally substituted alkyl and optionally substituted cycloalkyl;
or
the step of treating a compound of formula D with a hydrolase enzyme or with a trialkyltin hydroxide, where R₈ is C1-C6 unbranched alkyl

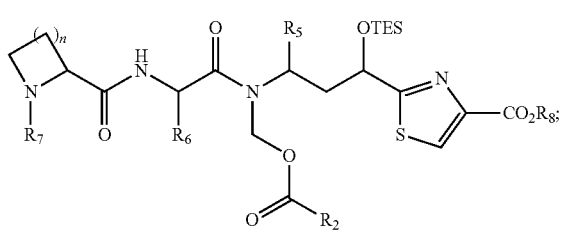

D where R₂ is selected from the group consisting of optionally substituted alkyl and optionally substituted cycloalkyl;
or
the step of treating a compound of formula F1 with a non-basic fluoride reagent

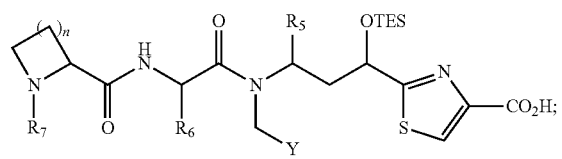

F1 or
the step of treating a compound of formula G1 with an acylating agent of formula R₄C(O)X₂, where X₂ is a leaving group

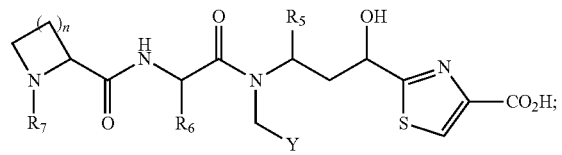

G1 or
the steps of
c) forming an active ester intermediate from a compound of formula H1

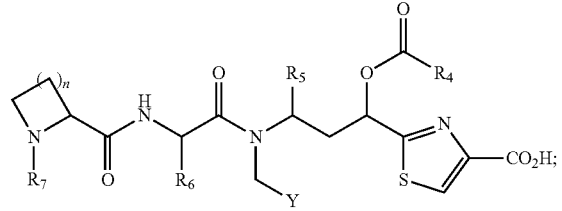

H1 and
d) reacting the active ester intermediate with a compound of the formula I

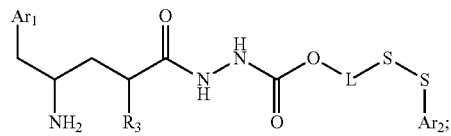

I or a combination thereof.

2. The process of claim 1 comprising the step of treating a compound of formula A with triethylsilyl chloride and imidazole in an aprotic solvent, where R₈ is C1-C6 unbranched alkyl

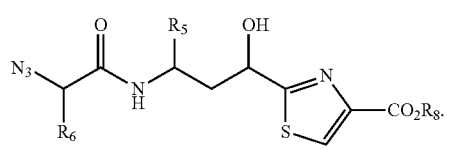

A

3. The process of claim 1 comprising the step of treating a compound of formula B with a base and a compound of the formula ClCH₂OC(O)R₂ in an aprotic solvent at a temperature from about −78° C. to about 0° C.; wherein the molar ratio of the compound of the formula ClCH₂OC(O)R₂ to the compound of formula B is from about 1 to about 1.5, where R₂ is selected from the group consisting of optionally substituted alkyl and optionally substituted cycloalkyl and R₈ is C1-C6 unbranched alkyl

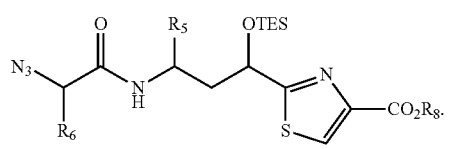

B

4. The process of claim 1 comprising the steps of
a) preparing a compound of formula (E1) from a compound of formula E, where X₁ is a leaving group

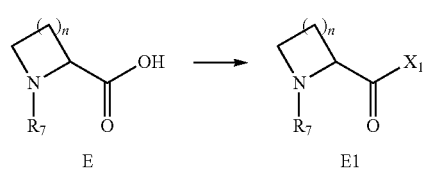

and
b) treating a compound of formula C under reducing conditions in the presence of the compound of formula E1, where R₈ is C1-C6 unbranched alkyl

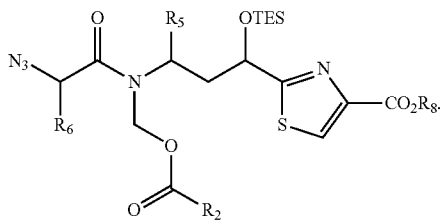

where $R_2$ is selected from the group consisting of optionally substituted alkyl and optionally substituted cycloalkyl.

5. The process of claim 1 comprising the step of treating a compound of formula D with a hydrolase enzyme or a trialkyltin hydroxide, where $R_8$ is C1-C6 unbranched alkyl

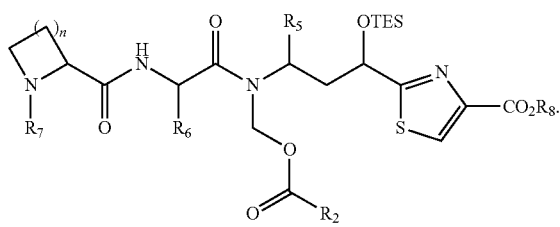

where $R_2$ is selected from the group consisting of optionally substituted alkyl and optionally substituted cycloalkyl.

6. The process of claim 1 comprising the step of treating a compound of formula G1 with an acylating agent of formula $R_4C(O)X_2$, where $X_2$ is a leaving group

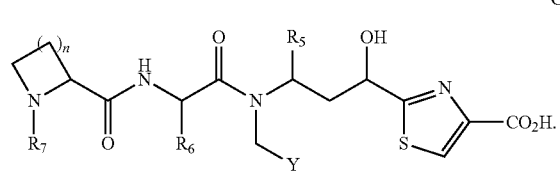

7. The process of claim 1 comprising the steps of
c) forming an active ester intermediate from a compound of formula H1

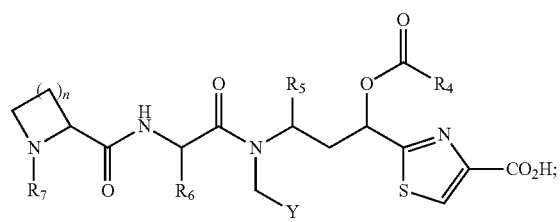

and
d) reacting the active ester intermediate with a compound of the formula I

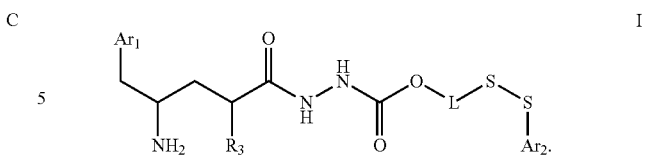

8. The process of claim 1 wherein Y is $R_2C(O)O$, where $R_2$ is selected from the group consisting of optionally substituted alkyl and optionally substituted cycloalkyl.
9. The process of claim 8 wherein $R_2$ is n-butyl.
10. The process of claim 1 wherein $R_3$ is methyl.
11. The process of claim 1 wherein $Ar_1$ is 4-hydroxyphenyl.
12. The process of claim 1 wherein $R_4$ is methyl.
13. The process of claim 1 wherein $R_5$ is iso-propyl.
14. The process of claim 1 wherein $R_7$ is methyl.
15. The process of claim 1 wherein $Ar_e$ is 3-nitro-2-pyridyl.
16. The process of claim 1 wherein L is $-(C(R)_2)_pCR^aR^b-$.
17. The process of claim 1 wherein p is 1.
18. A compound of the formula

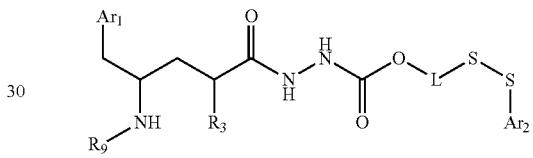

or a salt or solvate thereof;
wherein
$Ar_1$ is optionally substituted aryl or optionally substituted heteroaryl;
$Ar_2$ is optionally substituted aryl or optionally substituted heteroaryl;
L is selected from the group consisting of

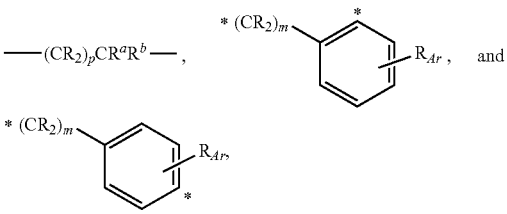

where p is an integer from about 1 to about 3, m is an integer from about 1 to about 4, and * indicates the points of attachment;
$R^a$, $R^b$, and R are each independently selected in each instance from the group consisting of hydrogen and alkyl; or any two of $R^a$, $R^b$, and R are taken together with the attached carbon atom(s) to form a carbocyclic ring;
$R_{Ar}$ represents 0 to 4 substituents selected from the group consisting of amino, or derivatives thereof, hydroxy or derivatives thereof, halo, thio or derivatives thereof, alkyl, haloalkyl, heteroalkyl, aryl, arylalkyl, arylheteroalkyl, heteroaryl, heteroarylalkyl, heteroarylheteroalkyl, nitro, sulfonic acids and derivatives thereof, and carboxylic acids and derivatives thereof;

$R_3$ is optionally substituted alkyl; and
$R_9$ is hydrogen or an amine protecting group.

19. The compound of claim 18 wherein $Ar_2$ is 3-nitro-2-pyridyl.

20. The compound of claim 18 wherein $Ar_1$ is 4-substituted phenyl.

* * * * *